(12) United States Patent
Chu et al.

(10) Patent No.: US 11,179,367 B2
(45) Date of Patent: *Nov. 23, 2021

(54) PHARMACEUTICAL COMPOSITIONS FOR TREATING CYSTIC FIBROSIS

(71) Applicant: Vertex Pharmaceuticals Incorporated, Boston, MA (US)

(72) Inventors: Cathy Chu, Cambridge, MA (US); Varsha Dhamankar, Watertown, MA (US); Eleni Dokou, Cambridge, MA (US); Eric L. Haseltine, Melrose, MA (US); Samuel Moskowitz, Waban, MA (US); Sarah Robertson, Somerville, MA (US); David Waltz, Waban, MA (US); Weichao George Chen, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,222

(22) Filed: Feb. 4, 2019

(65) Prior Publication Data

US 2019/0240197 A1    Aug. 8, 2019

Related U.S. Application Data

(60) Provisional application No. 62/626,567, filed on Feb. 5, 2018, provisional application No. 62/657,522, filed on Apr. 13, 2018.

(51) Int. Cl.
| | |
|---|---|
| *A61K 31/4045* | (2006.01) |
| *A61K 31/443* | (2006.01) |
| *A61K 31/404* | (2006.01) |
| *A61P 11/00* | (2006.01) |
| *A61K 31/4439* | (2006.01) |
| *A61K 31/47* | (2006.01) |
| *A61P 25/28* | (2006.01) |

(52) U.S. Cl.
CPC ........ *A61K 31/4045* (2013.01); *A61K 31/404* (2013.01); *A61K 31/443* (2013.01); *A61K 31/4439* (2013.01); *A61K 31/47* (2013.01); *A61P 11/00* (2018.01); *A61P 25/28* (2018.01)

(58) Field of Classification Search
CPC .............. C07D 401/04; C07D 231/20; A61K 31/4439; A61K 31/4045; A61K 2300/00
See application file for complete search history.

(56) References Cited

U.S. PATENT DOCUMENTS

| | | |
|---|---|---|
| 5,410,061 A | 4/1995 | Gilmore et al. |
| 6,441,004 B1 | 8/2002 | Faull et al. |
| 6,787,651 B2 | 9/2004 | Stolle et al. |
| 6,949,572 B2 | 9/2005 | Bertinato et al. |
| 6,979,692 B2 | 12/2005 | Bertinato et al. |
| 7,368,573 B2 | 5/2008 | Bertinato et al. |
| 8,058,299 B2 | 11/2011 | Bolin et al. |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,206,877 B2 * | 2/2019 | Phenix ................. A61K 31/47 |
| 10,208,053 B2 | 2/2019 | Strohbach et al. |
| 10,258,624 B2 | 4/2019 | Miller et al. |
| 10,570,115 B2 | 2/2020 | Alcacio et al. |
| 10,654,829 B2 | 5/2020 | Dhamankar et al. |
| 10,793,547 B2 * | 10/2020 | Abela ................... A61P 11/00 |
| 2002/0055631 A1 | 5/2002 | Augeri et al. |
| 2002/0086887 A1 | 7/2002 | Augeri et al. |
| 2004/0006237 A1 | 1/2004 | Dolitzky et al. |
| 2005/0171185 A1 | 8/2005 | Yamasaki et al. |

(Continued)

FOREIGN PATENT DOCUMENTS

| | | |
|---|---|---|
| AU | 2013231151 A1 | 10/2013 |
| AU | 2013270464 A1 | 1/2014 |

(Continued)

OTHER PUBLICATIONS

Anilkumar, G.N. et al. (2011) "II. Novel HCV NS5b polymerase inhibitors: Discovery of indole C2 acyl sulfonamides" *Biogranic & Medicinal Chemistry Letters*, 22(1):713-717.

(Continued)

*Primary Examiner* — Theodore R. Howell
*Assistant Examiner* — George W Kosturko
(74) *Attorney, Agent, or Firm* — Finnegan, Henderson, Farabow, Garrett & Dunner, LLP

(57) ABSTRACT

A pharmaceutical composition comprising Compound I:

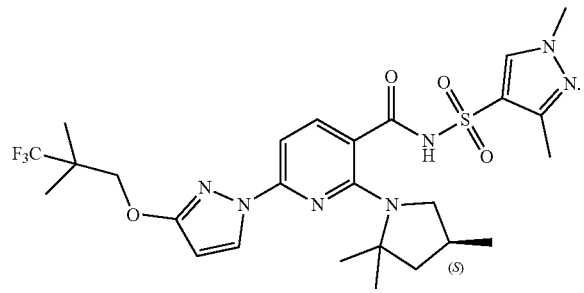

Methods of treating cystic fibrosis comprising administering one or more of such pharmaceutical compositions to a patient.

13 Claims, 22 Drawing Sheets

(56) References Cited

U.S. PATENT DOCUMENTS

| | | |
|---|---|---|
| 2005/0197376 A1 | 9/2005 | Kayakiri et al. |
| 2007/0105833 A1 | 5/2007 | Ruah et al. |
| 2010/0227888 A1 | 9/2010 | Ruah et al. |
| 2011/0098311 A1* | 4/2011 | Van Goor ............... A61P 19/00 514/255.05 |
| 2011/0165118 A1 | 7/2011 | Chan et al. |
| 2013/0072483 A1 | 3/2013 | Wenge et al. |
| 2013/0267493 A1 | 10/2013 | Bhattacharya et al. |
| 2013/0317000 A1 | 11/2013 | Chowdhury et al. |
| 2013/0317001 A1 | 11/2013 | Andrez et al. |
| 2014/0080825 A1 | 3/2014 | Hadida-Ruah et al. |
| 2014/0296200 A1 | 10/2014 | Brown et al. |
| 2015/0320736 A1 | 11/2015 | Phenix et al. |
| 2015/0322002 A1 | 11/2015 | Dehnhardt et al. |
| 2018/0099932 A1 | 4/2018 | Altenbach et al. |
| 2018/0141954 A1 | 5/2018 | Strohbach et al. |
| 2018/0162839 A1 | 6/2018 | Abela et al. |
| 2018/0170938 A1 | 6/2018 | Strohbach et al. |
| 2018/0244611 A1 | 8/2018 | Altenbach et al. |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0153000 A1 | 5/2019 | Munoz et al. |
| 2019/0240197 A1 | 8/2019 | Chu et al. |
| 2019/0269683 A1 | 9/2019 | Miller et al. |
| 2020/0138798 A1 | 5/2020 | Chen et al. |
| 2020/0171015 A1 | 6/2020 | Haseltine et al. |
| 2020/0283405 A1 | 9/2020 | Alcacio et al. |
| 2020/0369608 A1 | 11/2020 | Angell et al. |
| 2020/0392109 A1 | 12/2020 | Dhamankar et al. |
| 2021/0032272 A1 | 2/2021 | Abela et al. |
| 2021/0047295 A1 | 2/2021 | Abela et al. |

FOREIGN PATENT DOCUMENTS

| | | |
|---|---|---|
| CA | 2145473 A1 | 9/1995 |
| EP | 0 194 599 A2 | 9/1986 |
| EP | 0 673 930 A1 | 9/1995 |
| EP | 1 318 978 B1 | 2/2006 |
| JP | 10-114654 A | 5/1998 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/31226 A1 | 7/1998 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2004/111014 A1 | 12/2004 |
| WO | WO 2005/049018 A1 | 6/2005 |
| WO | WO 2005/054191 A1 | 6/2005 |
| WO | WO 2005/070006 A2 | 8/2005 |
| WO | WO 2005/075435 A1 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/002421 A2 | 1/2006 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/113327 A2 | 10/2007 |
| WO | WO 2007/117715 A2 | 10/2007 |
| WO | WO 2007/134279 A2 | 11/2007 |
| WO | WO 2008/005457 A2 | 1/2008 |
| WO | WO 2008/100867 A2 | 8/2008 |
| WO | WO 2008/127399 A2 | 10/2008 |
| WO | WO 2008/141385 A1 | 11/2008 |
| WO | WO 2009/006315 A1 | 1/2009 |
| WO | WO 2009/027730 A1 | 3/2009 |
| WO | WO 2009/032116 A1 | 3/2009 |
| WO | WO 2009/038683 A2 | 3/2009 |
| WO | WO 2009/064848 A1 | 5/2009 |
| WO | WO 2009/071947 A2 | 6/2009 |
| WO | WO 2009/073757 A1 | 6/2009 |
| WO | WO 2009/076142 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/019239 A2 | 2/2010 |
| WO | WO 2010/022307 A2 | 2/2010 |
| WO | WO 2010/025295 A2 | 3/2010 |
| WO | WO 2010/053471 A1 | 5/2010 |
| WO | WO 2010/054138 A2 | 5/2010 |
| WO | WO 2010/065824 A2 | 6/2010 |
| WO | WO 2010/083441 A2 | 7/2010 |
| WO | WO 2010/102758 A2 | 9/2010 |
| WO | WO 2010/108162 A1 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/019413 A1 | 2/2011 |
| WO | WO 2011/068560 A1 | 6/2011 |
| WO | WO 2011/072241 A1 | 6/2011 |
| WO | WO 2011/102514 A1 | 8/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/128251 A1 | 10/2011 |
| WO | WO 2011/133751 A2 | 10/2011 |
| WO | WO 2011/133951 A1 | 10/2011 |
| WO | WO 2011/150016 A1 | 12/2011 |
| WO | WO 2012/027247 A2 | 3/2012 |
| WO | WO 2012/027731 A2 | 3/2012 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/166415 A1 | 12/2012 |
| WO | WO 2012/170061 A1 | 12/2012 |
| WO | WO 2013/033068 A1 | 3/2013 |
| WO | WO 2013/037955 A1 | 3/2013 |
| WO | WO 2013/038373 A1 | 3/2013 |

(56) References Cited

FOREIGN PATENT DOCUMENTS

| | | |
|---|---|---|
| WO | WO 2013/041602 A1 | 3/2013 |
| WO | WO 2013/070961 A1 | 5/2013 |
| WO | WO 2013/082102 A1 | 6/2013 |
| WO | WO 2013/112804 A1 | 8/2013 |
| WO | WO 2013/118805 A1 | 8/2013 |
| WO | WO 2013/130669 A1 | 9/2013 |
| WO | WO 2013/158121 A1 | 10/2013 |
| WO | WO 2013/177224 A1 | 11/2013 |
| WO | WO 2013/185112 A1 | 12/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/105484 A1 | 6/2016 |
| WO | WO 2016/105485 A2 | 6/2016 |
| WO | WO 2016/128529 A1 | 8/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 | |
| WO | WO 2018/116185 A1 | 6/2018 | |
| WO | WO-2018107100 A1 * | 6/2018 | ........... C07D 401/04 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/026075 A1 | 10/2019 |
| WO | WO 2019/191620 A1 | 10/2019 |
| WO | WO 2019/200246 A1 | 10/2019 |

OTHER PUBLICATIONS

Atzrodt J, Derdau V, Fey T, Zimmermann J. "The Renaissance of H/D Exchange" Angew. Chem. Int. Ed. 2007: 46, 7744-7765.

Atzrodt J, Derdau V, Kerr W, Reid M. "C—H functionalization for hydrogen isotope exchange" Angew. Chem. Int. Ed. 2018: 57, 3022-3047.

Borhade, S.R. et al. (2013) "Synthesis of Novel Aryl and Heteroaryl Acyl Sulfonimidamides via Pd-Catalyzed Carbonylation Using a Nongaseous Precursor" Organic Lett, 15(5):1056-1059.

Braman, V.; Liu, J. F.; Harbeson, S.; Uttamsingh, V.; Bridson, G.; Wu, L.; Shipley, J. E. "Preliminary Clinical Outcomes for CTP-354, a Novel Subtype-Selective GABA(A) Modulator" Presented at the American Neurological Association (ANA) 2014 Annual Meeting, Baltimore, MD, Oct. 12-14, 2014.

Byrn, S. et al. (1995) "Pharmaceutical solids: a strategic approach to regulatory considerations," (12): 945-954.

Caira, M. R. (1998) "Crystalline Polymorphism of Organic Compounds," Topics in Current Chemistry, 163-208.

Cargnin S, Serafini M, Pirali T. "A primer of deuterium in drug design" Future Med. Chem. 2019; 11(16): 2039-2042.

Chen, Y. (Jan. 26, 2016) "N-Monoacylation of Sulfonimidamides" Synthesis, 48(7):1019-1028.

Czeskis B, Elmore, CS, Haight A, Hesk D, Maxwell BD, Miller SA, Raglione T, Schildknegt K, Traverse JF, Wang P. "Deuterated active pharmaceutical ingredients: a science-based proposal for synthesis, analysis, and control. Part 1: Framing the problem" J. Label. Compd. Radiopharm. 2019, 62: 690-694. DOI: 10.1002/jlcr.3743.

Dao HT, Li C, Michaudel Q, Maxwell BD, Baran PS. J. Am. Chem. Soc. 2015; 137, 8046-8049.

Database CAPLUS, Accession No. 1965:51408. Abstract of French Patent No. FR M2868, filed Nov. 23, 1964, by Roussel—UCLAF [online]. Retrieved Jan. 6, 2017 (1 page).

Database CAPLUS, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).

Database Pubchem, CID: 20050716. Compound Summary, 1-[2-[[2-[(2-Amino-3-methylbutanoyl)amino]-3-methylpentanoyl]amino]-3-phenylpropanoyl]pyrrolidine-2-carboxylic acid. NIH, U.S. National Library of Medicine, National Center for Biotechnology Information; Modify Date: Nov. 30, 2019. [online]. Retrieved from https://pubchem.ncbi.nlm.nih.gov/compound/20050716, on Dec. 3, 2019 (7 pages).

Database Pubchem, CID: 20091118. Compound Summary, [4-(5-Hexylpyrimidin-2-yl)phenyl] 2-methoxypropanoate. NIH, U.S. National Library of Medicine, National Center for Biotechnology Information; Modify Date: Nov. 30, 2019. [online]. Retrieved from https://pubchem.ncbi.nlm.nih.gov/compound/20091118, on Dec. 3, 2019 (9 pages).

Database Pubchem, CID: 20120819. Compound Summary, 4-(Cyclopentyloxy)-3-fluorobenzene-1-sulfonyl chloride. NIH, U.S. National Library of Medicine, National Center for Biotechnology Information; Modify Date: Nov. 30, 2019. [online]. Retrieved from https://pubchem.ncbi.nlm.nih.gov/compound/20120819, on Dec. 3, 2019 (8 pages).

Database Pubchem, CID: 2545578. Compound Summary, T5339296. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).

Database Pubchem, CID: 44419393. Compound Summary, CHEMBL374189. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).

Database Pubchem, CID: 49774135. Compound Summary, SCHEMBL13395127. NIH, U.S. National Library of Medicine, National Center for Biotechnology Information; Modify Date: Jan.

(56) References Cited

OTHER PUBLICATIONS 16, 2016 [online]. Retrieved from https://pubchem.ncbi.nlm.nih.gov/compound/49774135, on Jan. 22, 2016 (10 pages).
Database Pubchem, CID: 58132855. Compound Summary, SCHEMBL831192. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).
Dorwald, F. A. (2006) "Side Reactions in Organic Synthesis" Wiley: VCH, Weinheim p. IX of Preface p. 1-15.
Gant TG. "Using Deuterium in Drug Discovery: Leaving the Label in the Drug" J Med. Chem. 2014; 57(9): 3595-3611.
Halford B. "The deuterium switcheroo" Chemical & Engineering News 2016; 94(27), 32-36.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2015/54316: International Search Report and Written Opinion, dated Feb. 5, 2016 (11 pages).
International Patent Application No. PCT/US2017/025381: International Search Report and Written Opinion, dated Jun. 6, 2017 (11 pages).
International Patent Application No. PCT/US2017/054611: International Search Report and Written Opinion, dated Jan. 3, 2018 (10 pages).
International Patent Application No. PCT/US2017/065425: International Search Report and Written Opinion, dated Feb. 27, 2018 (10 pages).
International Patent Application No. PCT/US2018/036610: International Search Report and Written Opinion, dated Sep. 19, 2018 (9 pages).
International Patent Application No. PCT/US2018/040427: International Search Report and Written Opinion, dated Oct. 9, 2018 (15 pages).
International Patent Application No. PCT/US2018/042415: International Search Report and Written Opinion, dated Oct. 31, 2018 (12 pages).
International Patent Application No. PCT/US2018/042486: International Search Report and Written Opinion, dated Nov. 7, 2018 (13 pages).
International Patent Application No. PCT/US2018/044963: International Search Report and Written Opinion, dated Sep. 25, 2018 (15 pages).
International Patent Application No. PCT/US2018/056772: International Search Report and Written Opinion, dated Jan. 29, 2019 (13 pages).
International Patent Application No. PCT/US2018/063871: International Search Report and Written Opinion, dated Feb. 25, 2019 (16 pages).
International Patent Application No. PCT/US2019/016537: International Search Report and Written Opinion, dated Apr. 23, 2019 (13 pages).
International Patent Application No. PCT/US2018/064522: International Search Report and Written Opinion, dated Jun. 25, 2019 (21 pages).
International Patent Application No. PCT/US2019/018042: International Search Report and Written Opinion, dated Apr. 17, 2019 (10 pages).
International Patent Application No. PCT/US2019/024890: International Search Report and Written Opinion, dated Jun. 17, 2019 (13 pages).
International Patent Application No. PCT/US2019/026075: International Search Report and Written Opinion, dated Jun. 17, 2019 (13 pages).
International Patent Application No. PCT/US2019/027202: International Search Report and Written Opinion, dated Jun. 17, 2019 (10 pages).
Jain, B.C. et al. (1947) "Studies in Sulphanilamides. Part XIII. Reaction With Dicarboxylic Acids. Some New N1- and N4-Acyl and Heterocycic Derivatives" *Journal of the Indian Chemical Society*, 24:173-176.
Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.
Lai, J.T. et al. (1980) "Rearrangement of 2,2,6,6-tetramethyl-4-piperidone in phase-transfer catalyzed reactions," *Journal of Organic Chemistry*, 45(8):1513-1514.
Liu, J. F. et al. "CTP-354: a Novel Deuterated Subtype-Selective GABA(A) Modulator for Treatment of Neuropathic Pain, Spasticity and Anxiety Disorders" Presented at the American College of Neuropsychopharmacology (ACNP) 51st Annual Meeting, Hollywood, FL, Dec. 2-6, 2012.
Matter, H. et al. (2002) "Design and Quantitative Structure-Activity Relationship of 3-Amidinobenzyl-1H-indole-2-carboxamides as Potent, Nonchiral, and Selective Inhibitors of Blood Coagulation Factor Xa" *Journal of Medicinal Chemistry*, 45(13):2749-2769.
Maxwell BD, Tran SB, Lago M, Li J, and Bonacorsi Jr SJ. "The syntheses of [14C]BMS-823778 for use in a human ADME clinical study and of [13CD313CD2]BMT-094817, a stable-isotope labeled standard of a newly detected human metabolite" J. Label. Compd. Radiopharm. 2016; 59, 255-259.
Norman, P. (2014) "Novel picolinamide-based cystic fibrosis transmembrane regulator modulators: evaluation of WO2013038373, WO2013038376, WO2013038381, WO2013038386, and WO2013038390," *Expert Opinion on Therapeutic Patents*, 24(7):829-837.
Notman, N. (2016) "2Heavy drugs gaining momentum" [online] Retrieved from the internet: https://www.chemistryworld.com/features/2heavy-drugs-gaining-momentum/1010186.article, on Oct. 7, 2019.
Passarella, D. et al. (2001) "Cyclodimerization of indol-2-ylacetylenes. An example of intermolecular enyne-alkyne cycloaddition" *Journal of the Chemical Society, Perkin Transactions 1*, 127-129.
Pirali T, Serafini M, Cargnin S, Genazzani AA. "Applications of Deuterium in Medicinal Chemistry" J Med. Chem. 2019; 62(11): 5276-5297.
Rosebraugh, C.J. (2015) "Highlights of Presecribing Information for Orkambi," [online] Retrieved from the Internet: https://www.accessdata.fda.gov/drugsatfda_docs/label/2015/206038Orig1s000lbl.pdf, on Aug. 24, 2017.
Schmidt C. "First deuterated drug approved" Nat. Biotechnol. 2017, 35, 493-494.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" *Journal für Pracktische Chemie*, 331(3):503-506.
Tullis, E. et al. (2018) "Preliminary safety and efficacy of triple-combination CFTR modulator regimens," *Respirology*, 23(51):33.
U.S. Appl. No. 16/620,265, filed Dec. 6, 2019, by Chen et al.
U.S. Appl. No. 16/625,028, filed Dec. 20, 2019, by Chu et al.
U.S. Appl. No. 16/625,028, filed Jan. 17, 2020, by Haseltine et al.
U.S. Appl. No. 16/635,346, filed Jan. 30, 2020, by Angell et al.
U.S. Appl. No. 16/836,155, filed Mar. 31, 2020, by Miller et al.
Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.
Venkatesh, S. et al. (2000) "Role of the development scientist in compound lead selection and optimization" *J. Pharm. Sci.* 89(2), 145-154.
Verado, G. et al. (1999) "Reductive One Batch Synthesis of N-Substituted Pyrrolidines from Primary Amines and 2,5-Dimethoxytetrahydrofuran" *Synthesis*, (1):74-79.
Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.

(56) References Cited

OTHER PUBLICATIONS

Vertex Pharmaceuticals, Inc. (Jul. 18, 2017) "Vertex Announces Positive Phase 1 & Phase 2 Data from Three Different Triple Combination Regimens in People with Cystic Fibrosis Who Have One F508del Mutation and One Minimal Function Mutation (F508del/Min)", Retrieved from the Internet: URL: http://investors.vrtx.com/news-releases/news-release-details/vertex/announces-positive-phase-1-phase-2-data-three-different [retrieved on Mar. 27, 2019].

Vertex Pharmaceuticals, Inc. (Nov. 3, 2017) "Vertex announces presentations of data at North American Cystic Fibrosis Conference that Demonstrate Important Progress Toward Goal of Helping All People with CF," Health and Medicine Week, vol. 3, p. 196.

Vodak, D. (2014) "Design and Development of HPMCAS-Based Spray-Dried Dispersions," 303-322.

Wainwright, C.E. et al. (2015) "Lumacaftor-Ivacaftor in Patients with Cystic Fibrosis Homozygous for Phe508del CFTR," *The New England Journal of Medicine*, 373(3):220-231.

Willson T. M. et al. (1996) "Bone targeted drugs 2. Synthesis of estrogens with hydroxyapatite affinity," Bioorg. & Med. Chem. Lett., (6):1047-1050.

Winn, M. et al. (1993) "2-(Alkylamino)nicotinic Acid and Analogs. Potent Angiotensin II Antagonists" *Journal of Medicinal Chemistry*, 36(18):2676-2688.

Yarnell AT. "Heavy-Hydrogen Drugs Turn Heads, Again" Chemical & Engineering News 2009; 87(25), 36-39.

Bhattacharya, S. et al. (1999) Polymorphism in Pharmaceutical Solids: Thermoanalytical and Crystallographic Methods (Brittain H. ed., 2d ed. Informa Healthcare USA, Inc. 2009) 318-335.

Boyle, M. "A CFTR corrector (lumacaftor) and a CFTR potentiator (ivacaftor) for treatment of patients with cystic fibrosis who have a phe508del CFTR mutation: a phase 2 randomised controlled trial," The Lancet Respiratory Medicine (Jul. 1, 2014) Retrieved from the Internet: https://www-clinicalkeycom-ez03.infotrieve.com/#!/content/playContent/1-s2.0S2213260014701328?returnurl=null&referrer=null.

Garg, V. et al. "Pharmacokinetic and Drug-Drug Interaction Profiles of the Combination of Tezacaftor/Ivacaftor", Clinical and Translational Science—CTS, vol. 12, No. 3, Jan. 29, 2019 (Jan. 29, 2019), pp. 267-275, XP055719490, US ISSN: 1752-8054, DOI: 10.1111/cts.12610.

International Patent Application No. PCT/US2020/028699: International Search Report and Written Opinion, dated Jul. 20, 2020 (9 pages).

International Patent Application No. PCT/US2020/034199: International Search Report and Written Opinion, dated Aug. 11, 2020 (15 pages).

Ivanisevic, I. (2011) "Uses of X-Ray Powder Diffraction in the Pharmaceutical Industry," Pharm. Form. Qual. 30-33.

Kieltsch, I. et al. Laureates: Awards and Honors SCS Fall Meeting 2007 260 Recent Advances in Electrophilic CF 3-Transfer Using Hypervalent Iodine(III) Reagents 11, A Chimia Chimia Schweizerische Chemische Gesellschaft ISSN, vol. 62, No. 62, Jan. 1, 2008 (Jan. 1, 2008), pp. 260-263, XP055591571, DOI: 10.2533/chimia.2008.260.

Montemayor, Kristina et al. "Unmasking catamenial hemoptysis in the era of CFTR modulator therapy", Journal of Cystic Fibrosis, Elsevier, NL, vol. 19, No. 4, Jan. 24, 2020 (Jan. 24, 2020), XP086202454, ISSN: 1569-1993, DOI: 10.1016/J.JCF.2020.01.005 [retrieved on Jan. 24, 2020].

NCT03029455 "A Study to Evaluate Safety and Pharmacokinetics of VX-659 in Healthy Subjects and in Adults With Cystic Fibrosis". Vertex Pharmaceuticals Incorporated, Retrieved from the Internet: https://clinicaltrials.gov/ct2/show/study/NCT03029455.

Peter Grootenhuis. (2012). In Peter Grootenhuis. https://en.wikipedia.org/w/index.php?title=Peter_Grootenhuis&oldid=997787974. Accessed Jan. 25, 2021.

Qun, C. et al. "Synthesis of 3,3,3-trifluoro-2,2-dimethylpropionic acid", Huaxue Shiji—Chemical Reagents, Beijing : Huaxue Huaxue Shiji Keji Qingbao Zhongxinzhan, CN, vol. 38, No. 4, Jan. 1, 2016 (Jan. 1, 2016), pp. 386-388, XP009513488, ISSN: 0258-3283, DOI: 10.13822/J.CNKI.HXSJ.2016.04.026.

Table 2 : List of the mutations or SNP tested in this study (https://www.jmdjournal.org/cms/10.2353/jmoldx.2008.080056/attachment/2286a276-d0b2-4a8a-83f8-8273bef9a761/mmc1.doc). Accessed Jan. 25, 2021.

Tsong-Long H. et al. "Synthesis and pharmacological characterization of 2-aminobenzaldehyde oxime analogs as dual inhibitors of neutrophil elastase and proteinase 3", Bioorganic & Medicinal Chemistry, vol. 23, No. 5, Jan. 16, 2015, pp. 1123-1134, XP029199003.

"Vertex Provides Update on Ongoing Phase 3 Program for VX-661 in Combination with Ivacaftor for the Treatment of Cystic Fibrosis" (Aug. 15, 2016) Retrieved from the Internet: https://www.businesswire.com/news/home/20160815006099/en/Vertex-Update-Ongoing-Phase-3-Program-VX-661.

* cited by examiner

FIG. 1A

| Mutation cDNA Name | Mutation Protein Name | Mutation Legacy Name |
|---|---|---|
| c1A>G | | M1V |
| c.54-5940_273+10250del21kb | pSer18ArgfsX16 | CFTRdele2,3 |
| c.91C>T | p.Arg31Cys | R31C |
| c.115C>T | p.Gin39X | Q39X |
| c.137C>A | p.Ala46Asp | A46O |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88llefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.llel05SerfsX2 | 444delA |
| c.325_327delTATinsG | p.Tyrl09GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.llel48LeufsX5 | 574delA |
| c.443T>C | p.lle148Thr | I148T |

FIG. 1B

| Mutation cDNA Name | Mutation Protein Name | Mutation Legacy Name |
|---|---|---|
| c.489+1G>T | No protein name | 621+1G->T |
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| C.59SOT | p.His199Tyr | H199Y |
| C.613CM | p.Pro205Ser | P205S |
| c.617T>G | p.Leu20GTrp | L206W |
| C.6580T | p.Gln220X | Q220X |
| c.580T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ele | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 10799C>A] | p.[Gln359Lys;Thr360Lys] | Q359K/T360K |
| c.1081delT | p.Trp361GlyfsX8 | 1213delT |
| c.1116+1G>A | No protein name | 1248+1G->A |

FIG. 1C

| Mutation cDNA Name | Mutation Protein Name | Mutation Legacy Name |
|---|---|---|
| c.1127_1128insA | p.Gln378AlafsX4 | 1259insA |
| c.1153_1154insAT | p.Asn386IlefsX3 | 1288insTA |
| c.1202G>A or c.1203G>A | p.Trp401X | W401X |
| c.1209+1G>A | No protein name | 1341+1G->A |
| c.1210-12[5] | No protein name | 5T |
| c.1210-12(7] | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | ' p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1G47T>G | p.Ser549Arg | S549R |
| | | |

FIG. 1D

| Mutation cDNA Name | Mutation Protein Name | Mutation Legacy Name |
|---|---|---|
| c.1646G>A | p.Ser549Asn | S549N |
| c.1650delA | p.Gly551ValfsX8 | 1782delA |
| c.1651G>A | p.Gly551Ser | G551S |
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | pSer641ArgfsX5 | 2055del9->A |
| c.1973_1985del13insAGAAA | p.Arg658 LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |

FIG. 1E

| Mutation cDNA Name | Mutation Protein Name | Mutation Legacy Name |
|---|---|---|
| c.2051_2052delAAinsG | p.Lys684SerfsX38 | 2183AA->G+ |
| c.2051_2052delAAinsG | p.Lys684SerfsX38 | 2183delAA->G# |
| c.2052_2053insA | p.Gln685ThrfsX4 | 2184insA |
| c.2052delA | p.Lys684AsnfsX38 | 2184delA |
| c.2125O>T | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547O>A | p.Tyr849X | Y849X |
| c.2551C>T | p.Arg851X | R851X |
| c.2583delT | p.Phe861LeufsX3 | 2711delT |
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |

FIG. 1F

| Mutation cDNA Name | Mutation Protein Name | Mutation Legacy Name |
|---|---|---|
| c.2737_2738insG | | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |

FIG. 1G

| Mutation cDNA Name | Mutation Protein Name | Mutation Legacy Name |
|---|---|---|
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |
| c.3485G>T | p.Arg1162Leu | R1162L |
| c.3528delC | p.Lys1177SerfsX15 | 3659delC |
| c.3535_3536insTCAA | p.Thr1179IlefsX7 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC->T |
| c.3715-1G>A | No protein name | 3850-1G->A |
| c.3731G>A | p.Gly1244Glu | G1244E |
| c.3744delA | p. Lys1250ArgfsX9 | 3876delA |
| c.3752G>A | p.Ser1251Asn | S1251N |
| c.3763T>C | p.Ser1255Pro | S1255P |
| c.37640A | p.Ser1255X | S1255X |
| c.3773_3774insT | p.Leu1258PhefsX7 | 3905insT |
| c.3808G>A | p.Asp1270Asn | D1270N |
| c.3346G>A | p.Trp12S2X | W1282X |

FIG. 1H

| Mutation cDNA Name | Mutation Protein Name | Mutation Legacy Name |
|---|---|---|
| c.3873+1G>A | No protein name | 4005+1G->A |
| c.3883delA | p.Ile1295PhefsX33 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |
| c.4251delA | p.Glu1418ArgfsX14 | 4382delA |
| c.4296_4297insGA | p.Ser1435GlyfsX14 | 4428insGA |

PHARMACEUTICAL COMPOSITIONS FOR TREATING CYSTIC FIBROSIS

This application claims priority to U.S. provisional applications 62/626,567, filed Feb. 5, 2018, and 62/657,522, filed Apr. 13, 2018. The disclosures of both provisional applications are incorporated herein by reference in their entirety.

One aspect of the invention provides pharmaceutical compositions comprising modulators of Cystic Fibrosis Transmembrane Conductance Regulator (CFTR). Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence, and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Accordingly, there is a need for novel treatments of CFTR mediated diseases.

Disclosed herein are pharmaceutical compositions comprising Compound I and/or pharmaceutically acceptable salts thereof, Compound II and/or pharmaceutically acceptable salts thereof, and Compound III-d or Compound III and/or pharmaceutically acceptable salts thereof. Compound I can be depicted as having the following structure:

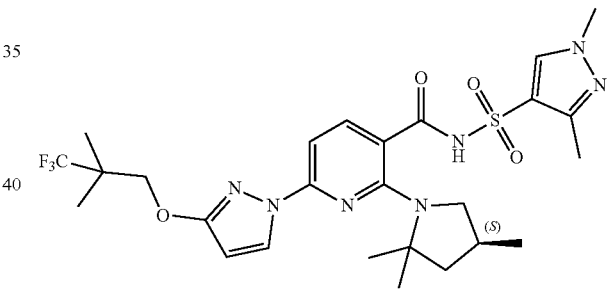

A chemical name for Compound I is N-(1,3-dimethylpyrazol-4-yl)sulfonyl-6-[3-(3,3,3-trifluoro-2,2-dimethyl-propoxy)pyrazol-1-yl]-2-[(4 S)-2,2,4-trimethylpyrrolidin-1-yl]pyridine-3-carboxamide. PCT Application No. PCT/US2017/065425, incorporated herein by reference, discloses Compound I, a method of making Compound I, a method of making Form A of Compound I, and that Compound I is a CFTR modulator with an $EC_{50}$ of 0.07 μM. In some embodiments, Compound I is amorphous.

In some embodiments, Compound I is Form A. In some embodiments, crystalline Form A is characterized by an X-ray powder diffractogram having a signal at least one two-theta value chosen from 6.6±0.2, 7.6±0.2, 9.6±0.2, 12.4±0.2, 13.1±0.2, 15.2±0.2, 16.4±0.2, 18.2±0.2, and 18.6±0.2. In some embodiments, crystalline Form A is characterized by an X-ray powder diffractogram having a signal at at least three two-theta values chosen from 6.6±0.2, 7.6±0.2, 9.6±0.2, 12.4±0.2, 13.1±0.2, 15.2±0.2, 16.4±0.2, 18.2±0.2, and 18.6±0.2. In some embodiments, crystalline Form A is characterized by an X-ray powder diffractograph having a signal at at least three two-theta values chosen from 6.6±0.2, 9.6±0.2, 13.1±0.2, 15.2±0.2, 18.2±0.2, and 18.6±0.2. In some embodiments, crystalline Form A is characterized by an X-ray powder diffractograph having a signal at three two-theta values of 6.6±0.2, 13.1±0.2, 18.2±0.2. In some embodiments, crystalline Form A is characterized by an X-ray powder diffractograph having a signal at six two-theta values of 6.6±0.2, 9.6±0.2, 13.1±0.2, 15.2±0.2, 18.2±0.2, and 18.6±0.2. In some embodiments, Crystalline Form A is characterized by an X-ray powder diffractogram substantially similar to that in FIG. 4A. In some embodiments, Crystalline Form A is characterized by an X-ray powder diffractogram substantially similar to that in FIG. 4B. Crystalline Form A was found to be the most thermodynamically stable form and to provide good bioavailability.

Compound II can be depicted as having the following structure:

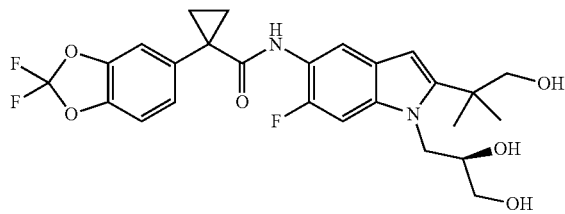 [SMILES: CC(C)(CO)c1cc2cc(NC(=O)C3(c4ccc5c(c4)OC(F)(F)O5)CC3)c(F)cc2n1C[C@@H](O)CO]

A chemical name for Compound II is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide;

Compound III-d can be depicted as having the following structure:

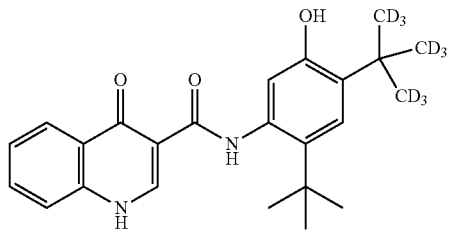 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

A chemical name for Compound III-d is N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide;

Compound III can be depicted as having the following structure:

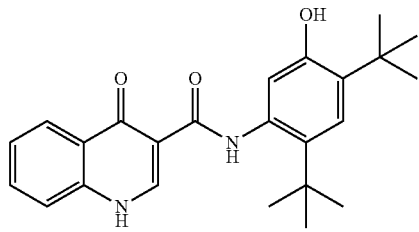 [SMILES: CC(C)(C)c1cc(C(C)(C)C)c(NC(=O)c2c[nH]c3ccccc3c2=O)cc1O]

A chemical name for Compound III is N-(5-hydroxy-2,4-di-tert-butyl-phenyl)-4-oxo-1H-quinoline-3-carboxamide.

BRIEF DESCRIPTION OF THE DRAWINGS

FIGS. 1A-1H is a representative list of CFTR genetic mutations.

DEFINITIONS

Figure 2A:
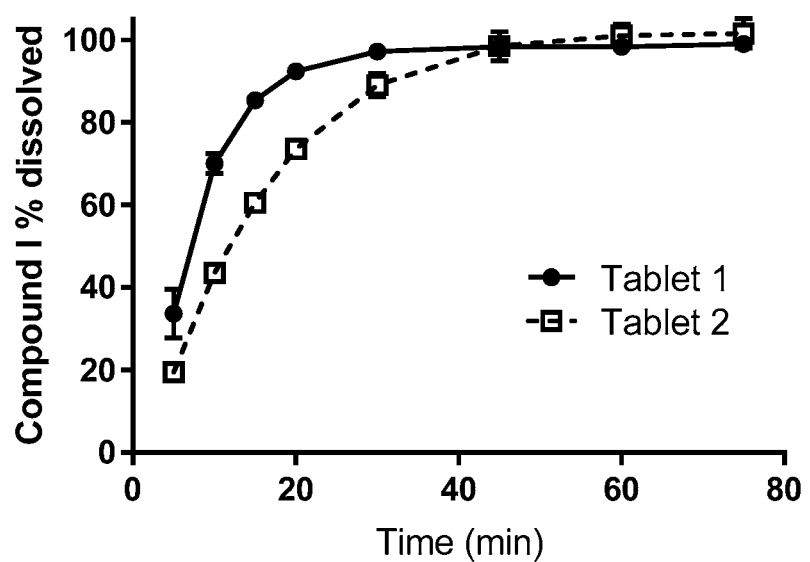
FIG. 2A is dissolution data for Compound I.

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compound I, Compound II, and their pharmaceutically acceptable salts thereof disclosed herein are CFTR correctors.

As used herein, the term "CFTR potentiator" refers to a compound that increases the channel activity of CFTR protein located at the cell surface, resulting in enhanced ion transport. Compound III-d and Compound III disclosed herein are CFTR potentiators.

As used herein, the term "active pharmaceutical ingredient" ("API") refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describe pharmaceutically acceptable salts in detail in *J. Pharmaceutical Sciences*, 1977, 66, 1-19.

Suitable pharmaceutically acceptable salts are, for example, those disclosed in S. M. Berge, et al. J. Pharmaceutical Sciences, 1977, 66, 1-19. For example, Table 1 of that article provides the following pharmaceutically acceptable salts:

TABLE 1

| Acetate | Iodide | Benzathine |
|---|---|---|
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methyl sulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teoclate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and N+(C1-4 alkyl)$_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

As used herein, the term "XRPD" refers to the analytical characterization method of X-ray powder diffraction. XRPD patterns can be recorded at ambient conditions in transmission or reflection geometry using a diffractometer.

As used herein, the terms "X-ray powder diffractogram," "X-ray powder diffraction pattern," "XRPD pattern" interchangeably refer to an experimentally obtained pattern plotting signal positions (on the abscissa) versus signal intensities (on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) chosen from . . . ."

A "signal" or "peak" as used herein refers to a point in the XRPD pattern where the intensity as measured in counts is at a local. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta," "a signal at [a] two-theta value[ ] of . . . " and/or "a signal at at least . . . two-theta value(s) chosen from . . . " refer to X-ray reflection positions as measured and observed in X-ray powder diffraction experiments (° 2θ).

The repeatability of the angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

The term "X-ray powder diffractogram having a signal at . . . two-theta values" as used herein refers to an XRPD pattern that contains X-ray reflection positions as measured and observed in X-ray powder diffraction experiments (° 2θ).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. For example, an amorphous material is a solid material having no sharp characteristic crystalline peak(s) in its X-ray power diffraction (XRPD) pattern (i.e., is not crystalline as determined by XRPD). Instead, one or more broad peaks (e.g., halos) appear in its XRPD pattern. Broad peaks are characteristic of an amorphous solid. See, e.g., US 2004/0006237 for a comparison of XRPDs of an amorphous material and crystalline material.

As used herein, the term "substantially amorphous" refers to a solid material having little or no long range order in the position of its molecules. For example, substantially amorphous materials have less than 15% crystallinity (e.g., less than 10% crystallinity or less than 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constituting the continuous phase. Or, a solid dispersion includes the drug constituting the dispersed phase, and the polymer constituting the continuous phase.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The term "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

Pharmaceutical Compositions

Disclosed herein is a pharmaceutical composition comprising a first solid dispersion and a second solid dispersion, wherein the pharmaceutical composition comprises (a) 25 mg to 250 mg of Compound I:

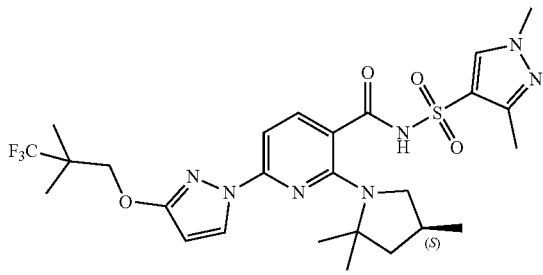

(b) a first solid dispersion comprising 20 mg to 150 mg of Compound II:

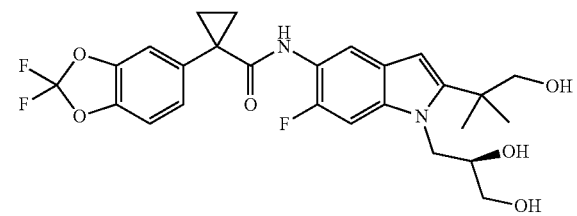 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and (c) a second solid dispersion comprising 25 mg to 200 mg of Compound III-d:

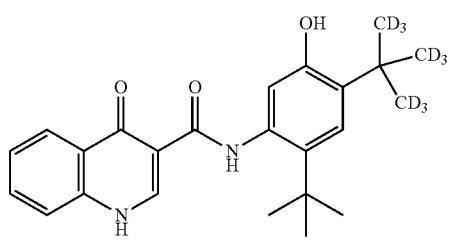 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

or
Compound III:

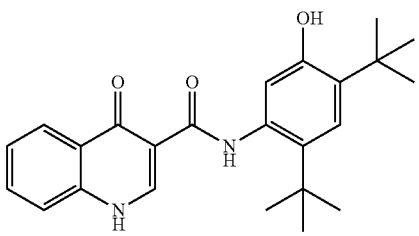 [SMILES: CC(C)(C)c1cc(C(C)(C)C)c(NC(=O)c2c[nH]c3ccccc3c2=O)cc1O]

and 10 wt % to 30 wt % of a polymer relative to the total weight of the second solid dispersion. In some embodiments, the pharmaceutical composition is a single tablet In some embodiments, each of Compound II and Compound III-d is independently substantially amorphous. In some embodiments, each of Compound II and Compound III-d is independently crystalline. In some embodiments, each of Compound II and Compound III-d or Compound III is independently a mixture of forms (crystalline and/or amorphous).

Solid Dispersions

In some embodiments, the pharmaceutical compositions (e.g., tablets) disclosed herein comprise a first solid dispersion comprising Compound II and a second solid dispersion comprising Compound III-d or Compound III.

In some embodiments, each of the first and second solid dispersions independently comprise a plurality of particles having a mean particle diameter of 5 to 100 microns. In some embodiments, each of the first and second solid dispersions independently comprise a plurality of particles having a mean particle diameter of 15 to 40 microns. In some embodiments, each of the first and second solid dispersions independently comprise a plurality of particles having a mean particle diameter of 15 microns.

In some embodiments, the first solid dispersions and the first spray dried dispersions of the disclosure independently comprise substantially amorphous Compound II. In some embodiments, the second solid dispersions and the second spray dried dispersions of the disclosure independently comprises substantially amorphous Compound III-d or Compound III.

In some embodiments, the solid dispersions and the spray dried dispersions of the disclosure can comprise other excipients, such as polymers and/or surfactants. Any suitable polymers and surfactants known in the art can be used in the disclosure. Certain exemplary polymers and surfactants are as described below.

Solid dispersions of any one of Compounds II, III-d, or III may be prepared by any suitable method known in the art, e.g., spray drying, lyophilizing, hot melting, or cyrogrounding/cryomilling techniques. For example, see WO2015/160787. Typically such spray drying, lyophilizing, hot melting or cyrogrounding/cryomilling techniques generates an amorphous form of API (e.g., Compounds II, III-d, or III).

Spray drying is a process that converts a liquid feed to a dried particulate form. Optionally, a secondary drying process such as fluidized bed drying or vacuum drying may be used to reduce residual solvents to pharmaceutically acceptable levels. Typically, spray drying involves contacting a highly dispersed liquid suspension or solution, and a sufficient volume of hot gas to produce evaporation and drying of the liquid droplets. The preparation to be spray dried can be any solution, coarse suspension, slurry, colloidal dispersion, or paste that may be atomized using the selected spray drying apparatus. In one procedure, the preparation is sprayed into a current of warm filtered gas that evaporates the solvent and conveys the dried product to a collector (e.g. a cyclone). The spent gas is then exhausted with the solvent, or alternatively the spent air is sent to a condenser to capture and potentially recycle the solvent. Commercially available types of apparatus may be used to conduct the spray drying. For example, commercial spray dryers are manufactured by Buchi Ltd. And Niro (e.g., the PSD line of spray driers manufactured by Niro) (see, US 2004/0105820; US 2003/0144257).

Techniques and methods for spray drying may be found in Perry's Chemical Engineering Handbook, 6th Ed., R. H. Perry, D. W. Green & J. O. Maloney, eds.), McGraw-Hill book co. (1984); and Marshall "Atomization and Spray-Drying" 50, Chem. Eng. Prog. Monogr. Series 2 (1954).

Removal of the solvent may require a subsequent drying step, such as tray drying, fluid bed drying, vacuum drying, microwave drying, rotary drum drying or biconical vacuum drying.

In one embodiment, the solid dispersions and the spray dried dispersions of the disclosure are fluid bed dried.

In one process, the solvent includes a volatile solvent, for example a solvent having a boiling point of less than 100° C. In some embodiments, the solvent includes a mixture of solvents, for example a mixture of volatile solvents or a mixture of volatile and non-volatile solvents. Where mixtures of solvents are used, the mixture can include one or more non-volatile solvents, for example, where the non-volatile solvent is present in the mixture at less than 15%, e.g., less than 12%, less than 10%, less than 8%, less than 5%, less than 3%, or less than 2%.

In some processes, solvents are those solvents where the API(s) (e.g., Compound II and/or Compound III-d and/or Compound III) has solubilities of at least 10 mg/ml, (e.g., at least 15 mg/ml, 20 mg/ml, 25 mg/ml, 30 mg/ml, 35 mg/ml, 40 mg/ml, 45 mg/ml, 50 mg/ml, or greater). In other processes, solvents include those solvents where the API(s) (e.g., Compound II and/or Compound III-d and/or Compound III) has a solubility of at least 20 mg/ml.

Exemplary solvents that could be tested include acetone, cyclohexane, dichloromethane or methylene chloride (DCM), N,N-dimethylacetamide (DMA), N,N-dimethylformamide (DMF), 1,3-dimethyl-2-imidazolidinone (DMI), dimethyl sulfoxide (DMSO), dioxane, ethyl acetate, ethyl ether, glacial acetic acid (HAc), methyl ethyl ketone (MEK), N-methyl-2-pyrrolidinone (NMP), methyl tert-butyl ether (MTBE), tetrahydrofuran (THF), pentane, acetonitrile, methanol, ethanol, isopropyl alcohol, isopropyl acetate, and toluene. Exemplary co-solvents include DCM/methanol, acetone/DMSO, acetone/DMF, acetone/water, MEK/water, THF/water, dioxane/water. In a two solvent system, the solvents can be present from 0.1% to 99.9% w/w. In some preferred embodiments, water is a co-solvent with acetone where water is present from 0.1% to 15%, for example 9% to 11%, e.g., 10%. In some preferred embodiments, water is a co-solvent with MEK where water is present from 0.1% to 15%, for example 9% to 11%, e.g., 10%. In some embodiments the solvent system includes three solvents. Certain exemplary solvents include those described above, for example, MEK, DCM, water, methanol, IPA, and mixtures thereof.

The particle size and the temperature drying range may be modified to prepare an optimal solid dispersion. As would be appreciated by skilled practitioners, a small particle size would lead to improved solvent removal. Applicants have found however, that smaller particles may result in low bulk density that, under some circumstances do not provide optimal solid dispersions for downstream processing such as tableting.

A solid dispersion (e.g., a spray dried dispersion) disclosed herein may optionally include a surfactant. A surfactant or surfactant mixture would generally decrease the interfacial tension between the solid dispersion and an aqueous medium. An appropriate surfactant or surfactant mixture may also enhance aqueous solubility and bioavailability of the API(s) (e.g., Compound II and/or Compound III-d and/or Compound III) from a solid dispersion. The surfactants for use in connection with the disclosure include, but are not limited to, sorbitan fatty acid esters (e.g., Spans®), polyoxyethylene sorbitan fatty acid esters (e.g., Tweens®), sodium lauryl sulfate (SLS), sodium dodecylbenzene sulfonate (SDBS) dioctyl sodium sulfosuccinate (Docusate sodium), dioxycholic acid sodium salt (DOSS), Sorbitan Monostearate, Sorbitan Tristearate, hexadecyltrimethyl ammonium bromide (HTAB), Sodium N-lauroylsarcosine, Sodium Oleate, Sodium Myristate, Sodium Stearate, Sodium Palmitate, Gelucire 44/14, ethylenediamine tetraacetic acid (EDTA), Vitamin E d-alpha tocopheryl polyethylene glycol 1000 succinate (TPGS), Lecithin, Glutanic acid monosodium monohydrate, Labrasol, PEG 8 caprylic/capric glycerides, Transcutol, diethylene glycol monoethyl ether, Solutol HS-15, polyethylene glycol/hydroxystearate, Taurocholic Acid, Pluronic F68, Pluronic F108, and Pluronic F127 (or any other polyoxyethylene-polyoxypropylene co-polymers (Pluronics®) or saturated polyglycolized glycerides (Gelucirs®)). Specific examples of such surfactants that may be used in connection with this disclosure include, but are not limited to, Span 65, Span 25, Tween 20, Capryol 90, Pluronic F108, sodium lauryl sulfate (SLS), Vitamin E TPGS, pluronics and copolymers.

In some embodiments, SLS is used as a surfactant in the solid dispersion of Compound III-d and/or III.

The amount of the surfactant (e.g., SLS) relative to the total weight of the solid dispersion may be between 0.1-15% w/w. For example, it is from 0.5% to 10%, such as from 0.5 to 5%, e.g., 0.5 to 4%, 0.5 to 3%, 0.5 to 2%, 0.5 to 1%, or 0.5%.

In certain embodiments, the amount of the surfactant relative to the total weight of the solid dispersion is at least 0.1% or at least 0.5%. In these embodiments, the surfactant would be present in an amount of no more than 15%, or no more than 12%, 11%, 10%, 9%, 8%, 7%, 6%, 5%, 4%, 3%, 2% or 1%. In some embodiments, the surfactant is in an amount of 0.5% by weight.

Candidate surfactants (or other components) can be tested for suitability for use in the disclosure in a manner similar to that described for testing polymers.

One aspect of the disclosure provides a method of generating a spray dried dispersion comprising (i) providing a mixture of one or more APIs and a solvent; and (ii) forcing the mixture through a nozzle and subjecting the mixture to spray drying conditions to generate the spray dried dispersion.

Another aspect of the disclosure provides a method of generating a spray dried dispersion comprising: (i) providing a mixture comprising one or more APIs and a solvent(s); and (ii) forcing the mixture out of a nozzle under spray drying conditions to generate a spray dried dispersion.

Another aspect of the disclosure provides a method of generating a spray dried dispersion comprising (i) spraying a mixture through a nozzle, wherein the mixture comprises one or more APIs and a solvent; and (ii) forcing the mixture through a nozzle under spray drying conditions to generate a particle that comprises the APIs.

Another aspect of the disclosure provides a spray dried dispersion comprising one or more APIs, wherein the dispersion is substantially free of a polymer, and wherein the spray dried dispersion is generated by (i) providing a mixture that consists essentially of one or more APIs and a solvent; and (ii) forcing the mixture through a nozzle under spray drying conditions to generate the spray dried dispersion.

Another aspect of the disclosure provides a spray dried dispersion comprising one or more APIs, wherein the dispersion is generated by (i) providing a mixture that comprising one or more APIs, a polymer(s), and a solvent(s); and (ii) forcing the mixture through a nozzle under spray drying conditions to generate the spray dried dispersion.

Another aspect of the disclosure provides a spray dried dispersion comprising a particle, wherein the particle comprises one or more APIs and a polymer(s), and wherein the spray dried dispersion is generated by (i) spraying a mixture through a nozzle, wherein the mixture comprises one or more APIs and a solvent; and (ii) forcing the mixture through a nozzle under spray drying conditions to generate the spray dried dispersion.

Another aspect of the disclosure provides a spray dried dispersion comprising a particle, wherein the particle comprises one or more APIs, and the particle is substantially free of a polymer, and wherein the spray dried dispersion is generated by (i) spraying a mixture through a nozzle, wherein the mixture comprises one or more APIs and a solvent; and (ii) forcing the mixture through a nozzle under spray drying conditions to generate the spray dried dispersion.

In some embodiments, the one or more APIs are selected from Compound II, Compound III-d, and Compound III.

Some embodiments further comprise further drying the spray dried dispersion. For example, the spray dried dispersion is dried under reduced pressure. In other examples, the spray dried dispersion is dried at a temperature of from 50° C. to 100° C.

In some embodiments, the solvent comprises a polar organic solvent. Examples of polar organic solvents include methylethyl ketone, THF, DCM, methanol, or IPA, or any combination thereof, such as, for example DCM/methanol. In other examples, the solvent further comprises water. For instance, the solvent could be methylethyl ketone/water, THF/water, or methylethyl ketone/water/IPA. For example, the ratio of the polar organic solvent to water is from 70:30 to 95:5 by volume. In other instances, the ratio of the polar organic solvent to water is 90:10 by volume.

Some embodiments further comprise filtering the mixture before it is forced through the nozzle. Such filtering can be accomplished using any suitable filter media having a suitable pore size.

Some embodiments further comprise applying heat to the mixture as it enters the nozzle. This heating can be accomplished using any suitable heating element.

In some embodiments, the nozzle comprises an inlet and an outlet, and the inlet is heated to a temperature that is less than the boiling point of the solvent.

In some embodiments, the mixture is forced through the nozzle by a pressurized gas. Examples of suitable pressurized gases include those pressurized gas that are inert to the first agent, the second agent, and the solvent. In one example, the pressurized gas comprises elemental nitrogen.

In some embodiments, the pressurized gas has a positive pressure of from 90 psi to 150 psi.

In some embodiments, a pharmaceutically acceptable composition of the disclosure comprising substantially amorphous API(s) (e.g., Compound II, Compound III-d, and Compound III) may be prepared by non-spray drying techniques, such as, for example, cyrogrounding/cryomilling techniques. A composition comprising substantially amorphous API(s) (e.g., Compound II, Compound III-d, and Compound III) may also be prepared by hot melt extrusion techniques.

In some embodiments, the solid dispersions (e.g., spray dried dispersions) of the disclosure comprise a polymer(s). Any suitable polymers known in the art can be used in the disclosure. Exemplary suitable polymers include polymers selected from cellulose-based polymers, polyoxyethylene-based polymers, polyethylene-propylene glycol copolymers, vinyl-based polymers, PEO-polyvinyl caprolactam-based polymers, and polymethacrylate-based polymers.

The cellulose-based polymers include a methylcellulose, a hydroxypropyl methylcellulose (HPMC) (hypromellose), a hypromellose phthalate (HPMC-P), a hypromellose acetate succinate, and co-polymers thereof. The polyoxyethylene-based polymers include a polyethylene-propylene glycol, a polyethylene glycol, a poloxamer, and co-polymers thereof. The vinyl-based polymers include a polyvinylpyrrolidine (PVP), and PVP/VA. The PEO-polyvinyl caprolactam-based polymers include a polyethylene glycol, polyvinyl acetate and polyvinylcaprolactame-based graft copolymer (e.g., Soluplus®). The polymethacrylate-based polymers are synthetic cationic and anionic polymers of dimethylaminoethyl methacrylates, methacrylic acid, and methacrylic acid esters in varying ratios. Several types are commercially available and may be obtained as the dry powder, aqueous dispersion, or organic solution. Examples of such polymethacrylate-based polymers include a poly (methacrylic acid, ethyl acrylate) (1:1), a dimethylaminoethyl methacrylate-methylmethacrylate copolymer, and an Eudragit®.

In some embodiments, the cellulose-based polymer is a hypromellose acetate succinate (also known as hydroxypropyl methylcellulose acetate succinate or HMPCAS) and a hypromellose (also known as hydroxypropyl methylcellulose or HPMC), or a combination of hypromellose acetate succinate and a hypromellose. HPMCAS is available in various grades based on the content of acetyl and succinoyl groups (wt %) in the HPMCAS molecule and on particle size. For example, HPMCAS grades L, M, and H are available. HPMCAS-H is a grade that contains about 10-14 wt % of acetyl groups and about 4-8 wt % of succinoyl groups. Each HPMCAS grade is available in two particle sizes, F (fine) and G (granular). HPMC comes in various types (for example, HPMC E, F, J, and K-types). HPMC E type means that there are about 28-30% methoxy groups and about 7-12% hydroxpropoxy groups. There are various E grades ranging from low to high viscosity. For example, E3 means the viscosity is about 2.4-3.6 millipascal seconds (mPa·s) for HPMC measured at 2% in water at 20° C.; E15 means the viscosity is about 12-18 mPa·s for the HPMC measured at 2% in water at 20° C.; and E50 means the viscosity is about 40-60 mPa·s for the HPMC measured at 2% in water at 20° C.

In some embodiments, the cellulose-based polymer is a hypromellose acetate succinate and a hypromellose, or a combination of hypromellose acetate succinate and a hypromellose.

In some embodiments, the cellulose-based polymer is hypromellose E15, hypromellose acetate succinate L or hypromellose acetate succinate H.

In some embodiments, the polyoxyethylene-based polymer or polyethylene-propylene glycol copolymer is a polyethylene glycol or a pluronic.

In some embodiments, the polyoxyethylene-based polymer or polyethylene-propylene glycol copolymer is polyethylene glycol 3350 or poloxamer 407.

In some embodiments, the vinyl-based polymer is a vinylpolyvinylpyrrolidine-based polymer, such as polyvinylpyrrolidine K30 or polyvinylpyrrolidine VA 64.

In some embodiments, the polymethacrylate polymer is Eudragit L100-55 or Eudragit® E PO.

In some embodiments, the polymer(s) is selected from cellulosic polymers such as HPMC and/or HPMCAS.

In one embodiment, a polymer is able to dissolve in aqueous media. The solubility of the polymers may be pH independent or pH dependent. The latter include one or more enteric polymers. The term "enteric polymer" refers to a polymer that is preferentially soluble in the less acidic environment of the intestine relative to the more acid environment of the stomach, for example, a polymer that is insoluble in acidic aqueous media but soluble when the pH is above 5-6. An appropriate polymer is chemically and biologically inert. In order to improve the physical stability of the solid dispersions, the glass transition temperature (Tg) of the polymer is as high as possible. For example, polymers that have a glass transition temperature at least equal to or greater than the glass transition temperature of the API. Other polymers have a glass transition temperature that is within 10 to 15° C. of the API.

Additionally, the hygroscopicity of the polymers is as low, e.g., less than 10%. For the purpose of comparison in this application, the hygroscopicity of a polymer or composition is characterized at 60% relative humidity. In some preferred embodiments, the polymer has less than 10% water absorption, for example less than 9%, less than 8%, less than 7%, less than 6%, less than 5%, less than 4%, less than 3%, or less than 2% water absorption. The hygroscopicity can also affect the physical stability of the solid dispersions. Generally, moisture adsorbed in the polymers can greatly reduce the Tg of the polymers as well as the resulting solid dispersions, which will further reduce the physical stability of the solid dispersions as described above.

In one embodiment, the polymer is one or more water-soluble polymer(s) or partially water-soluble polymer(s). Water-soluble or partially water-soluble polymers include but are not limited to, cellulose derivatives (e.g., hydroxypropylmethylcellulose (HPMC), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins (e.g., β-cyclodextin) and copolymers and derivatives thereof, including for example PVP-VA (polyvinylpyrrollidone-vinyl acetate).

In some embodiments, the polymer is hydroxypropylmethylcellulose (HPMC), such as HPMC E50, HPMC E15, or HPMC E3.

As discussed herein, the polymer can be a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP), or polymethacrylates (e.g., Eudragit® S). In some embodiments, the polymer is hydroxypropyl methyl cellulose acetate succinate (HPMCAS). In some embodiments, the polymer is hydroxypropyl methyl cellulose acetate succinate HG grade (HPMCAS-HG).

In yet another embodiment, the polymer is a polyvinylpyrrolidone co-polymer, for example, avinylpyrrolidone/vinyl acetate co-polymer (PVP/VA).

In embodiments where Compound II, Compound III-d, or Compound III forms a solid dispersion with a polymer, for example with an HPMC, HPMCAS, or PVP/VA polymer, the amount of polymer relative to the total weight of the solid dispersion ranges from 0.1% to 99% by weight. Unless otherwise specified, percentages of drug, polymer and other excipients as described within a dispersion are given in weight percentages. The amount of polymer is typically at least 20%, and preferably at least 30%, for example, at least 35%, at least 40%, at least 45%, or 50% (e.g., 49.5%). The amount is typically 99% or less, and preferably 80% or less, for example 75% or less, 70% or less, 65% or less, 60% or less, or 55% or less. In one embodiment, the polymer is in an amount of up to 50% of the total weight of the dispersion (and even more specifically, between 40% and 50%, such as 49%, 49.5%, or 50%).

In some embodiments, the API (e.g., Compound II, Compound III-d, or Compound III) and polymer are present in roughly equal amounts in weight, for example each of the polymer and the drug make up half of the percentage weight of the dispersion. For example, the polymer is present in 49.5 wt % and Compound II, Compound III-d, or Compound III is present in 50 wt %. In another embodiment Compound II, Compound III-d, or Compound III is present in an amount greater than half of the percentage weight of the dispersions. For example, the polymer is present in 20 wt % and Compound II, Compound III-d, or Compound III is present in 80 wt %. In other embodiments, the polymer is present in 19.5 wt % and Compound II, Compound III-d, or Compound III is present in 80 wt %.

In some embodiments, the API (e.g., Compound II, Compound III-d, or Compound III) and the polymer combined represent 1% to 20% w/w total solid content of the spray drying solution prior to spray drying. In some embodiments, Compound II, Compound III-d, or Compound III, and the polymer combined represent 5% to 15% w/w total solid content of the spray drying solution prior to spray drying. In some embodiments, Compound II, Compound III-d, or Compound III and the polymer combined represent 11% w/w total solid content of the spray drying solution prior to spray drying.

In some embodiments, the dispersion further includes other minor ingredients, such as a surfactant (e.g., SLS). In some embodiments, the surfactant is present in less than 10% of the dispersion, for example less than 9%, less than 8%, less than 7%, less than 6%, less than 5%, less than 4%, less than 3%, less than 2%, 1%, or 0.5%.

In embodiments including a polymer, the polymer is present in an amount effective for stabilizing the solid dispersion. Stabilizing includes inhibiting or preventing, the crystallization of an API (e.g., Compound II, Compound III-d, or Compound III). Such stabilizing would inhibit the conversion of the API from amorphous to crystalline form. For example, the polymer would prevent at least a portion (e.g., 5%, 10%, 15%, 20%, 25%, 30%, 35%, 40%, 45%, 50%, 55%, 60%, 65%, 70%, 75%, or greater) of the API from converting from an amorphous to a crystalline form. Stabilization can be measured, for example, by measuring the glass transition temperature of the solid dispersion, measuring the amount of crystalline material, measuring the rate of relaxation of the amorphous material, or by measuring the solubility or bioavailability of the API.

In some embodiments, the polymers for use in the disclosure have a glass transition temperature of no less than 10-15° C. lower than the glass transition temperature of API. In some instances, the glass transition temperature of the polymer is greater than the glass transition temperature of API, and in general at least 50° C. higher than the desired storage temperature of the drug product. For example, at least 100° C., at least 105° C., at least 105° C., at least 110° C., at least 120° C., at least 130° C., at least 140° C., at least 150° C., at least 160° C., at least 160° C., or greater.

In some embodiments, the polymers for use in the disclosure have similar or better solubility in solvents suitable for spray drying processes relative to that of an API (e.g., Compound II, Compound III-d, or Compound III). In some embodiments, the polymer will dissolve in one or more of the same solvents or solvent systems as the API.

In some embodiments, the polymers for use in the disclosure can increase the solubility of an API (e.g., Compound II, Compound III-d, or Compound III) in aqueous and physiologically relative media either relative to the solubility of the API in the absence of polymer or relative to the solubility of the API when combined with a reference polymer. For example, the polymers can increase the solubility of Compound II, Compound III-d, or Compound III by reducing the amount of amorphous Compound II, Compound III-d, or Compound III that converts to a crystalline form(s), either from a solid amorphous dispersion or from a liquid suspension.

In some embodiments, the polymers for use in the disclosure can decrease the relaxation rate of the amorphous substance.

In some embodiments, the polymers for use in the disclosure can increase the physical and/or chemical stability of an API (e.g., Compound II, Compound III-d, or Compound III).

In some embodiments, the polymers for use in the disclosure can improve the manufacturability of an API (e.g., Compound II, Compound III-d, or Compound III).

In some embodiments, the polymers for use in the disclosure can improve one or more of the handling, administration or storage properties of an API (e.g., Compound II, Compound III-d, or Compound III).

In some embodiments, the polymers for use in the disclosure have little or no unfavorable interaction with other pharmaceutical components, for example excipients.

The suitability of a candidate polymer (or other component) can be tested using the spray drying methods (or other methods) described herein to form an amorphous composition. The candidate composition can be compared in terms of stability, resistance to the formation of crystals, or other properties, and compared to a reference preparation, e.g., a preparation of neat amorphous Compound I, Compound II, Compound III-d, or Compound III. For example, a candidate composition could be tested to determine whether it inhibits the time to onset of solvent mediated crystallization, or the percent conversion at a given time under controlled conditions, by at least 50%, 75%, or 100% as well as the reference preparation, or a candidate composition could be tested to determine if it has improved bioavailability or solubility relative to crystalline Compound I, Compound II, Compound III-d, or Compound III.

In some embodiments, the first solid dispersion comprises a cellulose polymer. For example, the first solid dispersion comprises hydroxypropyl methylcellulose (HPMC). In some embodiments, the first solid dispersion comprises a weight ratio of HPMC to Compound II ranging from 1:10 to 1:1. In some instances, the weight ratio of HPMC to Compound II is from 1:3 to 1:5.

In some embodiments, the second solid dispersion comprises a cellulose polymer. For example, the second solid dispersion comprises hydroxypropyl methylcellulose acetate succinate (HPMCAS).

In some embodiments, each of the first and second solid dispersions comprises a plurality of particles having a mean particle diameter of 5 to 100 microns. In some embodiments, the particles have a mean particle diameter of 5 to 30 microns. In some embodiments, the particles have a mean particle diameter of 15 microns.

In some embodiments, the first solid dispersion comprises from 70 wt % to 90 wt % (e.g., from 75 wt % to 85 wt %) of Compound II.

In some embodiments, the second solid dispersion comprises from 70 wt % to 90 wt % (e.g., from 75 wt % to 85 wt %) of Compound III-d or III.

In some embodiments, each of the first and second solid dispersions is a spray dried dispersion.

In some embodiments, the pharmaceutical composition disclosed herein further comprise one or more pharmaceutically acceptable excipients, such as pharmaceutically acceptable vehicles, adjuvants, or carriers.

Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutically acceptable composition, its use is contemplated to be within the scope of this disclosure.

In one embodiment, the pharmaceutical composition of the disclosure comprise one or more fillers, a disintegrant, and a lubricant.

Fillers suitable for the pharmaceutical compositions disclosed herein are compatible with the other ingredients of the pharmaceutical compositions, i.e., they do not substantially reduce the solubility, the hardness, the chemical stability, the physical stability, or the biological activity of the pharmaceutical compositions. Exemplary fillers include: celluloses, modified celluloses, (e.g. sodium carboxymethyl cellulose, ethyl cellulose hydroxymethyl cellulose, hydroxypropylcellulose), cellulose acetate, microcrystalline cellulose, calcium phosphates, dibasic calcium phosphate, starches (e.g. corn starch, potato starch), sugars (e.g., mannitol, lactose, sucrose, or the like), or any combination thereof. In one embodiment, the filler is microcrystalline cellulose.

In some embodiments, the pharmaceutical compositions comprises one or more fillers in an amount of at least 5 wt % (e.g., at least 20 wt %, at least 30 wt %, or at least 40 wt %) by weight of the pharmaceutical composition. For example, the pharmaceutical compositions comprise from 10 wt % to 60 wt % (e.g., from 20 wt % to 55 wt %, from 25 wt % to 50 wt %, or from 27 wt % to 45 wt %) of filler, by weight of the pharmaceutical composition. In another example, the pharmaceutical composition s comprise at least 20 wt % (e.g., at least 30 wt % or at least 40 wt %) of microcrystalline cellulose, for example MCC Avicel PH102 or Avicel PH101, by weight of the pharmaceutical composition. In yet another example, the pharmaceutical compositions comprise from 10 wt % to 60 wt % (e.g., from 20 wt % to 55 wt % or from 25 wt % to 45 wt %) of microcellulose, by weight of the pharmaceutical composition.

Disintegrants suitable for the pharmaceutical compositions disclosed herein can enhance the dispersal of the pharmaceutical compositions and are compatible with the other ingredients of the pharmaceutical compositions, i.e., they do not substantially reduce the chemical stability, the physical stability, the hardness, or the biological activity of the pharmaceutical compositions. Exemplary disintegrants include croscarmellose sodium, sodium starch glycolate, crospovidone or a combination thereof. In one embodiment, the disintegrant is croscarmellose sodium.

In some embodiments, the pharmaceutical compositions disclosed herein comprise disintegrant in an amount of 10 wt % or less (e.g., 7 wt % or less, 6 wt % or less, or 5 wt % or less) by weight of the pharmaceutical composition. For example, the pharmaceutical compositions comprise from 1 wt % to 10 wt % (e.g., from 1.5 wt % to 7.5 wt % or from 2.5 wt % to 6 wt %) of disintegrant, by weight of the pharmaceutical composition. In another example, the pharmaceutical compositions comprise 10 wt % or less (e.g., 7 wt % or less, 6 wt % or less, or 5 wt % or less) of croscarmellose sodium, by weight of the pharmaceutical composition. In yet another example, the pharmaceutical compositions comprise from 1 wt % to 10 wt % (e.g., from 1.5 wt % to 7.5 wt % or from 2.5 wt % to 6 wt %) of croscarmellose sodium, by weight of the pharmaceutical composition. In some examples, the pharmaceutical compositions comprise from 0.1% to 10 wt % (e.g., from 0.5 wt % to 7.5 wt % or from 1.5 wt % to 6 wt %) of disintegrant, by weight of the pharmaceutical composition. In still other embodiments, the pharmaceutical compositions comprise from 0.5% to 10 wt % (e.g., from 1.5 wt % to 7.5 wt % or from 2.5 wt % to 6 wt %) of disintegrant, by weight of the pharmaceutical composition.

In some embodiments, the pharmaceutical compositions disclosed herein comprise a lubricant. A lubricant can prevent adhesion of a mixture component to a surface (e.g., a surface of a mixing bowl, a granulation roll, a compression die and/or punch). A lubricant can also reduce interparticle friction within the granulate and improve the compression and ejection of compressed pharmaceutical compositions from a granulator and/or die press. A suitable lubricant for the pharmaceutical compositions disclosed herein is compatible with the other ingredients of the pharmaceutical compositions, i.e., they do not substantially reduce the solubility, the hardness, or the biological activity of the pharmaceutical compositions. Exemplary lubricants include magnesium stearate, sodium stearyl fumarate, calcium stearate, zinc stearate, sodium stearate, stearic acid, aluminum stearate, leucine, glyceryl behenate, hydrogenated vegetable oil or any combination thereof. In embodiment, the lubricant is magnesium stearate.

In one embodiment, the pharmaceutical compositions comprise a lubricant in an amount of 5 wt % or less (e.g., 4.75 wt %, 4.0 wt % or less, or 3.00 wt % or less, or 2.0 wt % or less) by weight of the pharmaceutical composition. For example, the pharmaceutical compositions comprise from 5 wt % to 0.10 wt % (e.g., from 4.5 wt % to 0.5 wt % or from 3 wt % to 1 wt %) of lubricant, by weight of the pharmaceutical composition. In another example, the pharmaceutical compositions comprise 5 wt % or less (e.g., 4.0 wt % or less, 3.0 wt % or less, or 2.0 wt % or less, or 1.0 wt % or less)

of magnesium stearate, by weight of the pharmaceutical composition. In yet another example, the pharmaceutical compositions comprise from 5 wt % to 0.10 wt % (e.g., from 4.5 wt % to 0.15 wt % or from 3.0 wt % to 0.50 wt %) of magnesium stearate, by weight of the pharmaceutical composition.

In some embodiments, the pharmaceutical compositions disclosed herein are tablets.

Any suitable spray dried dispersions of Compound II, Compound III-d, and Compound III can be used for the pharmaceutical compositions disclosed herein. Some examples for Compound II and its pharmaceutically acceptable salts can be found in WO 2011/119984 and WO 2014/015841, all of which are incorporated herein by reference. Some examples for Compound III and its pharmaceutically acceptable salts can be found in WO 2007/134279, WO 2010/019239, WO 2011/019413, WO 2012/027731, and WO 2013/130669, all of which are incorporated herein by reference.

Pharmaceutical compositions comprising Compound II and Compound III are disclosed in PCT Publication No. WO 2015/160787, incorporated herein by reference. An exemplary embodiment is shown in the following Table 2:

TABLE 2

Examplary Tablet Comprising 100 mg Compound II and 150 mg Compound III.

| | Ingredient | Amount per tablet (mg) |
|---|---|---|
| Intra-granular | Compound II SDD (spray dried dispersion) (80 wt % Compound II; 20 wt % HPMC) | 125 |
| | Compound III SDD (80 wt % Compound III; 19.5 wt % HPMCAS-HG; 0.5 wt % sodium lauryl sulfate) | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated Tablet | | 591.9 |
| Film coat | Opadry | 17.7 |
| Total coated Tablet | | 609.6 |

Pharmaceutical compositions comprising Compound III are disclosed in PCT Publication No. WO 2010/019239, incorporated herein by reference. An exemplary embodiment is shown in the following Table 3:

TABLE 3

Ingredients for Exemplary Tablet of Compound III.

| Tablet Formulation | Percent Dose % Wt./Wt. | Dose (mg) | Batch (g) |
|---|---|---|---|
| Compound III SDD (80 wt % Compound III; 19.5 wt % HPMCAS-HG; 0.5 wt % sodium lauryl sulfate) | 34.1% | 187.5 | 23.9 |
| Microcrystalline cellulose | 30.5% | 167.8 | 21.4 |
| Lactose | 30.4% | 167.2 | 21.3 |
| Sodium croscarmellose | 3% | 16.5 | 2.1 |

TABLE 3-continued

Ingredients for Exemplary Tablet of Compound III.

| Tablet Formulation | Percent Dose % Wt./Wt. | Dose (mg) | Batch (g) |
|---|---|---|---|
| SLS | 0.5% | 2.8 | 0.4 |
| Colloidal silicon dioxide | 0.5% | 2.8 | 0.4 |
| Magnesium stearate | 1% | 5.5 | 0.7 |
| Total | 100% | 550 | 70 |

Additional pharmaceutical compositions comprising Compound III are disclosed in PCT Publication No. WO 2013/130669, incorporated herein by reference. Exemplary mini-tablets (~2 mm diameter, ~2 mm thickness, each mini-tablet weighing 6.9 mg) was formulated to have 50 mg of Compound III per 26 mini-tablets and 75 mg of Compound III per 39 mini-tablets using the amounts of ingredients recited in Table 4, below.

TABLE 4

Ingredients for mini-tablets for 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Compound III SDD (80 wt % Compound III; 19.5 wt % HPMCAS-HG; 0.5 wt % sodium lauryl sulfate) | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.1 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.2 |
| Total | 100 | 178.6 | 268 | 5003.2 |

In some embodiments, the pharmaceutical compositions disclosed herein comprise:

| Component | mg per pharmaceutical composition |
|---|---|
| intragranular: | |
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| microcrystalline cellulose | 75 to 85 mg |
| croscarmellose sodium (CCS) | 25 to 35 mg |
| extragranular: | |
| microcrystalline cellulose | 115 to 120 mg |
| magnesium stearate | 3 to 7 mg |

In some embodiments, the pharmaceutical compositions disclosed herein comprise:

| Component | mg per pharmaceutical composition |
|---|---|
| intragranular: | |
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| croscarmellose sodium (CCS) | 20 to 25 mg |
| extragranular: | |
| microcrystalline cellulose | 85 to 95 mg |
| magnesium stearate | 2 to 6 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| croscarmellose sodium (CCS) | 25 to 35 mg |
| microcrystalline cellulose | 195 to 200 mg |
| magnesium stearate | 3 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| croscarmellose sodium (CCS) | 20 to 25 mg |
| microcrystalline cellulose | 85 to 95 mg |
| magnesium stearate | 2 to 6 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| croscarmellose sodium (CCS) | 20 to 30 mg |
| microcrystalline cellulose | 135 to 145 mg |
| magnesium stearate | 2 to 6 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| croscarmellose sodium (CCS) | 35 to 40 mg |
| lactose monohydrate | 105 to 115 mg |
| microcrystalline cellulose | 220 to 230 mg |
| colloidal silicon dioxide | 1 to 5 mg |
| magnesium stearate | 4 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| croscarmellose sodium (CCS) | 20 to 30 mg |
| lactose monohydrate | 40 to 50 mg |
| microcrystalline cellulose | 90 to 100 mg |
| colloidal silicon dioxide | 1 to 5 mg |
| magnesium stearate | 2 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| croscarmellose sodium (CCS) | 20 to 30 mg |
| microcrystalline cellulose | 135 to 145 mg |
| colloidal silicon dioxide | 1 to 5 mg |
| magnesium stearate | 2 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III-d, 19.5 wt % hypromellose acetate succinate, and 0.5 wt % sodium lauryl sulfate | 90 to 95 mg |
| croscarmellose sodium (CCS) | 20 to 30 mg |
| microcrystalline cellulose | 135 to 145 mg |
| magnesium stearate | 2 to 7 mg |

In some embodiments, the pharmaceutical compositions disclosed herein comprise:

| Component | mg per pharmaceutical composition |
|---|---|
| intragranular: | |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| microcrystalline cellulose | 75 to 85 mg |
| croscarmellose sodium (CCS) | 25 to 35 mg |
| extragranular: | |
| microcrystalline cellulose | 115 to 120 mg |
| magnesium stearate | 3 to 7 mg |

In some embodiments, the pharmaceutical compositions disclosed herein comprise:

| Component | mg per pharmaceutical composition |
|---|---|
| intragranular: | |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 20 to 25 mg |
| microcrystalline cellulose | 85 to 9 mg |
| extragranular: | |
| microcrystalline cellulose | 115 to 120 mg |
| magnesium stearate | 2 to 7 mg |

In some embodiments, the pharmaceutical compositions disclosed herein comprise:

| Component | mg per pharmaceutical composition |
|---|---|
| intragranular: | |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 20 to 25 mg |
| extragranular: | |
| microcrystalline cellulose | 85 to 95 mg |
| magnesium stearate | 2 to 6 mg |

In some embodiments, the pharmaceutical compositions disclosed herein comprise:

| Component | mg per pharmaceutical composition |
|---|---|
| intragranular: | |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 20 to 25 mg |
| extragranular: | |
| microcrystalline cellulose | 270 to 275 mg |
| magnesium stearate | 2 to 7 mg |

In some embodiments, the pharmaceutical compositions disclosed herein comprise:

| Component | mg per pharmaceutical composition |
|---|---|
| intragranular: | |
| Compound I | 90 to 110 mg |
| solid dispersion containing 80 wt % Compound II, 20 wt% hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 20 to 25 mg |
| microcrystalline cellulose | 85 to 90 mg |
| extragranular: | |
| croscarmellose sodium (CCS) | 5 to 10 mg |
| microcrystalline cellulose | 105 to 115 mg |
| magnesium stearate | 2 to 7 mg |

In some embodiments, the pharmaceutical compositions disclosed herein comprise:

| Component | mg per pharmaceutical composition |
|---|---|
| intragranular: | |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| microcrystalline cellulose | 105 to 115 mg |
| extragranular: | |
| croscarmellose sodium (CCS) | 25 to 35 mg |
| microcrystalline cellulose | 85 to 90 mg |
| magnesium stearate | 2 to 7 mg |

In some embodiments, the pharmaceutical compositions disclosed herein comprise:

| Component | mg per pharmaceutical composition |
| --- | --- |
| intragranular: | |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| microcrystalline cellulose | 195 to 200 mg |
| extragranular: | |
| croscarmellose sodium (CCS) | 25 to 35 mg |
| magnesium stearate | 2 to 7 mg |

In some embodiments, the pharmaceutical compositions disclosed herein comprise:

| Component | mg per pharmaceutical composition |
| --- | --- |
| intragranular: | |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 12 to 17 mg |
| microcrystalline cellulose | 60 to 70 mg |
| extragranular: | |
| Compound I | 90 to 110 mg |
| microcrystalline cellulose | 95 to 105 mg |
| magnesium stearate | 2 to 7 mg |

In some embodiments, the pharmaceutical compositions disclosed herein comprise:

| Component | mg per pharmaceutical composition |
| --- | --- |
| intragranular: | |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 10 to 20 mg |
| microcrystalline cellulose | 60 to 70 mg |
| extragranular: | |
| Compound I | 90 to 110 mg |
| microcrystalline cellulose | 195 to 205 mg |
| magnesium stearate | 2 to 7 mg |

In some embodiments, the pharmaceutical compositions disclosed herein comprise:

| Component | mg per pharmaceutical composition |
| --- | --- |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 25 to 35 mg |
| microcrystalline cellulose | 195 to 205 mg |
| magnesium stearate | 2 to 7 mg |

In some embodiments, the pharmaceutical compositions disclosed herein comprise:

| Component | mg per pharmaceutical composition |
| --- | --- |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 20 to 25 mg |
| microcrystalline cellulose | 200 to 210 mg |
| magnesium stearate | 2 to 7 mg |

In some embodiments, the pharmaceutical compositions disclosed herein comprise:

| Component | mg per pharmaceutical composition |
| --- | --- |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 20 to 25 mg |
| microcrystalline cellulose | 85 to 95 mg |
| magnesium stearate | 2 to 6 mg |

In some embodiments, the pharmaceutical compositions disclosed herein comprise:

| Component | mg per pharmaceutical composition |
| --- | --- |
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 20 to 25 mg |
| microcrystalline cellulose | 270 to 275 mg |
| magnesium stearate | 2 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 25 to 35 mg |
| microcrystalline cellulose | 195 to 205 mg |
| magnesium stearate | 2 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 25 to 35 mg |
| microcrystalline cellulose | 195 to 205 mg |
| magnesium stearate | 2 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 25 to 35 mg |
| microcrystalline cellulose | 195 to 200 mg |
| magnesium stearate | 2 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 12 to 17 mg |
| microcrystalline cellulose | 160 to 170 mg |
| magnesium stearate | 2 to 7 mg |

In some embodiments, the pharmaceutical compositions disclosed herein comprise:

| Component | mg per pharmaceutical composition |
|---|---|
| Compound I | 90 to 110 mg |
| solid dispersion containing 80 wt % Compound II, 20 wt % hypromellose | 60 to 65 mg |
| solid dispersion containing 80 wt % Compound III, 19.5 wt % hypromellose acetate succinate, and 0.5 wt % sodium lauryl sulfate | 90 to 95 mg |
| croscarmellose sodium (CCS) | 10 to 20 mg |
| microcrystalline cellulose | 260 to 270 mg |
| magnesium stearate | 2 to 7 mg |

In some embodiments, the pharmaceutical compositions disclosed herein comprise:

| Component | Composition (% w/w) (based on the total weight of the pharmaceutical composition) |
|---|---|
| Compound (I) | 12 wt % to 30 wt % |
| Compound (II) | 5 wt % to 15 wt % |
| Compound III-d or Compound (III) | 10 wt % to 25 wt % |
| Croscarmellose sodium | 3 wt %-8 wt % |
| Microcrystalline cellulose | 20 wt % to 45 wt % |
| Magnesium stearate | 0.5 wt % to 2 wt % |

In some embodiments, the pharmaceutical composition disclosed herein comprise:

| Component | Composition (% w/w) (based on the total weight of the pharmaceutical composition) |
|---|---|
| Compound (I) | 18% to 23 wt % |
| Compound (II) | 8 wt % to 12 wt % |
| Compound III-d or Compound (III) | 13% to 18 wt % |
| Croscarmellose sodium | 3 wt %-7 wt % |
| Microcrystalline cellulose | 35 wt % to 45 wt % |
| Magnesium stearate | 0.5 wt % to 1.5 wt % |

In some embodiments, the pharmaceutical compositions disclosed herein comprise:

| Component | Composition (% w/w) (based on the total weight of the pharmaceutical composition) |
|---|---|
| Compound (I) | 15% to 25 wt % |
| Compound (II) | 5 wt % to 10 wt % |
| Compound III-d or Compound (III) | 7 wt % to 15 wt % |
| Croscarmellose sodium | 3 wt %-7 wt % |
| Microcrystalline cellulose | 30 wt % to 50 wt % |
| Magnesium stearate | 0.5 wt % to 1.5 wt % |

In some embodiments, the pharmaceutical compositions disclosed herein comprise:

| Component | Composition (% w/w) (based on the total weight of the pharmaceutical composition) |
|---|---|
| Compound (I) | 20% to 25 wt % |
| Compound (II) | 7 wt % to 15wt % |
| Compound III-d or Compound (III) | 15% to 20 wt % |
| Croscarmellose sodium | 3 wt %-7 wt % |
| Microcrystalline cellulose | 15 wt % to 25 wt % |
| Magnesium stearate | 0.5 wt % to 1.5 wt % |

In some embodiments, the pharmaceutical compositions disclosed herein comprise:

| Component | Composition (% w/w) (based on the total weight of the pharmaceutical composition) |
|---|---|
| Compound (I) | 20% to 25 wt % |
| Compound (II) | 7 wt % to 15 wt |
| Compound III-d or Compound (III) | 15% to 20 wt % |
| Croscarmellose sodium | 3 wt %-7 wt % |
| Microcrystalline cellulose | 25 wt % to 35 wt % |
| Magnesium stearate | 0.5 wt % to 1.5 wt % |

In some embodiments, the pharmaceutical compositions disclosed herein comprise:

| Component | Composition (% w/w) (based on the total weight of the pharmaceutical composition) |
|---|---|
| Compound (I) | 22% to 28 wt % |
| Compound (II) | 10 wt % to 15 wt % |
| Compound III-d or Compound (III) | 15% to 25 wt % |
| Croscarmellose sodium | 3 wt %-7 wt % |
| Microcrystalline cellulose | 15 wt % to 25 wt % |
| Magnesium stearate | 0.5 wt % to 1.5 wt % |

In some embodiments, the pharmaceutical compositions disclosed herein comprise:

| Component | Composition (% w/w) (based on the total weight of the pharmaceutical composition) |
|---|---|
| Compound (I) | 15% to 20 wt % |
| Compound (II) | 7 wt % to 15 wt % |
| Compound III-d or Compound (III) | 10 wt % to 15 wt % |
| Croscarmellose sodium | 3 wt %-5 wt % |
| Microcrystalline cellulose | 45 wt % to 55 wt % |
| Magnesium stearate | 0.5 wt % to 1.5 wt % |

In some embodiments, the pharmaceutical compositions disclosed herein comprise:

| Component | Composition (% w/w) (based on the total weight of the pharmaceutical composition) |
|---|---|
| Compound (I) | 20.5 ± 0.5 |
| Compound (II) | 10.2 ± 0.5 |
| Compound III-d or Compound (III) | 15.4 ± 0.5 |
| Croscarmellose sodium | 6.0 ± 0.5 |
| Microcrystalline cellulose | 40.5 ± 0.5 |
| Magnesium stearate | 1.0 ± 0.5 |

In some embodiments, the pharmaceutical compositions disclosed herein comprise:

| | Component | Composition (% w/w) (based on the total weight of the pharmaceutical composition) |
|---|---|---|
| IG (Intragradular) | Compound (I) | 20.5 ± 0.5 |
| | Compound (II) | 10.2 ± 0.5 |
| | Compound III-d or Compound (III) | 15.4 ± 0.5 |
| | Croscarmellose sodium | 6.0 ± 0.5 |
| | Microcrystalline cellulose | 16.5 ± 0.5 |
| EG (Extragradular) | Microcrystalline cellulose | 24.0 ± 0.5 |
| | Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 26.9 ± 0.5 |
| Compound (II) | 16.8 ± 0.5 |
| Compound III-d or Compound (III) | 25.3 ± 0.5 |
| Croscarmellose sodium | 6.0 ± 0.5 |
| Microcrystalline cellulose | 24.0 ± 0.5 |
| Magnesium stearate | 1.0 ± 0.5 |

In some embodiments, the pharmaceutical compositions disclosed herein comprise:

| | Component | Composition (% w/w) (based on the total weight of the pharmaceutical composition) |
|---|---|---|
| IG | Compound (I) | 26.9 ± 0.5 |
| | Compound (II) | 16.8 ± 0.5 |
| | Compound III-d or Compound (III) | 25.3 ± 0.5 |
| | Croscarmellose sodium | 6.0 ± 0.5 |
| EG | Microcrystalline cellulose | 24.0 ± 0.5 |
| | Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 23.4 ± 0.5 |
| Compound (II) | 11.7 ± 0.5 |

| Component | Composition (% w/w) (based on the total weight of the pharmaceutical composition) |
|---|---|
| Compound III-d or Compound (III) | 17.6 ± 0.5 |
| Croscarmellose sodium | 6.0 ± 0.5 |
| Microcrystalline cellulose | 33.0 ± 0.5 |
| Magnesium stearate | 1.0 ± 0.5 |

In some embodiments, the pharmaceutical compositions disclosed herein comprise:

| | Component | Composition (% w/w) (based on the total weight of the pharmaceutical composition) |
|---|---|---|
| IG | Compound (I) | 23.42 ± 0.5 |
| | Compound (II) | 11.7 ± 0.5 |
| | Compound III-d or Compound (III) | 17.6 ± 0.5 |
| | Microcrystalline cellulose | 33.0 ± 0.5 |
| | Croscarmellose sodium | 6.0 ± 0.5 |
| EG | Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 20.5 ± 0.5 |
| Compound (II) | 10.3 ± 0.5 |
| Compound III-d or Compound (III) | 15.4 ± 0.5 |
| Croscarmellose sodium | 6.0 ± 0.5 |
| Microcrystalline cellulose | 40.5 ± 0.5 |
| Magnesium stearate | 1.0 ± 0.5 |

In some embodiments, the pharmaceutical compositions disclosed herein comprise:

| | Component | Composition (% w/w) (based on the total weight of the pharmaceutical composition) |
|---|---|---|
| IG | Compound (I) | 20.5 ± 0.5 |
| | Compound (II) | 10.3 ± 0.5 |
| | Compound III-d or Compound (III) | 15.4 ± 0.5 |
| | Croscarmellose sodium | 6.0 ± 0.5 |
| | Microcrystalline cellulose | 16.5 ± 0.5 |
| EG | Microcrystalline cellulose | 24.0 ± 0.5 |
| | Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 20.5 ± 0.5 |
| Compound (II) | 12.8 ± 0.5 |
| Compound III-d or Compound (III) | 19.2 ± 0.5 |
| Croscarmellose sodium | 4.5 ± 0.5 |
| Microcrystalline cellulose | 40.0 ± 0.5 |
| Magnesium stearate | 1.0 ± 0.5 |

In some embodiments, the pharmaceutical compositions disclosed herein comprise:

| | Component | Composition (% w/w) (based on the total weight of the pharmaceutical composition) |
|---|---|---|
| IG | Compound (I) | 20.5 ± 0.5 |
| | Compound (II) | 12.8 ± 0.5 |
| | Compound III-d or Compound (III) | 19.2 ± 0.5 |
| | Croscarmellose sodium | 4.5 ± 0.5 |
| | Microcrystalline cellulose | 18.0 ± 0.5 |
| EG | Microcrystalline cellulose | 24.0 ± 0.5 |
| | Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 26.9 ± 0.5 |
| Compound (II) | 13.5 ± 0.5 |
| Compound III-d or Compound (III) | 20.2 ± 0.5 |
| Croscarmellose sodium | 6.0 ± 0.5 |
| Microcrystalline cellulose | 24.0 ± 0.5 |
| Magnesium stearate | 1.0 ± 0.5 |

In some embodiments, the pharmaceutical compositions disclosed herein comprise:

| | Component | Composition (% w/w) (based on the total weight of the pharmaceutical composition) |
|---|---|---|
| IG | Compound (I) | 26.9 ± 0.5 |
| | Compound (II) | 13.5 ± 0.5 |
| | Compound III-d or Compound (III) | 20.2 ± 0.5 |
| | Croscarmellose sodium | 6.00 ± 0.5 |
| EG | Microcrystalline cellulose | 24.0 ± 0.5 |
| | Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 18.0 ± 0.5 |
| Compound (II) | 9.0 ± 0.5 |
| Compound III-d or Compound (III) | 13.5 ± 0.5 |
| Croscarmellose sodium | 4.0 ± 0.5 |
| Microcrystalline cellulose | 49.0 ± 0.5 |
| Magnesium stearate | 1.0 ± 0.5 |

In some embodiments, the pharmaceutical compositions disclosed herein comprise:

|     | Component | Composition (% w/w) (based on the total weight of the pharmaceutical composition) |
|-----|-----------|---|
| IG  | Compound (I) | 18.0 ± 0.5 |
|     | Compound (II) | 9.0 ± 0.5 |
|     | Compound III-d or Compound (III) | 13.5 ± 0.5 |
|     | Croscarmellose sodium | 4.0 ± 0.5 |
| EG  | Microcrystalline cellulose | 49.0 ± 0.5 |
|     | Magnesium stearate | 1.0 ± 0.5 |

In some embodiments, the pharmaceutical compositions disclosed herein comprise:

| Component | Composition (% w/w) (based on the total weight of the pharmaceutical composition) |
|-----------|---|
| Compound (I) | 20.5 ± 0.5 |
| Compound (II) | 10.3 ± 0.5 |
| Compound III-d or Compound (III) | 15.4 ± 0.5 |
| Croscarmellose sodium | 6.0 ± 0.5 |
| Microcrystalline cellulose | 40.5 ± 0.5 |
| Magnesium stearate | 1.0 ± 0.5 |

In some embodiments, the pharmaceutical compositions disclosed herein comprise:

|     | Component | Composition (% w/w) (based on the total weight of the pharmaceutical composition) |
|-----|-----------|---|
| IG  | Compound (I) | 20.5 ± 0.5 |
|     | Compound (II) | 10.3 ± 0.5 |
|     | Compound III-d or Compound (III) | 15.4 ± 0.5 |
|     | Croscarmellose sodium | 4.5 ± 0.5 |
|     | Microcrystalline cellulose | 18.0 ± 0.5 |
| EG  | Croscarmellose sodium | 1.5 ± 0.5 |
|     | Microcrystalline cellulose | 22.5 ± 0.5 |
|     | Magnesium stearate | 1.00 ± 0.5 |

In some embodiments, the pharmaceutical compositions disclosed herein comprise:

|     | Component | Composition (% w/w) (based on the total weight of the pharmaceutical composition) |
|-----|-----------|---|
| IG  | Compound (I) | 20.5 ± 0.5 |
|     | Compound (II) | 12.8 ± 0.5 |
|     | Compound III-d or Compound (III) | 19.2 ± 0.5 |
|     | Microcrystalline cellulose | 22.5 ± 0.5 |
| EG  | Croscarmellose sodium | 6.0 ± 0.5 |
|     | Microcrystalline cellulose | 18.0 ± 0.5 |
|     | Magnesium stearate | 1.0 ± 0.5 |

In some embodiments, the pharmaceutical compositions disclosed herein comprise:

|     | Component | Composition (% w/w) (based on the total weight of the pharmaceutical composition) |
|-----|-----------|---|
| IG  | Compound (I) | 20.5 ± 0.5 |
|     | Compound (II) | 10.3 ± 0.5 |
|     | Compound III-d or Compound (III) | 15.4 ± 0.5 |
|     | Croscarmellose sodium | 4.5 ± 0.5 |
|     | Microcrystalline cellulose | 18 ± 0.5 |
| EG  | Croscarmellose sodium | 1.5 ± 0.5 |
|     | Microcrystalline cellulose | 22.5 ± 0.5 |
|     | Magnesium stearate | 1 ± 0.5 |

In some embodiments, the pharmaceutical compositions disclosed herein comprise:

|     | Component | Composition (% w/w) (based on the total weight of the tablet) |
|-----|-----------|---|
| IG  | Compound (I) | 20.5 ± 0.5 |
|     | Compound (II) | 10.3 ± 0.5 |
|     | Compound III-d or Compound (III) | 15.4 ± 0.5 |
|     | Croscarmellose sodium | 4.5 ± 0.5 |
|     | Microcrystalline cellulose | 18.0 ± 0.5 |
| EG  | Croscarmellose sodium | 1.5 ± 0.5 |
|     | Microcrystalline cellulose | 22.5 ± 0.5 |
|     | Magnesium stearate | 1.00 ± 0.5 |

In some embodiments, the pharmaceutical compositions disclosed herein comprise:

|     | Component | Composition (% w/w) (based on the total weight of the pharmaceutical composition) |
|-----|-----------|---|
| IG  | Compound (I) | 20.5 ± 0.5 |
|     | Compound (II) | 10.2 ± 0.5 |
|     | Compound III-d or Compound (III) | 15.4 ± 0.5 |
|     | Microcrystalline cellulose | 40.5 ± 0.5 |
| EG  | Croscarmellose sodium | 6.0 ± 0.5 |
|     | Magnesium stearate | 1.0 ± 0.5 |

In some embodiments, the pharmaceutical compositions disclosed herein comprise:

| Component | Composition (% w/w) (based on the total weight of the pharmaceutical composition) |
|-----------|---|
| Compound (I) | 22.7 ± 0.5 |
| Compound (II) | 11.3 ± 0.5 |
| Compound III-d or Compound (III) | 17.0 ± 0.5 |
| Croscarmellose sodium | 3.4 ± 0.5 |
| Microcrystalline cellulose | 37.6 ± 0.5 |
| Magnesium stearate | 1.0 ± 0.5 |

In some embodiments, the pharmaceutical compositions disclosed herein comprise:

| | Component | Composition (% w/w) (based on the total weight of the pharmaceutical composition) |
|---|---|---|
| IG | Compound (II) | 11.3 ± 0.5 |
| | Compound III-d or Compound (III) | 17.0 ± 0.5 |
| | Croscarmellose sodium | 3.4 ± 0.5 |
| | Microcrystalline cellulose | 14.9 ± 0.5 |
| EG | Compound (I) | 22.7 ± 0.5 |
| | Microcrystalline cellulose | 22.7 ± 0.5 |
| | Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 18.4 ± 0.5 |
| Compound (II) | 9.2 ± 0.5 |
| Compound III-d or Compound (III) | 13.8 ± 0.5 |
| Croscarmellose sodium | 2.7 ± 0.5 |
| Microcrystalline cellulose | 49.0 ± 0.5 |
| Magnesium stearate | 1.0 ± 0.5 |

In some embodiments, the pharmaceutical compositions disclosed herein comprise:

| | Component | Composition (% w/w) (based on the total weight of the pharmaceutical composition) |
|---|---|---|
| IG | Compound (II) | 9.2 ± 0.5 |
| | Compound III-d or Compound (III) | 13.8 ± 0.5 |
| | Croscarmellose sodium | 2.7 ± 0.5 |
| | Microcrystalline cellulose | 12.1 ± 0.5 |
| EG | Compound (I) | 18.4 ± 0.5 |
| | Microcrystalline cellulose | 36.9 ± 0.5 |
| | Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 15.6 ± 0.5 |
| Compound (II) | 9.8 ± 0.5 |
| Compound III-d or Compound (III) | 14.6 ± 0.5 |
| Croscarmellose sodium | 6.0 ± 0.5 |
| Lactose monohydrate | 17.5 ± 0.5 |
| Microcrystalline cellulose | 35.0 ± 0.5 |
| Colloidal silicon dioxide | 0.5 ± 0.5 |
| Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 23.4 ± 0.5 |
| Compound (II) | 11.7 ± 0.5 |
| Compound III-d or Compound (III) | 17.6 ± 0.5 |
| Croscarmellose sodium | 6.0 ± 0.5 |
| Lactose monohydrate | 10.8 ± 0.5 |
| Microcrystalline cellulose | 21.7 ± 0.5 |
| Colloidal silicon dioxide | 0.5 ± 0.5 |
| Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 23.4 ± 0.5 |
| Compound (II) | 11.7 ± 0.5 |
| Compound III-d or Compound (III) | 17.6 ± 0.5 |
| Croscarmellose sodium | 6.0 ± 0.5 |
| Microcrystalline cellulose | 32.5 ± 0.5 |
| Colloidal silicon dioxide | 0.5 ± 0.5 |
| Magnesium stearate | 1.0 ± 0.5 |

In some embodiments, the pharmaceutical compositions disclosed herein comprise:

| Component | Composition (% w/w) (based on the total weight of the pharmaceutical composition) |
|---|---|
| Compound (I) | 23.4 ± 0.5 |
| Compound (II) | 11.7 ± 0.5 |
| Compound III-d or Compound (III) | 17.6 ± 0.5 |
| Croscarmellose sodium | 6.0 ± 0.5 |
| Microcrystalline cellulose | 33.0 ± 0.5 |
| Magnesium stearate | 1.0 ± 0.5 |

In some embodiments, the pharmaceutical compositions disclosed herein comprise:

(A) an intragranular portion that comprises:
(a) 10 mg to 110 mg of Compound I;
(b) 25 mg to 70 mg of a first solid dispersion comprising 80 wt % Compound II relative to the total weight of the first solid dispersion; and 20 wt % of a hydroxypropyl methylcellulose relative to the total weight of the first solid dispersion; and
(c) 85 mg to 195 mg, of a second solid dispersion comprising 80 wt % of Compound III relative to the total weight of the second solid dispersion; 0.5 wt % of sodium lauryl sulfate relative to the total weight of the second solid dispersion; and 19.5 wt % of a hydroxypropyl methylcellulose acetate succinate to the total weight of the second solid dispersion;
(d) 10 mg to 45 mg of croscarmellose sodium; and
(e) 40 mg to 115 mg of microcrystalline cellulose; and
(B) an extragranular portion that comprises:
(f) 55 mg to 165 mg of microcrystalline cellulose; and
(g) 2 mg to 7 mg of magnesium stearate.

In some embodiments, the pharmaceutical compositions disclosed herein comprise:

(A) an intragranular portion that comprises:
 (a) 95 mg to 105 mg of Compound I;
 (b) 60 mg to 65 mg of a first solid dispersion comprising 80 wt % Compound II relative to the total weight of the first solid dispersion and 20 wt % of a hydroxypropyl methylcellulose relative to the total weight of the first solid dispersion;
 (c) 185 mg to 190 mg of a second solid dispersion comprising 80 wt % of Compound III relative to the total weight of the second solid dispersion; 0.5 wt % of sodium lauryl sulfate relative to the total weight of the second solid dispersion; and 19.5 wt % of a hydroxypropyl methylcellulose acetate succinate to the total weight of the second solid dispersion;
 (d) 35 mg to 45 mg of croscarmellose sodium;
 (e) 105 mg to 115 mg of microcrystalline cellulose; and
(B) an extragranular portion that comprises:
 (f) 155 mg to 165 mg of said microcrystalline cellulose; and
 (g) 2 mg to 7 mg of magnesium stearate.

In some embodiments, the pharmaceutical compositions disclosed herein comprise:

(A) an intragranular portion that comprises:
 (a) 45 mg to 55 mg of Compound I;
 (b) 25 mg to 55 mg of a first solid dispersion comprising 80 wt % Compound II relative to the total weight of the first solid dispersion and 20 wt % of a hydroxypropyl methylcellulose relative to the total weight of the first solid dispersion;
 (c) 90 mg to 100 mg of a second solid dispersion comprising 80 wt % of Compound III relative to the total weight of the second solid dispersion; 0.5 wt % of sodium lauryl sulfate relative to the total weight of the second solid dispersion; and 19.5 wt % of a hydroxypropyl methylcellulose acetate succinate to the total weight of the second solid dispersion;
 (d) 15 mg to 25 mg of croscarmellose sodium;
 (e) 50 mg to 60 mg of microcrystalline cellulose; and
(B) an extragranular portion that comprises:
 (f) 75 mg to 85 mg of microcrystalline cellulose; and
 (g) 2 mg to 7 mg of magnesium stearate.

In some embodiments, the pharmaceutical compositions disclosed herein comprise:

(A) an intragranular portion that comprises:
 (a) 45 mg to 55 mg of Compound I;
 (b) 60 mg to 65 mg of a first solid dispersion comprising 80 wt % Compound II relative to the total weight of the first solid dispersion and 20 wt % of a hydroxypropyl methylcellulose relative to the total weight of the first solid dispersion;
 (c) 185 mg to 190 mg of a second solid dispersion comprising 80 wt % of Compound III relative to the total weight of the second solid dispersion; 0.5 wt % of sodium lauryl sulfate relative to the total weight of the second solid dispersion; and 19.5 wt % of a hydroxypropyl methylcellulose acetate succinate to the total weight of the second solid dispersion;
 (d) 30 mg to 40 mg of croscarmellose sodium;
 (e) 90 mg to 100 mg of microcrystalline cellulose; and
(B) an extragranular portion that comprises:
 (f) 130 mg to 145 mg of microcrystalline cellulose; and
 (g) 2 mg to 7 mg of magnesium stearate.

In some embodiments, the pharmaceutical compositions disclosed herein comprise:

(A) an intragranular portion that comprises:
 (a) 20 mg to 30 mg of Compound I;
 (b) 30 mg to 35 mg of a first solid dispersion comprising 80 wt % Compound II relative to the total weight of the first solid dispersion and 20 wt % of a hydroxypropyl methylcellulose relative to the total weight of the first solid dispersion;
 (c) 90 mg to 100 mg of a second solid dispersion comprising 80 wt % of Compound III relative to the total weight of the second solid dispersion; 0.5 wt % of sodium lauryl sulfate relative to the total weight of the second solid dispersion; and 19.5 wt % of a hydroxypropyl methylcellulose acetate succinate to the total weight of the second solid dispersion;
 (d) 15 mg to 25 mg of croscarmellose sodium;
 (e) 45 mg to 50 mg of microcrystalline cellulose; and
(B) an extragranular portion that comprises:
 (f) 65 mg to 70 mg of microcrystalline cellulose; and
 (g) 2 mg to 7 mg of magnesium stearate.

In some embodiments, the pharmaceutical compositions disclosed herein comprise:

(A) an intragranular portion that comprises:
 (a) 20 mg to 30 mg of Compound I;
 (b) 60 mg to 65 mg of a first solid dispersion comprising 80 wt % Compound II relative to the total weight of the first solid dispersion and 20 wt % of a hydroxypropyl methylcellulose relative to the total weight of the first solid dispersion;
 (c) 185 mg to 190 mg of a second solid dispersion comprising 80 wt % of Compound III relative to the total weight of the second solid dispersion; 0.5 wt % of sodium lauryl sulfate relative to the total weight of the second solid dispersion; and 19.5 wt % of a hydroxypropyl methylcellulose acetate succinate to the total weight of the second solid dispersion;
 (d) 35 mg to 45 mg of croscarmellose sodium;
 (e) 80 mg to 90 mg of microcrystalline cellulose; and
(B) an extragranular portion that comprises:
 (f) 120 mg to 130 mg of microcrystalline cellulose; and
 (g) 2 mg to 7 mg of magnesium stearate.

In some embodiments, the pharmaceutical compositions disclosed herein comprise:

(A) an intragranular portion that comprises:
 (a) 10 mg to 15 mg of Compound I;
 (b) 25 mg to 35 mg of a first solid dispersion comprising 80 wt % Compound II relative to the total weight of the first solid dispersion and 20 wt % of a hydroxypropyl methylcellulose relative to the total weight of the first solid dispersion;
 (c) 90 mg to 100 mg of a second solid dispersion comprising 80 wt % of Compound III relative to the total weight of the second solid dispersion; 0.5 wt % of sodium lauryl sulfate relative to the total weight of the second solid dispersion; and 19.5 wt % of a hydroxypropyl methylcellulose acetate succinate to the total weight of the second solid dispersion;
 (d) 10 mg to 20 mg of croscarmellose sodium;
 (e) 40 mg to 50 mg of microcrystalline cellulose; and
(B) an extragranular portion that comprises:
 (f) 60 mg to 65 mg of microcrystalline cellulose; and
 (g) 2 mg to 7 mg of magnesium stearate.

In some embodiments, the pharmaceutical compositions disclosed herein comprise:

|  | Material Name | mg per tablet |
|---|---|---|
| Intra Granular | Compound I | 100.0 ± 0.5 |
|  | Compound II SDD (80 wt % Compound II and 20 wt % HPMC) | 62.5 ± 0.5 |
|  | Compound III SDD (80 wt % Compound III, 19.5 wt % HPMCAS, and 0.5 wt % sodium lauryl sulfate) | 93.8 ± 0.5 |
|  | Croscarmellose sodium | 29.3 ± 0.5 |
|  | Microcrystalline cellulose | 80.5 ± 0.5 |
| Extra Granular | Microcrystalline cellulose | 117.1 ± 0.5 |
|  | Magnesium stearate | 4.9 ± 0.5 |
|  | Coating | 14.6 ± 0.5 |

In some embodiments, the pharmaceutical compositions disclosed herein comprise:

|  | Ingredient | Amount per tablet (mg) |
|---|---|---|
| Intra-granular | Compound I | 100.0 ± 0.5 |
|  | Compound II SDD (80 wt % Compound II and 20 wt % HPMC) | 62.5 ± 0.5 |
|  | Compound III SDD (80 wt % Compound III, 19.5 wt % HPMCAS, and 0.5 wt % sodium lauryl sulfate) | 187.6 ± 0.5 |
|  | Croscarmellose Sodium | 29.3 ± 0.5 |
|  | Microcrystalline cellulose | 80.5 ± 0.5 |
| Extra-granular | Microcrystalline cellulose | 117.1 ± 0.5 |
|  | Magnesium Stearate | 4.9 ± 0.5 |

In some embodiments, the pharmaceutical compositions disclosed herein comprise:

|  | Ingredient | Amount per tablet (mg) |
|---|---|---|
| Intra-granular | Compound I | 100.0 ± 0.5 |
|  | Compound II SDD (80 wt % Compound II and 20 wt % HPMC) | 62.4 ± 0.5 |
|  | Compound III SDD (80 wt % Compound III, 19.5 wt % HPMCAS, and 0.5 wt % sodium lauryl sulfate) | 187.6 ± 0.5 |
|  | Croscarmellose Sodium | 22.3 ± 0.5 |
| Extra-granular | Microcrystalline cellulose | 89.1 ± 0.5 |
|  | Magnesium Stearate | 3.7 ± 0.5 |

In some embodiments, the pharmaceutical compositions disclosed herein comprise:

| Ingredient | Amount per tablet (mg) |
|---|---|
| Compound I | 100 ± 0.5 |
| Compound II SDD (80 wt % Compound II and 20 wt % HPMC) | 62.5 ± 0.5 |
| Compound III SDD (80 wt % Compound III, 19.5 wt % HPMCAS, and 0.5 wt % sodium lauryl sulfate) | 187.6 ± 0.5 |
| Microcrystalline cellulose | 140.9 ± 0.5 |
| Croscarmellose Sodium | 25.6 ± 0.5 |
| Magnesium stearate | 4.3 ± 0.5 |

In some embodiments, the pharmaceutical compositions disclosed herein comprise:

|  | Ingredient | Amount per tablet (mg) |
|---|---|---|
| Intra-granular | Compound I | 100 ± 0.5 |
|  | Compound II SDD (80 wt % Compound II and 20 wt % HPMC) | 62.5 ± 0.5 |
|  | Compound III SDD (80 wt % Compound III, 19.5 wt % HPMCAS, and 0.5 wt % sodium lauryl sulfate) | 187.5 ± 0.5 |
|  | Croscarmellose sodium | 40 ± 0.5 |
|  | Microcrystalline cellulose | 110 ± 0.5 |
| Extra-granular | Microcrystalline cellulose | 160 ± 0.5 |
|  | Magnesium stearate | 6.7 ± 0.5 |
|  | Film coat | 20 ± 0.5 |

In some embodiments, the pharmaceutical compositions disclosed herein comprise:

|  | Ingredient | Amount per tablet (mg) |
|---|---|---|
| Intra-granular | Compound I | 50 ± 0.5 |
|  | Compound II SDD (80 wt % Compound II and 20 wt % HPMC) | 31.2 ± 0.5 |
|  | Compound III SDD (80 wt % Compound III, 19.5 wt % HPMCAS, and 0.5 wt % sodium lauryl sulfate) | 93.7 ± 0.5 |
|  | Croscarmellose sodium | 20 ± 0.5 |
|  | Microcrystalline cellulose | 55 ± 0.5 |
| Extra-granular | Microcrystalline cellulose | 80 ± 0.5 |
|  | Magnesium stearate | 3.3 ± 0.5 |
|  | Film coat | 10 ± 0.5 |

In some embodiments, the pharmaceutical compositions disclosed herein comprise:

|  | Ingredient | Amount per tablet (mg) |
|---|---|---|
| Intra-granular | Compound I | 50 ± 0.5 |
|  | Compound II SDD (80 wt % Compound II and 20 wt % HPMC) | 62.5 ± 0.5 |
|  | Compound III SDD (80 wt % Compound III, 19.5 wt % HPMCAS, and 0.5 wt % sodium lauryl sulfate) | 187.5 ± 0.5 |
|  | Croscarmellose sodium | 34.3 ± 0.5 |
|  | Microcrystalline cellulose | 94.3 ± 0.5 |
| Extra-granular | Microcrystalline cellulose | 137.1 ± 0.5 |
|  | Magnesium stearate | 5.7 ± 0.5 |
|  | Film coat | 17.1 ± 0.5 |

In some embodiments, the pharmaceutical compositions disclosed herein comprise:

|  | Ingredient | Amount per tablet (mg) |
|---|---|---|
| Intra-granular | Compound I | 25 ± 0.5 |
|  | Compound II SDD (80 wt % Compound II and 20 wt % HPMC) | 31.2 ± 0.5 |

-continued

| | Ingredient | Amount per tablet (mg) |
|---|---|---|
| | Compound III SDD (80 wt % Compound III, 19.5 wt % HPMCAS, and 0.5 wt % sodium lauryl sulfate) | 93.7 ± 0.5 |
| | Croscarmellose sodium | 17.1 ± 0.5 |
| | Microcrystalline cellulose | 47.1 ± 0.5 |
| Extra-granular | Microcrystalline cellulose | 68.6 ± 0.5 |
| | Magnesium stearate | 2.9 ± 0.5 |
| | Film coat | 8.6 ± 0.5 |

In some embodiments, the pharmaceutical compositions disclosed herein comprise:

| | Ingredient | Amount per tablet (mg) |
|---|---|---|
| Intra-granular | Compound I | 25 ± 0.5 |
| | Compound II SDD (80 wt % Compound II and 20 wt % HPMC) | 62.5 ± 0.5 |
| | Compound III SDD (80 wt % Compound III, 19.5 wt % HPMCAS, and 0.5 wt % sodium lauryl sulfate) | 187.5 ± 0.5 |
| | Croscarmellose sodium | 31.4 ± 0.5 |
| | Microcrystalline cellulose | 86.4 ± 0.5 |
| Extra-granular | Microcrystalline cellulose | 125.7 ± 0.5 |
| | Magnesium stearate | 5.2 ± 0.5 |
| | Film coat | 15.7 ± 0.5 |

In some embodiments, the pharmaceutical compositions disclosed herein comprise:

| | Ingredient | Amount per tablet (mg) |
|---|---|---|
| Intra-granular | Compound I | 12.5 ± 0.5 |
| | Compound II SDD (80 wt % Compound II and 20 wt % HPMC) | 31.2 ± 0.5 |
| | Compound III SDD (80 wt % Compound III, 19.5 wt % HPMCAS, and 0.5 wt % sodium lauryl sulfate) | 93.7 ± 0.5 |
| | Croscarmellose sodium | 15.7 ± 0.5 |
| | Microcrystalline cellulose | 43.2 ± 0.5 |
| Extra-granular | Microcrystalline cellulose | 62.9 ± 0.5 |
| | Magnesium stearate | 2.6 ± 0.5 |
| | Film coat | 7.9 ± 0.5 |

In some embodiments, the pharmaceutical compositions disclosed herein are tablets.

Processes of Making Tablets

The tablets of the disclosure can be produced by compacting or compressing an admixture or composition, for example, powder or granules, under pressure to form a stable three-dimensional shape (e.g., a tablet). As used herein, "tablet" includes compressed pharmaceutical dosage unit forms of all shapes and sizes, whether coated or uncoated. In some embodiments, the methods of preparing the tablets disclosed herein comprise (a) mixing Compound I and the first and second solid dispersions to form a first mixture; and (b) compressing a tablet mixture comprising the first mixture into a tablet. As used herein, the term "mixing" include mixing, blending and combining. In some embodiments, the tablet mixture further comprises one or more pharmaceutically acceptable excipients, and the methods further comprise mixing the first mixture with said one or more excipients to form the tablet mixture. Mixing the first mixture with one or more excipients can be performed in one or more steps. In one embodiment, the one or more excipients are mixed to form a second mixture; and the first and second mixtures are mixed together to form the tablet mixture prior to the compression step. In one embodiment, the one or more excipients can be mixed with the first mixture in more than one parts, for example, some excipients mixed with the first mixture first and the other excipients followed later. In some embodiments, the tablets disclosed herein an intra-granular part and an extra-grandular part as described above, and one or more excipients included in the intra-granular part are mixed to form a second mixture, and one or more excipients included in the extra-granular part are mixed to form a third mixture, and the first mixture are combined with the second mixture, and the combined first and second mixtures are combined with the third mixture to form a tablet mixture.

In some embodiments, the methods of preparing the tablets disclosed herein comprise: (a) mixing Compound I and the first and second solid dispersions to form a first mixture; (b) mixing the first mixture with one or more of microcrystalline cellulose, croscarmellose sodium and magnesium stearate to form a tablet mixture; and (c) compressing the tablet mixture into a tablet.

In some embodiments, the methods of preparing the tablets disclosed herein comprise:
(a) mixing Compound I and the first and second solid dispersions described above to form a first mixture; (b) mixing one or more of microcrystalline cellulose, croscarmellose sodium and magnesium stearate in an intra-granular part to form a second mixture; (c) mixing one or more of microcrystalline cellulose, croscarmellose sodium, and magnesium stearate in an extra-granular part to form a third mixture; (d) mixing the first, second, and third mixtures to form a tablet mixture; and (e) compressing the tablet mixture comprising the first, second and third mixtures into a tablet. It is noted that steps (a), (b), and (c) may occur in any order.

In some embodiments, the methods disclosed herein further comprise coating the tablet.

In some embodiments, the methods disclosed herein further comprise granulating the first, second, and/or third mixtures prior to the compression the tablet mixture. Any suitable methods known in the art for granulation and compression of pharmaceutical compositions can be used. It is noted that step (a) can occur prior to step (b) or step (b) can occur prior to step (a).

Granulation and Compression

In some embodiments, solid forms, including powders comprising one or more APIs (e.g., Compound I, Compound II, Compound III-d and/or Compound III) and the included pharmaceutically acceptable excipients (e.g. filler, diluent, disintegrant, surfactant, glidant, binder, lubricant, or any combination thereof) can be subjected to a dry granulation process. The dry granulation process causes the powder to agglomerate into larger particles having a size suitable for further processing. Dry granulation can improve the flowability of a mixture to produce tablets that comply with the demand of mass variation or content uniformity.

In some embodiments, formulations can be produced using one or more mixing and dry granulations steps. The order and the number of the mixing by granulation. At least one of the excipients and the API(s) can be subject to dry granulation or wet high shear granulation or twin screw wet granulation before compression into tablets. Dry granulation can be carried out by a mechanical process, which transfers energy to the mixture without any use of any liquid substances (neither in the form of aqueous solutions, solutions based on organic solutes, or mixtures thereof) in contrast to wet granulation processes, also contemplated herein. Generally, the mechanical process requires compaction such as the one provided by roller compaction. An example of an alternative method for dry granulation is slugging. In some embodiments, wet granulations instead of the dry granulation can be used.

In some embodiments, roller compaction is a granulation process comprising mechanical compacting of one or more substances. In some embodiments, a pharmaceutical composition comprising an admixture of powders is pressed, that is roller compacted, between two rotating rollers to make a solid sheet that is subsequently crushed in a sieve to form a particulate matter. In this particulate matter, a close mechanical contact between the ingredients can be obtained. An example of roller compaction equipment is Minipactor® a Gerteis 3W-Polygran from Gerteis Maschinen+Processengineering AG.

In some embodiments, tablet compression according to the disclosure can occur without any use of any liquid substances (neither in the form of aqueous solutions, solutions based on organic solutes, or mixtures thereof), i.e., a dry granulation process. In a typical embodiment the resulting core or tablet has a tensile strength in the range of from 0.5 MPa to 3.0 MPa; such as 1.0 to 2.5 MPa, such as in the range of 1.5 to 2.0 MPa.

In some embodiments, the ingredients are weighed according to the formula set herein. Next, all of the intragranular ingredients are sifted and mixed well. The ingredients can be lubricated with a suitable lubricant, for example, magnesium stearate. The next step can comprise compaction/slugging of the powder admixture and sized ingredients. Next, the compacted or slugged blends are milled into granules and may optionally be sifted to obtain the desired size. Next, the granules can be further blended or lubricated with, for example, magnesium stearate. Next, the granular composition of the disclosure can be compressed on suitable punches into various pharmaceutical formulations in accordance with the disclosure. Optionally the tablets can be coated with a film coat.

Another aspect of the disclosure provides a method for producing a pharmaceutical composition comprising an admixture of a composition comprising one or more APIs (e.g., Compound I, Compound II, Compound III-d and/or Compound III); and one or more excipients selected from: one or more fillers, a diluent, a binder, a glidant, a surfactant, a lubricant, a disintegrant, and compressing the composition into a tablet.

Coating

In some embodiments, the tablets disclosed herein can be coated with a film coating and optionally labeled with a logo, other image and/or text using a suitable ink. In still other embodiments, the tablets disclosed herein can be coated with a film coating, waxed, and optionally labeled with a logo, other image and/or text using a suitable ink. Suitable film coatings and inks are compatible with the other ingredients of the tablets, e.g., they do not substantially reduce the solubility, the chemical stability, the physical stability, the hardness, or the biological activity of the tablets. The suitable colorants and inks can be any color and are water based or solvent based. In one embodiment, the tablets disclosed herein are coated with a colorant and then labeled with a logo, other image, and/or text using a suitable ink.

In some embodiments, the tablets disclosed herein are coated with a film that comprises 2-6 wt % by the weight of the uncoated tablet. In some embodiments, the film comprises one or more colorants and/or pigments. In some embodiments, the tablets disclosed herein are coated with a film that comprises one or more colorants and/or pigments and wherein the film comprises 2-5 wt % by the weight of the uncoated tablet. In some embodiments, the tablets disclosed herein are coated with a film that comprises one or more colorants and/or pigments and wherein the film comprises 2-4 wt % by the weight of the uncoated tablet. The colored tablets can be labeled with a logo and text indicating the strength of the active ingredient in the tablet using a suitable ink.

Methods of Treatment

The tablets disclosed herein can be administered once a day, twice a day, or three times a day. In some embodiments, one or more of the tablets are administered per dosing. In some embodiments, two tablets per dosing are administered. In some embodiments, two tablets per dosing are administered once a day. In some embodiments, two tablets per dosing are administered twice a day. An effective amount of the APIs (e.g., Compound (I)) is administered to the patient with or using one or more tablets disclosed herein.

The tablets disclosed herein are useful for treating cystic fibrosis.

In some aspects, the tablets disclosed herein can be employed in combination therapies. In some embodiments, the tablets disclosed herein can be administered concurrently with, prior to, or subsequent to, at least one active pharmaceutical ingredients or medical procedures.

In some embodiments, the pharmaceutical compositions are a tablet. In some embodiments, the tablets are suitable for oral administration.

The tablets disclosed herein, optionally with additional active pharmaceutical ingredients or medical procedures are useful for treating cystic fibrosis in a patient.

Compounds I, II, III-d, and III are as depicted above. Compound IV is depicted as having the following structure:

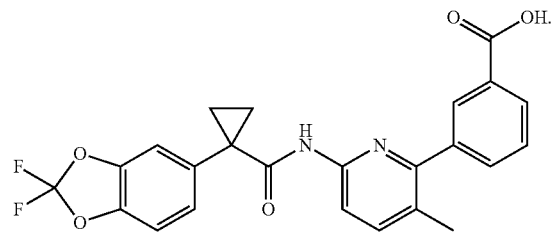 [SMILES: Cc1ccc(NC(=O)C2(c3ccc4c(c3)OC(F)(F)O4)CC2)nc1-c1cccc(C(=O)O)c1]

A chemical name for Compound IV is 3-(6-(1-(2,2-difluorobenzo[d][1,3]dioxol-5-yl)cyclopropanecarboxamido)-3-methylpyridin-2-yl)benzoic acid.

A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes.

In some embodiments, disclosed herein methods of treating, lessening the severity of, or symptomatically treating cystic fibrosis in a patient comprising administering an effective amount of a compound, pharmaceutically acceptable salt thereof, or a deuterated analog of any of the foregoing; or a pharmaceutical composition, of this disclosure to a patient, such as a human, wherein said patient has cystic fibrosis. In some embodiments, the patient has an F508del/minimal function (MF) genotype, F508del/F508del genotype (homozygous for the F508del mutation), F508del/gating genotype, or F508del/residual function (RF) genotype. In some embodiments the patient is heterozygous and has one F508del mutation.

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance. Table C below includes a non-exclusive list of CFTR minimal function mutations, which are detectable by an FDA-cleared genotyping assay. In some embodiments, a mutation is considered a MF mutation if it meets at least 1 of the following 2 criteria:
(1) biological plausibility of no translated protein (genetic sequence predicts the complete absence of CFTR protein), or
(2) in vitro testing that supports lack of responsiveness to Compound II, Compound III or the combination of Compound II and Compound III, and evidence of clinical severity on a population basis (as reported in large patient registries).

In some embodiments, the minimal function mutations are those that result in little-to-no functioning CFTR protein and are not responsive in vitro to Compound II, Compound III, or the combination of Compound II and Compound III.

In some embodiments, the minimal function mutations are those that are not responsive in vitro to Compound II, Compound III, or the combination of Compound II and Compound III. In some embodiments, the minimal function mutations are mutations based on in vitro testing met the following criteria in in vitro experiments:
baseline chloride transport that was <10% of wildtype CFTR, and
an increase in chloride transport of <10% over baseline following the addition of TEZ, IVA, or TEZ/IVA in the assay.

In some embodiments, patients with at least one minimal function mutation exhibit evidence of clinical severity as defined as:
average sweat chloride >86 mmol/L, and
prevalence of pancreatic insufficiency (PI) >50%.

Patients with an F508del/minimal function genotype are defined as patients that are heterozygous F508del-CFTR with a second CFTR allele containing a minimal function mutation. In some embodiments, patients with an F508del/minimal function genotype are patients that are heterozygous F508del-CFTR with a second CFTR allele containing a mutation that results in a CFTR protein with minimal CFTR function (little-to-no functioning CFTR protein) and that is not responsive in vitro to Compound II, Compound III, or the combination of Compound II and Compound III.

In some embodiments, minimal function mutations can be determined using 3 major sources:
biological plausibility for the mutation to respond (i.e., mutation class)
evidence of clinical severity on a population basis (per CFTR2 patient registry; accessed on 15 Feb. 2016)
average sweat chloride >86 mmol/L, and
prevalence of pancreatic insufficiency (PI) >50%
in vitro testing
mutations resulting in baseline chloride transport <10% of wild-type CFTR were considered minimal function
mutations resulting in chloride transport <10% of wild-type CFTR following the addition of Compound II and/or Compound III were considered nonresponsive.

As used herein, a "residual function mutations" refer to are Class II through V mutations that have some residual chloride transport and result in a less severe clinical phenotype. Residual function mutations are mutation in the CFTR gene that result in reduced protein quantity or function at the cell surface which can produce partial CFTR activity.

Non-limiting examples of CFTR gene mutations known to result in a residual function phenotype include a CFTR residual function mutation selected from 2789+5G→A, 3849+1 OkbC→T, 3272-26A→G, 711+3A→G, E56K, P67L, R74W, D11OE, D11OH, R117C, L206W, R347H, R352Q, A455E, D579G, E831X, S945L, S977F, F1052V, R1070W, F1074L, D1 152H, D1270N, E193K, and K1060T. For example, CFTR mutations that cause defective mRNA splicing, such as 2789+507 A, result in reduced protein synthesis, but deliver some functional CFTR to the surface of the cell to provide residual function. Other CFTR mutations that reduce conductance and/or gating, such as R1 17H, result in a normal quantity of CFTR channels at the surface of the cell, but the functional level is low, resulting in residual function. In some embodiments, the CFTR residual function mutation is selected from R117H, S1235R, I1027T, R668C, G576A, M470V, L997F, R75Q, R1070Q, R31C, D614G, G1069R, R1162L, E56K, A1067T, E193K, and K1060T. In some embodiments, the CFTR residual function mutation is selected from R117H, S1235R, I1027T, R668C, G576A, M470V, L997F, R75Q, R1070Q, R31C, D614G, G1069R, R1162L, E56K, and A1067T.

Residual CFTR function can be characterized at the cellular (in vitro) level using cell based assays, such as an FRT assay (Van Goar, F. et al. (2009) PNAS Vol. 106, No. 44, 18825-18830; and Van Goor, F. et al. (2011) PNAS Vol. 108, No. 46, 18843-18846), to measure the amount of chloride transport through the mutated CFTR channels. Residual function mutations result in a reduction but not complete elimination of CFTR dependent ion transport. In some embodiments, residual function mutations result in at least about 10% reduction of CFTR activity in an FRT assay. In some embodiments, the residual function mutations result in up to about 90% reduction in CFTR activity in an FRT assay.

Patients with an F508del/residual function genotype are defined as patients that are heterozygous F508del-CFTR with a second CFTR allele that contains a mutation that results in reduced protein quantity or function at the cell surface which can produce partial CFTR activity.

Patients with an F508del/gating mutation genotype are defined as patients that are heterozygous F508del-CFTR with a second CFTR allele that contains a mutation associated with a gating defect and clinically demonstrated to be responsive to Compound III. Examples of such mutations include: G178R, S549N, S549R, G551D, G551S, G1244E, S1251N, S1255P, and G1349D.

In some embodiments, the methods of treating, lessening the severity of, or symptomatically treating cystic fibrosis disclosed herein are each independently produces an increase in chloride transport above the baseline chloride transport of the patient.

In some embodiments, in the methods of treating, lessening the severity of, or symptomatically treating cystic fibrosis disclosed herein, the patient is heterozygous for F508del, and the other CFTR genetic mutation is any CF-causing mutation. In some embodiments, the patient is heterozygous for F508del, and the other CFTR genetic mutation is any CF-causing mutation, and is expected to be and/or is responsive to any of the novel compounds disclosed herein, such as Compound I, Compound II, Compound III and/or Compound IV genotypes based on in vitro and/or clinical data. In some embodiments, the patient is heterozygous for F508del, and the other CFTR genetic mutation is any CF-causing mutation, and is expected to be and/or is responsive to any combinations of (i) the novel compounds disclosed herein, such as Compound I, and (ii) Compound II, and/or Compound III and/or Compound IV genotypes based on in vitro and/or clinical data.

In some embodiments, in the methods of treating, lessening the severity of, or symptomatically treating cystic fibrosis disclosed herein, the patient possesses a CFTR genetic mutation selected from any of the mutations listed in Table A.

TABLE A

| CF Mutations |
| --- |
| 078delT |
| 1078delT |
| I1234V |
| 1154insTC |
| 1161delC |
| 1213delT |
| 1248 + 1G→A |
| 1249 − 1G→A |
| 124del23bp |
| 1259insA |
| 1288insTA |
| 1341 + 1G->A |
| 1342 − 2A->C |
| 1461ins4 |
| 1471delA |
| 1497delGG |
| 1507del |
| 1525 − 1G→A |
| 1525 − 2A→G |
| 1548delG |
| 1577delTA |
| 1609delCA |
| 1677delTA |
| 1716G/A |
| 1717 − 1G→A |
| 1717 − 8G→A |
| 1782delA |
| 1811 + 1.6kbA->G |
| 1811 + 1G->C |
| 1811 + 1.6kbA→G |
| 1811 + 1G→C |
| 1812 − 1G->A |
| 1898 + 1G->A |
| 1812 − 1G→A |
| 1824delA |
| 182delT 1119delA |
| 185 + 1G→T |
| 1898 + 1G->T |
| 1898 + 1G→A |
| 1898 + 1G→C |

TABLE A-continued

| CF Mutations |
| --- |
| 1898 + 3A->G |
| 1898 + 5G->T |
| 1924del7 |
| 1949del84 |
| 2043delG |
| 2055del9→A |
| 2105-2117del13insAGAAA |
| 2118del14 |
| 2143delT |
| 2183AA->G+ |
| 2183AA→G |
| 2183AA→G$^a$ |
| 2183delAA->G# |
| 2183delAA→G |
| 2184delA |
| 2184insA |
| 2307insA |
| 2347delG |
| 2556insAT |
| 2585delT |
| 2594delGT |
| 2622 + 1G->A |
| 2622 + IG->A |
| 2659delC |
| 2711delT |
| 271delT |
| 2721del11 |
| 2732insA |
| 2789 + 2insA |
| 2789 + 5G→A |
| 2790 − 1G→C |
| 2790 − IG->C |
| 2869insG |
| 2896insAG |
| 2942insT |
| 2957delT |
| 296 + 1G→A |
| 2991del32 |
| 3007delG |
| 3028delA |
| 3040G→C |
| 306insA |
| 306insA 1138insG |
| 3120G→A |
| 3121 − 1G→A |
| 3121 − 2A→G |
| 3121 − 977_3499 + 248 del2515 |
| 3132delTG |
| 3141del9 |
| 3171delC |
| 3195del6 |
| 3199del6 |
| 3272 − 26A->G |
| 3500 − 2A→G |
| 3600 + 2insT |
| 365-366insT |
| 3659delC |
| 3667ins4 |
| 3737delA |
| 3791delC |
| 3821delT |
| 3849 + 10kbC→T |
| 3849 + IOkbC->T |
| 3850 − 1G→A |
| 3850 − 3T->G |
| 3850 − IG->A |
| 3876delA |
| 3878delG |
| 3905InsT |
| 3905insT |
| 394delTT |
| 4005 + 1G->A |
| 4005 + 2T->C |
| 4005 + 1G→A |
| 4005 + IG->A |
| 4010del4 |
| 4015delA |
| 4016insT |

TABLE A-continued

| CF Mutations |
|---|
| 4021dupT |
| 4040delA |
| 405 + 1G→A |
| 405 + 3A→C |
| 405 + IG->A |
| 406 − 1G→A |
| 406 − IG->A |
| 4209TGTT->A |
| 4209TGTT→AA |
| 4279insA |
| 4326delTC |
| 4374 + 1G→T |
| 4374 + IG->T |
| 4382delA |
| 4428insGA |
| 442delA |
| 457TAT→G |
| 541delC |
| 574delA |
| 5T |
| 621 + 1G→T |
| 621 + 3A->G |
| 663delT |
| 663delT 1548delG |
| 675del4 |
| 711 + 1G->T |
| 711 + 3A->G |
| 711 + 1G→T |
| 711 + 3A→G |
| 711 + 5G→A |
| 712 − 1G->T |
| 7T |
| 852del22 |
| 935delA |
| 991del5 |
| A1006E |
| A120T |
| A234D |
| A349V |
| A455E |
| A613T |
| A46D |
| A46Db |
| A559T |
| A559Tb |
| A561E |
| C276X |
| C524R |
| C524X |
| CFTRdel2,3 |
| CFTRdele22-23 |
| D110E |
| D110H |
| D1152H |
| D1270N |
| D192G |
| D443Y |
| D513G |
| D579G |
| D614G |
| D836Y |
| D924N |
| D979V |
| E1104X |
| E116K |
| E1371X |
| E193K |
| E193X |
| E403D |
| E474K |
| E56K |
| E585X |
| E588V |
| E60K |
| E822K |
| E822X |
| E831X |
| E92K |

TABLE A-continued

| CF Mutations |
|---|
| E92X |
| F1016S |
| F1052V |
| F1074L |
| F1099L |
| F191V |
| F311del |
| F311L |
| F508C |
| F508del |
| F575Y |
| G1061R |
| G1069R |
| G1244E |
| G1249R |
| G126D |
| G1349D |
| G149R |
| G178R |
| G194R |
| G194V |
| G27R |
| G27X |
| G314E |
| G330X |
| G458V |
| G463V |
| G480C |
| G542X |
| G550X |
| G551D |
| G551S |
| G576A |
| G622D |
| G628R |
| G628R(G->A) |
| G970D |
| G673X |
| G85E |
| G91R |
| G970R |
| G970R |
| H1054D |
| H1085P |
| H1085R |
| H1375P |
| H139R |
| H199R |
| H199Y |
| H609R |
| H939R |
| I1005R |
| I1027T |
| I1234V |
| I1269N |
| I1366N |
| I148T |
| I175V |
| I3336K |
| I502T |
| I506S |
| I506T |
| I507del |
| I507del |
| I601F |
| I618T |
| I807M |
| I980K |
| IVS14b + 5G->A |
| K710X |
| K710X |
| K710X |
| L102R |
| L1065P |
| L1077P |
| L1077Pb |
| L1254X |
| L1324P |

TABLE A-continued

| CF Mutations |
|---|
| L1335P |
| L138ins |
| L1480P |
| L15P |
| L165S |
| L206W |
| L218X |
| L227R |
| L320V |
| L346P |
| L453S |
| L467P |
| L467Pb |
| L558S |
| L571S |
| L732X |
| L927P |
| L967S |
| L997F |
| M1101K |
| M1101R |
| M152V |
| M1T |
| M1V |
| M265R |
| M470V |
| M952I |
| M952T |
| N1303K |
| P205S |
| P574H |
| P5L |
| P67L |
| P750L |
| P99L |
| Q1100P |
| Q1291H |
| Q1291R |
| Q1313X |
| Q1382X |
| Q1411X |
| Q1412X |
| Q220X |
| Q237E |
| Q237H |
| Q452P |
| Q290X |
| Q359K/T360K |
| Q39X |
| Q414 |
| Q414X |
| E585X |
| Q493X |
| Q525X |
| Q552X |
| Q685X |
| Q890X |
| Q890X |
| Q98R |
| Q98X |
| R1066C |
| R1066H |
| R1066M |
| R1070Q |
| R1070W |
| R1102X |
| R1158X |
| R1162L |
| R1162X |
| R117C |
| R117G |
| R117H |
| R117L |
| R117P |
| R1283M |
| R1283S |
| R170H |
| R258G |
| R31C |
| R31L |
| R334L |
| R334Q |
| R334W |
| R347H |
| R347L |
| R347P |
| R352Q |
| R352W |
| R516G |
| R553Q |
| R553X |
| R560K |
| R560S |
| R560T |
| R668C |
| R709X |
| R74W |
| R751L |
| R75Q |
| R75X |
| R764X |
| R792G |
| R792X |
| R851X |
| R933G |
| S1118F |
| S1159F |
| S1159P |
| S1196X |
| S1235R |
| S1251N |
| S1255P |
| S1255X |
| S13F |
| S341P |
| S434X |
| S466X |
| S489X |
| S492F |
| S4X |
| S549N |
| S549R |
| S549R(A->C) |
| S549R(T->G) |
| S589N |
| S737F |
| S912L |
| S912X |
| S945L |
| S977F |
| T1036N |
| T1053I |
| T1246I |
| T338I |
| T604I |
| V1153E |
| V1240G |
| V1293G |
| V201M |
| V232D |
| V456A |
| V456F |
| V520F |
| V562I |
| V754M |
| W1089X |
| W1098C |
| W1098R |
| W1098X |
| W1204X |
| W1282R |
| W1282X |
| W361R |
| W401X |
| W496X |
| W57G |

TABLE A-continued

CF Mutations

W57R
W57X
W846X
Y1014C
Y1032C
Y1092X
Y109N
Y122X
Y161D
Y161S
Y563D
Y563N
Y569C
Y569D
Y569Db
Y849X
Y913C
Y913X

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D1100E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C, 621+3A->G, 1949del84, 3141del9, 3195del6, 3199del6, 3905InsT, 4209TGTT->A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G->A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, 1980K, L102R, L1324P, L1335P, L138ins, L1480P, L15P, L165S, L320V, L346P, L453S, L571S, L967S, M1101R, M152V, M1T, M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A->C), S549R(T->G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, the patient has at least one combination mutation chosen from: G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C, and 621+3A->G.

In some embodiments, the patient has at least one combination mutation chosen from: 1949del84, 3141del9, 3195del6, 3199del6, 3905InsT, 4209TGTT->A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G->A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, 1980K, L102R, L1324P, L1335P, L138ins, L1480P, L15P, L165S, L320V, L346P, L453S, L571S, L967S, M1101R, M152V, M1T, M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A->C), S549R(T->G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, in the methods of treating, lessening the severity of, or symptomatically treating cystic fibrosis disclosed herein, the patient possesses a CFTR genetic mutation G551D. In some embodiments, the patient is homozygous for the G551D genetic mutation. In some embodiments, the patient is heterozygous for the G551D genetic mutation. In some embodiments, the patient is heterozygous for the G551D genetic mutation, having the G551D mutation on one allele and any other CF-causing mutation on the other allele. In some embodiments, the patient is heterozygous for the G551D genetic mutation on one allele and the other CF-causing genetic mutation on the other allele is any one of F508del, G542X, N1303K, W1282X, R117H, R553X, 1717-1G->A, 621+1G->T, 2789+5G->A, 3849+10kbC->T, R1162X, G85E, 3120+1G->A, ΔI507, 1898+1G->A, 3659delC, R347P, R560T, R334W, A455E, 2184delA, or 711+1G->T. In some embodiments, the patient is heterozygous for the G551D genetic mutation, and the other CFTR genetic mutation is F508del. In some embodiments, the patient is heterozygous for the G551D genetic mutation, and the other CFTR genetic mutation is R117H.

In some embodiments, in the methods of treating, lessening the severity of, or symptomatically treating cystic fibrosis disclosed herein, the patient possesses a CFTR genetic mutation F508del. In some embodiments, the patient is homozygous for the F508del genetic mutation. In some embodiments, the patient is heterozygous for the F508del genetic mutation wherein the patient has the F508del genetic mutation on one allele and any CF-causing genetic mutation on the other allele. In some embodiments, the patient is heterozygous for F508del, and the other CFTR genetic mutation is any CF-causing mutation, including, but not limited to G551D, G542X, N1303K, W1282X, R117H, R553X, 1717-1G->A, 621+1G->T, 2789+5G->A, 3849+10kbC->T, R1162X, G85E, 3120+1G->A, ΔI507, 1898+1G->A, 3659delC, R347P, R560T, R334W, A455E, 2184delA, or 711+1G->T. In some embodiments, the patient is heterozygous for F508del, and the other CFTR genetic mutation is G551D. In some embodiments, the patient is heterozygous for F508del, and the other CFTR genetic mutation is R117H.

In some embodiments, the patient has at least one combination mutation chosen from:
D443Y;G576A;R668C,
F508C;S1251N,
G576A; R668C,
G970R; M470V,
R74W;D 1270N,
R74W;V201M, and
R74W;V201M;D 1270N.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V and G1069R. In some embodiments, the patient possesses a CFTR genetic mutation selected from G178R, G551S, G970R, G1244E, S1255P, G1349D, S549N, S549R and S1251N. In some embodiments, the patient possesses a CFTR genetic mutation selected from E193K, F1052V and G1069R. In some embodiments, the method produces an increase in chloride transport relative to baseline chloride transport of the patient of the patient.

In some embodiments, in the methods of treating, lessening the severity of, or symptomatically treating cystic fibrosis disclosed herein, the patient possesses a CFTR genetic mutation selected from R117C, D110H, R347H, R352Q, E56K, P67L, L206W, A455E, D579G, S1235R, S945L, R1070W, F1074L, D110E, D1270N and D1152H.

In some embodiments, the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G. In some embodiments, the patient possesses a CFTR genetic mutation selected from 1717-1G->A, 1811+1.6kbA->G, 2789+5G->A, 3272-26A->G and 3849+10kbC->T. In some embodiments, the patient possesses a CFTR genetic mutation selected from 2789+5G->A and 3272-26A->G.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and human CFTR mutations selected from F508del, R117H, and G551D.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C, 621+3A->G, and a CFTR mutation selected from F508del, R117H, and G551D; and a CFTR mutations selected from F508del, R117H, and G551D.

In some embodiments, the patient possesses a CFTR genetic mutation selected from G178R, G551S, G970R, G1244E, S1255P, G1349D, S549N, S549R, S1251N, E193K, F1052V and G1069R, and a human CFTR mutation selected from F508del, R117H, and G551D. In some embodiments, the patient possesses a CFTR genetic mutation selected from G178R, G551S, G970R, G1244E, S1255P, G1349D, S549N, S549R and S1251N, and a human CFTR mutation selected from F508del, R117H, and G551D. In some embodiments, the patient possesses a CFTR genetic mutation selected from E193K, F1052V and G1069R, and a human CFTR mutation selected from F508del, R117H, and G551D.

In some embodiments, the patient possesses a CFTR genetic mutation selected from R117C, D110H, R347H, R352Q, E56K, P67L, L206W, A455E, D579G, S1235R, S945L, R1070W, F1074L, D110E, D1270N and D1152H, and a human CFTR mutation selected from F508del, R117H, and G551D.

In some embodiments, the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G551D. In some embodiments, the patient possesses a CFTR genetic mutation selected from 1717-1G->A, 1811+1.6kbA->G, 2789+5G->A, 3272-26A->G and 3849+10kbC->T, and a human CFTR mutation selected from F508del, R117H, and G551D. In some embodiments, the patient possesses a CFTR genetic mutation selected from 2789+5G->A and 3272-26A->G, and a human CFTR mutation selected from F508del, R117H.

In some embodiments, the patient is heterozygous having a CF-causing mutation on one allele and a CF-causing mutation on the other allele. In some embodiments, the patient is heterozygous for F508del, and the other CFTR genetic mutation is any CF-causing mutation, including, but not limited to F508del on one CFTR allele and a CFTR mutation on the second CFTR allele that is associated with minimal CFTR function, residual CFTR function, or a defect in CFTR channel gating activity.

In some embodiments, the CF-causing mutation is selected from Table A. In some embodiments, the CF-causing mutation is selected from Table B. In some embodiments, the CF-causing mutation is selected from Table C. In some embodiments, the CF-causing mutation is selected from FIG. 3. In some embodiments, the patient is heterozygous having a CF-causing mutation on one CFTR allele selected from the mutations listed in the table from FIG. 3 and a CF-causing mutation on the other CFTR allele is selected from the CFTR mutations listed in Table B:

TABLE B

CFTR Mutations

| | | |
|---|---|---|
| Q39X | S1196X | 4382delA |
| W57X | W1204X | 4016insT |
| E60X | S1255X | 2347delG |
| R75X | W1282X | 3007delG |
| E92X | Q1313X | 574delA |
| Q98X | 621 + 1G→T | 2711delT |
| Y122X | 711 + 1G→T | 3791delC |
| L218X | 711 + 5G→A | CFTRdele22-23 |
| Q220X | 712-1G→T | 457TAT→G |
| C276X | 405 + 1G→A | 2043delG |
| Q290X | 405 + 3A→C | 2869insG |
| G330X | 406-1G→A | 3600 + 2insT |
| W401X | 621 + 1G→T | 3737delA |
| Q414X | 1248 + 1G→A | 4040delA |
| S434X | 1341 + 1G→A | 541delC |
| S466X | 1717 - 1G→A | A46D |

TABLE B-continued

CFTR Mutations

| | | |
|---|---|---|
| S489X | 1811 + 1.6kbA→G | T338I |
| Q493X | 1811 + 1G→C | R347P |
| W496X | 1812 - 1G→A | L927P |
| Q525X | 1898 + 1G→A | G85E |
| G542X | 2622 + 1G→A | S341P |
| Q552X | 3120 + 1G→A | L467P |
| R553X | 3120G→A | I507del |
| E585X | 3850 - 1G→A | V520F |
| G673X | 4005 + 1G→A | A559T |
| R709X | 4374 + 1G→T | R560T |
| K710X | 663delT | R560S |
| L732X | 2183AA→G | A561E |
| R764X | CFTRdel2,3 | Y569D |
| R785X | 3659delC | L1065P |
| R792X | 394delTT | R1066C |
| E822X | 2184insA | R1066M |
| W846X | 3905insT | L1077P |
| R851X | 2184delA | H1085R |
| Q890X | 1078delT | M1101K |
| S912X | 1154insTC | N1303K |
| W1089X | 2183delAA→G | 3849 + 10kbC→T |
| Y1092X | 2143delT | 3272 - 26A→G |
| E1104X | 1677delTA | 711 + 3A→G |
| R1158X | 3876delA | E56K |
| R1162X | 2307insA | P67L |
| R74W | E831X | S549N |
| D110E | S945L | S549R |
| D110H | S977F | G551D |
| R117C | F1052V | G551S |
| L206W | R1070W | G1244E |
| R347H | F1074L | S1251N |
| R352Q | D1152H | S1255P |
| A455E | D1270N | G1349D |
| D579G | G178R | |

TABLE C

CFTR Mutations

| Criteria | Mutation | | | | |
|---|---|---|---|---|---|
| Truncation mutations or nonsense mutations % PI >50% and/or SwCl⁻ >86 mmol/L no full-length protein | S4X | C276X | G542X | R792X | E1104X |
| | G27X | Q290X | G550X | E822X | R1158X |
| | Q39X | G330X | Q552X | W846X | R1162X |
| | W57X | W401X | R553X | Y849X | S1196X |
| | E60X | Q414X | E585X | R851X | W1204X |
| | R75X | S434X | G673X | Q890X | L1254X |
| | E92X | S466X | Q685X | S912X | S1255X |
| | Q98X | S489X | R709X | Y913X | W1282X |
| | Y122X | Q493X | K710X | W1089X | Q1313X |
| | E193X | W496X | L732X | Y1092X | E1371X |
| | L218X | C524X | R764X | W1098X | Q1382X |
| | Q220X | Q525X | R785X | R1102X | Q1411X |
| Splice mutations or Carnonical splice mutations % PI >50% and/or SwCl⁻ >86 mmol/L no or little mature mRNA | 185 + 1G→T | 711 + 5G→A | 1717 - 8G→A | 2622 + 1G→A | 3121 - 1G→A |
| | 296 + 1G→A | 712 - 1G→T | 1717 - 1G→A | 2790 - 1G→C | 3500 - 2A→G |
| | 405 + 1G→A | 1248 + 1G→A | 1811 + 1G→C | 3040G→C | 3600 + 2insT |
| | 405 + 3A→C | 1249 - 1G→A | 1811 + 1.6kbA→G | (G970R) | 3850 - 1G→A |
| | 406 - 1G→A | 1341 + 1G→A | 1812 - 1G→A | 3120G→A | 4005 + 1G→A |
| | 621 + 1G→T | 1525 - 2A→G | 1898 + 1G→A | 3120 + 1G→A | 4374 + 1G→T |
| | 711 + 1G→T | 1525 - 1G→A | 1898 + 1G→C | 3121 - 2A→G | |
| Small (≤3 nucleotide) insertion/deletion (ins/del) frameshift mutations % PI >50% and/or SwCl⁻ >86 mmol/L garbled and/or truncated protein | 182delT | 1119delA | 1782delA | 2732insA | 3876delA |
| | 306insA | 1138insG | 1824delG | 2869insG | 3878delG |
| | 365-366insT | 1154insTC | 2043delG | 2896insAG | 3905insT |
| | 394delTT | 1161delC | 2143delT | 2942insT | 4016insT |
| | 442delA | 1213delT | 2183AA→G ᵃ | 2957delT | 4021dupT |
| | 444delA | 1259insA | 2184delA | 3007delG | 4040delA |
| | 457TAT→G | 1288insTA | 2184insA | 3028delA | 4279insA |
| | 541delC | 1471delA | 2307insA | 3171delC | 4326delTC |
| | 574delA | 1497delGG | 2347delG | 3659delC | |
| | 663delT | 1548delG | 2585delT | 3737delA | |
| | 935delA | 1609del CA | 2594delGT | 3791delC | |
| | 1078delT | 1677delTA | 2711delT | 3821delT | |
| Non-small (>3 nucleotide) insertion/deletion | CFTRdele2,3 | 1461ins4 | | 2991del32 | |
| | CFTRdele22,23 | 1924del7 | | 3667ins4 | |
| | 124del23bp | 2055del9→A | | 4010del4 | |

TABLE C-continued

CFTR Mutations

| Criteria | Mutation | | | |
|---|---|---|---|---|
| (ins/del) frameshift mutations % PI >50% and/or SwCl⁻ >86 mmol/L garbled and/or truncated protein | 852del22 991del5 | 2105-2117del13insAGAAA 2721del11 | | 4209TGTT→*AA |
| Class II, III, IV mutations not responsive to Compound III alone or in combination with Compound II or Compound IV/or Missense muatations that: % PI >50% and/or SwCl >86 mmol/L AND Not responsive in vitro to Compound III alone or in combination with Compound II or Compound IV | A46D[b] G85E R347P L467P[b] I507del | V520F A559T[b] R560T R560S A561E | Y569D[b] L1065P R1066C L1077P[b] M1101K | N1303K |

Note:
% PI: percentage of F508del-CFTR heterozygous patients in the CFTR2 patient registry who are pancreatic insufficient;
SwCl⁻: mean sweat chloride of F508del-CFTR heterozygous patients in the CFTR2 patient registry
[a]Also known as 2183delAA→G.
[b]Unpublished data.

In some embodiments, the patient is: with F508del/MF (F/MF) genotypes (heterozygous for F508del and an MF mutation not expected to respond to CFTR modulators, such as Compound III); with F508del/F508del (F/F) genotype (homozygous for F508del); and/or with F508del/gating (F/G) genotypes (heterozygous for F508del and a gating mutation known to be CFTR modulator-responsive (e.g., Compound III-responsive). In some embodiments, the patient with F508del/MF (F/MF) genotypes has a MF mutation that is not expected to respond to Compound II, Compound III, and both of Compound II and Compound III. In some embodiments, the patient with F508del/MF (F/MF) genotypes has any one of the MF mutations in Table C.

In some embodiments, the patient is heterozygous for F508del, and the other CFTR genetic mutation is any CF-causing mutation, including truncation mutations, splice mutations, small (≤3 nucleotide) insertion or deletion (ins/del) frameshift mutations; non-small (>3 nucleotide) insertion or deletion (ins/del) frameshift mutations; and Class II, III, IV mutations not responsive to Compound III alone or in combination with Compound II or Compound IV.

In some embodiments, the patient is heterozygous for F508del, and the other CFTR genetic mutation is a truncation mutation. In some specific embodiments, the truncation mutation is a truncation mutation listed in Table C.

In some embodiments, the patient is heterozygous for F508del, and the other CFTR genetic mutation is a splice mutation. In some specific embodiments, the splice mutation is a splice mutation listed in Table C.

In some embodiments, the patient is heterozygous for F508del, and the other CFTR genetic mutation is a small (≤3 nucleotide) insertion or deletion (ins/del) frameshift mutation. In some specific embodiments, the small (≤3 nucleotide) insertion or deletion (ins/del) frameshift mutation is a small (≤3 nucleotide) insertion or deletion (ins/del) frameshift mutation listed in Table C.

In some embodiments, the patient is heterozygous for F508del, and the other CFTR genetic mutation is any CF-causing mutation expected to be and/or is responsive to, based on in vitro and/or clinical data, any combination of (i) a novel compound chosen from those disclosed herein (e.g., compounds of Formula (I), (II), (III), (IV), or (V), and pharmaceutically acceptable salts thereof, and their deuterated derivatives), and (ii) Compound II, and/or Compound III, and/or Compound IV.

In some embodiments, the patient is heterozygous for F508del, and the other CFTR genetic mutation is any CF-causing mutation expected to be and/or is responsive, based on in vitro and/or clinical data, to the triple combination of a novel compound chosen from those disclosed herein (e.g., compounds of Formula (I), (II), (III), (IV), or (V), and pharmaceutically acceptable salts thereof, and their deuterated derivatives), and Compound II, and Compound III.

In some embodiments, the patient is heterozygous for F508del, and the other CFTR genetic mutation is a non-small (>3 nucleotide) insertion or deletion (ins/del) frameshift mutation. In some specific embodiments, the non-small (>3 nucleotide) insertion or deletion (ins/del) frameshift mutation is a non-small (>3 nucleotide) insertion or deletion (ins/del) frameshift mutation listed in Table 5B.

In some embodiments, the patient is heterozygous for F508del, and the other CFTR genetic mutation is a Class II, III, IV mutations not responsive to Compound III alone or in combination with Compound II or Compound IV. In some specific embodiments, the Class II, III, IV mutations not responsive to Compound III alone or in combination with Compound II or Compound IV is a Class II, III, IV mutations not responsive to Compound III alone or in combination with Compound II or Compound IV listed in Table C.

In some embodiments, the patient is heterozygous for F508del, and the other CFTR genetic mutation is any mutation listed in Table C.

In some embodiments, the patient is heterozygous for F508del, and the other CFTR genetic mutation is any mutation, but other than F508del, listed in Table A, B, C, and FIG. 3.

In some embodiments, the patient is heterozygous for F508del, and the other CFTR genetic mutation is any mutation listed in Table A. In some embodiments, the patient is heterozygous for F508del, and the other CFTR genetic mutation is any mutation listed in Table B. In some embodiments, the patient is heterozygous for F508del, and the other CFTR genetic mutation is any mutation listed in Table C. In some embodiments, the patient is heterozygous for F508del, and the other CFTR genetic mutation is any mutation listed in FIG. 3.

In some embodiments, the patient is homozygous for F508del.

In some embodiments, the patient is heterozygous having one CF-causing mutation on one CFTR allele selected from the mutations listed in the table from FIG. 3 and another CF-causing mutation on the other CFTR allele is selected from the CFTR mutations listed in Table C.

In some embodiments, the composition disclosed herein is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl— concentrations, or ex vivo biochemical or histochemical techniques to monitor cell surface density. Using such methods, residual CFTR activity can be readily detected for patients that are heterozygous or homozygous for a variety of different mutations, including patients heterozygous for the most common mutation, F508del, as well as other mutations such as the G551D mutation, or the R117H mutation. In some embodiments, compositions disclosed herein are useful for treating, lessening the severity of, or symptomatically treating cystic fibrosis in patients who exhibit little to no residual CFTR activity. In some embodiments, compositions disclosed herein are useful for treating, lessening the severity of, or symptomatically treating cystic fibrosis in patients who exhibit little to no residual CFTR activity in the apical membrane of respiratory epithelia.

In some embodiments, the compositions disclosed herein are useful for treating or lessening the severity of cystic fibrosis in patients who exhibit residual CFTR activity using pharmacological methods. Such methods increase the amount of CFTR present at the cell surface, thereby inducing a hitherto absent CFTR activity in a patient or augmenting the existing level of residual CFTR activity in a patient.

In some embodiments, the compositions disclosed herein are useful for treating or lessening the severity of cystic fibrosis in patients with certain genotypes exhibiting residual CFTR activity.

In some embodiments, compositions disclosed herein are useful for treating, lessening the severity of, or symptomatically treating cystic fibrosis in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel.

In some embodiments of the methods of treating cystic fibrosis disclosed herein, the absolute change in patient's percent predicted forced expiratory volume in one second ($ppFEV_1$) after 15 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 40% relative to the ppFEV1 of the patient prior to said administration.

In some embodiments of the methods of treating cystic fibrosis disclosed herein, the absolute change in patient's percent predicted forced expiratory volume in one second ($ppFEV_1$) after 29 days of administration of at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from 3% to 40% relative to the ppFEV1 of the patient prior to said administration.

In some embodiments of the methods of treating cystic fibrosis disclosed herein, the absolute change in the patient's sweat chloride after 15 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from −2 to −65 mmol/L from baseline, i.e., relative to the sweat chloride of the patient prior to said administration. In some embodiments, the absolute change in sweat chloride of said patient ranges from −5 to −65 mmol/L. In some embodiments, the absolute change in sweat chloride of said patient ranges from −10 to −65 mmol/L. In some embodiments, the absolute change in sweat chloride of said patient ranges from −2 to −65 mmol/L.

In some embodiments of the methods of treating cystic fibrosis disclosed herein, the absolute change in the patient's sweat chloride after 29 days of administration of at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from −2 to −65 mmol/L from baseline, i.e., relative to the sweat chloride of the patient prior to said administration. In some embodiments, the absolute change in sweat chloride of said patient ranges from −5 to −65 mmol/L. In some embodiments, the absolute change in sweat chloride of said patient ranges from −10 to −65 mmol/L. In some embodiments, the absolute change in sweat chloride of said patient ranges from −2 to −65 mmol/L.

In some embodiments, the triple combinations are administered to a patient who has one F508del mutation and one minimal function mutation, and who has not taken any of said at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof.

In some embodiments, the triple combinations are administered to a patient has two copies of F508del mutation, and wherein patient has taken at least one compound chosen from Compound II and pharmaceutically acceptable salts thereof, and at least one compound chosen from Compound III or III-d and pharmaceutically acceptable salts thereof, but not any of said at least one compound chosen from Compound I and pharmaceutically acceptable salts thereof.

In some embodiments, the absolute change in patient's ppFEV$_1$ after 15 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 35% relative to the ppFEV1 of the patient prior to said administration.

In some embodiments, the absolute change in patient's ppFEV$_1$ after 29 days of administration of at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from 3% to 35% relative to the ppFEV1 of the patient prior to said administration.

In some embodiments, the absolute change in a patient's ppFEV$_1$ relative to the ppFEV1 of the patient prior to such administration of the triple combinations can be calculated as (postbaseline value-baseline value). The baseline value is defined as the most recent non-missing measurement collected before the first dose of study drug in the Treatment Period (Day 1).

The exact amount of API(s) and tablets comprising such API(s) required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of API(s) and tablets comprising such API(s) of this disclosure will be decided by the attending physician within the scope of sound medical judgment. The specific effective dose level for any particular patient or organism will depend upon a variety of factors including the disorder being treated and the severity of the disorder; the activity of the specific API employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure also is directed to methods of treatment using isotope-labelled compounds of the afore-mentioned compounds, which have the same structures as disclosed herein except that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively.

The isotope-labelled compounds and salts can be used in a number of beneficial ways. They can be suitable for medicaments and/or various types of assays, such as substrate tissue distribution assays. For example, tritium ($^3$H)- and/or carbon-14 ($^{14}$C)-labelled compounds are particularly useful for various types of assays, such as substrate tissue distribution assays, due to relatively simple preparation and excellent detectability. For example, deuterium ($^2$H)-labelled ones are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2$H)-labelled ones. In some specific embodiments, the isotope-labelled compounds and salts are deuterium ($^2$H)-labelled, wherein one or more hydrogen atoms therein have been replaced by deuterium. In chemical structures, deuterium is represented as "$^2$H" or "D."

The deuterium ($^2$H)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417; and T. G. Gant "Using deuterium in drug discovery: leaving the label in the drug" J. Med. Chem. 2014, 57, 3595-3611, relevant portions of which are independently incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

One of ordinary skill in the art would understand that deuteration of one or more metabolically labile positions on a compound or active metabolite may lead to improvement of one or more superior DMPK properties while maintaining biological activity as compared to the corresponding hydrogen analogs. The superior DMPK property or properties may have an impact on the exposure, half-life, clearance, metabolism, and/or even food requirements for optimal absorption of the drug product. Deuteration may also change the metabolism at other non-deuterated positions of the deuterated compound.

Compound III-d as used herein includes the deuterated compound disclosed in U.S. Pat. No. 8,865,902 (which is incorporated herein by reference), and CTP-656.

As mentioned above, Compound III-d is:

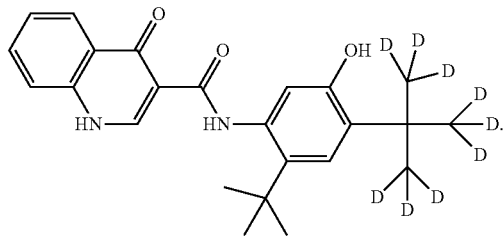

Exemplary embodiments of the disclosure include:
1. A single tablet comprising
   (a) 25 mg to 150 mg of Compound I:

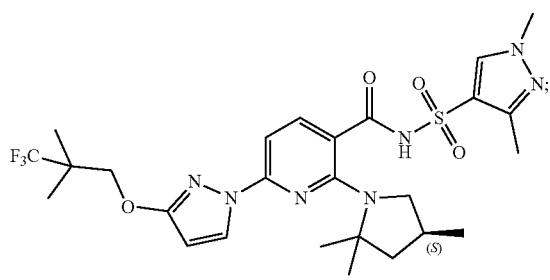

(b) a first solid dispersion comprising 20 mg to 150 mg of Compound II:

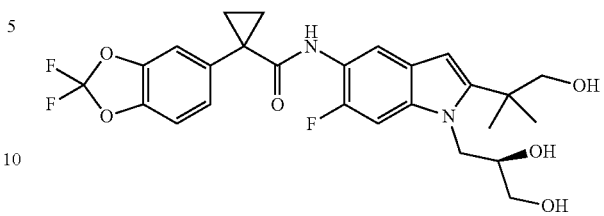

and 10 wt % to 30 wt % of a polymer relative to the total weight of the first solid dispersion; and
   (c) a second solid dispersion comprising 25 mg to 200 mg of Compound III-d:

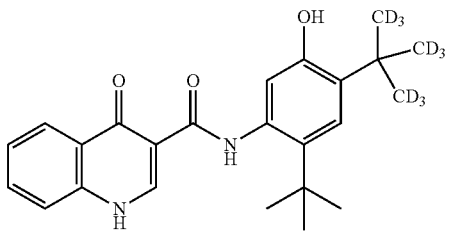 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and 10 wt % to 30 wt % of a polymer relative to the total weight of the second solid dispersion.

2. The single tablet of embodiment 1, wherein at least one of the first or second solid dispersions is a spray-dried dispersion.

3. The single tablet of embodiment 1, wherein both of the first and second solid dispersions are spray-dried dispersions.

4. The single tablet of embodiment 1, wherein said polymer in the first solid dispersion is hydroxypropyl methylcellulose; and said polymer in the second solid dispersion is hydroxypropyl methylcelluloseacetate succinate.

5. The single tablet of embodiment 1, wherein said polymer in the first solid dispersion is HPMC E15; and said polymer in the second solid dispersion is hydroxypropyl methylcelluloseacetate succinate H.

6. The single tablet of embodiment 1, wherein said polymer in the first solid dispersion is HPMC E15; and said polymer in the second solid dispersion is hydroxypropyl methylcelluloseacetate succinate HG.

6a. The single tablet of embodiment 1, wherein Compound I is Crystalline Form A.

6b. The single tablet of embodiment 6a, wherein Compound I Crystalline Form A is in substantially pure form.

6c. The single tablet of embodiment 6a, wherein Compound I Crystalline Form A is characterized by an X-ray powder diffractogram having a signal at at least three two-theta values chosen from 6.6±0.2, 7.6±0.2, 9.6±0.2, 12.4±0.2, 13.1±0.2, 15.2±0.2, 16.4±0.2, 18.2±0.2, and 18.6±0.2.

6d. The single tablet of embodiment 6a, wherein Compound I Crystalline Form A is characterized by an X-ray powder diffractograph having a signal at at least three two-theta values chosen from 6.6±0.2, 9.6±0.2, 7.6±0.2, 15.2±0.2, 12.4±0.2, and 16.4±0.2.

6e. The single tablet of embodiment 6a, wherein Compound I Crystalline Form A is characterized by an X-ray powder diffractograph having a signal at three two-theta values of 6.6±0.2, 9.6±0.2, 15.2±0.2.

6f. The single tablet of embodiment 6a, wherein Compound I Crystalline Form A is characterized by an X-ray powder diffractograph having a signal at six two-theta values of 6.6±0.2, 9.6±0.2, 7.6±0.2, 15.2±0.2, 12.4±0.2, and 16.4±0.2.

Figure 4A:
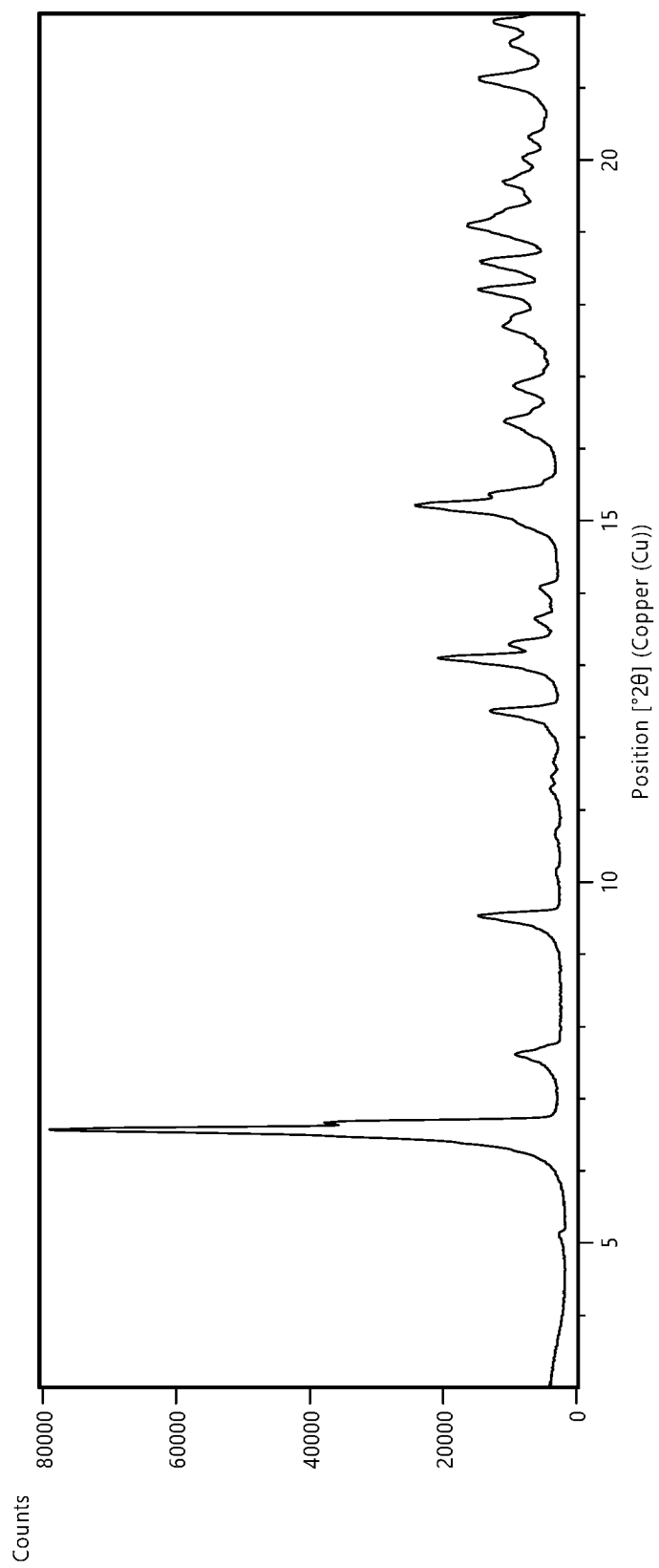
FIG. 4A is an XRPD of Form A of Compound 1.

6g. The single tablet of embodiment 6a, wherein Compound I Crystalline Form A is characterized by an X-ray powder diffractogram substantially similar to that in FIG. 4A.

Figure 4B:
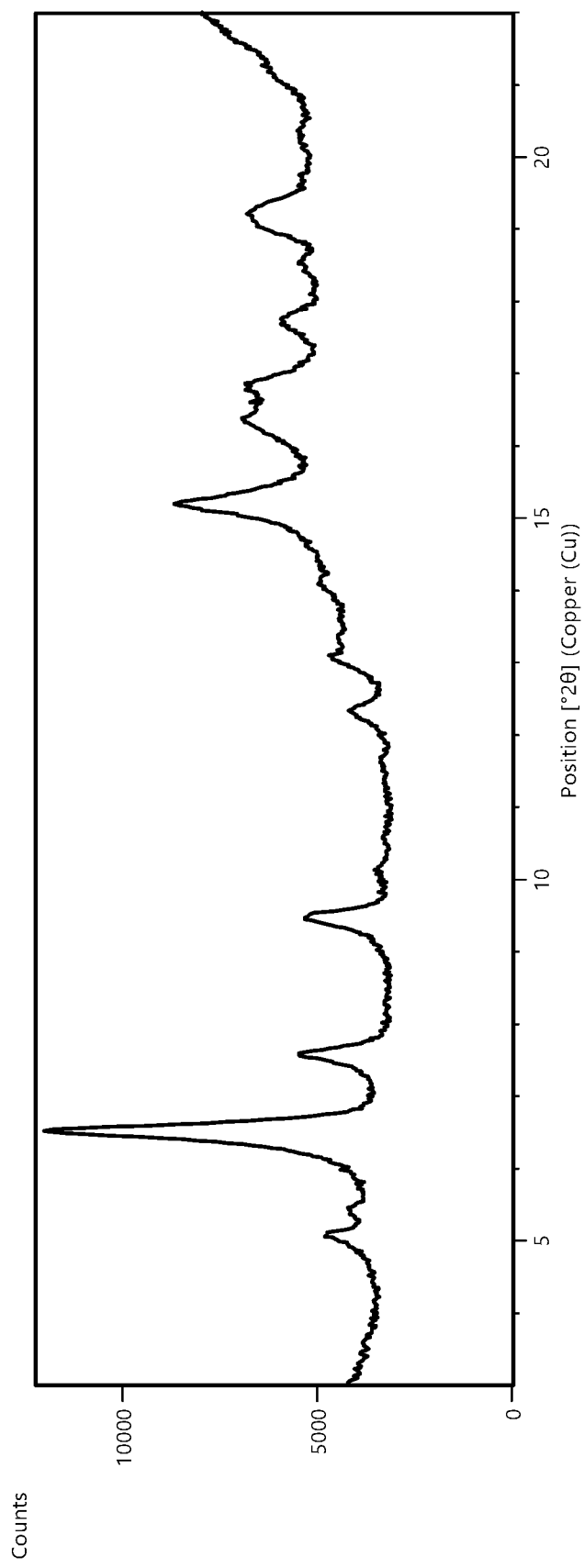
FIG. 4B is an XRPD of a tablet with the composition of Tablet 4.

6h. The single tablet of embodiment 6a, wherein Compound I Crystalline Form A is characterized by an X-ray powder diffractogram substantially similar to that in FIG. 4B.

7. The single tablet of any one of embodiments 1-6g, comprising 80 mg to 120 mg of Compound I.

8. The single tablet of any one of embodiments 1-6g, comprising 80 mg to 120 mg, 85 mg to 115 mg, 90 mg to 110 mg, or 95 mg to 105 mg of Compound I.

9. The single tablet of any one of embodiments 1-6g, comprising 100 mg of Compound I.

10. The single tablet of any one of embodiments 1-6g, comprising 75 mg to 125 mg of Compound I.

11. The single tablet of any one of embodiments 1-10, wherein the first solid dispersion comprises 25 mg to 75 mg of Compound II.

12. The single tablet of any one of embodiments 1-10, wherein the first solid dispersion comprises 50 mg of Compound II.

13. The single tablet of any one of embodiments 1-12, wherein the second solid dispersion comprises 25 mg to 50 mg, 25 mg to 75 mg, 50 mg to 100 mg, or 75 mg to 125 mg of Compound III-d.

14. The single tablet of any one of embodiments 1-12, wherein the second solid dispersion comprises 75 mg of Compound III-d.

15. The single tablet of any one of embodiments 1-6, comprising
50 mg to 125 mg of Compound I; and wherein
the first solid dispersion comprises 25 mg to 75 mg of Compound II; and
the second solid dispersion comprises 75 mg to 125 mg of Compound III-d.

16. The single tablet of any one of embodiments 1-6, comprising
75 mg to 125 mg of Compound I; and wherein
the first solid dispersion comprises 50 mg of Compound II; and
the second solid dispersion comprises 75 mg of Compound III-d.

17. The single tablet of any one of embodiments 1-6, comprising
100 mg of Compound I; and wherein
the first solid dispersion comprises 50 mg of Compound II; and
the second solid dispersion comprises 75 mg of Compound III-d.

18. The single tablet of any one of embodiments 1-17, wherein the second solid dispersion further comprises 0.5% sodium lauryl sulfate relative to the total weight of the second solid dispersion.

19. The single tablet of any one of embodiments 1-18, further comprising one or more pharmaceutically acceptable excipients chosen from one or more fillers, disintegrants, lubricants, and glidants.

20. The single tablet of embodiment 19, wherein fillers are chosen from microcrystalline cellulose, silicified microcrystalline cellulose, lactose monohydrate, dicalcium phosphate, mannitol, copovidone, hydroxypropyl cellulose, hydroxypropyl methylcellulose, methyl cellulose, ethyl cellulose, starch, Maltodextrin, agar, and guar gum.

21. The single tablet of embodiment 19, wherein disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose.

22. The single tablet of embodiment 19, wherein lubricants are chosen from magnesium stearate, sodium stearyl fumarate, calcium stearate, sodium stearate, stearic acid, and talc.

23. The single tablet of embodiment 19, wherein glidants are colloidal silicon dioxide.

24. The single tablet of any one of embodiments 1-23, wherein Compound I is substantially crystalline, and wherein each of Compounds II and III-d are independently substantially amorphous.

25. A pharmaceutical composition comprising:
(a) 10 wt % to 30 wt % of Compound I:

relative to the total weight of the pharmaceutical composition;

(b) 10 wt % to 30 wt % of a first solid dispersion relative to the total weight of the pharmaceutical composition, wherein the first solid dispersion comprises 70 wt % to 90 wt % of Compound II relative to the total weight of the first solid dispersion:

and 10 wt % to 30 wt % of a polymer relative to the total weight of the first solid dispersion; and (c) 10 wt % to 30 wt % of a second solid dispersion relative to the total weight of the pharmaceutical composition; wherein the second solid dispersion comprises 70 wt % to 90 wt % of Compound III-d relative to the total weight of the second solid dispersion:

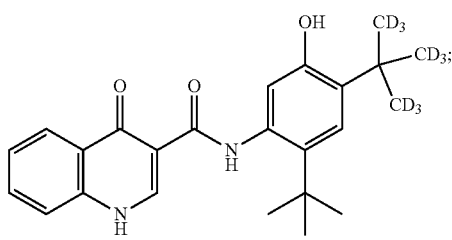 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and 10 wt % to 30 wt % of a polymer relative to the total weight of the second solid dispersion.

26. The pharmaceutical composition of embodiment 25, wherein at least one of the first or second solid dispersions is a spray-dried dispersion.

27. The pharmaceutical composition of embodiment 25, wherein both of the first and second solid dispersions are spray-dried dispersions.

28. The pharmaceutical composition of embodiment 25, wherein said polymer in the first solid dispersion is hydroxypropyl methylcellulose; and said polymer in the second solid dispersion is hydroxypropyl methylcellulose acetate succinate.

29. The pharmaceutical composition of embodiment 25, wherein said polymer in the first solid dispersion is hydroxypropyl methylcellulose (HPMC E15); and said polymer in the second solid dispersion is hydroxypropyl methylcellulose acetate succinate H.

30. The pharmaceutical composition of embodiment 25, wherein:
the first solid dispersion comprises 70 wt % to 85 wt % of Compound II relative to the total weight of the first solid dispersion, and the polymer is hydroxypropyl methylcellulose in an amount of 15 wt % to 30 wt % relative to the total weight of the first solid dispersion; and
the second solid dispersion comprises 70 wt % to 85 wt % of Compound III-d relative to the total weight of the second solid dispersion, 0.5% sodium lauryl sulfate relative to the total weight of the second solid dispersion, and the polymer is hydroxypropyl methylcellulose acetate succinate in an amount of 14.5 wt % to 29.5 wt % relative to the total weight of the second solid dispersion.

31. The pharmaceutical composition of any one of embodiments 25-30, wherein the first solid dispersion comprises 75 wt % to 85 wt % of Compound II relative to the total weight of the first solid dispersion.

32. The pharmaceutical composition of any one of embodiments 25-31, wherein the first solid dispersion comprises 80 wt % of Compound II relative to the total weight of the first solid dispersion; and 20 wt % of hydroxypropyl methylcellulose relative to the total weight of the first solid dispersion.

33. The pharmaceutical composition of any one of embodiments 25-32, wherein the second solid dispersion comprises 75 wt % to 85 wt % of Compound III-d relative to the total weight of the second solid dispersion.

34. The pharmaceutical composition of any one of embodiments 25-33, wherein the second solid dispersion comprises 80 wt % of Compound III-d relative to the total weight of the second solid dispersion; 0.5% of sodium lauryl sulfate relative to the total weight of the second solid dispersion, and 19.5 wt % of hydroxypropyl methylcellulose acetate succinate relative to the total weight of the second solid dispersion.

35. The pharmaceutical composition of any one of embodiments 25-34, further comprising one or more pharmaceutically acceptable excipients chosen from one or more fillers, disintegrants, lubricants, and glidants.

36. The pharmaceutical composition of embodiment 35, wherein fillers are chosen from microcrystalline cellulose, silicified microcrystalline cellulose, lactose monohydrate, dicalcium phosphate, mannitol, copovidone, hydroxypropyl cellulose, hydroxypropyl methylcellulose, methyl cellulose, ethyl cellulose, starch, Maltodextrin, agar, and guar gum.

37. The pharmaceutical composition of embodiment 35, wherein disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose.

38. The pharmaceutical composition of embodiment 35, wherein lubricants are chosen from magnesium stearate, sodium stearyl fumarate, calcium stearate, sodium stearate, stearic acid, and talc.

39. The pharmaceutical composition of embodiment 35, wherein glidants are colloidal silicon dioxide.

40. The pharmaceutical composition of any one of embodiments 25-39, wherein Compound I is substantially crystalline, and wherein each of Compounds II and III-d is independently substantially amorphous.

41. The pharmaceutical composition of any one of embodiments 25-40, wherein the pharmaceutical composition is a tablet.

42. The pharmaceutical composition of any one of embodiments 25-40, wherein the pharmaceutical composition is in the form of granules.

43. A pharmaceutical composition comprising:
(a) Compound I:

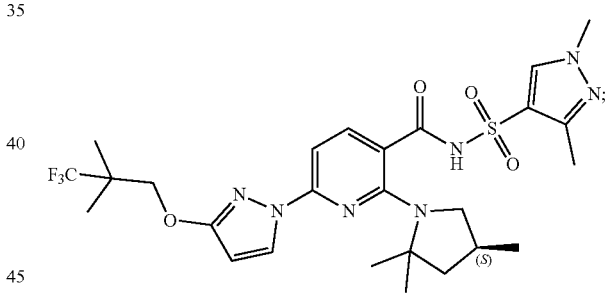

(b) a first solid dispersion,
wherein the first solid dispersion comprises 70 wt % to 90 wt % of Compound II relative to the total weight of the first solid dispersion:

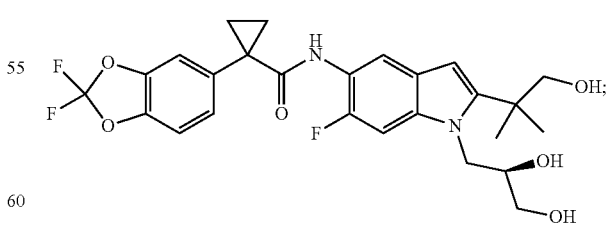

and 10 wt % to 30 wt % of a polymer; and
(c) a second solid dispersion;
wherein the second solid dispersion comprises 70 wt % to 90 wt % of Compound III-d relative to the total weight of the second solid dispersion:

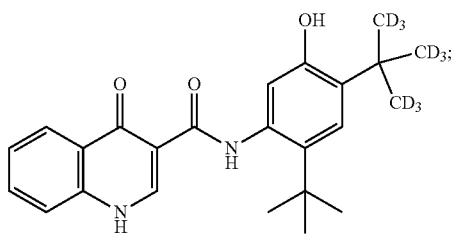 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and 10 wt % to 30 wt % of a polymer, wherein
The weight ratio of Compound I in (a): Compound II in (b): Compound III-d in (c) ranges from 1-4:2:3.

43a. The pharmaceutical composition of embodiment 43, wherein the weight ratio of Compound I in (a): Compound II in (b): Compound III-d in (c) is 2:2:3.

43b. The pharmaceutical composition of embodiment 43, wherein the weight ratio of Compound I in (a): Compound II in (b): Compound III-d in (c) is 1:2:3.

43c. The pharmaceutical composition of embodiment 43, wherein the weight ratio of Compound I in (a): Compound II in (b): Compound III-d in (c) is 4:2:3.

44. The pharmaceutical composition of embodiment 43, wherein at least one of the second or third solid dispersions is a spray-dried dispersion.

45. The pharmaceutical composition of embodiment 43, wherein both of the first and second solid dispersions are spray-dried dispersions.

46. The pharmaceutical composition of embodiment 43, wherein said polymer in the first solid dispersion is hydroxypropyl methylcellulose; and said polymer in the second solid dispersion is hydroxypropyl methylcellulose acetate succinate.

47. The pharmaceutical composition of embodiment 43, wherein said polymer in the first solid dispersion is hydroxypropyl methylcellulose (HPMC E15); and said polymer in the second solid dispersion is hydroxypropyl methylcellulose acetate succinate H.

48. The pharmaceutical composition of embodiment 43, wherein:
the first solid dispersion comprises 70 wt % to 85 wt % of Compound II relative to the total weight of the first solid dispersion, and the polymer is hydroxypropyl methylcellulose in an amount of 15 wt % to 30 wt % relative to the total weight of the first solid dispersion; and the second solid dispersion comprises 70 wt % to 85 wt % of Compound III-d relative to the total weight of the second solid dispersion, 0.5% sodium lauryl sulfate relative to the total weight of the second solid dispersion, and the polymer is hydroxypropyl methylcellulose acetate succinate in an amount of 14.5 wt % to 29.5 wt % relative to the total weight of the second solid dispersion.

49. The pharmaceutical composition of any one of embodiments 43-48, wherein the first solid dispersion comprises 75 wt % to 85 wt % of Compound II relative to the total weight of the first solid dispersion.

50. The pharmaceutical composition of any one of embodiments 43-49, wherein the first solid dispersion comprises 80 wt % of Compound II relative to the total weight of the first solid dispersion; and 20 wt % of hydroxypropyl methylcellulose relative to the total weight of the first solid dispersion.

51. The pharmaceutical composition of any one of embodiments 43-50, wherein the second solid dispersion comprises 75 wt % to 85 wt % of Compound III-d relative to the total weight of the second solid dispersion.

52. The pharmaceutical composition of any one of embodiments 43-51, wherein the second solid dispersion comprises 80 wt % of Compound III-d relative to the total weight of the second solid dispersion; 0.5% of sodium lauryl sulfate relative to the total weight of the second solid dispersion, and 19.5 wt % of hydroxypropyl methylcellulose acetate succinate relative to the total weight of the second solid dispersion.

53. The pharmaceutical composition of any one of embodiments 43-42, further comprising one or more pharmaceutically acceptable excipients chosen from one or more fillers, disintegrants, lubricants, and glidants.

54. The pharmaceutical composition of embodiment 53, wherein fillers are chosen from microcrystalline cellulose, silicified microcrystalline cellulose, lactose monohydrate, dicalcium phosphate, mannitol, copovidone, hydroxypropyl cellulose, hydroxypropyl methylcellulose, methyl cellulose, ethyl cellulose, starch, Maltodextrin, agar, and guar gum.

55. The pharmaceutical composition of embodiment 53, wherein disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose.

56. The pharmaceutical composition of embodiment 53, wherein lubricants are chosen from magnesium stearate, sodium stearyl fumarate, calcium stearate, sodium stearate, stearic acid, and talc.

57. The pharmaceutical composition of embodiment 53, wherein glidants are colloidal silicon dioxide.

58. The pharmaceutical composition of any one of embodiments 43-57, wherein Compound I is substantially crystalline, and wherein each of Compounds II and III-d is independently substantially amorphous.

59. The pharmaceutical composition of any one of embodiments 43-58, wherein the pharmaceutical composition is a tablet.

60. The pharmaceutical composition of any one of embodiments 43-58, wherein the pharmaceutical composition is in the form of granules.

61. A single tablet comprising:
(a) 25 mg to 125 mg of Compound I:

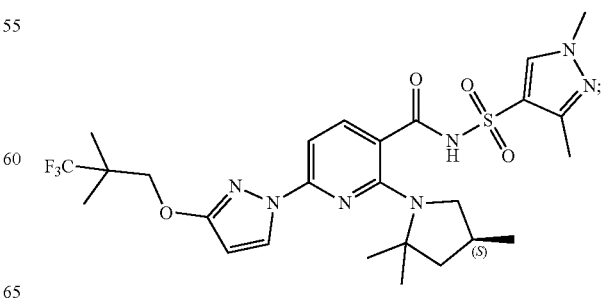

(b) 60 mg to 65 mg of a first solid dispersion comprising 80 wt % Compound II relative to the total weight of the first solid dispersion:

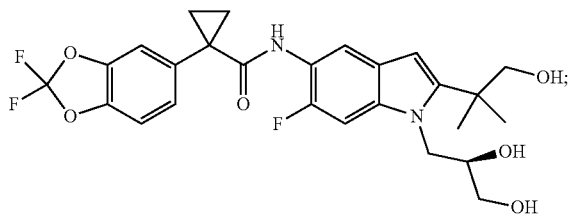 [SMILES: CC(C)(CO)c1cc2cc(NC(=O)C3(c4ccc5c(c4)OC(F)(F)O5)CC3)c(F)cc2n1C[C@@H](O)CO]

and 20 wt % of a hydroxypropyl methylcellulose relative to the total weight of the first solid dispersion; and
(c) 90 mg to 95 mg of a second solid dispersion comprising 80 wt % of Compound III-d relative to the total weight of the second solid dispersion:

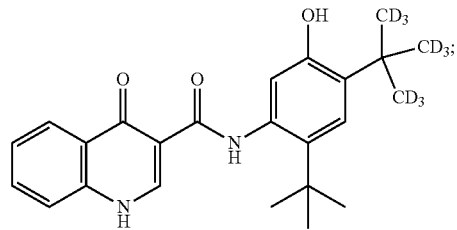 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

0.5 wt % of sodium lauryl sulfate relative to the total weight of the second solid dispersion; and 19.5 wt % of a hydroxypropyl methylcellulose acetate succinate to the total weight of the second solid dispersion
(d) 75 mg to 230 mg of microcrystalline cellulose;
(e) 20 mg to 45 mg of croscarmellose sodium; and
(f) 2 mg to 7 mg of magnesium stearate.
62. The single tablet of embodiment 61, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 75 mg to 85 mg of said microcrystalline cellulose;
(e) 25 mg to 35 mg of said croscarmellose sodium; and
(B) wherein the extra-granular part comprises:
(a) 115 mg to 120 mg of said microcrystalline cellulose; and
(b) 3 mg to 7 mg of magnesium stearate.
63. The single tablet of embodiment 61, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium; and
(B) wherein the extra-granular part comprises:
(a) 85 mg to 95 mg of said microcrystalline cellulose; and
(b) 2 mg to 6 mg of magnesium stearate.
64. The single tablet of embodiment 61, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 200 mg of said microcrystalline cellulose; and
(f) 3 mg to 7 mg of magnesium stearate.

65. The single tablet of embodiment 61, comprising
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 85 mg to 95 mg of said microcrystalline cellulose; and
(f) 2 mg to 6 mg of magnesium stearate.
66. The single tablet of embodiment 61, comprising
(a) 90 mg to 110 mg of Compound I;
(b) 60 mg to 65 mg of said first solid dispersion;
(c) 90 mg to 95 mg of said second solid dispersion;
(d) 20 mg to 30 mg of said croscarmellose sodium;
(e) 135 mg to 145 mg of said microcrystalline cellulose; and
(f) 2 mg to 6 mg of magnesium stearate.
67. The single tablet of embodiment 61, comprising
(a) 90 mg to 110 mg of Compound I;
(b) 60 mg to 65 mg of said first solid dispersion;
(c) 90 mg to 95 mg of said second solid dispersion;
(d) 35 mg to 40 mg of said croscarmellose sodium;
(e) 105 mg to 115 mg of lactose monohydrate;
(f) 220 mg to 230 mg of said microcrystalline cellulose;
(g) 1 mg to 5 mg of colloidal silicon dioxide; and
(h) 4 mg to 7 mg of magnesium stearate.
68. The single tablet of embodiment 61, comprising
(a) 90 mg to 110 mg of Compound I;
(b) 60 mg to 65 mg of said first solid dispersion;
(c) 90 mg to 95 mg of said second solid dispersion;
(d) 20 mg to 30 mg of said croscarmellose sodium;
(e) 40 mg to 50 mg of lactose monohydrate;
(f) 90 mg to 100 mg of said microcrystalline cellulose;
(g) 1 mg to 5 mg of colloidal silicon dioxide; and
(h) 2 mg to 7 mg of magnesium stearate.
69. The single tablet of embodiment 61, comprising
(a) 90 mg to 110 mg of Compound I;
(b) 60 mg to 65 mg of said first solid dispersion;
(c) 90 mg to 95 mg of said second solid dispersion;
(d) 20 mg to 30 mg of said croscarmellose sodium;
(e) 135 mg to 145 mg of said microcrystalline cellulose;
(f) 1 mg to 5 mg of colloidal silicon dioxide; and
(g) 2 mg to 7 mg of magnesium stearate.
70. The single tablet of embodiment 61, comprising
(a) 90 mg to 110 mg of Compound I;
(b) 60 mg to 65 mg of said first solid dispersion;
(c) 90 mg to 95 mg of said second solid dispersion;
(d) 20 mg to 30 mg of said croscarmellose sodium;
(e) 135 mg to 145 mg of said microcrystalline cellulose; and
(f) 2 mg to 7 mg of magnesium stearate.
71. A single tablet comprising
(a) 25 mg to 150 mg of Compound I:

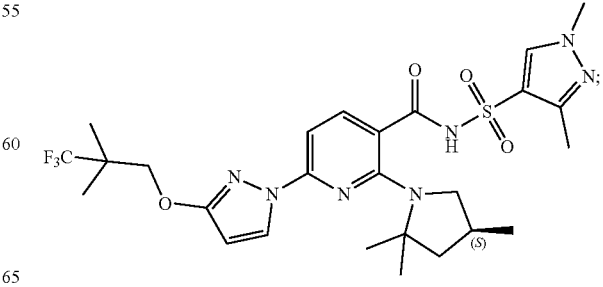

(b) a first solid dispersion comprising 20 mg to 150 mg of Compound II:

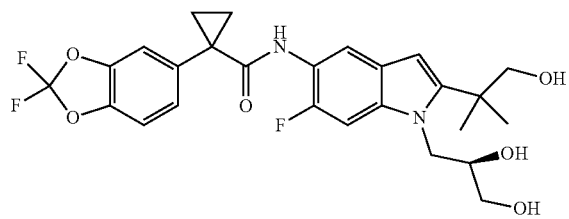 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and (c) a second solid dispersion comprising 25 mg to 200 mg of Compound III:

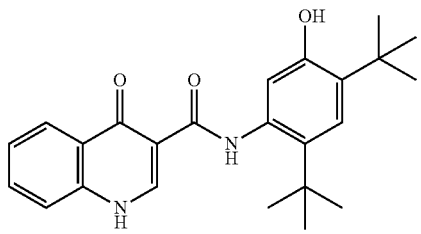 [SMILES: CC(C)(C)c1cc(C(C)(C)C)c(NC(=O)c2c[nH]c3ccccc3c2=O)cc1O]

and 10 wt % to 30 wt % of a polymer relative to the total weight of the second solid dispersion.

72. The single tablet of embodiment 71, wherein at least one of the first or second solid dispersions is a spray-dried dispersion.

73. The single tablet of embodiment 71, wherein both of the first and second solid dispersions are spray-dried dispersions.

74. The single tablet of embodiment 71, wherein said polymer in the first solid dispersion is hydroxypropyl methylcellulose; and said polymer in the second solid dispersion is hydroxypropyl methylcellulose acetate succinate.

75. The single tablet of embodiment 71, wherein said polymer in the first solid dispersion is HPMC E15; and said polymer in the second solid dispersion is hydroxypropyl methylcellulose acetate succinate H.

76. The single tablet of embodiment 71, wherein said polymer in the first solid dispersion is HPMC E15; and said polymer in the second solid dispersion is hydroxypropyl methylcellulose acetate succinate HG.

77. The single tablet of any one of embodiments 71-76, comprising 80 mg to 120 mg of Compound I.

78. The single tablet of any one of embodiments 71-76, comprising 80 mg to 120 mg, 85 mg to 115 mg, 90 mg to 110 mg, or 95 mg to 105 mg of Compound I.

79. The single tablet of any one of embodiments 71-76, comprising 100 mg of Compound I.

80. The single tablet of any one of embodiments 71-76, comprising 75 mg to 125 mg of Compound I.

81. The single tablet of any one of embodiments 71-80, wherein the first solid dispersion comprises 25 mg to 75 mg of Compound II.

82. The single tablet of any one of embodiments 71-80, wherein the first solid dispersion comprises 50 mg of Compound II.

83. The single tablet of any one of embodiments 71-82, wherein the second solid dispersion comprises 25 mg to 50 mg, 25 mg to 75 mg, 50 mg to 100 mg, or 75 mg to 125 mg of Compound III.

84. The single tablet of any one of embodiments 71-82, wherein the second solid dispersion comprises 75 mg of Compound III.

85. The single tablet of any one of embodiments 71-76, comprising
50 mg to 125 mg of Compound I; and wherein
the first solid dispersion comprises 25 mg to 75 mg of Compound II; and
the second solid dispersion comprises 75 mg to 125 mg of Compound III.

86. The single tablet of any one of embodiments 71-82, comprising
75 mg to 125 mg of Compound I; and wherein
the first solid dispersion comprises 50 mg of Compound II; and
the second solid dispersion comprises 75 mg of Compound III.

87. The single tablet of any one of embodiments 71-82, comprising
100 mg of Compound I; and wherein
the first solid dispersion comprises 50 mg of Compound II; and
the second solid dispersion comprises 75 mg of Compound III.

88. The single tablet of any one of embodiments 71-87, wherein the second solid dispersion further comprises 0.5% sodium lauryl sulfate relative to the total weight of the second solid dispersion.

89. The single tablet of any one of embodiments 71-88, further comprising one or more pharmaceutically acceptable excipients chosen from one or more fillers, disintegrants, lubricants, and glidants.

90. The single tablet of embodiment 89, wherein fillers are chosen from microcrystalline cellulose, silicified microcrystalline cellulose, lactose monohydrate, dicalcium phosphate, mannitol, copovidone, hydroxypropyl cellulose, hydroxypropyl methylcellulose, methyl cellulose, ethyl cellulose, starch, Maltodextrin, agar, and guar gum.

91. The single tablet of embodiment 89, wherein disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose.

92. The single tablet of embodiment 89, wherein lubricants are chosen from magnesium stearate, sodium stearyl fumarate, calcium stearate, sodium stearate, stearic acid, and talc.

93. The single tablet of embodiment 89, wherein glidants are colloidal silicon dioxide.

94. The single tablet of any one of embodiments 71-93, wherein Compound I is substantially crystalline, and wherein each of Compounds II and III are independently substantially amorphous.

95. A pharmaceutical composition comprising:
(a) 10 wt % to 30 wt % of Compound I:

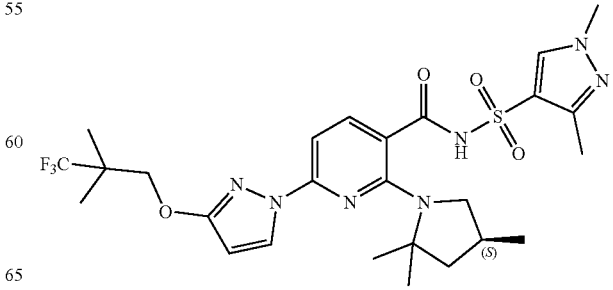

relative to the total weight of the pharmaceutical composition;

(b) 8 wt % to 30 wt % of a first solid dispersion relative to the total weight of the pharmaceutical composition, wherein the first solid dispersion comprises 70 wt % to 90 wt % of Compound II relative to the total weight of the first solid dispersion:

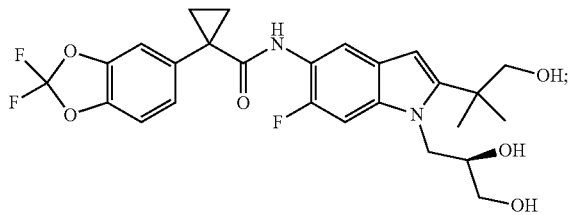 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and (c) 10 wt % to 30 wt % of a second solid dispersion relative to the total weight of the pharmaceutical composition; wherein the second solid dispersion comprises 70 wt % to 90 wt % of Compound III relative to the total weight of the second solid dispersion:

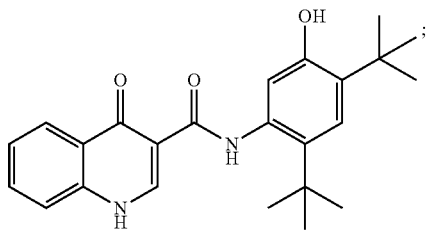 [SMILES: CC(C)(C)c1cc(C(C)(C)C)c(NC(=O)c2c[nH]c3ccccc3c2=O)cc1O]

and 10 wt % to 30 wt % of a polymer relative to the total weight of the second solid dispersion.

96. The pharmaceutical composition of embodiment 95, wherein at least one of the second or third solid dispersions is a spray-dried dispersion.

97. The pharmaceutical composition of embodiment 95, wherein both of the first and second solid dispersions are spray-dried dispersions.

98. The pharmaceutical composition of embodiment 95, wherein said polymer in the first solid dispersion is hydroxypropyl methylcellulose; and said polymer in the second solid dispersion is hydroxypropyl methylcellulose acetate succinate.

99. The pharmaceutical composition of embodiment 95, wherein said polymer in the first solid dispersion is hydroxypropyl methylcellulose (HPMC E15); and said polymer in the second solid dispersion is hydroxypropyl methylcellulose acetate succinate H.

100. The pharmaceutical composition of embodiment 95, wherein:
the first solid dispersion comprises 70 wt % to 85 wt % of Compound II relative to the total weight of the first solid dispersion, and the polymer is hydroxypropyl methylcellulose in an amount of 15 wt % to 30 wt % relative to the total weight of the first solid dispersion; and
the second solid dispersion comprises 70 wt % to 85 wt % of Compound III relative to the total weight of the second solid dispersion, 0.5% sodium lauryl sulfate relative to the total weight of the second solid dispersion, and the polymer is hydroxypropyl methylcellulose acetate succinate in an amount of 14.5 wt % to 29.5 wt % relative to the total weight of the second solid dispersion.

101. The pharmaceutical composition of any one of embodiments 95-100, wherein the first solid dispersion comprises 75 wt % to 85 wt % of Compound II relative to the total weight of the first solid dispersion.

102. The pharmaceutical composition of any one of embodiments 95-100, wherein the first solid dispersion comprises 80 wt % of Compound II relative to the total weight of the first solid dispersion; and 20 wt % of hydroxypropyl methylcellulose relative to the total weight of the first solid dispersion.

103. The pharmaceutical composition of any one of embodiments 95-102, wherein the second solid dispersion comprises 75 wt % to 85 wt % of Compound III relative to the total weight of the second solid dispersion.

104. The pharmaceutical composition of any one of embodiments 95-103, wherein the second solid dispersion comprises 80 wt % of Compound III relative to the total weight of the second solid dispersion; 0.5% of sodium lauryl sulfate relative to the total weight of the second solid dispersion, and 19.5 wt % of hydroxypropyl methylcellulose acetate succinate relative to the total weight of the second solid dispersion.

105. The pharmaceutical composition of any one of embodiments 95-104, further comprising one or more pharmaceutically acceptable excipients chosen from one or more fillers, disintegrants, and lubricants.

106. The pharmaceutical composition of embodiment 105, wherein fillers are chosen from microcrystalline cellulose, silicified microcrystalline cellulose, lactose, dicalcium phosphate, mannitol, copovidone, hydroxypropyl cellulose, hydroxypropyl methylcellulose, methyl cellulose, ethyl cellulose, starch, Maltodextrin, agar, and guar gum.

107. The pharmaceutical composition of embodiment 105, wherein disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose.

108. The pharmaceutical composition of embodiment 105, wherein lubricants are chosen from magnesium stearate, sodium stearyl fumarate, calcium stearate, sodium stearate, stearic acid, and talc.

109. The pharmaceutical composition of any one of embodiments 95-108, wherein Compound I is substantially crystalline, and wherein each of Compounds II and III is independently substantially amorphous.

110. The pharmaceutical composition of any one of embodiments 95-109, wherein the pharmaceutical composition is a tablet.

111. The pharmaceutical composition of any one of embodiments 95-109, wherein the pharmaceutical composition is in the form of granules.

112. A pharmaceutical composition comprising:
(a) Compound I:

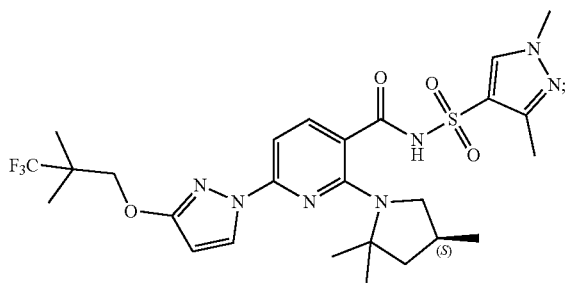

(b) a first solid dispersion comprising 70 wt % to 90 wt % of Compound II relative to the total weight of the first solid dispersion:

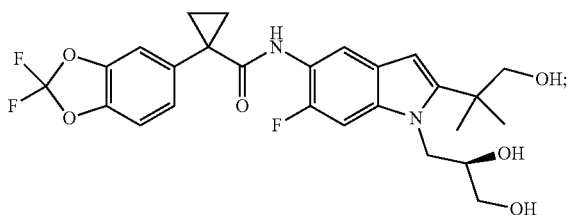 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and
(c) a second solid dispersion comprising 70 wt % to 90 wt % of Compound III relative to the total weight of the second solid dispersion:

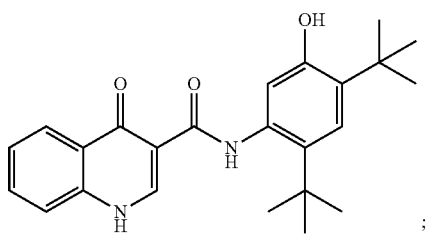 [SMILES: CC(C)(C)c1cc(C(C)(C)C)c(NC(=O)c2c[nH]c3ccccc3c2=O)cc1O]

and 10 wt % to 30 wt % of a polymer relative to the total weight of the second solid dispersion, wherein
the weight ratio of Compound I in (a): Compound II in (b): Compound III-d in (c) ranges from 2:4:5 to 6:1:1.

113. The pharmaceutical composition of embodiment 112, wherein at least one of the second or third solid dispersions is a spray-dried dispersion.

114. The pharmaceutical composition of embodiment 112, wherein both of the first and second solid dispersions are spray-dried dispersions.

115. The pharmaceutical composition of embodiment 112, wherein said polymer in the first solid dispersion is hydroxypropyl methylcellulose; and said polymer in the second solid dispersion is hydroxypropyl methylcellulose acetate succinate.

116. The pharmaceutical composition of embodiment 112, wherein said polymer in the first solid dispersion is hydroxypropyl methylcellulose (HPMC E15); and said polymer in the second solid dispersion is hydroxypropyl methylcellulose acetate succinate H.

117. The pharmaceutical composition of embodiment 112, wherein:
the first solid dispersion comprises 70 wt % to 85 wt % of Compound II relative to the total weight of the first solid dispersion, and the polymer is hydroxypropyl methylcellulose in an amount of 15 wt % to 30 wt % relative to the total weight of the first solid dispersion; and
the second solid dispersion comprises 70 wt % to 85 wt % of Compound III relative to the total weight of the second solid dispersion, 0.5% sodium lauryl sulfate relative to the total weight of the second solid dispersion, and the polymer is hydroxypropyl methylcellulose acetate succinate in an amount of 14.5 wt % to 29.5 wt % relative to the total weight of the second solid dispersion.

118. The pharmaceutical composition of any one of embodiments 112-117, wherein the first solid dispersion comprises 75 wt % to 85 wt % of Compound II relative to the total weight of the first solid dispersion.

119. The pharmaceutical composition of any one of embodiments 112-117, wherein the first solid dispersion comprises 80 wt % of Compound II relative to the total weight of the first solid dispersion; and 20 wt % of hydroxypropyl methylcellulose relative to the total weight of the first solid dispersion.

120. The pharmaceutical composition of any one of embodiments 112-119, wherein the second solid dispersion comprises 75 wt % to 85 wt % of Compound III relative to the total weight of the second solid dispersion.

121. The pharmaceutical composition of any one of embodiments 112-120, wherein the second solid dispersion comprises 80 wt % of Compound III relative to the total weight of the second solid dispersion; 0.5% of sodium lauryl sulfate relative to the total weight of the second solid dispersion, and 19.5 wt % of hydroxypropyl methylcellulose acetate succinate relative to the total weight of the second solid dispersion.

122. The pharmaceutical composition of any one of embodiments 112-121, further comprising one or more pharmaceutically acceptable excipients chosen from one or more fillers, disintegrants, and lubricants.

123. The pharmaceutical composition of embodiment 122, wherein fillers are chosen from microcrystalline cellulose, silicified microcrystalline cellulose, lactose, dicalcium phosphate, mannitol, copovidone, hydroxypropyl cellulose, hydroxypropyl methylcellulose, methyl cellulose, ethyl cellulose, starch, Maltodextrin, agar, and guar gum.

124. The pharmaceutical composition of embodiment 122, wherein disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose.

125. The pharmaceutical composition of embodiment 122, wherein lubricants are chosen from magnesium stearate, sodium stearyl fumarate, calcium stearate, sodium stearate, stearic acid, and talc.

126. The pharmaceutical composition of any one of embodiments 112-125, wherein Compound I is substantially crystalline, and wherein each of Compounds II and III is independently substantially amorphous.

127. The pharmaceutical composition of any one of embodiments 112-126, wherein the pharmaceutical composition is a tablet.

128. The pharmaceutical composition of any one of embodiments 112-126, wherein the pharmaceutical composition is in the form of granules.

129. A single tablet comprising:
(a) 25 mg to 125 mg of Compound I:

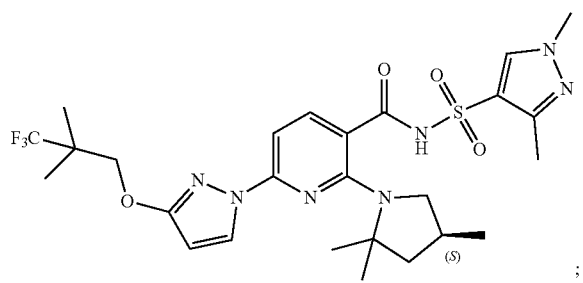

(b) 60 mg to 65 mg of a first solid dispersion comprising 80 wt % Compound II relative to the total weight of the first solid dispersion:

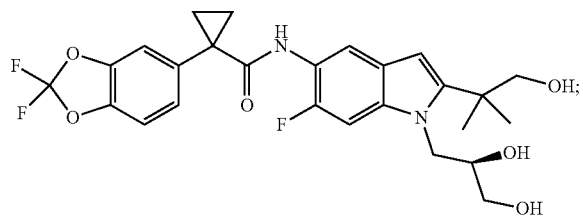 [SMILES: CC(C)(CO)c1cc2cc(NC(=O)C3(c4ccc5c(c4)OC(F)(F)O5)CC3)c(F)cc2n1C[C@@H](O)CO]

and 20 wt % of a hydroxypropyl methylcellulose relative to the total weight of the first solid dispersion; and
(c) 90 mg to 95 mg of a second solid dispersion comprising 80 wt % of Compound III relative to the total weight of the second solid dispersion:

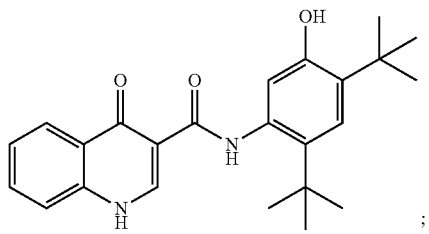 [SMILES: CC(C)(C)c1cc(C(C)(C)C)c(NC(=O)c2c[nH]c3ccccc3c2=O)cc1O]

0.5 wt % of sodium lauryl sulfate relative to the total weight of the second solid dispersion; and 19.5 wt % of a hydroxypropyl methylcellulose acetate succinate to the total weight of the second solid dispersion
(d) 85 mg to 275 mg of microcrystalline cellulose;
(e) 10 mg to 35 mg of croscarmellose sodium; and
(f) 2 mg to 7 mg of magnesium stearate.

130. The single tablet of embodiment 129, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 75 mg to 85 mg of said microcrystalline cellulose; and
(B) wherein the extra-granular part comprises:
(a) 115 mg to 120 mg of said microcrystalline cellulose; and
(b) 3 mg to 7 mg of magnesium stearate.

131. The single tablet of embodiment 129, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 85 mg to 90 mg of said microcrystalline cellulose; and
(B) wherein the extra-granular part comprises:
(a) 115 mg to 120 mg of microcrystalline cellulose; and
(b) 2 mg to 7 mg of magnesium stearate.

132. The single tablet of embodiment 129, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium; and
(B) wherein the extra-granular part comprises:
(a) 85 mg to 95 mg of microcrystalline cellulose; and
(b) 2 mg to 6 mg of magnesium stearate.

133. The single tablet of embodiment 129, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium; and
(B) wherein the extra-granular part comprises:
(a) 270 mg to 275 mg of microcrystalline cellulose; and
(b) 2 mg to 7 mg of magnesium stearate.

134. The single tablet of embodiment 129, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 85 mg to 90 mg of said microcrystalline cellulose; and
(B) wherein the extra-granular part comprises:
(a) 5 mg to 10 mg of said croscarmellose sodium;
(b) 105 mg to 115 mg of microcrystalline cellulose; and
(c) 2 mg to 7 mg of magnesium stearate.

135. The single tablet of embodiment 129, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 105 mg to 115 mg of said microcrystalline cellulose; and
(B) wherein the extra-granular part comprises:
(a) 25 mg to 35 mg of said croscarmellose sodium;
(b) 85 mg to 90 mg of microcrystalline cellulose; and
(c) 2 mg to 7 mg of magnesium stearate.

136. The single tablet of embodiment 129, wherein the tablet comprises an intra-granular part and extra-granular part, and
(A) wherein the intra-granular part comprises:
(a) 90 mg to 110 mg of Compound I;
(b) 60 mg to 65 mg of said first solid dispersion;
(c) 90 mg to 95 mg of said second solid dispersion;
(d) 195 mg to 200 mg of said microcrystalline cellulose; and
(B) wherein the extra-granular part comprises:
(a) 25 mg to 35 mg of said croscarmellose sodium; and
(b) 2 mg to 7 mg of magnesium stearate.

137. The single tablet of embodiment 129, wherein the tablet comprises an intra-granular part and extra-granular part, and
(A) wherein the intra-granular part comprises:
(a) 60 mg to 65 mg of said first solid dispersion;
(b) 90 mg to 95 mg of said second solid dispersion;

(c) 12 mg to 17 mg of said croscarmellose sodium;
(d) 60 mg to 70 mg of said microcrystalline cellulose; and
(B) wherein the extra-granular part comprises:
(a) 90 mg to 110 mg of Compound I;
(b) 95 mg to 105 mg of microcrystalline cellulose; and
(c) 2 mg to 7 mg of magnesium stearate.
138. The single tablet of embodiment 129, wherein the tablet comprises an intra-granular part and extra-granular part, and
(A) wherein the intra-granular part comprises:
(a) 60 mg to 65 mg of said first solid dispersion;
(b) 90 mg to 95 mg of said second solid dispersion;
(c) 10 mg to 20 mg of said croscarmellose sodium;
(d) 60 mg to 70 mg of said microcrystalline cellulose; and
(B) wherein the extra-granular part comprises:
(a) 90 mg to 110 mg of Compound I;
(b) 195 mg to 205 mg of microcrystalline cellulose; and
(c) 2 mg to 7 mg of magnesium stearate.
139. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.
140. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 200 mg to 210 mg of said microcrystalline cellulose; and
(f) 2 mg to 7 mg of magnesium stearate.
141. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 85 mg to 95 mg of said microcrystalline cellulose; and
(f) 2 mg to 6 mg of magnesium stearate.
142. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 270 mg to 275 mg of said microcrystalline cellulose; and
(f) 2 mg to 7 mg of magnesium stearate.
143. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.
144. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.
145. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 200 mg of said microcrystalline cellulose; and
(f) 2 mg to 7 mg of magnesium stearate.

146. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 12 mg to 17 mg of said croscarmellose sodium;
(e) 160 mg to 170 mg of said microcrystalline cellulose; and
(f) 2 mg to 7 mg of magnesium stearate.
147. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 10 mg to 20 mg of said croscarmellose sodium;
(e) 260 mg to 270 mg of said microcrystalline cellulose; and
(f) 2 mg to 7 mg of magnesium stearate.
148. A pharmaceutical composition comprising
(a) 10 wt % to 30 wt % Compound I relative to the total weight of the pharmaceutical composition:

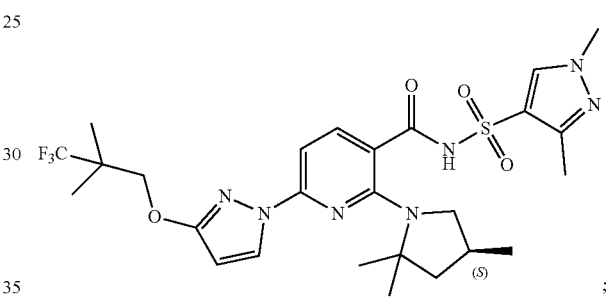

;

(b) 5 wt % to 15 wt % of Compound II relative to the total weight of the pharmaceutical composition:

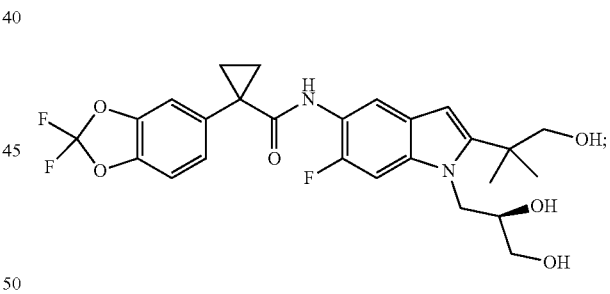

(c) 10 wt % to 25 wt % of Compound III or Compound III-d relative to the total weight of the pharmaceutical composition:

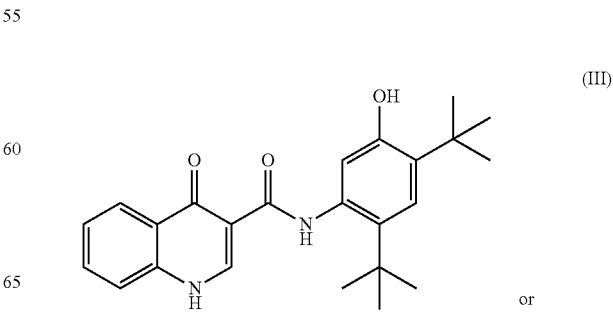

or

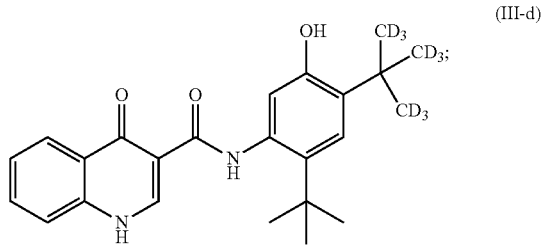

(d) 20 wt % to 45 wt % of microcrystalline cellulose relative to the total weight of the pharmaceutical composition;
(e) 3 wt %-8 wt % of croscarmellose sodium relative to the total weight of the pharmaceutical composition; and
(f) 0.5 wt % to 2 wt % of magnesium stearate relative to the total weight of the pharmaceutical composition.

149. The pharmaceutical composition of embodiment 148, wherein the pharmaceutical composition comprises:
(a) 18% to 23 wt % Compound I relative to the total weight of the pharmaceutical composition;
(b) 8 wt % to 12 wt % of Compound II relative to the total weight of the pharmaceutical composition;
(c) 13 wt % to 18 wt % of Compound III or Compound III-d relative to the total weight of the pharmaceutical composition;
(d) 35 wt % to 45 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.

150. The pharmaceutical composition of embodiment 148, wherein the pharmaceutical composition comprises:
(a) 15% to 25 wt % Compound I relative to the total weight of the pharmaceutical composition;
(b) 5 wt % to 10 wt % of Compound II relative to the total weight of the pharmaceutical composition;
(c) 7 wt % to 15 wt % of Compound III or Compound III-d relative to the total weight of the pharmaceutical composition;
(d) 30 wt % to 50 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.

151. The pharmaceutical composition of embodiment 148, wherein the pharmaceutical composition comprises:
(a) 20% to 25 wt % Compound I relative to the total weight of the pharmaceutical composition;
(b) 7 wt % to 15 wt % of Compound II relative to the total weight of the pharmaceutical composition;
(c) 15 wt % to 20 wt % of Compound III or Compound III-d relative to the total weight of the pharmaceutical composition;
(d) 15 wt % to 25 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.

152. The pharmaceutical composition of embodiment 148, wherein the pharmaceutical composition comprises:
(a) 20% to 25 wt % Compound I relative to the total weight of the pharmaceutical composition;
(b) 7 wt % to 15 wt % of Compound II relative to the total weight of the pharmaceutical composition;
(c) 15 wt % to 20 wt % of Compound III or Compound III-d relative to the total weight of the pharmaceutical composition;
(d) 25 wt % to 35 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.

153. The pharmaceutical composition of embodiment 148, wherein the pharmaceutical composition comprises:
(a) 22% to 28 wt % Compound I relative to the total weight of the pharmaceutical composition;
(b) 10 wt % to 15 wt % of Compound II relative to the total weight of the pharmaceutical composition;
(c) 15 wt % to 25 wt % of Compound III or Compound III-d relative to the total weight of the pharmaceutical composition;
(d) 15 wt % to 25 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.

154. The pharmaceutical composition of embodiment 148, wherein the pharmaceutical composition comprises:
(a) 15% to 20 wt % Compound I relative to the total weight of the pharmaceutical composition;
(b) 7 wt % to 15 wt % of Compound II relative to the total weight of the pharmaceutical composition;
(c) 10 wt % to 15 wt % of Compound III or Compound III-d relative to the total weight of the pharmaceutical composition;
(d) 45 wt % to 55 wt % of microcrystalline cellulose relative to the total weight of the pharmaceutical composition;
(e) 3 wt %-5 wt % of croscarmellose sodium relative to the total weight of the pharmaceutical composition; and
(f) 0.5 wt % to 1.5 wt % of magnesium stearate relative to the total weight of the pharmaceutical composition.

155. The pharmaceutical composition of any one of embodiments 148-154, wherein the pharmaceutical composition is a tablet.

156. A method of treating cystic fibrosis in a patient comprising orally administering to the patient one or more of the single tablet or pharmaceutical composition of any one of embodiments 1-155.

157. The method of embodiment 156, wherein one or more of the single tablets or pharmaceutical compositions are administered once daily.

158. The method of embodiment 156, wherein one or more of the single tablets or pharmaceutical compositions are administered twice daily.

159. The method of embodiment 156, wherein two tablets are administered once daily.

160. The method according to any one of embodiments 156-159, wherein said patient has cystic fibrosis is chosen from patients with F508del/minimal function genotypes, patients with F508del/F508del genotypes, patients with F508del/gating genotypes, and patients with F508del/residual function genotypes.

161. The method of embodiment 160, wherein the patient with a F508del/minimal function genotype has a minimal function mutation chosen from:

| Mutation | | | | |
|---|---|---|---|---|
| S4X | C276X | G542X | R792X | E1104X |
| G27X | Q290X | G550X | E822X | R1158X |
| Q39X | G330X | Q552X | W846X | R1162X |
| W57X | W401X | R553X | Y849X | S1196X |
| E60X | Q414X | E585X | R851X | W1204X |
| R75X | S434X | G673X | Q890X | L1254X |
| E92X | S466X | Q685X | S912X | S1255X |
| Q98X | S489X | R709X | Y913X | W1282X |
| Y122X | Q493X | K710X | W1089X | Q1313X |
| E193X | W496X | L732X | Y1092X | E1371X |
| L218X | C524X | R764X | W1098X | Q1382X |
| Q220X | Q525X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 405 + 1G→A | 1248 + 1G→A | 1811 + 1G→C | 3040G→C | 3600 + 2insT |
| 405 + 3A→C | 1249 − 1G→A | 1811 + 1.6kbA→G | (G970R) | 3850 − 1G→A |
| 406 − 1G→A | 1341 + 1G→A | 1812 − 1G→A | 3120G→A | 4005 + 1G→A |
| 621 + 1G→T | 1525 − 2A→G | 1898 + 1G→A | 3120 + 1G→A | 4374 + 1G→T |
| 711 + 1G→T | 1525 − 1G→A | 1898 + 1G→C | 3121 − 2A→G | |
| 182delT | 1119delA | 1782delA | 2732insA | 3876delA |
| 306insA | 1138insG | 1824delA | 2869insG | 3878delG |
| 365-366insT | 1154insTC | 2043delG | 2896insAG | 3905insT |
| 394delTT | 1161delC | 2143delT | 2942insT | 4016insT |
| 442delA | 1213delT | 2183AA→G$^a$ | 2957delT | 4021dupT |
| 444delA | 1259insA | 2184delA | 3007delG | 4040delA |
| 457TAT→G | 1288insTA | 2184insA | 3028delA | 4279insA |
| 541delC | 1471delA | 2307insA | 3171delC | 4326delTC |
| 574delA | 1497delGG | 2347delG | 3659delC | |
| 663delT | 1548delG | 2585delT | 3737delA | |
| 935delA | 1609delCA | 2594delGT | 3791delC | |
| 1078delT | 1677delTA | 2711delT | 3821delT | |
| CFTRdele2,3 | | 1461ins4 | 2991del32 | |
| CFTRdele22,23 | | 1924del7 | 3199del6$^a$ | |
| 124del23bp | | 2055del9→A | 3667ins4 | |
| 852del22 | | 2105-2117del13insAGAAA | 4010del4 | |
| 991del5 | | 2721del11 | 4209TGTT→AA | |
| A46D$^b$ | V520F | Y569D$^b$ | N1303K | |
| G85E | A559T$^b$ | L1065P | | |
| R347P | R560T | R1066C | | |
| L467P$^b$ | R560S | L1077P$^b$ | | |
| I507del | A561E | M1101K | | |

162. The method of embodiment 160, wherein the patient with a F508del/gating genotype has a gating mutation chosen from G178R, S549N, S549R, G551D, G551S, G1244E, S1251N, S1255P, and G1349D.

163. The method of embodiment 160, wherein the patient with a F508del/residual function genotype has a residual function mutation chosen from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, K1060T, R117H, S1235R, I1027T, R668C, G576A, M470V, L997F, R75Q, R1070Q, R31C, D614G, G1069R, R1162L, E56K, A1067T, E193K, and K1060T.

164. A method of preparing a single tablet of any one of embodiments 1, 41, 59, 61, 71, 110, 127, 129, or 155, comprising
(a) mixing Compound I and the first and second solid dispersions to form a first mixture; and
(b) compressing a tablet mixture comprising the first mixture into a tablet.

165. The method of embodiment 164, wherein the tablet mixture further comprises one or more pharmaceutically acceptable excipients, and the method further comprises mixing the first mixture with said one or more excipients to form the tablet mixture.

166. The method of embodiment 164 or 165, further comprising coating the tablet.

167. A method of preparing a single tablet of embodiment 61 or 129, comprising
(a) mixing Compound I and the first and second solid dispersions to form a first mixture;
(b) mixing the first mixture with said microcrystalline cellulose, croscarmellose sodium and magnesium stearate to form a tablet mixture; and (c) compressing the tablet mixture into a tablet.

168. The method of embodiment 167, further comprising coating the tablet.

Additional exemplary embodiments of the disclosure include:

1. A pharmaceutical composition comprising
(a) 25 mg to 250 mg of Compound I:

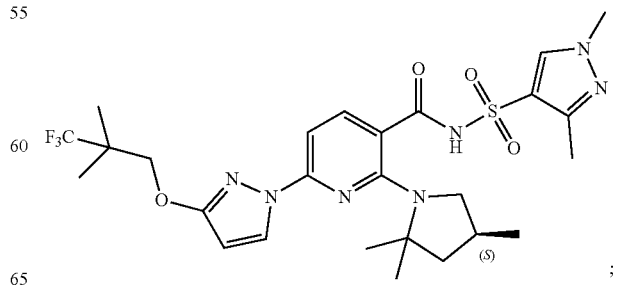

(b) a first solid dispersion comprising 20 mg to 150 mg of Compound II:

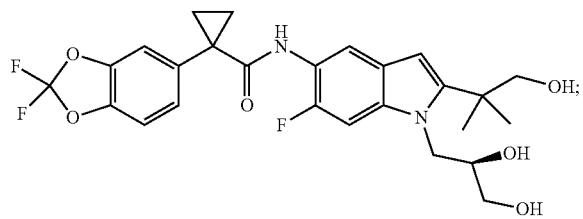 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and (c) a second solid dispersion comprising 25 mg to 200 mg of Compound III-d:

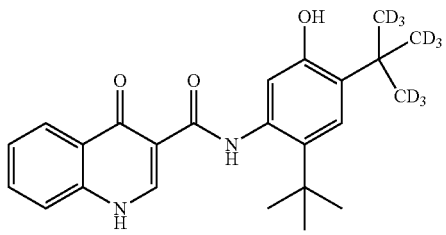 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and 10 wt % to 30 wt % of a polymer relative to the total weight of the second solid dispersion.

2. The pharmaceutical composition of embodiment 1, wherein at least one of the first or second solid dispersions is a spray-dried dispersion.

3. The pharmaceutical composition of embodiment 1, wherein both of the first and second solid dispersions are spray-dried dispersions.

4. The pharmaceutical composition of embodiment 1, wherein said polymer in the first solid dispersion is hydroxypropyl methylcellulose; and said polymer in the second solid dispersion is hydroxypropyl methylcelluloseacetate succinate.

5. The pharmaceutical composition of embodiment 1, wherein said polymer in the first solid dispersion is HPMC E15; and said polymer in the second solid dispersion is hydroxypropyl methylcelluloseacetate succinate H.

6. The pharmaceutical composition of embodiment 1, wherein said polymer in the first solid dispersion is HPMC E15; and said polymer in the second solid dispersion is hydroxypropyl methylcelluloseacetate succinate HG.

7. The pharmaceutical composition of any one of embodiments 1-6, comprising 25 mg to 75 mg or 80 mg to 120 mg of Compound I.

8. The pharmaceutical composition of any one of embodiments 1-6, comprising 80 mg to 120 mg, 85 mg to 115 mg, 90 mg to 110 mg, or 95 mg to 105 mg of Compound I.

9. The pharmaceutical composition of any one of embodiments 1-6, comprising 25 mg, 50 mg, or 100 mg of Compound I.

10. The pharmaceutical composition of any one of embodiments 1-6, comprising 75 mg to 125 mg of Compound I.

11. The pharmaceutical composition of any one of embodiments 1-10, wherein the first solid dispersion comprises 25 mg to 75 mg of Compound II.

12. The pharmaceutical composition of any one of embodiments 1-10, wherein the first solid dispersion comprises 50 mg of Compound II.

13. The pharmaceutical composition of any one of embodiments 1-12, wherein the second solid dispersion comprises 25 mg to 50 mg, 25 mg to 75 mg, 50 mg to 100 mg, 75 mg to 125 mg, or 125 mg to 175 mg of Compound III-d.

14. The pharmaceutical composition of any one of embodiments 1-12, wherein the second solid dispersion comprises 75 mg or 150 mg of Compound III-d.

15. The pharmaceutical composition of any one of embodiments 1-6, comprising 50 mg to 125 mg of Compound I; and wherein the first solid dispersion comprises 25 mg to 75 mg of Compound II; and the second solid dispersion comprises 75 mg to 125 mg of Compound III-d.

16. The pharmaceutical composition of any one of embodiments 1-6, comprising (a) 75 mg to 125 mg of Compound I; and wherein the first solid dispersion comprises 50 mg of Compound II; and the second solid dispersion comprises 75 mg of Compound III-d; or (b) 100 mg of Compound I; and wherein the first solid dispersion comprises 50 mg of Compound II; and the second solid dispersion comprises 75 mg of Compound III-d.

17. The pharmaceutical composition of any one of embodiments 1-17, wherein the second solid dispersion further comprises 0.5% sodium lauryl sulfate relative to the total weight of the second solid dispersion.

18. The pharmaceutical composition of any one of embodiments 1-18, further comprising one or more pharmaceutically acceptable excipients chosen from one or more fillers, disintegrants, lubricants, and glidants.

19. The pharmaceutical composition of embodiment 19, wherein:

fillers are chosen from microcrystalline cellulose, silicified microcrystalline cellulose, lactose monohydrate, dicalcium phosphate, mannitol, copovidone, hydroxypropyl cellulose, hydroxypropyl methylcellulose, methyl cellulose, ethyl cellulose, starch, Maltodextrin, agar, and guar gum;

disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose;

lubricants are chosen from magnesium stearate, sodium stearyl fumarate, calcium stearate, sodium stearate, stearic acid, and talc; and glidants are colloidal silicon dioxide.

20. The pharmaceutical composition of any one of embodiments 1-19, wherein Compound I is substantially crystalline, and wherein each of Compounds II and III-d are independently substantially amorphous.

21. The pharmaceutical composition of any one of embodiments 1-20, wherein the pharmaceutical composition is a tablet or in the form of granules.

22. The pharmaceutical composition of embodiment 1, further comprising microcrystalline cellulose; croscarmellose sodium; and optionally magnesium stearate.

23. The pharmaceutical composition of embodiment 22, wherein the pharmaceutical composition comprises 50 mg to 250 mg of microcrystalline cellulose; 10 mg to 45 mg of croscarmellose sodium; and optionally 1 mg to 10 mg of magnesium stearate.

24. The pharmaceutical composition of any one of embodiments 1-23, wherein the weight ratio of Compound I in (a): Compound II in (b): Compound III-d in (c) is 4:2:3, 2:2:3, or 1:2:3.

25. A pharmaceutical composition comprising:
(a) 10 wt % to 30 wt % of Compound I:

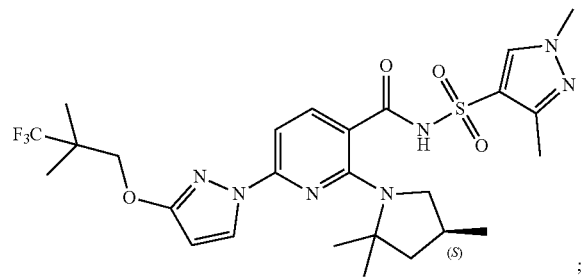

relative to the total weight of the pharmaceutical composition;
(b) 10 wt % to 30 wt % of a first solid dispersion relative to the total weight of the pharmaceutical composition, wherein the first solid dispersion comprises 70 wt % to 90 wt % of Compound II relative to the total weight of the first solid dispersion:

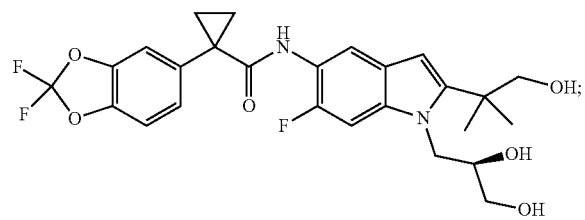 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and
(c) 10 wt % to 30 wt % of a second solid dispersion relative to the total weight of the pharmaceutical composition; wherein the second solid dispersion comprises 70 wt % to 90 wt % of Compound III-d relative to the total weight of the second solid dispersion:

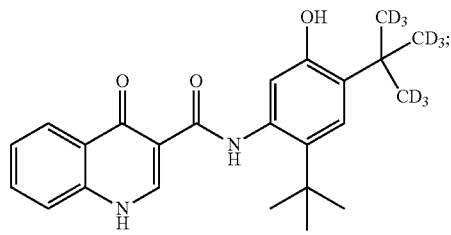 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and 10 wt % to 30 wt % of a polymer relative to the total weight of the second solid dispersion.
26. The pharmaceutical composition of embodiment 25, wherein at least one of the first or second solid dispersions is a spray-dried dispersion.
27. The pharmaceutical composition of embodiment 25, wherein both of the first and second solid dispersions are spray-dried dispersions.
28. The pharmaceutical composition of embodiment 25, wherein said polymer in the first solid dispersion is hydroxypropyl methylcellulose; and said polymer in the second solid dispersion is hydroxypropyl methylcellulose acetate succinate.
29. The pharmaceutical composition of embodiment 25, wherein said polymer in the first solid dispersion is hydroxypropyl methylcellulose (HPMC E15); and said polymer in the second solid dispersion is hydroxypropyl methylcellulose acetate succinate H.
30. The pharmaceutical composition of embodiment 25, wherein:
the first solid dispersion comprises 70 wt % to 85 wt % of Compound II relative to the total weight of the first solid dispersion, and the polymer is hydroxypropyl methylcellulose in an amount of 15 wt % to 30 wt % relative to the total weight of the first solid dispersion; and
the second solid dispersion comprises 70 wt % to 85 wt % of Compound III-d relative to the total weight of the second solid dispersion, 0.5% sodium lauryl sulfate relative to the total weight of the second solid dispersion, and the polymer is hydroxypropyl methylcellulose acetate succinate in an amount of 14.5 wt % to 29.5 wt % relative to the total weight of the second solid dispersion.
31. The pharmaceutical composition of any one of embodiments 25-30, wherein the first solid dispersion comprises 75 wt % to 85 wt % of Compound II relative to the total weight of the first solid dispersion.
32. The pharmaceutical composition of any one of embodiments 25-31, wherein the first solid dispersion comprises 80 wt % of Compound II relative to the total weight of the first solid dispersion; and 20 wt % of hydroxypropyl methylcellulose relative to the total weight of the first solid dispersion.
33. The pharmaceutical composition of any one of embodiments 25-32, wherein the second solid dispersion comprises 75 wt % to 85 wt % of Compound III-d relative to the total weight of the second solid dispersion.
34. The pharmaceutical composition of any one of embodiments 25-33, wherein the second solid dispersion comprises 80 wt % of Compound III-d relative to the total weight of the second solid dispersion; 0.5% of sodium lauryl sulfate relative to the total weight of the second solid dispersion, and 19.5 wt % of hydroxypropyl methylcellulose acetate succinate relative to the total weight of the second solid dispersion.
35. The pharmaceutical composition of any one of embodiments 25-34, further comprising one or more pharmaceutically acceptable excipients chosen from one or more fillers, disintegrants, lubricants, and glidants.
36. The pharmaceutical composition of embodiment 35, wherein:
filler are chosen from microcrystalline cellulose, silicified microcrystalline cellulose, lactose monohydrate, dicalcium phosphate, mannitol, copovidone, hydroxypropyl cellulose, hydroxypropyl methylcellulose, methyl cellulose, ethyl cellulose, starch, Maltodextrin, agar, and guar gum;
disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose;
lubricants are chosen from magnesium stearate, sodium stearyl fumarate, calcium stearate, sodium stearate, stearic acid, and talc; and
glidants are colloidal silicon dioxide.
37. The pharmaceutical composition of any one of embodiments 25-36, wherein Compound I is substantially crystalline, and wherein each of Compounds II and III-d is independently substantially amorphous.
38. The pharmaceutical composition of any one of embodiments 25-37, wherein the pharmaceutical composition is a tablet or in the form of granules.

39. The pharmaceutical composition of embodiment 35, further comprising microcrystalline cellulose; croscarmellose sodium; and magnesium stearate.
40. The pharmaceutical composition of embodiment 39, wherein the pharmaceutical composition comprises 50 mg to 250 mg of microcrystalline cellulose; 10 mg to 45 mg of croscarmellose sodium; and optionally 1 mg to 10 mg of magnesium stearate.
41. The pharmaceutical composition of embodiment 39, wherein the pharmaceutical composition comprises 15 wt % to 45 wt % of microcrystalline cellulose relative to the total weight of the pharmaceutical composition; 1 wt % to 10 wt % of croscarmellose sodium; and optionally 0.5 wt % to 3 wt % mg of magnesium stearate.
42. The pharmaceutical composition of any one of embodiments 25-41, wherein the weight ratio of Compound I in (a): Compound II in (b): Compound III-d in (c) is 4:2:3, 2:2:3 or 1:2:3.
43. A pharmaceutical composition comprising:
(a) Compound I:

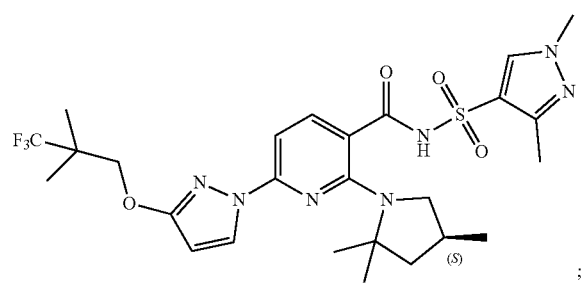

(b) a first solid dispersion,
wherein the first solid dispersion comprises 70 wt % to 90 wt % of Compound II relative to the total weight of the first solid dispersion:

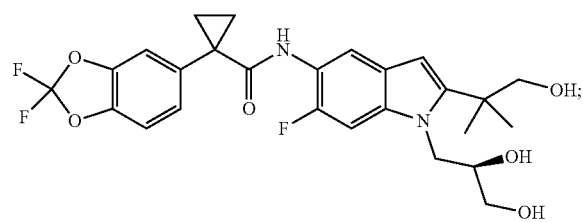 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer; and
(c) a second solid dispersion;
wherein the second solid dispersion comprises 70 wt % to 90 wt % of Compound III-d relative to the total weight of the second solid dispersion:

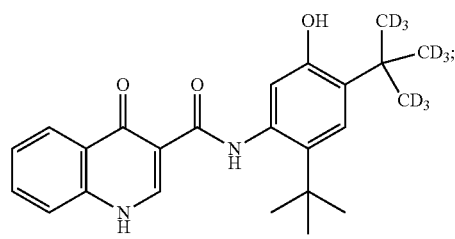 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

and 10 wt % to 30 wt % of a polymer, wherein the weight ratio of Compound I in (a): Compound II in (b): Compound III-d in (c) ranges from 1-4:2:3.
44. The pharmaceutical composition of embodiment 43, wherein at least one of the second or third solid dispersions is a spray-dried dispersion.
45. The pharmaceutical composition of embodiment 43, wherein both of the first and second solid dispersions are spray-dried dispersions.
46. The pharmaceutical composition of embodiment 43, wherein said polymer in the first solid dispersion is hydroxypropyl methylcellulose; and said polymer in the second solid dispersion is hydroxypropyl methylcellulose acetate succinate.
47. The pharmaceutical composition of embodiment 43, wherein said polymer in the first solid dispersion is hydroxypropyl methylcellulose (HPMC E15); and said polymer in the second solid dispersion is hydroxypropyl methylcellulose acetate succinate H.
48. The pharmaceutical composition of embodiment 43, wherein:
the first solid dispersion comprises 70 wt % to 85 wt % of Compound II relative to the total weight of the first solid dispersion, and the polymer is hydroxypropyl methylcellulose in an amount of 15 wt % to 30 wt % relative to the total weight of the first solid dispersion; and
the second solid dispersion comprises 70 wt % to 85 wt % of Compound III-d relative to the total weight of the second solid dispersion, 0.5% sodium lauryl sulfate relative to the total weight of the second solid dispersion, and the polymer is hydroxypropyl methylcellulose acetate succinate in an amount of 14.5 wt % to 29.5 wt % relative to the total weight of the second solid dispersion.
49. The pharmaceutical composition of any one of embodiments 43-48, wherein the first solid dispersion comprises 75 wt % to 85 wt % of Compound II relative to the total weight of the first solid dispersion.
50. The pharmaceutical composition of any one of embodiments 43-49, wherein the first solid dispersion comprises 80 wt % of Compound II relative to the total weight of the first solid dispersion; and 20 wt % of hydroxypropyl methylcellulose relative to the total weight of the first solid dispersion.
51. The pharmaceutical composition of any one of embodiments 43-50, wherein the second solid dispersion comprises 75 wt % to 85 wt % of Compound III-d relative to the total weight of the second solid dispersion.
52. The pharmaceutical composition of any one of embodiments 43-51, wherein the second solid dispersion comprises 80 wt % of Compound III-d relative to the total weight of the second solid dispersion; 0.5% of sodium lauryl sulfate relative to the total weight of the second solid dispersion, and 19.5 wt % of hydroxypropyl methylcellulose acetate succinate relative to the total weight of the second solid dispersion.
53. The pharmaceutical composition of any one of embodiments 43-52, further comprising one or more pharmaceutically acceptable excipients chosen from one or more fillers, disintegrants, lubricants, and glidants.
54. The pharmaceutical composition of embodiment 53, wherein:
fillers are chosen from microcrystalline cellulose, silicified microcrystalline cellulose, lactose monohydrate, dicalcium phosphate, mannitol, copovidone, hydroxypropyl cellulose, hydroxypropyl methylcellulose, methyl cellulose, ethyl cellulose, starch, Maltodextrin, agar, and guar gum;
disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose;
lubricants are chosen from magnesium stearate, sodium stearyl fumarate, calcium stearate, sodium stearate, stearic acid, and talc; and
glidants are colloidal silicon dioxide.

55. The pharmaceutical composition of any one of embodiments 43-54, wherein Compound I is substantially crystalline, and wherein each of Compounds II and III-d is independently substantially amorphous.

56. The pharmaceutical composition of any one of embodiments 43-55, wherein the pharmaceutical composition is a tablet or in the form of granules.

57. The pharmaceutical composition of any one of embodiments 43-56, wherein the weight ratio of Compound I in (a): Compound II in (b): Compound III-d in (c) is 4:2:3, 2:2:3 or 1:2:3.

58. The pharmaceutical composition of embodiment 43, further comprising microcrystalline cellulose; croscarmellose sodium; and magnesium stearate.

59. The pharmaceutical composition of embodiment 58, wherein the pharmaceutical composition comprises 50 mg to 250 mg of microcrystalline cellulose; 10 mg to 45 mg of croscarmellose sodium; and optionally 1 mg to 10 mg of magnesium stearate.

60. The pharmaceutical composition of embodiment 58, wherein the pharmaceutical composition comprises 15 wt % to 45 wt % of microcrystalline cellulose relative to the total weight of the pharmaceutical composition; 1 wt % to 10 wt % of croscarmellose sodium; and optionally 0.5 wt % to 3 wt % mg of magnesium stearate.

61. A single tablet comprising:
(a) 25 mg to 125 mg of Compound I:

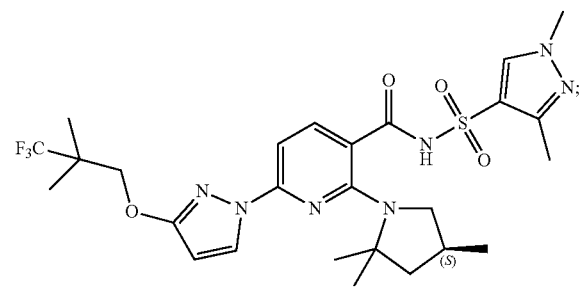

(b) 60 mg to 65 mg of a first solid dispersion comprising 80 wt % Compound II relative to the total weight of the first solid dispersion:

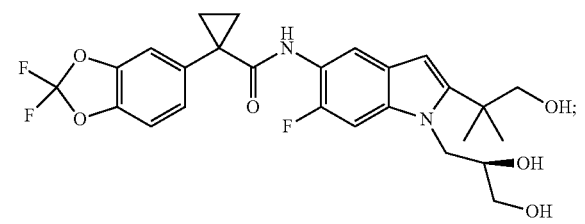 [SMILES: CC(C)(CO)c1cc2cc(NC(=O)C3(c4ccc5c(c4)OC(F)(F)O5)CC3)c(F)cc2n1C[C@@H](O)CO]

and 20 wt % of a hydroxypropyl methylcellulose relative to the total weight of the first solid dispersion; and
(c) 90 mg to 95 mg of a second solid dispersion comprising 80 wt % of Compound III-d relative to the total weight of the second solid dispersion:

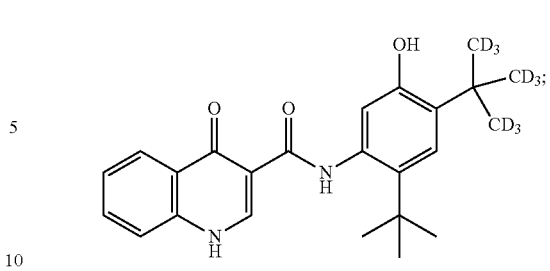

0.5 wt % of sodium lauryl sulfate relative to the total weight of the second solid dispersion; and 19.5 wt % of a hydroxypropyl methylcellulose acetate succinate to the total weight of the second solid dispersion
(d) 75 mg to 230 mg of microcrystalline cellulose;
(e) 20 mg to 45 mg of croscarmellose sodium; and
(f) 2 mg to 7 mg of magnesium stearate.

62. The single tablet of embodiment 61, comprising:
(a) 90 mg to 110 mg or 35 mg to 75 mg of Compound I;
(b) 60 mg to 65 mg of said first solid dispersion;
(c) 90 mg to 95 mg of said second solid dispersion;
(d) 190 mg to 205 mg of said microcrystalline cellulose;
(e) 25 mg to 35 mg of said croscarmellose sodium; and
(f) 3 mg to 7 mg of magnesium stearate.

63. The single tablet of embodiment 61, comprising:
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 85 mg to 95 mg of said microcrystalline cellulose; and
(f) 2 mg to 6 mg of magnesium stearate.

64. The single tablet of embodiment 61, comprising:
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 200 mg of said microcrystalline cellulose; and
(f) 3 mg to 7 mg of magnesium stearate.

65. The single tablet of embodiment 61, comprising:
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 85 mg to 95 mg of said microcrystalline cellulose; and
(f) 2 mg to 6 mg of magnesium stearate.

66. The single tablet of embodiment 61, comprising:
(a) 90 mg to 110 mg of Compound I;
(b) 60 mg to 65 mg of said first solid dispersion;
(c) 90 mg to 95 mg of said second solid dispersion;
(d) 20 mg to 30 mg of said croscarmellose sodium;
(e) 135 mg to 145 mg of said microcrystalline cellulose; and
(f) 2 mg to 6 mg of magnesium stearate.

67. The single tablet of embodiment 61, comprising:
(a) 90 mg to 110 mg of Compound I;
(b) 60 mg to 65 mg of said first solid dispersion;
(c) 90 mg to 95 mg of said second solid dispersion;
(d) 35 mg to 40 mg of said croscarmellose sodium;
(e) 105 mg to 115 mg of lactose monohydrate;
(f) 220 mg to 230 mg of said microcrystalline cellulose;
(g) 1 mg to 5 mg of colloidal silicon dioxide; and
(h) 4 mg to 7 mg of magnesium stearate.

68. The single tablet of embodiment 61, comprising:
(a) 90 mg to 110 mg of Compound I;
(b) 60 mg to 65 mg of said first solid dispersion;
(c) 90 mg to 95 mg of said second solid dispersion;
(d) 20 mg to 30 mg of said croscarmellose sodium;

(e) 40 mg to 50 mg of lactose monohydrate;
(f) 90 mg to 100 mg of said microcrystalline cellulose;
(g) 1 mg to 5 mg of colloidal silicon dioxide; and
(h) 2 mg to 7 mg of magnesium stearate.

69. The single tablet of embodiment 61, comprising:
(a) 90 mg to 110 mg of Compound I;
(b) 60 mg to 65 mg of said first solid dispersion;
(c) 90 mg to 95 mg of said second solid dispersion;
(d) 20 mg to 30 mg of said croscarmellose sodium;
(e) 135 mg to 145 mg of said microcrystalline cellulose;
(f) 1 mg to 5 mg of colloidal silicon dioxide; and
(g) 2 mg to 7 mg of magnesium stearate.

70. The single tablet of embodiment 61, comprising:
(a) 90 mg to 110 mg of Compound I;
(b) 60 mg to 65 mg of said first solid dispersion;
(c) 90 mg to 95 mg of said second solid dispersion;
(d) 20 mg to 30 mg of said croscarmellose sodium;
(e) 135 mg to 145 mg of said microcrystalline cellulose; and
(f) 2 mg to 7 mg of magnesium stearate.

71. A pharmaceutical composition comprising
(a) 15 mg to 250 mg of Compound I:

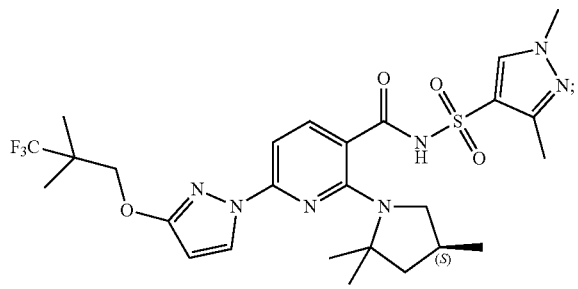

(b) a first solid dispersion comprising 10 mg to 150 mg of Compound II:

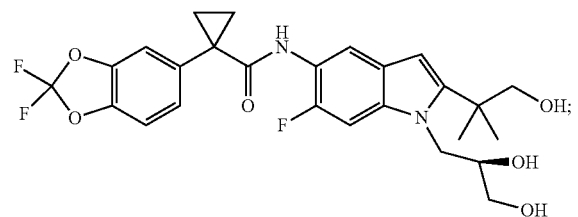 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt of a polymer relative to the total weight of the first solid dispersion; and (c) a second solid dispersion comprising 25 mg to 200 mg of Compound III:

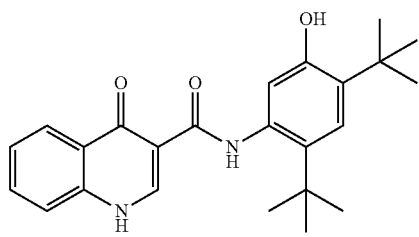 [SMILES: CC(C)(C)c1cc(C(C)(C)C)c(NC(=O)c2c[nH]c3ccccc3c2=O)cc1O]

and 10 wt % to 30 wt % of a polymer relative to the total weight of the second solid dispersion.

72. The pharmaceutical composition of embodiment 71, wherein at least one of the first or second solid dispersions is a spray-dried dispersion.

73. The pharmaceutical composition of embodiment 71, wherein both of the first and second solid dispersions are spray-dried dispersions.

74. The pharmaceutical composition of embodiment 71, wherein said polymer in the first solid dispersion is hydroxypropyl methylcellulose; and said polymer in the second solid dispersion is hydroxypropyl methylcellulose acetate succinate.

75. The pharmaceutical composition of embodiment 71, wherein said polymer in the first solid dispersion is HPMC E15; and said polymer in the second solid dispersion is hydroxypropyl methylcellulose acetate succinate H.

76. The pharmaceutical composition of embodiment 71, wherein said polymer in the first solid dispersion is HPMC E15; and said polymer in the second solid dispersion is hydroxypropyl methylcellulose acetate succinate HG.

77. The pharmaceutical composition of any one of embodiments 71-76, comprising 25 mg to 75 mg or 80 mg to 120 mg of Compound I.

78. The pharmaceutical composition of any one of embodiments 71-76, comprising 80 mg to 120 mg, 85 mg to 115 mg, 90 mg to 110 mg, or 95 mg to 105 mg of Compound I.

79. The pharmaceutical composition of any one of embodiments 71-76, comprising 25 mg, 50 mg, or 100 mg of Compound I.

80. The pharmaceutical composition of any one of embodiments 71-76, comprising 75 mg to 125 mg of Compound I.

81. The pharmaceutical composition of any one of embodiments 71-80, wherein the first solid dispersion comprises 25 mg to 75 mg of Compound II.

82. The pharmaceutical composition of any one of embodiments 71-80, wherein the first solid dispersion comprises 50 mg of Compound II.

83. The pharmaceutical composition of any one of embodiments 71-82, wherein the second solid dispersion comprises 25 mg to 50 mg, 25 mg to 75 mg, 50 mg to 100 mg, 75 mg to 125 mg, or 125 mg to 175 mg of Compound III.

84. The pharmaceutical composition of any one of embodiments 71-82, wherein the second solid dispersion comprises 75 mg of Compound III.

85. The pharmaceutical composition of any one of embodiments 71-76, comprising
(a) 50 mg to 125 mg of Compound I; and wherein
the first solid dispersion comprises 25 mg to 75 mg of Compound II; and
the second solid dispersion comprises 50 mg to 175 mg of Compound III; or
(b) 70 mg to 240 mg of Compound I; and wherein
the first solid dispersion comprises 30 mg to 120 mg of Compound II; and
the second solid dispersion comprises 50 mg to 170 mg of Compound III; or
(c) 30 mg to 120 mg of Compound I; and wherein
the first solid dispersion comprises 15 mg to 60 mg of Compound II; and
the second solid dispersion comprises 20 mg to 90 mg of Compound III; or
(d) 30 mg to 120 mg of Compound I; and wherein
the first solid dispersion comprises 15 mg to 60 mg of Compound II; and the second solid dispersion comprises 50 mg to 170 mg of Compound III; or
(e) 15 mg to 55 mg of Compound I; and wherein
the first solid dispersion comprises 10 mg to 50 mg of Compound II; and
the second solid dispersion comprises 20 mg to 90 mg of Compound III.

86. The pharmaceutical composition of any one of embodiments 71-76, comprising
(a) 75 mg to 125 mg of Compound I; and wherein
the first solid dispersion comprises 50 mg of Compound II; and
the second solid dispersion comprises 75 mg of Compound III; or
(b) 100 mg of Compound I; and wherein
the first solid dispersion comprises 50 mg of Compound II; and
the second solid dispersion comprises 75 mg of Compound III; or
(c) 200 mg of Compound I; and wherein
the first solid dispersion comprises 100 mg of Compound II; and
the second solid dispersion comprises 150 mg of Compound III; or
(d) 100 mg of Compound I; and wherein
the first solid dispersion comprises 50 mg of Compound II; and
the second solid dispersion comprises 150 mg of Compound III; or
(e) 50 mg of Compound I; and wherein
the first solid dispersion comprises 25 mg of Compound II; and
the second solid dispersion comprises 75 mg of Compound III; or
(f) 100 mg of Compound I; and wherein
the first solid dispersion comprises 100 mg of Compound II; and
the second solid dispersion comprises 150 mg of Compound III; or
(g) 50 mg of Compound I; and wherein
the first solid dispersion comprises 50 mg of Compound II; and
the second solid dispersion comprises 75 mg of Compound III; or
(h) 50 mg of Compound I; and wherein
the first solid dispersion comprises 50 mg of Compound II; and
the second solid dispersion comprises 150 mg of Compound III; or
(i) 25 mg of Compound I; and wherein
the first solid dispersion comprises 25 mg of Compound II; and
the second solid dispersion comprises 150 mg of Compound III; or
(j) 25 mg of Compound I; and wherein
the first solid dispersion comprises 50 mg of Compound II; and
the second solid dispersion comprises 150 mg of Compound III; or
(k) 12.5 mg of Compound I; and wherein
the first solid dispersion comprises 25 mg of Compound II; and
the second solid dispersion comprises 75 mg of Compound III; or
(l) 30 mg to 70 mg of Compound I; and wherein
the first solid dispersion comprises 15 mg to 40 mg of Compound II; and
the second solid dispersion comprises 20 mg to 55 mg of Compound III; or
(m) 70 mg to 130 mg of Compound I; and wherein
the first solid dispersion comprises 30 mg to 70 mg of Compound II; and
the second solid dispersion comprises 50 mg to 100 mg of Compound III.

87. The pharmaceutical composition of any one of embodiments 71-86, wherein the second solid dispersion further comprises 0.5% sodium lauryl sulfate relative to the total weight of the second solid dispersion.

88. The pharmaceutical composition of any one of embodiments 71-87, further comprising one or more pharmaceutically acceptable excipients chosen from one or more fillers, disintegrants, lubricants, and glidants.

89. The pharmaceutical composition of embodiment 88, wherein:
said fillers are chosen from microcrystalline cellulose, silicified microcrystalline cellulose, lactose monohydrate, dicalcium phosphate, mannitol, copovidone, hydroxypropyl cellulose, hydroxypropyl methylcellulose, methyl cellulose, ethyl cellulose, starch, Maltodextrin, agar, and guar gum;
said disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose;
said lubricants are chosen from magnesium stearate, sodium stearyl fumarate, calcium stearate, sodium stearate, stearic acid, and talc; and
said glidants are chosen from colloidal silicon dioxides.

90. The pharmaceutical composition any one of embodiments 71-89, wherein Compound I is substantially crystalline, and wherein each of Compounds II and III are independently substantially amorphous.

91. The pharmaceutical composition of embodiment 71, further comprising microcrystalline cellulose; croscarmellose sodium; and optionally magnesium stearate.

92. The pharmaceutical composition of embodiment 91, wherein the pharmaceutical composition comprises 50 mg to 250 mg of microcrystalline cellulose; 10 mg to 45 mg of croscarmellose sodium; and optionally 1 mg to 10 mg of magnesium stearate.

93. The pharmaceutical composition of any one of embodiments 71-92, wherein the pharmaceutical composition comprises 25 mg to 250 mg of Compound I in (a): said first solid dispersion comprises 20 mg to 150 mg of Compound II in (b): and said second solid dispersion comprises 25 mg to 200 mg of Compound III.

94. The pharmaceutical composition of any one of embodiments 1-23, wherein the weight ratio of Compound I in (a): Compound II in (b): Compound III in (c) is 4:2:3, 2:1:3, 2:2:3, 1:1:3, 1:2:3, or 1:2:6.

95. A pharmaceutical composition comprising:
(a) 10 wt % to 30 wt % of Compound I:

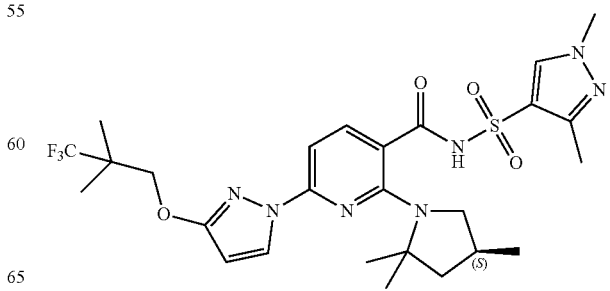

relative to the total weight of the pharmaceutical composition;
(b) 8 wt % to 30 wt % of a first solid dispersion relative to the total weight of the pharmaceutical composition, wherein the first solid dispersion comprises 70 wt % to 90 wt % of Compound II relative to the total weight of the first solid dispersion:

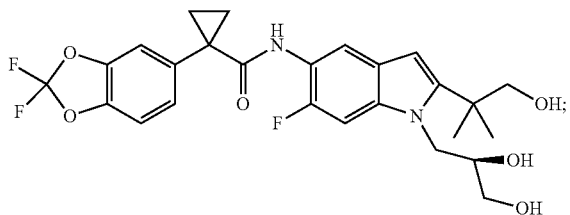 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and
(c) 10 wt % to 45 wt % of a second solid dispersion relative to the total weight of the pharmaceutical composition; wherein the second solid dispersion comprises 70 wt % to 90 wt % of Compound III relative to the total weight of the second solid dispersion:

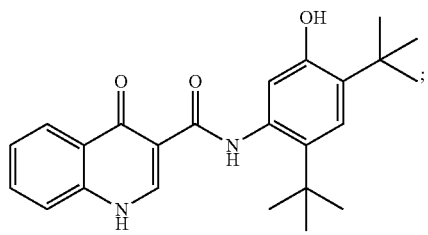 [SMILES: CC(C)(C)c1cc(C(C)(C)C)c(NC(=O)c2c[nH]c3ccccc3c2=O)cc1O]

and 10 wt % to 30 wt % of a polymer relative to the total weight of the second solid dispersion.

96. The pharmaceutical composition of embodiment 95, wherein at least one of the second or third solid dispersions is a spray-dried dispersion.

97. The pharmaceutical composition of embodiment 95, wherein both of the first and second solid dispersions are spray-dried dispersions.

98. The pharmaceutical composition of embodiment 95, wherein said polymer in the first solid dispersion is hydroxypropyl methylcellulose; and said polymer in the second solid dispersion is hydroxypropyl methylcellulose acetate succinate.

99. The pharmaceutical composition of embodiment 95, wherein said polymer in the first solid dispersion is hydroxypropyl methylcellulose (HPMC E15); and said polymer in the second solid dispersion is hydroxypropyl methylcellulose acetate succinate H.

100. The pharmaceutical composition of embodiment 95, wherein:
the first solid dispersion comprises 70 wt % to 85 wt % of Compound II relative to the total weight of the first solid dispersion, and the polymer is hydroxypropyl methylcellulose in an amount of 15 wt % to 30 wt % relative to the total weight of the first solid dispersion; and
the second solid dispersion comprises 70 wt % to 85 wt % of Compound III relative to the total weight of the second solid dispersion, 0.5% sodium lauryl sulfate relative to the total weight of the second solid dispersion, and the polymer is hydroxypropyl methylcellulose acetate succinate in an amount of 14.5 wt % to 29.5 wt % relative to the total weight of the second solid dispersion.

101. The pharmaceutical composition of any one of embodiments 95-100, wherein the first solid dispersion comprises 75 wt % to 85 wt % of Compound II relative to the total weight of the first solid dispersion.

102. The pharmaceutical composition of any one of embodiments 95-100, wherein the first solid dispersion comprises 80 wt % of Compound II relative to the total weight of the first solid dispersion; and 20 wt % of hydroxypropyl methylcellulose relative to the total weight of the first solid dispersion.

103. The pharmaceutical composition of any one of embodiments 95-102, wherein the second solid dispersion comprises 75 wt % to 85 wt % of Compound III relative to the total weight of the second solid dispersion.

104. The pharmaceutical composition of any one of embodiments 95-103, wherein the second solid dispersion comprises 80 wt % of Compound III relative to the total weight of the second solid dispersion; 0.5% of sodium lauryl sulfate relative to the total weight of the second solid dispersion, and 19.5 wt % of hydroxypropyl methylcellulose acetate succinate relative to the total weight of the second solid dispersion.

105. The pharmaceutical composition of any one of embodiments 95-104, further comprising one or more pharmaceutically acceptable excipients chosen from one or more fillers, disintegrants, and lubricants.

106. The pharmaceutical composition of embodiment 105, wherein:
said fillers are chosen from microcrystalline cellulose, silicified microcrystalline cellulose, lactose, dicalcium phosphate, mannitol, copovidone, hydroxypropyl cellulose, hydroxypropyl methylcellulose, methyl cellulose, ethyl cellulose, starch, Maltodextrin, agar, and guar gum;
said disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose; and
said lubricants are chosen from magnesium stearate, sodium stearyl fumarate, calcium stearate, sodium stearate, stearic acid, and talc.

107. The pharmaceutical composition of any one of embodiments 95-107, wherein the pharmaceutical composition is a tablet or in the form of granules.

108. The pharmaceutical composition of embodiment 95, further comprising microcrystalline cellulose; croscarmellose sodium; and optionally magnesium stearate.

109. The pharmaceutical composition of embodiment 108, wherein the pharmaceutical composition comprises 15 wt % to 45 wt % of microcrystalline cellulose relative to the total weight of the pharmaceutical composition; 1 wt % to 10 wt % of croscarmellose sodium; and optionally 0.5 wt % to 3 wt % mg of magnesium stearate.

110. The pharmaceutical composition of any one of embodiments 95-109, wherein the pharmaceutical composition comprises 10 wt % to 30 wt % of Compound I in (a); 8 wt % to 30 wt % of said first solid dispersion in (b); and 10 wt % to 30 wt % of said second solid dispersion in (c).

111. The pharmaceutical composition of any one of embodiments 95-110, wherein the weight ratio of Compound I in (a): Compound II in (b): Compound III in (c) is 4:2:3, 2:1:3, 2:2:3, 1:1:3, 1:2:3, or 1:2:6.

112. A pharmaceutical composition comprising:
(a) Compound I:

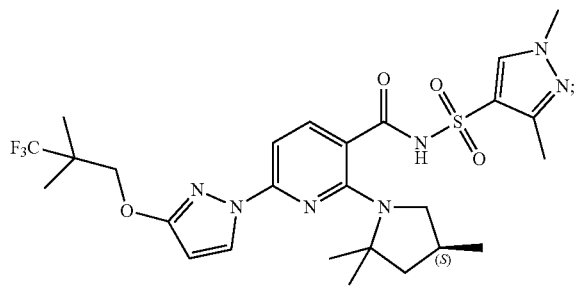

(b) a first solid dispersion comprising 70 wt % to 90 wt % of Compound II relative to the total weight of the first solid dispersion:

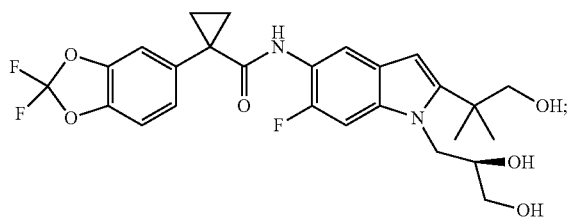 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and
(c) a second solid dispersion comprising 70 wt % to 90 wt % of Compound III relative to the total weight of the second solid dispersion:

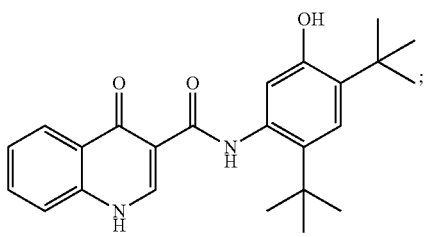 [SMILES: CC(C)(C)c1cc(C(C)(C)C)c(NC(=O)c2c[nH]c3ccccc3c2=O)cc1O]

and 10 wt % to 30 wt % of a polymer relative to the total weight of the second solid dispersion, wherein
the weight ratio of Compound I in (a): Compound II in (b): Compound III in (c) in a range of 4:2:3-6.

113. The pharmaceutical composition of embodiment 112, wherein at least one of the second or third solid dispersions is a spray-dried dispersion.

114. The pharmaceutical composition of embodiment 112, wherein both of the first and second solid dispersions are spray-dried dispersions.

115. The pharmaceutical composition of embodiment 112, wherein said polymer in the first solid dispersion is hydroxypropyl methylcellulose; and said polymer in the second solid dispersion is hydroxypropyl methylcellulose acetate succinate.

116. The pharmaceutical composition of embodiment 112, wherein said polymer in the first solid dispersion is hydroxypropyl methylcellulose (HPMC E15); and said polymer in the second solid dispersion is hydroxypropyl methylcellulose acetate succinate H.

117. The pharmaceutical composition of embodiment 112, wherein:
the first solid dispersion comprises 70 wt % to 85 wt % of Compound II relative to the total weight of the first solid dispersion, and the polymer is hydroxypropyl methylcellulose in an amount of 15 wt % to 30 wt % relative to the total weight of the first solid dispersion; and
the second solid dispersion comprises 70 wt % to 85 wt % of Compound III relative to the total weight of the second solid dispersion, 0.5% sodium lauryl sulfate relative to the total weight of the second solid dispersion, and the polymer is hydroxypropyl methylcellulose acetate succinate in an amount of 14.5 wt % to 29.5 wt % relative to the total weight of the second solid dispersion.

118. The pharmaceutical composition of any one of embodiments 112-117, wherein the first solid dispersion comprises 75 wt % to 85 wt % of Compound II relative to the total weight of the first solid dispersion.

119. The pharmaceutical composition of any one of embodiments 112-117, wherein the first solid dispersion comprises 80 wt % of Compound II relative to the total weight of the first solid dispersion; and 20 wt % of hydroxypropyl methylcellulose relative to the total weight of the first solid dispersion.

120. The pharmaceutical composition of any one of embodiments 112-119, wherein the second solid dispersion comprises 75 wt % to 85 wt % of Compound III relative to the total weight of the second solid dispersion.

121. The pharmaceutical composition of any one of embodiments 112-120, wherein the second solid dispersion comprises 80 wt % of Compound III relative to the total weight of the second solid dispersion; 0.5% of sodium lauryl sulfate relative to the total weight of the second solid dispersion, and 19.5 wt % of hydroxypropyl methylcellulose acetate succinate relative to the total weight of the second solid dispersion.

122. The pharmaceutical composition of any one of embodiments 112-121, further comprising one or more pharmaceutically acceptable excipients chosen from one or more fillers, disintegrants, and lubricants.

123. The pharmaceutical composition of embodiment 122, wherein:
said fillers are chosen from microcrystalline cellulose, silicified microcrystalline cellulose, lactose, dicalcium phosphate, mannitol, copovidone, hydroxypropyl cellulose, hydroxypropyl methylcellulose, methyl cellulose, ethyl cellulose, starch, Maltodextrin, agar, and guar gum;
said disintegrants are chosen from croscarmellose sodium, sodium starch glycolate, crospovidone, corn or pre-gelatinized starch, sodium carboxymethyl cellulose, calcium carboxymethyl cellulose, and microcrystalline cellulose; and
said lubricants are chosen from magnesium stearate, sodium stearyl fumarate, calcium stearate, sodium stearate, stearic acid, and talc.

124. The pharmaceutical composition of any one of embodiments 112-123, wherein Compound I is substantially crystalline, and wherein each of Compounds II and III is independently substantially amorphous.

125. The pharmaceutical composition of any one of embodiments 112-124, wherein the pharmaceutical composition is a tablet or in the form of granules.

126. The pharmaceutical composition of embodiment 112, further comprising microcrystalline cellulose; croscarmellose sodium; and magnesium stearate.

127. The pharmaceutical composition of embodiment 58, wherein the pharmaceutical composition comprises 15 wt % to 45 wt % of microcrystalline cellulose relative to the total weight of the pharmaceutical composition; 1 wt % to 10 wt % of croscarmellose sodium; and 0.5 wt % to 3 wt % mg of magnesium stearate.

128. The pharmaceutical composition of embodiment 58, wherein the weight ratio of Compound I in (a): Compound II in (b): Compound III in (c) in 4:2:3, 2:1:3, 2:2:3, 1:1:3, 1:2:3, or 1:2:6.

129. A single tablet comprising:
(a) 25 mg to 125 mg of Compound I:

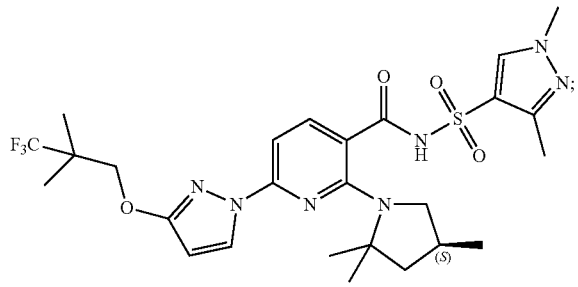

(b) 60 mg to 65 mg of a first solid dispersion comprising 80 wt % Compound II relative to the total weight of the first solid dispersion:

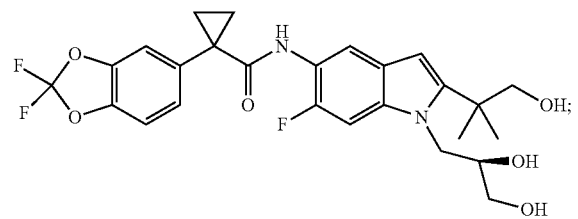 [SMILES: CC(C)(CO)c1cc2cc(NC(=O)C3(c4ccc5c(c4)OC(F)(F)O5)CC3)c(F)cc2n1C[C@@H](O)CO]

and 20 wt % of a hydroxypropyl methylcellulose relative to the total weight of the first solid dispersion; and
(c) 90 mg to 95 mg, to 65 mg to 190 mg of a second solid dispersion comprising 80 wt % of Compound III relative to the total weight of the second solid dispersion:

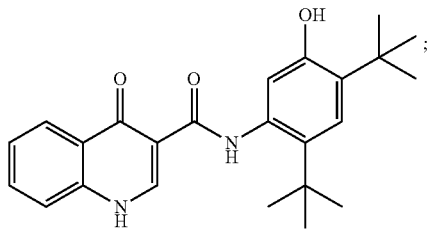 [SMILES: CC(C)(C)c1cc(C(C)(C)C)c(NC(=O)c2c[nH]c3ccccc3c2=O)cc1O]

0.5 wt % of sodium lauryl sulfate relative to the total weight of the second solid dispersion; and 19.5 wt % of a hydroxypropyl methylcellulose acetate succinate to the total weight of the second solid dispersion
(d) 85 mg to 275 mg of microcrystalline cellulose;
(e) 10 mg to 35 mg of croscarmellose sodium; and
(f) 2 mg to 7 mg of magnesium stearate.

130. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.

131. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.

132. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 20 mg to 25 mg of said croscarmellose sodium;
(e) 200 mg to 210 mg of said microcrystalline cellulose; and
(f) 2 mg to 7 mg of magnesium stearate.

133. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 20 mg to 25 mg of said croscarmellose sodium;
(e) 85 mg to 95 mg of said microcrystalline cellulose; and
(f) 2 mg to 6 mg of magnesium stearate.

134. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 20 mg to 25 mg of said croscarmellose sodium;
(e) 270 mg to 275 mg of said microcrystalline cellulose; and
(f) 2 mg to 7 mg of magnesium stearate.

135. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.

136. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.

137. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 12 mg to 17 mg of said croscarmellose sodium;
(e) 160 mg to 170 mg of said microcrystalline cellulose; and
(f) 2 mg to 7 mg of magnesium stearate.

138. The single tablet of embodiment 129, comprising
(a) 90 mg to 110 mg of Compound I;
(b) 60 mg to 65 mg of said first solid dispersion;
(c) 180 mg to 190 mg of said second solid dispersion;
(d) 10 mg to 20 mg of said croscarmellose sodium;
(e) 260 mg to 270 mg of said microcrystalline cellulose; and
(f) 2 mg to 7 mg of magnesium stearate.

139. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.

140. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 200 mg to 210 mg of said microcrystalline cellulose; and
(f) 2 mg to 7 mg of magnesium stearate.
141. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 85 mg to 95 mg of said microcrystalline cellulose; and
(f) 2 mg to 6 mg of magnesium stearate.
142. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 20 mg to 25 mg of said croscarmellose sodium;
(e) 270 mg to 275 mg of said microcrystalline cellulose; and
(f) 2 mg to 7 mg of magnesium stearate.
143. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.
144. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 205 mg of said microcrystalline cellulose; and
(f) 2 mg to 7 mg of magnesium stearate.
145. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 25 mg to 35 mg of said croscarmellose sodium;
(e) 195 mg to 200 mg of said microcrystalline cellulose; and
(f) 2 mg to 7 mg of magnesium stearate.
146. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 12 mg to 17 mg of said croscarmellose sodium;
(e) 160 mg to 170 mg of said microcrystalline cellulose; and
(f) 2 mg to 7 mg of magnesium stearate.
147. The single tablet of embodiment 129, comprising
(a) 90 mg to 110 mg of Compound I;
(b) 60 mg to 65 mg of said first solid dispersion;
(c) 90 mg to 95 mg of said second solid dispersion;
(d) 10 mg to 20 mg of said croscarmellose sodium;
(e) 260 mg to 270 mg of said microcrystalline cellulose; and
(f) 2 mg to 7 mg of magnesium stearate.

148. A single tablet comprising:
(a) 10 mg to 110 mg of Compound I:

(b) 25 mg to 70 mg of a first solid dispersion comprising 80 wt % Compound II relative to the total weight of the first solid dispersion:

and 20 wt % of a hydroxypropyl methylcellulose relative to the total weight of the first solid dispersion; and
(c) 85 mg to 195 mg, of a second solid dispersion comprising 80 wt % of Compound III relative to the total weight of the second solid dispersion:

0.5 wt % of sodium lauryl sulfate relative to the total weight of the second solid dispersion; and 19.5 wt % of a hydroxypropyl methylcellulose acetate succinate to the total weight of the second solid dispersion
(d) 10 mg to 45 mg of croscarmellose sodium; and
(e) 95 mg to 280 mg of microcrystalline cellulose; and
(f) 2 mg to 7 mg of magnesium stearate.
149. The single tablet of embodiment 148, comprising
(a) 95 mg to 105 mg of Compound I;
(b) 60 mg to 65 mg of said first solid dispersion;
(c) 185 mg to 190 mg of said second solid dispersion;
(d) 35 mg to 45 mg of said croscarmellose sodium;
(e) 260 mg to 280 mg of said microcrystalline cellulose; and
(f) 2 mg to 7 mg of magnesium stearate.
150. The single tablet of embodiment 148, comprising
(a) 45 mg to 55 mg of Compound I;
(b) 25 mg to 55 mg of said first solid dispersion;
(c) 90 mg to 100 mg of said second solid dispersion;

(d) 15 mg to 25 mg of said croscarmellose sodium;
(e) 125 mg to 145 mg of said microcrystalline cellulose; and
(f) 2 mg to 7 mg of magnesium stearate.
151. The single tablet of embodiment 148, comprising
(a) 45 mg to 55 mg of Compound I;
(b) 60 mg to 65 mg of said first solid dispersion;
(c) 185 mg to 190 mg of said second solid dispersion;
(d) 30 mg to 40 mg of said croscarmellose sodium;
(e) 220 mg to 245 mg of said microcrystalline cellulose; and
(f) 2 mg to 7 mg of magnesium stearate.
152. The single tablet of embodiment 148, comprising
(a) 20 mg to 30 mg of Compound I;
(b) 30 mg to 35 mg of said first solid dispersion;
(c) 90 mg to 100 mg of said second solid dispersion;
(d) 15 mg to 25 mg of said croscarmellose sodium;
(e) 110 mg to 120 mg of said microcrystalline cellulose; and
(f) 2 mg to 7 mg of magnesium stearate.
153. The single tablet of embodiment 148, comprising
(a) 20 mg to 30 mg of Compound I;
(b) 60 mg to 65 mg of said first solid dispersion;
(c) 185 mg to 190 mg of said second solid dispersion;
(d) 35 mg to 45 mg of said croscarmellose sodium;
(e) 200 mg to 220 mg of said microcrystalline cellulose; and
(f) 2 mg to 7 mg of magnesium stearate.
154. The single tablet of embodiment 148, comprising
(a) 10 mg to 15 mg of Compound I;
(b) 25 mg to 35 mg of said first solid dispersion;
(c) 90 mg to 100 mg of said second solid dispersion;
(d) 10 mg to 20 mg of said croscarmellose sodium;
(e) 100 mg to 115 mg of said microcrystalline cellulose; and
(f) 2 mg to 7 mg of magnesium stearate.
155. A pharmaceutical composition comprising
(a) 12 wt % to 30 wt % Compound I relative to the total weight of the pharmaceutical composition:

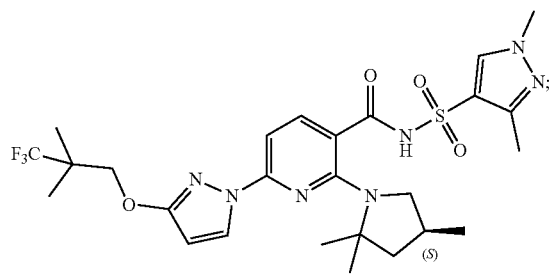

(b) 5 wt % to 15 wt % of Compound II relative to the total weight of the pharmaceutical composition:

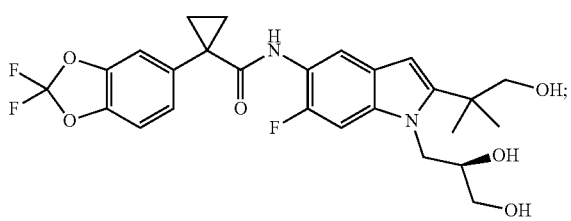 [SMILES: CC(C)(CO)c1cc2cc(NC(=O)C3(c4ccc5c(c4)OC(F)(F)O5)CC3)c(F)cc2n1C[C@@H](O)CO]

(c) 10 wt % to 25 wt % of Compound III or Compound III-d relative to the total weight of the pharmaceutical composition:

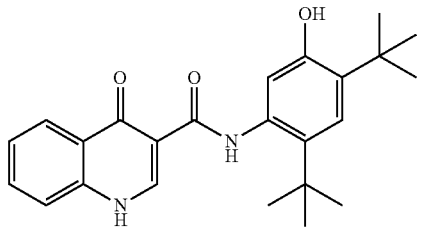

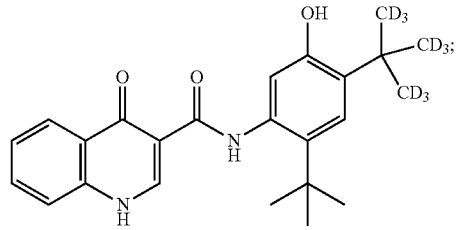

(d) 20 wt % to 45 wt % of microcrystalline cellulose relative to the total weight of the pharmaceutical composition;
(e) 3 wt %-8 wt % of croscarmellose sodium relative to the total weight of the pharmaceutical composition; and
(f) 0.5 wt % to 2 wt % of magnesium stearate relative to the total weight of the pharmaceutical composition.
156. The pharmaceutical composition of embodiment 155, wherein the pharmaceutical composition comprises:
(a) 18% to 23 wt % Compound I relative to the total weight of the pharmaceutical composition;
(b) 8 wt % to 12 wt % of Compound II relative to the total weight of the pharmaceutical composition;
(c) 13 wt % to 18 wt % of Compound III or Compound III-d relative to the total weight of the pharmaceutical composition;
(d) 35 wt % to 45 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.
157. The pharmaceutical composition of embodiment 155, wherein the pharmaceutical composition comprises:
(a) 15% to 25 wt % Compound I relative to the total weight of the pharmaceutical composition;
(b) 5 wt % to 10 wt % of Compound II relative to the total weight of the pharmaceutical composition;
(c) 7 wt % to 15 wt % of Compound III or Compound III-d relative to the total weight of the pharmaceutical composition;
(d) 30 wt % to 50 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.
158. The pharmaceutical composition of embodiment 155, wherein the pharmaceutical composition comprises:
(a) 20% to 25 wt % Compound I relative to the total weight of the pharmaceutical composition;
(b) 7 wt % to 15 wt % of Compound II relative to the total weight of the pharmaceutical composition;
(c) 15 wt % to 20 wt % of Compound III or Compound III-d relative to the total weight of the pharmaceutical composition;

(d) 15 wt % to 25 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.

159. The pharmaceutical composition of embodiment 155, wherein the pharmaceutical composition comprises:
(a) 20% to 25 wt % Compound I relative to the total weight of the pharmaceutical composition;
(b) 7 wt % to 15 wt % of Compound II relative to the total weight of the pharmaceutical composition;
(c) 15 wt % to 20 wt % of Compound III or Compound III-d relative to the total weight of the pharmaceutical composition;
(d) 25 wt % to 35 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.

160. The pharmaceutical composition of embodiment 155, wherein the pharmaceutical composition comprises:
(a) 22% to 28 wt % Compound I relative to the total weight of the pharmaceutical composition;
(b) 10 wt % to 15 wt % of Compound II relative to the total weight of the pharmaceutical composition;
(c) 15 wt % to 25 wt % of Compound III or Compound III-d relative to the total weight of the pharmaceutical composition;
(d) 15 wt % to 25 wt % of microcrystalline cellulose relative to the total weight of the pharmaceutical composition;
(e) 3 wt %-7 wt % of croscarmellose sodium relative to the total weight of the pharmaceutical composition; and
(f) 0.5 wt % to 1.5 wt % of magnesium stearate relative to the total weight of the pharmaceutical composition.

161. The pharmaceutical composition of embodiment 155, wherein the pharmaceutical composition comprises:
(a) 15% to 20 wt % Compound I relative to the total weight of the pharmaceutical composition;
(b) 7 wt % to 15 wt % of Compound II relative to the total weight of the pharmaceutical composition;
(c) 10 wt % to 15 wt % of Compound III or Compound III-d relative to the total weight of the pharmaceutical composition;
(d) 45 wt % to 55 wt % of microcrystalline cellulose relative to the total weight of the pharmaceutical composition;
(e) 3 wt %-5 wt % of croscarmellose sodium relative to the total weight of the pharmaceutical composition; and
(f) 0.5 wt % to 1.5 wt % of magnesium stearate relative to the total weight of the pharmaceutical composition.

162. A pharmaceutical composition comprising
(a) 12 wt % to 30 wt % Compound I relative to the total weight of the pharmaceutical composition:

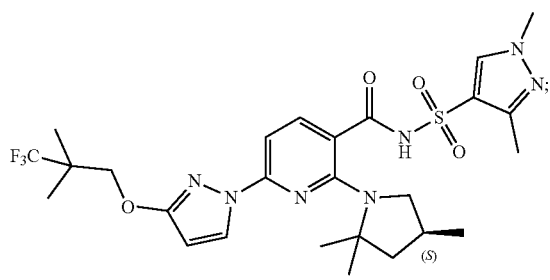

(b) 5 wt % to 15 wt % of Compound II relative to the total weight of the pharmaceutical composition:

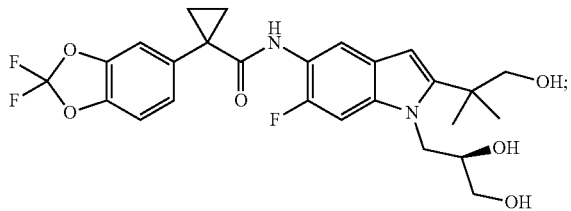 [SMILES: CC(C)(CO)c1cc2cc(NC(=O)C3(c4ccc5c(c4)OC(F)(F)O5)CC3)c(F)cc2n1C[C@@H](O)CO]

(c) 15 wt % to 35 wt % of Compound III relative to the total weight of the pharmaceutical composition:

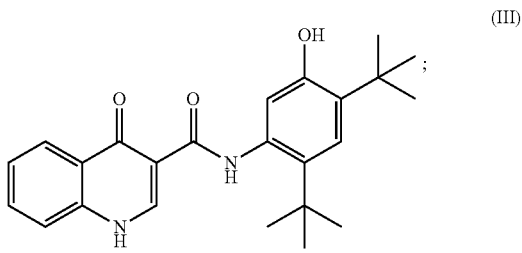 [SMILES: CC(C)(C)c1cc(C(C)(C)C)c(NC(=O)c2c[nH]c3ccccc3c2=O)cc1O]

(d) 15 wt % to 45 wt % of microcrystalline cellulose relative to the total weight of the pharmaceutical composition;
(e) 1 wt %-10 wt % of croscarmellose sodium relative to the total weight of the pharmaceutical composition; and
(f) 0.5 wt % to 3 wt % of magnesium stearate relative to the total weight of the pharmaceutical composition.

163. The pharmaceutical composition of any one of embodiments 155-162, wherein the pharmaceutical composition is a tablet.

164. The pharmaceutical composition or single tablet of any one of embodiments 1-163, wherein Compound I is Crystalline Form A.

165. The pharmaceutical composition or single tablet of embodiment 164, wherein Compound I Crystalline Form A is in substantially pure form.

166. The pharmaceutical composition or single tablet of embodiment 164, wherein Compound I Crystalline Form A is characterized by an X-ray powder diffractogram having a signal at at least three two-theta values chosen from 6.6±0.2, 7.6±0.2, 9.6±0.2, 12.4±0.2, 13.1±0.2, 15.2±0.2, 16.4±0.2, 18.2±0.2, and 18.6±0.2.

167. A method of treating cystic fibrosis in a patient comprising orally administering to the patient one or more of the single tablet or pharmaceutical composition of any one of embodiments 1-163.

168. The method of embodiment 167, wherein one or more of the single tablets or pharmaceutical compositions are administered once daily or twice daily.

169. The method of embodiment 168, wherein two tablets are administered once daily.

170. The method according to any one of embodiments 167-168, wherein said patient has cystic fibrosis is chosen from patients with F508del/minimal function genotypes, patients with F508del/F508del genotypes, patients with F508del/gating genotypes, and patients with F508del/residual function genotypes.

171. The method of embodiment 170, wherein the patient with a F508del/minimal function genotype has a minimal function mutation chosen from:

| Mutation | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 296 + 1G→T | 1248 + 1G→A | 1811 + 1G→C | 3040G→C | 3600 + 2insT |
| 405 + 1G→A | 1249 − 1G→A | 1811 + 1.6kbA→G | (G970R) | 3850 − 1G→A |
| 405 + 3A→C | 1341 + 1G→A | 1811 + 1643G→T | 3120G→A | 4005 + 1G→A |
| 406 − 1G→A | 1525 − 2A→G | 1812 − 1G→A | 3120 + 1G→A | 4374 + 1G→T |
| 621 + 1G→T | 1525 − 1G→A | 1898 + 1G→A | 3121-2A→G | |
| 711 + 1G→T | | 1898 + 1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |
| 365-366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G$^a$ | 3007delG | 4016insT |
| 457TAT→G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609del CA | 2594delGT | 3659delC | |
| CFTRdele1 | | CFTRdele16-17b | 1461ins4 | |
| CFTRdele2 | | CFTRdele17a,17b | 1924del7 | |
| CFTRdele2,3 | | CFTRdele17a-18 | 2055del9→A | |
| CFTRdele2-4 | | CFTRdele19 | 2105-2117del13insAGAAA | |
| CFTRdele3-10,14b-16 | | CFTRdele19-21 | 2372del8 | |
| CFTRdele4-7 | | CFTRdele21 | 2721del11 | |
| CFTRdele4-11 | | CFTRdele22-24 | 2991del32 | |
| CFTR50kbdel | | CFTRdele22,23 | 3121-977_3499 + 248del2515 | |
| CFTRdup6b-10 | | 124del23bp | 3667ins4 | |
| CFTRdele11 | | 602del14 | 4010del4 | |
| CFTRdele13,14a | | 852del22 | 4209TGTT→AA | |
| CFTRdele14b-17b | | 991del5 | | |
| A46D$^b$ | V520F | Y569D$^b$ | N1303K | |
| G85E | A559T$^b$ | L1065P | | |
| R347P | R560T | R1066C | | |
| L467P$^b$ | R560S | L1077P$^b$ | | |
| I507del | A561E | M1101K | | |

$^a$Also known as 2183delAA→G.

172. The method of embodiment 170, wherein the patient with a F508del/gating genotype has a gating mutation chosen from G178R, S549N, S549R, G551D, G551S, G1244E, S1251N, S1255P, and G1349D.

173. The method of embodiment 170, wherein the patient with a F508del/residual function genotype has a residual function mutation chosen from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, K1060T, R117H, S1235R, I1027T, R668C, G576A, M470V, L997F, R75Q, R1070Q, R31C, D614G, G1069R, R1162L, E56K, A1067T, E193K, and K1060T.

174. A method of preparing a single tablet of any one of embodiments 1, 41, 59, 61, 71, 110, 127, 129, 148, or 163, comprising (a) mixing Compound I and the first and second solid dispersions to form a first mixture; and (b) compressing a tablet mixture comprising the first mixture into a tablet.

175. The method of embodiment 174, wherein the tablet mixture further comprises one or more pharmaceutically acceptable excipients, and the method further comprises mixing the first mixture with said one or more excipients to form the tablet mixture.

176. The method of embodiment 173 or 174, further comprising coating the tablet.

177. A method of preparing a single tablet of embodiment 61 or 129, comprising (a) mixing Compound I and the first and second solid dispersions to form a first mixture;

(b) mixing the first mixture with said microcrystalline cellulose, croscarmellose sodium and magnesium stearate to form a tablet mixture; and (c) compressing the tablet mixture into a tablet.

178. The method of embodiment 177, further comprising coating the tablet.

179. A pharmaceutical composition having the following formulation:

| | Component | mg per tablet |
|---|---|---|
| Intragranular | Compound I | 50 |
| | a solid dispersion comprising: 80 wt % substantially amorphous Compound II, and 20 wt % HPMC | 31 |
| | a solid dispersion comprising: 80 wt % substantially amorphous Compound III, 19.5 wt % HPMCAS, and 0.5 wt % sodium lauryl sulfate | 47 |
| | Croscarmellose sodium | 15 |
| | Microcrystaline cellulose | 40 |
| Extragranular | Microcrystaline cellulose | 59 |
| | Magnesium stearate | 2 |
| | Total Core Tablet | 244 |
| | Film coat | 7 |
| | Total | 251 |

180. The pharmaceutical composition of any of embodiments 1-60, 71-128, 155-168, or 179, wherein the pharmaceutical composition is a tablet.

Methods of Preparing Compounds and Tablets

General Experimental Procedures

Reagents and starting materials were obtained by commercial sources unless otherwise stated and were used without purification. Proton and carbon NMR spectra were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

Final purity of compounds was determined by reversed phase UPLC using an Acquity UPLC BEH C18 column (50×2.1 mm, 1.7 μm particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+H]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30 m×0.25 mm×0.25 um_df) column, with a 2.0 mL/min flow rate (H$_2$ carrier gas), at an injection temperature of 220° C. and an oven temperature of 120° C., 15 minutes.

The powder x-ray diffraction measurements were performed using PANalytical's X-pert Pro diffractometer at room temperature with copper radiation (1.54060 Å). The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 3-40 degrees 2 theta with a step size of 0.017 degrees and a scan step time of 15.5 s.

Solid state $^{13}$C and $^{19}$F NMR data was obtained using Bruker-Biospin 400 MHz wide-bore spectrometer equipped with Bruker-Biospin 4 mm HFX probe was used. Samples were packed into 4 mm rotors and spun under Magic Angle Spinning (MAS) condition with typical spinning speed of 12.5 kHz. The proton relaxation time was estimated from $^1$H MAS T$_1$ saturation recovery relaxation experiment and used to set up proper recycle delay of the $^{13}$C cross-polarization (CP) MAS experiment. The fluorine relaxation time was estimated from $^{19}$F MAS T$_1$ saturation recovery relaxation experiment and used to set up proper recycle delay of the $^{19}$F MAS experiment. The CP contact time of CPMAS experiments was set to 2 ms. A CP proton pulse with linear ramp (from 50% to 100%) was employed. All spectra were externally referenced by adjusting the magnetic field to set carbon resonance of adamantane to 29.5 ppm. TPPM15 proton decoupling sequence was used with the field strength of approximately 100 kHz for both $^{13}$C and $^{19}$F acquisitions.

Final purity of compounds was determined by reversed phase UPLC using an Acquity UPLC BEH C18 column (50×2.1 mm, 1.7 μm particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+H]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30 m×0.25 mm×0.25 um_df) column, with a 2.0 mL/min flow rate (H2 carrier gas), at an injection temperature of 220° C. and an oven temperature of 120° C., 15 minutes.

Example 1. Synthesis of Compound I: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound I)

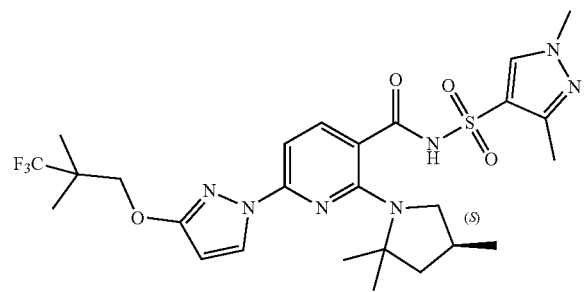

Part A: Synthesis of (4S)-2,2,4-trimethylpyrrolidine hydrochloride

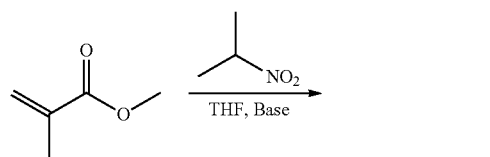

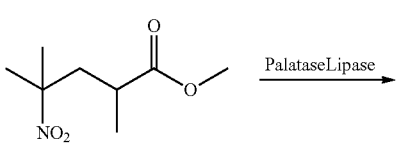

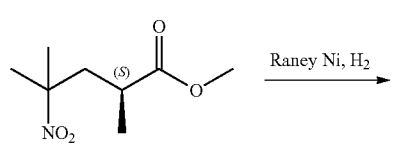

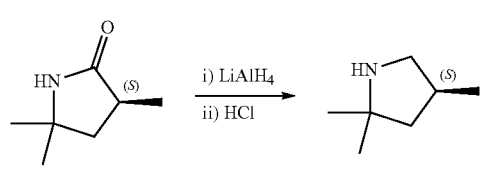

Step 1: methyl-2,4-dimethyl-4-nitro-pentanoate

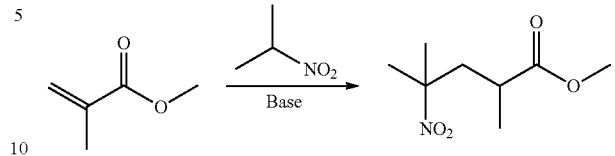

Tetrahydrofuran (THF, 4.5 L) was added to a 20 L glass reactor and stirred under N2 at room temperature. 2-Nitropropane (1.5 kg, 16.83 mol) and 1,8-diazabicyclo[5.4.0]undec-7-ene (DBU) (1.282 kg, 8.42 mol) were then charged to the reactor, and the jacket temperature was increased to 50° C. Once the reactor contents were close to 50° C., methyl methacrylate (1.854 kg, 18.52 mol) was added slowly over 100 minutes. The reaction temperature was maintained at or close to 50° C. for 21 hours. The reaction mixture was concentrated in vacuo then transferred back to the reactor and diluted with methyl tert-butyl ether (MTBE) (14 L). 2 M HCl (7.5 L) was added, and this mixture was stirred for 5 minutes then allowed to settle. Two clear layers were visible—a lower yellow aqueous phase and an upper green organic phase. The aqueous layer was removed, and the organic layer was stirred again with 2 M HCl (3 L). After separation, the HCl washes were recombined and stirred with MTBE (3 L) for 5 minutes. The aqueous layer was removed, and all of the organic layers were combined in the reactor and stirred with water (3 L) for 5 minutes. After separation, the organic layers were concentrated in vacuo to afford a cloudy green oil. Crude product was treated with MgSO$_4$ and filtered to afford methyl-2,4-dimethyl-4-nitro-pentanoate as a clear green oil (3.16 kg, 99% yield).

$^1$H NMR (400 MHz, Chloroform-d) δ 3.68 (s, 3H), 2.56-2.35 (m, 2H), 2.11-2.00 (m, 1H), 1.57 (s, 3H), 1.55 (s, 3H), 1.19 (d, J=6.8 Hz, 3H).

Step 2: Synthesis of methyl (2S)-2,4-dimethyl-4-nitro-pentanoate

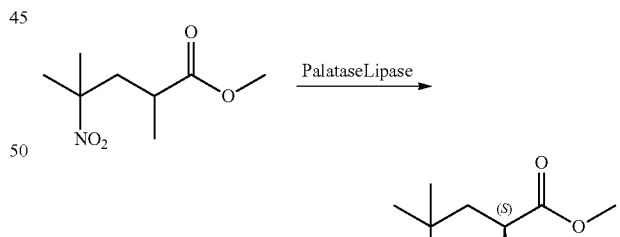

A reactor was charged with purified water (2090 L; 10 vol) and then potassium phosphate monobasic (27 kg, 198.4 moles; 13 g/L for water charge). The pH of the reactor contents was adjusted to pH 6.5 (±0.2) with 20% (w/v) potassium carbonate solution. The reactor was charged with racemic methyl-2,4-dimethyl-4-nitro-pentanoate (209 kg; 1104.6 moles), and Palatase 20000L lipase (13 L, 15.8 kg; 0.06 vol).

The reaction mixture was adjusted to 32+2° C. and stirred for 15-21 hours, and pH 6.5 was maintained using a pH stat with the automatic addition of 20% potassium carbonate solution. When the racemic starting material was converted to >98% ee of the S-enantiomer, as determined by chiral GC, external heating was switched off. The reactor was then charged with MTBE (35 L; 5 vol), and the aqueous layer was extracted with MTBE (3 times, 400-1000L). The combined organic extracts were washed with aqueous $Na_2CO_3$ (4 times, 522 L, 18% w/w 2.5 vol), water (523 L; 2.5 vol), and 10% aqueous NaCl (314 L, 1.5 vol). The organic layer was concentrated in vacuo to afford methyl (2S)-2,4-dimethyl-4-nitro-pentanoate as a mobile yellow oil (>98% ee, 94.4 kg; 45% yield).

Step 3: Synthesis of (3S)-3,5,5-trimethylpyrrolidin-2-one

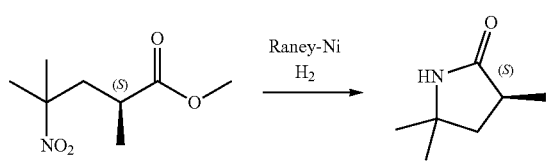

A 20 L reactor was purged with N2. The vessel was charged sequentially with DI water-rinsed, damp Raney® Ni (2800 grade, 250 g), methyl (2S)-2,4-dimethyl-4-nitro-pentanoate (1741 g, 9.2 mol), and ethanol (13.9 L, 8 vol). The reaction was stirred at 900 rpm, and the reactor was flushed with H2 and maintained at ~2.5 bar. The reaction mixture was then warmed to 60° C. for 5 hours. The reaction mixture was cooled and filtered to remove Raney nickel, and the solid cake was rinsed with ethanol (3.5 L, 2 vol). The ethanolic solution of the product was combined with a second equal sized batch and concentrated in vacuo to reduce to a minimum volume of ethanol (~1.5 volumes). Heptane (2.5 L) was added, and the suspension was concentrated again to ~1.5 volumes. This was repeated 3 times; the resulting suspension was cooled to 0-5° C., filtered under suction, and washed with heptane (2.5 L). The product was dried under vacuum for 20 minutes then transferred to drying trays and dried in a vacuum oven at 40° C. overnight to afford (3S)-3,5,5-trimethylpyrrolidin-2-one as a white crystalline solid (2.042 kg, 16.1 mol, 87%). $^1$H NMR (400 MHz, Chloroform-d) δ 6.39 (s, 1H), 2.62 (ddq, J=9.9, 8.6, 7.1 Hz, 1H), 2.17 (dd, J=12.4, 8.6 Hz, 1H), 1.56 (dd, J=12.5, 9.9 Hz, 1H), 1.31 (s, 3H), 1.25 (s, 3H), 1.20 (d, J=7.1 Hz, 3H).

Step 4: Synthesis of (4S)-2,2,4-trimethylpyrrolidine hydrochloride

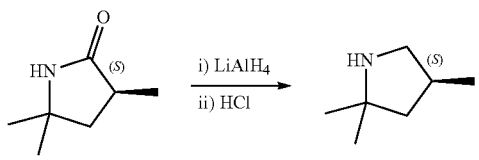

A glass lined 120 L reactor was charged with lithium aluminum hydride pellets (2.5 kg, 66 mol) and dry THF (60 L) and warmed to 30° C. The resulting suspension was charged with (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C., then cautiously quenched with the addition of ethyl acetate (EtOAc) (1.0 L, 10 moles), followed by a mixture of THF (3.4 L) and water (2.5 kg, 2.0 eq), and then a mixture of water (1.75 kg) with 50% aqueous sodium hydroxide (750 g, 2 equiv water with 1.4 equiv sodium hydroxide relative to aluminum), followed by 7.5 L water. After the addition was complete, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry. Isopropanol (8 L) was added and the solution was concentrated to near dryness by vacuum distillation. Isopropanol (4 L) was added, and the product was slurried by warming to about 50° C. MTBE (6 L) was added, and the slurry was cooled to 2-5° C. The product was collected by filtration and rinsed with 12 L MTBE and dried in a vacuum oven (55° C./300 torr/N2 bleed) to afford (4S)-2,2,4-trimethylpyrrolidine.HCl as a white, crystalline solid (6.21 kg, 75% yield). $^1$H NMR (400 MHz, DMSO-d6) δ 9.34 (br d, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Part B: Preparation of N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound I)

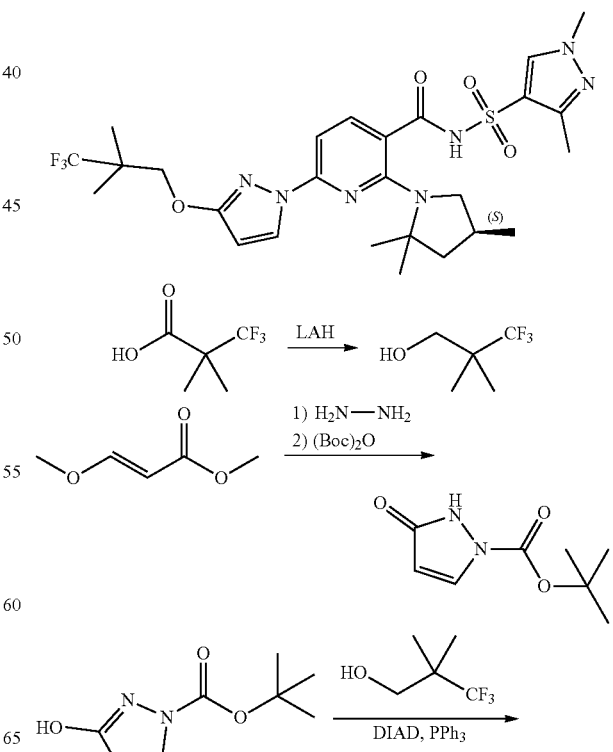

Preparation of Starting Materials

3,3,3-Trifluoro-2,2-dimethyl-propan-1-ol

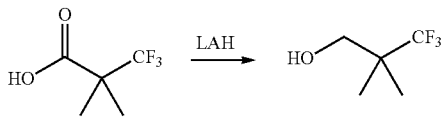

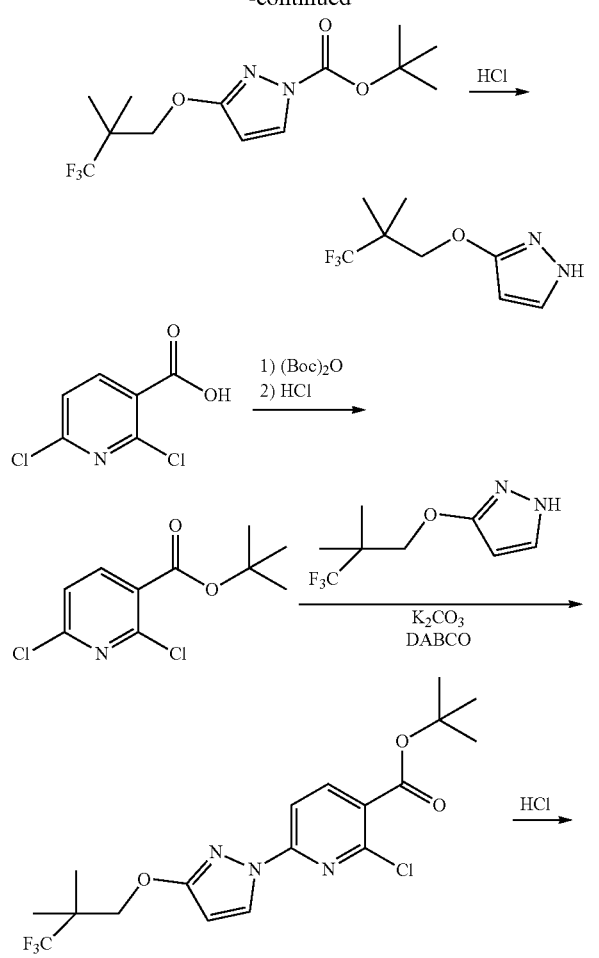

A 1 L 3 neck round bottom flask was fitted with a mechanical stirrer, a cooling bath, an addition funnel, and a J-Kem temperature probe. The vessel was charged with lithium aluminum hydride (LAH) pellets (6.3 g, 0.1665 mol) under a nitrogen atmosphere. The vessel was then charged with tetrahydrofuran (200 mL) under a nitrogen atmosphere. The mixture was allowed to stir at room temperature for 0.5 hours to allow the pellets to dissolve. The cooling bath was then charged with crushed ice in water and the reaction temperature was lowered to 0° C. The addition funnel was charged with a solution of 3,3,3-trifluoro-2,2-dimethyl-propanoic acid (20 g, 0.1281 mol) in tetrahydrofuran (60 mL) and the clear pale yellow solution was added drop wise over 1 hour. After the addition was complete the mixture was allowed to slowly warm to room temperature and stirring was continued for 24 hours. The suspension was cooled to 0° C. with a crushed ice-water in the cooling bath and then quenched by the very slow and drop wise addition of water (6.3 ml), followed by sodium hydroxide solution (15 weight %; 6.3 mL) and then finally with water (18.9 mL). The reaction temperature of the resulting white suspension was recorded at 5° C. The suspension was stirred at ~5° C. for 30 minutes and then filtered through a 20 mm layer of Celite. The filter cake was washed with tetrahydrofuran (2×100 mL). The filtrate was dried over sodium sulfate (150 g) and then filtered. The filtrate was concentrated under reduced pressure to provide a clear colorless oil (15 g) containing a mixture of the product 3,3,3-trifluoro-2,2-dimethyl-propan-1-ol in THF (73% weight of product ~10.95 g, and 27 wt. % THF as determined by 1H-NMR). The distillate from the rotary evaporation was distilled at atmospheric pressure using a 30 cm Vigreux column to provide 8.75 g of a residue containing 60% weight of THF and 40% weight of product (~3.5 g). The estimated total amount of product is 14.45 g (79% yield). 1H NMR (400 MHz, DMSO-d6) δ 4.99 (t, J=5.7 Hz, 1H), 3.38 (dd, J=5.8, 0.9 Hz, 2H), 1.04 (d, J=0.9 Hz, 6H).

tert-Butyl 3-oxo-2,3-dihydro-1H-pyrazole-1-carboxylate

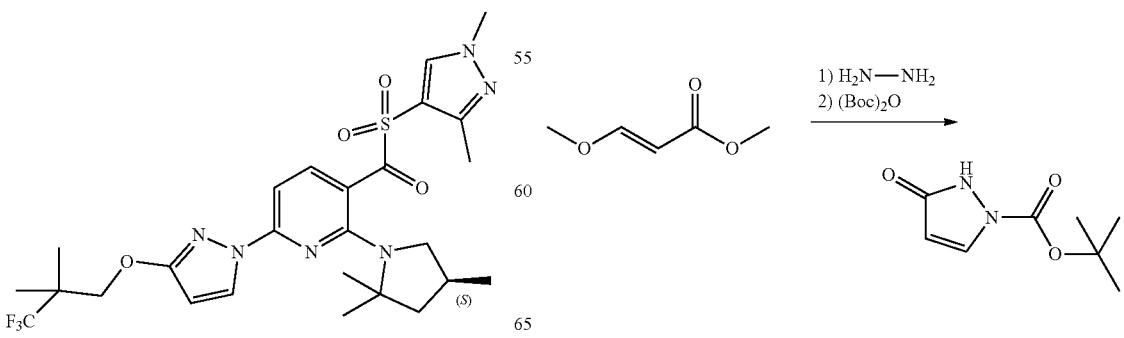

A 50L Syrris controlled reactor was started and jacket set to 20° C., stirring at 150 rpm, reflux condenser (10° C.) and nitrogen purge. MeOH (2.860 L) and methyl (E)-3-methoxyprop-2-enoate (2.643 kg, 22.76 mol) were added and the reactor was capped. The reaction was heated to an internal temperature of 40° C. and the system was set to hold jacket temp at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethyamine (2.483 kg, 3.420 L, 24.54 mol) was added portion wise (exothermic), maintaining reaction temp <30° C. A solution of Boc anhydride (di-tert-butyl dicarbonate) (4.967 kg, 5.228 L, 22.76 mol) in MeOH (2.860 L) was added portion wise maintaining temperature <45° C. The reaction mixture was stirred at 20° C. for 16 h. The reaction solution was partially concentrated to remove MeOH, resulting in a clear light amber oil. The resulting oil was transferred to the 50L reactor, stirred and added water (7.150 L) and heptane (7.150 L). The additions caused a small amount of the product to precipitate. The aqueous layer was drained into a clean container and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol), then began dropwise addition of acid. The jacket was set to 0° C. to absorb the quench exotherm. After addition (pH=5), the reaction mixture was stirred for 1 h. The solid was collected by filtration and washed with water (7.150 L), and washed a second time with water (3.575 L) and pulled dry. The crystalline solid was scooped out of the filter into a 20L rotovap bulb and heptane (7.150 L) was added. The mixture was slurried at 45° C. for 30 mins, and then distilled off 1-2 volumes of solvent. The slurry in the rotovap flask was filtered and the solids washed with heptane (3.575 L) and pulled dry. The solid was further dried in vacuo (50° C., 15 mbar) to give tert-Butyl 5-oxo-1H-pyrazole-2-carboxylate (2921 g, 71%) as coarse, crystalline solid. $^1$H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

Step A: tert-Butyl 3-(3,3,3-trifluoro-2,2-dimethyl-propoxy)pyrazole-1-carboxylate

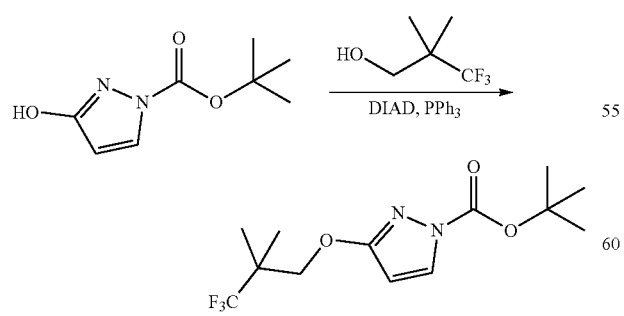

A mixture of 3,3,3-trifluoro-2,2-dimethyl-propan-1-ol (10 g, 70.36 mmol) and tert-butyl 3-hydroxypyrazole-1-carboxylate (12.96 g, 70.36 mmol) in toluene (130 mL) was treated with triphenyl phosphine (20.30 g, 77.40 mmol) followed by isopropyl N-isopropoxycarbonyliminocarbamate (14.99 mL, 77.40 mmol) and the mixture was stirred at 110° C. for 16 hours. The yellow solution was concentrated under reduced pressure, diluted with heptane (100 mL) and the precipitated triphenylphosphine oxide was removed by filtration and washed with heptane/toluene 4:1 (100 mL). The yellow filtrate was evaporated and the residue purified by silica gel chromatography with a linear gradient of ethyl acetate in hexane (0-40%) to give tert-butyl 3-(3,3,3-trifluoro-2,2-dimethyl-propoxy)pyrazole-1-carboxylate (12.3 g, 57%) as an off white solid. ESI-MS m/z calc. 308.13477, found 309.0 (M+1)$^+$; Retention time: 1.84 minutes. $^1$H NMR (400 MHz, DMSO-d6) δ 8.10 (d, J=3.0 Hz, 1H), 6.15 (d, J=3.0 Hz, 1H), 4.18 (s, 2H), 1.55 (s, 9H), 1.21 (s, 6H).

Step B: 3-(3,3,3-trifluoro-2,2-dimethyl-propoxy)-1H-pyrazole

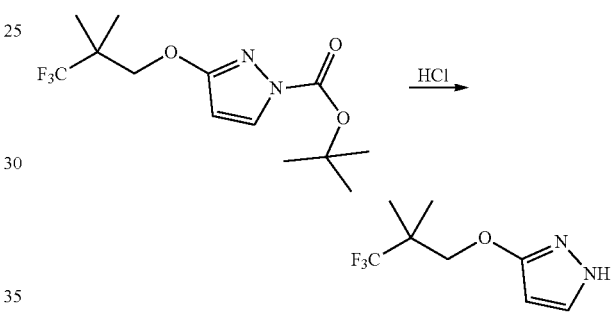

tert-Butyl 3-(3,3,3-trifluoro-2,2-dimethyl-propoxy)pyrazole-1-carboxylate (13.5 g, 43.79 mmol) was treated with 4 M hydrogen chloride in dioxane (54.75 mL, 219.0 mmol) and the mixture was stirred at 45° C. for 1 hour. The reaction mixture was evaporated to dryness and the residue was extracted with 1 M aqueous NaOH (100 ml) and methyl tert-butyl ether (100 ml), washed with brine (50 ml) and extracted with methyl tert-butyl ether (50 ml). The combined organic phases were dried, filtered and evaporated to give 3-(3,3,3-trifluoro-2,2-dimethyl-propoxy)-1H-pyrazole (9.0 g, 96%) as an off white waxy solid. ESI-MS m/z calc. 208.08235, found 209.0 (M+1)$^+$; Retention time: 1.22 minutes. $^1$H NMR (400 MHz, DMSO-d6) δ 11.91 (s, 1H), 7.52 (d, J=2.2 Hz, 1H), 5.69 (t, J=2.3 Hz, 1H), 4.06 (s, 2H), 1.19 (s, 6H).

Step C: tert-Butyl 2,6-dichloropyridine-3-carboxylate

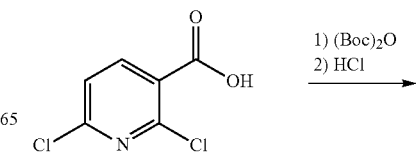

-continued

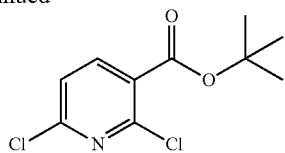

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and left to stir overnight at room temperature. At this point, HCl 1N (400 mL) was added and the mixture was stirred vigorously for about 10 minutes. The product was extracted with ethyl acetate (2×300 mL) and the combined organics layers were washed with water (300 mL) and brine (150 mL) and dried over sodium sulfate and concentrated under reduced pressure to give 12.94 g (96% yield) of tert-butyl 2,6-dichloropyridine-3-carboxylate as a colorless oil. ESI-MS m/z calc. 247.01668, found 248.1 (M+1)$^+$; Retention time: 2.27 minutes. $^1$H NMR (300 MHz, CDCl$_3$) ppm 1.60 (s, 9H), 7.30 (d, J=7.9 Hz, 1H), 8.05 (d, J=8.2 Hz, 1H).

Step D: tert-Butyl 2-chloro-6-[3-(3,3,3-trifluoro-2,2-dimethyl-propoxy)pyrazol-1-yl]pyridine-3-carboxylate

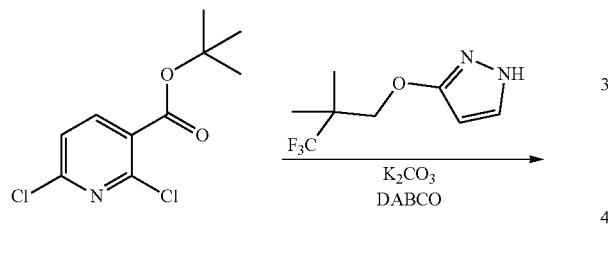

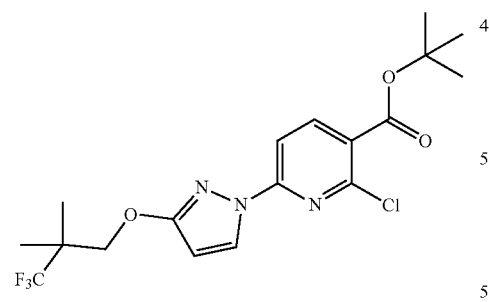

To a solution of tert-butyl 2,6-dichloropyridine-3-carboxylate (10.4 g, 41.9 mmol) and 3-(3,3,3-trifluoro-2,2-dimethyl-propoxy)-1H-pyrazole (9.0 g, 41.93 mmol) in DMF (110 mL) were added potassium carbonate (7.53 g, 54.5 mmol) and 1,4-diazabicyclo[2.2.2]octane (706 mg, 6.29 mmol) and the mixture was stirred at room temperature for 16 hours. The cream suspension was cooled in a cold water bath and cold water (130 mL) was slowly added. The thick suspension was stirred at room temperature for 1 hour, filtered and washed with plenty of water to give tert-butyl 2-chloro-6-[3-(3,3,3-trifluoro-2,2-dimethyl-propoxy)pyrazol-1-yl]pyridine-3-carboxylate (17.6 g, 99%) as an off white solid. ESI-MS m/z calc. 419.12234, found 420.0 (M+1)$^+$; Retention time: 2.36 minutes. $^1$H NMR (400 MHz, DMSO-d6) δ 8.44 (d, J=2.9 Hz, 1H), 8.31 (d, J=8.4 Hz, 1H), 7.76 (d, J=8.4 Hz, 1H), 6.26 (d, J=2.9 Hz, 1H), 4.27 (s, 2H), 1.57 (s, 9H), 1.24 (s, 6H).

Step E: 2-chloro-6-[3-(3,3,3-trifluoro-2,2-dimethyl-propoxy)pyrazol-1-yl]pyridine-3-carboxylic acid

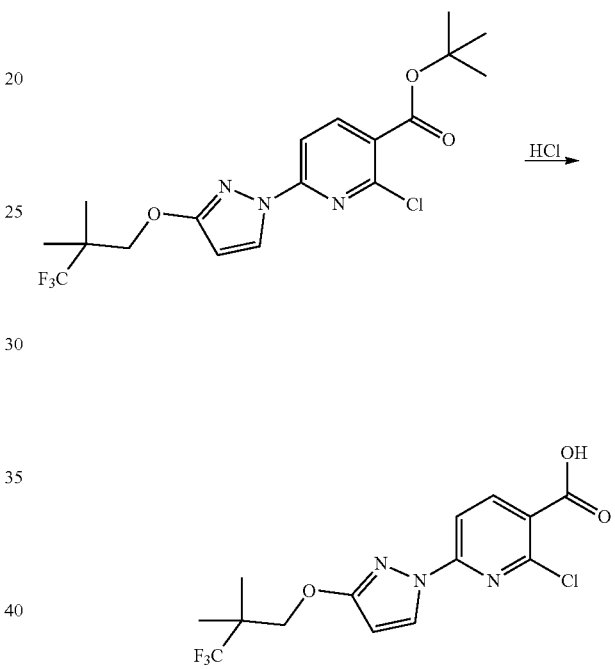

tert-Butyl 2-chloro-6-[3-(3,3,3-trifluoro-2,2-dimethyl-propoxy)pyrazol-1-yl]pyridine-3-carboxylate (17.6 g, 40.25 mmol) was suspended in isopropanol (85 mL) treated with hydrochloric acid (34 mL of 6 M, 201 mmol) and heated to reflux for 3 hours (went almost complete into solution at reflux and started to precipitate again). The suspension was diluted with water (51 mL) at reflux and left to cool to room temperature under stirring for 2.5 h. The solid was collected by filtration, washed with isopropanol/water 1:1 (50 mL), plenty of water and dried in a drying cabinet under vacuum at 45-50° C. with a nitrogen bleed overnight to give 2-chloro-6-[3-(3,3,3-trifluoro-2,2-dimethyl-propoxy)pyrazol-1-yl]pyridine-3-carboxylic acid (13.7 g, 91%) as an off white solid. ESI-MS m/z calc. 363.05975, found 364.0 (M+1)$^+$; Retention time: 1.79 minutes. $^1$H NMR (400 MHz, DMSO-d6) δ 13.61 (s, 1H), 8.44 (d, J=2.9 Hz, 1H), 8.39 (d, J=8.4 Hz, 1H), 7.77 (d, J=8.4 Hz, 1H), 6.25 (d, J=2.9 Hz, 1H), 4.28 (s, 2H), 1.24 (s, 6H).

Step F: 2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide

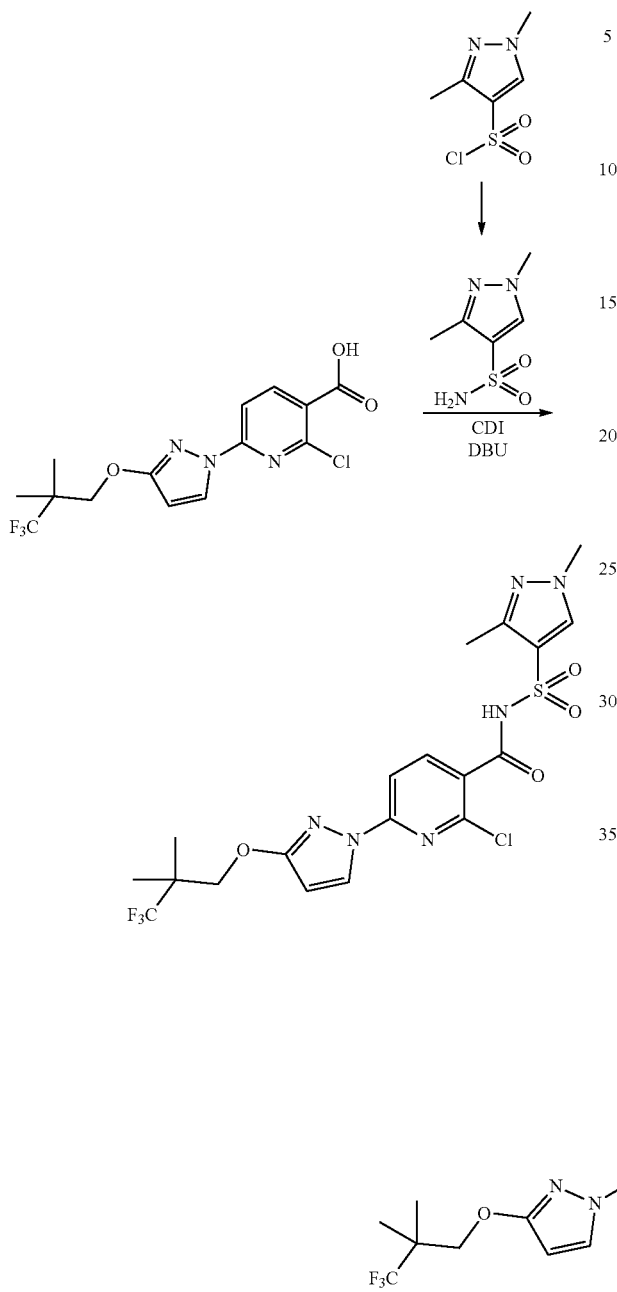

2-Chloro-6-[3-(3,3,3-trifluoro-2,2-dimethyl-propoxy)pyrazol-1-yl]pyridine-3-carboxylic acid (100 mg, 0.2667 mmol) and CDI (512 mg, 3.158 mmol) were combined in THF (582.0 µL) and the mixture was stirred at room temperature. Meanwhile, 1,3-dimethylpyrazole-4-sulfonyl chloride (62 mg, 0.3185 mmol) was combined with ammonia (in methanol) in a separate vial, instantly forming a white solid. After stirring for an additional 20 min, the volatiles were removed by evaporation, and 1 mL of dichloromethane was added to the solid residue, and was also evaporated. DBU (100 µL, 0.6687 mmol) was then added and the mixture stirred at 60° C. for 5 minutes, followed by addition of THF (1 mL) which was subsequently evaporated. The contents of the vial containing the CDI activated carboxylic acid in THF were then added to the vial containing the newly formed sulfonamide and DBU, and the reaction mixture was stirred for 4 hours at room temperature. The reaction mixture was diluted with 10 mL of ethyl acetate, and washed with 10 mL solution of citric acid (1 M). The aqueous layer was extracted with ethyl acetate (2×10 mL) and the combined organics were washed with brine, dried over sodium sulfate, and concentrated to give the product as white solid (137 mg, 99%) that was used in the next step without further purification. ESI-MS m/z calc. 520.09076, found 521.1 (M+1)$^+$; Retention time: 0.68 minutes.

Step G: N-(1,3-dimethylpyrazol-4-yl)sulfonyl-6-[3-(3,3,3-trifluoro-2,2-dimethyl-propoxy)pyrazol-yl]-2-[(4S)-2,2,4-trimethylpyrrolidin-1-yl]pyridine-3-carboxamide

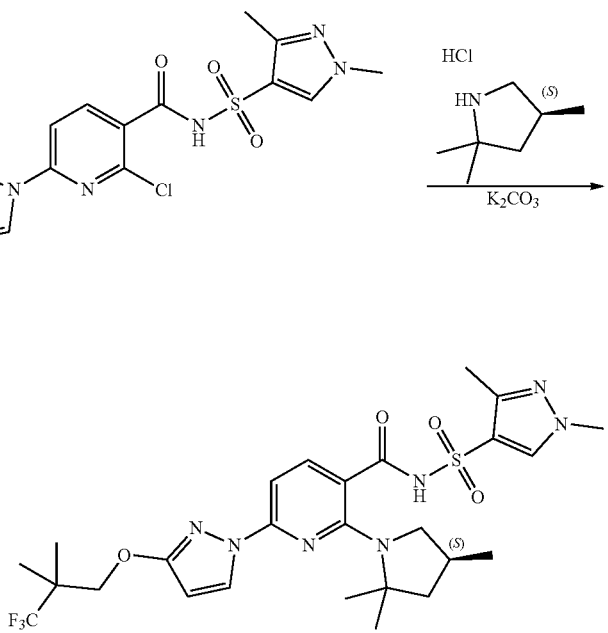

2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (137 mg, 0.2630 mmol), (4S)-2,2,4-trimethylpyrrolidine (Hydrochloride salt) (118 mg, 0.7884 mmol), and potassium carbonate (219 mg, 1.585 mmol) were combined in DMSO (685.0 µL) and the mixture was heated at 130° C. for 16 hours. The reaction was cooled to room temperature, and 1 mL of water was added. After stirring for 15 minutes, the contents of the vial were allowed to settle, and the liquid portion was removed via pipet and the remaining solids were dissolved with 20 mL of ethyl acetate and were washed with 1 M citric acid (15 mL). The layers were separated and the aqueous layer was extracted two additional times with 15 mL of ethyl acetate. The organics were combined, washed with brine, dried over sodium sulfate and concentrated. The resulting solid was further purified by silica gel chromatography eluting with a gradient of methanol in dichloromethane (0-10%) to give N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (72 mg, 41%) as a white solid. ESI-MS m/z calc. 597.2345, found 598.3 (M+1)$^+$; Retention time: 2.1 minutes. $^1$H NMR (400 MHz, DMSO) δ 12.36 (s, 1H), 8.37 (s, 1H), 8.22 (d, J=2.8 Hz, 1H), 7.74 (d, J=8.2 Hz, 1H), 6.93 (d, J=8.2 Hz, 1H), 6.17 (d, J=2.8 Hz, 1H), 4.23 (s, 2H), 3.81 (s, 3H), 2.56 (d, J=10.4 Hz, 1H), 2.41 (t, J=8.7 Hz, 1H), 2.32 (s, 3H), 2.18 (dd, J=12.4, 6.1 Hz, 1H), 1.87 (dd, J=11.7, 5.5 Hz, 1H), 1.55 (d, J=11.2 Hz, 6H), 1.42 (t, J=12.0 Hz, 1H), 1.23 (s, 6H), 0.81 (d, J=6.2 Hz, 3H).

Alternative Steps F and G

Alternative Step F: 2-chloro-N-((1,3-dimethyl-1H-pyrazol-4-yl)sulfonyl)-6-(3-(3,3,3-trifluoro-2,2-dimethylpropoxy)-1H-pyrazol-1-yl)nicotinamide

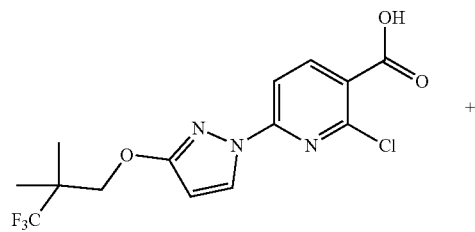

+

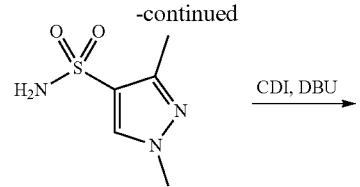

CDI, DBU →

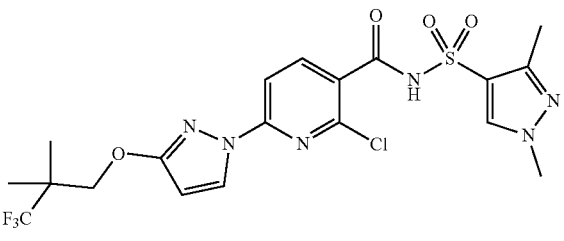

To a suspension of 2-chloro-6-[3-(3,3,3-trifluoro-2,2-dimethyl-propoxy)pyrazol-1-yl]pyridine-3-carboxylic acid (20.0 g, 53.89 mmol) in THF (78.40 mL) was added solid carbonyldiimidazole (approximately 10.49 g, 64.67 mmol) portion wise and the resulting solution was stirred at room temperature (slight exotherm from 18-21° C. was observed). After 1 h, solid 1,3-dimethylpyrazole-4-sulfonamide (approximately 11.33 g, 64.67 mmol) was added, followed by DBU (approximately 9.845 g, 9.671 mL, 64.67 mmol) in two equal portions over 1 min (exotherm from 19 to 35° C.). The reaction mixture was stirred at room temperature for 16 h. The reaction mixture was diluted with ethyl acetate (118 mL) and then HCl (approximately 107.8 mL of 2 M, 215.6 mmol). The phases were separated and the aqueous phase was extracted with ethyl acetate (78 mL). The combined organics were washed with water (39.2 mL), then brine (40 mL), dried over sodium sulfate and concentrated. The resulting foam was crystallized from a 1:1 isopropanol:heptane mixture (80 mL) to afford 2-chloro-N-((1,3-dimethyl-1H-pyrazol-4-yl)sulfonyl)-6-(3-(3,3,3-trifluoro-2,2-dimethyl-propoxy)-1H-pyrazol-1-yl)nicotinamide (26.1 g, 93%) as a white solid. ESI-MS m/z calc. 520.0, found 520.9 (M+1)$^+$; Retention time: 1.83 minutes.

Alternative Step G: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide

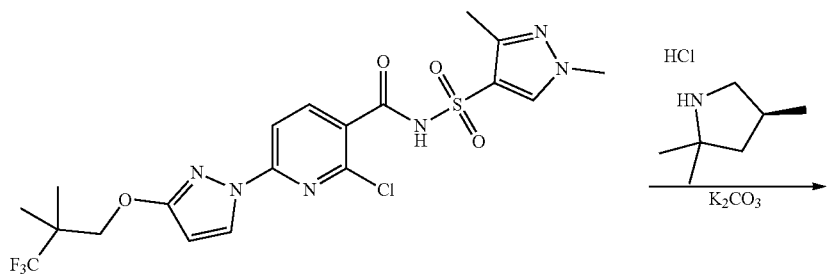

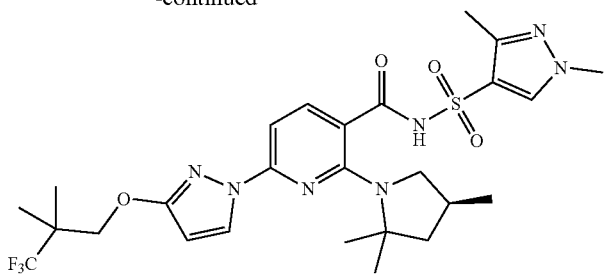

2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (20.0 g, 38.39 mmol), (4S)-2,2,4-trimethylpyrrolidine (Hydrochloride salt) (approximately 14.36 g, 95.98 mmol), and K2CO3 (approximately 26.54 g, 192.0 mmol) were combined in DMSO (80.00 mL) and 1,2-diethoxyethane (20.00 mL) in a 500-mL flask with reflux condenser. The reaction mixture was heated at 120° C. for 16 h then cooled to room temperature. The reaction was diluted with DCM (200.0 mL) and HCl (approximately 172.8 mL of 2 M, 345.5 mmol); aqueous pH ~1. The phases were separated, and the aqueous phase was extracted with DCM (100.0 mL). The organic phases were combined, washed with water (100.0 mL) (3×), and dried (Na2SO4) to afford an amber solution. The solution was filtered through a DCM-packed silica gel bed (80 g; 4 g/g) and washed with 20% EtOAc/DCM (5×200 mL). The combined filtrate/washes were concentrated to afford 22.2 g of an off-white powder. The powder was slurried in MTBE (140 mL) for 30 min. The solid was collected by filtration (paper/sintered-glass) to afford 24 g after air-drying. The solid was transferred to a drying dish and vacuum-dried (40° C./200 torr/N2 bleed) overnight to afford 20.70 g (90%) of a white powder. ESI-MS m/z calc. 597.2345, found 598.0 (M+1)+; Retention time: 2.18 minutes.

$^1$H NMR (400 MHz, Chloroform-d) δ 13.85 (s, 1H), 8.30 (d, J=8.6 Hz, 1H), 8.23 (d, J=2.8 Hz, 1H), 8.08 (s, 1H), 7.55 (d, J=8.5 Hz, 1H), 5.98 (d, J=2.8 Hz, 1H), 4.24 (s, 2H), 3.86 (s, 3H), 3.44 (dd, J=10.3, 8.4 Hz, 1H), 3.09 (dd, J=10.3, 7.8 Hz, 1H), 2.67-2.52 (m, 1H), 2.47 (s, 3H), 2.12 (dd, J=12.3, 7.8 Hz, 1H), 1.70 (dd, J=12.4, 9.6 Hz, 1H), 1.37 (s, 3H), 1.33 (s, 3H), 1.27 (s, 6H), 1.20 (d, 3H).

Alternative Synthesis of 3-(3,3,3-trifluoro-2,2-dimethyl-propoxy)-1H-pyrazole

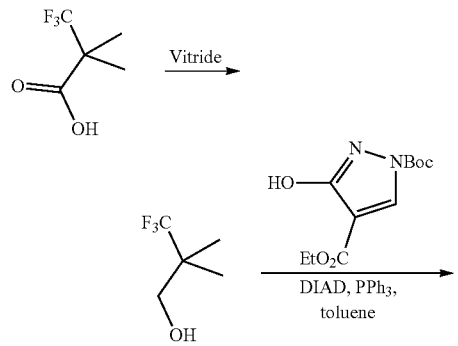

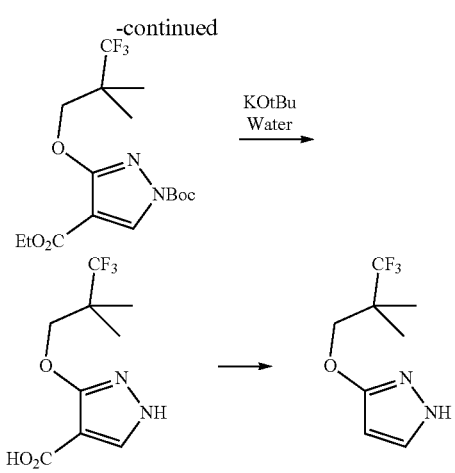

Step 1: Preparation of 3,3,3-trifluoro-2,2-dimethylpropan-1-ol

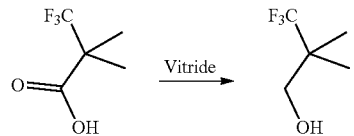

A reactor was loaded with toluene (300 mL) and 3,3,3-trifluoro-2,2-dimethylpropanoic acid (30 g, 192.2 mmol), capped, purged under nitrogen. The reaction was set to control the internal temperature to 40° C. A solution of Vitride (65% in toluene. approximately 119.6 g of 65% w/w, 115.4 mL of 65% w/w, 384.4 mmol) was set up for addition via syringe, and addition was begun at 40° C., with the target addition temperature between 40 and 50° C. The reaction was stirred at 40° C. for 90 min. The reaction was cooled to 10° C. then the remaining Vitride was quenched with slow addition of water (6 mL). A solution of 15% aq NaOH (30 mL) was added in portions, and solids precipitated half way through the base addition. Water (60.00 mL) was added. The mixture was warmed to 30° C. and held for at least 15 mins. The mixture was then cooled to 20° C. The aqueous layer was removed. The organic layer was washed with water (60 mL×3), and then washed with brine (60 mL). The washed organic layer was dried under Na2SO4, followed with MgSO4. The mix was filtered through Celite, and the cake washed with toluene (60.00 mL) and pulled dry. The product 3,3,3-trifluoro-2,2-dimethyl-propan-1-ol (22.5 g, 82%) was obtained as clear colorless solution.

Step 2: Preparation of 1-(tert-butyl) 4-ethyl 3-(3,3,3-trifluoro-2,2-dimethylpropoxy)-1H-pyrazole-1,4-dicarboxylate

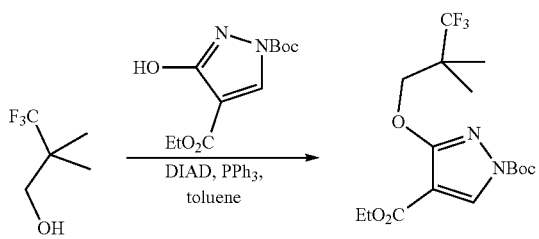

A reactor was charged with 3,3,3-trifluoro-2,2-dimethylpropan-1-ol (17.48 g, 123.0 mmol) solution in toluene (250 g), 1-(tert-butyl) 4-ethyl 3-hydroxy-1H-pyrazole-1,4-dicarboxylate (30.0 g, 117.1 mmol), and PPh$_3$ (35.33 g, 134.7 mmol). The reaction was heated to 40° C. DIAD (26.09 mL, 134.7 mmol) was weighed and placed into a syringe and added over 10 minutes while maintaining an internal temperature ranging between 40 and 50° C. The reaction was then heated to 100° C. over 30 minutes. After holding at 100° C. for 30 minutes, the reaction was complete, and the mixture was cooled to 70° C. over 15 minutes. Heptane (180.0 mL) was added, and the jacket was cooled to 15° C. over 1 hour. (TPPO began crystallizing at −35° C.). The mixture stirring at 15° C. was filtered (fast), the cake was washed with a pre-mixed solution of toluene (60 mL) and heptane (60 mL) and then pulled dry. The clear solution was concentrated to a waxy solid (45° C., vacuum, rotovap). Crude 1-(tert-butyl) 4-ethyl 3-(3,3,3-trifluoro-2,2-dimethylpropoxy)-1H-pyrazole-1,4-dicarboxylate (53.49 g) was obtained as a waxy solid, (~120% of theoretical mass recovered).

Step 3: Preparation of 3-(3,3,3-trifluoro-2,2-dimethylpropoxy)-1H-pyrazole-4-carboxylic acid

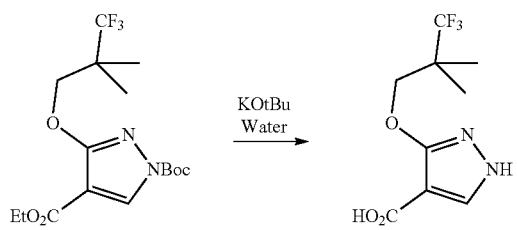

A solution of 1-(tert-butyl) 4-ethyl 3-(3,3,3-trifluoro-2,2-dimethylpropoxy)-1H-pyrazole-1,4-dicarboxylate (50.0 g, 131 mmol) in 2-methyltetrahydrofuran (500 mL) was prepared in a reactor and stirred at 40° C. Portions of KOt-Bu (80.85 g, 720.5 mmol) were then added over 30 minutes. Addition was exothermic. After 20 53.49 g UPLC-MS showed complete removal of the Boc group, so water (3.53 g, 3.53 mL, 196 mmol) was added drop-wise addition via syringe over 20 min to keep the reaction temperature between 40-50° C. The mixture was then stirred for 17 hours to complete the reaction. The mixture was then cooled to 20° C. and water (400 mL) was added. The stirring was stopped and the layers were separated. The desired product in the aqueous layer was returned to the reactor and the organic layer was discarded. The aqueous layer was washed with 2-Me-THF (200 mL). Isopropanol (50. mL) was added followed by dropwise addition of aqueous HCl (131 mL of 6.0 M, 786.0 mmol) to adjust the pH to <3 while maintaining the temperature below 30° C. The resulting solid was then isolated by filtration and the filter cake washer with water (100 mL) then pulled dry until a sticky cake was obtained. The solids were then dried under vacuum at 55° C. to afford 3-(3,3,3-trifluoro-2,2-dimethylpropoxy)-1H-pyrazole-4-carboxylic acid (23.25 g) as an off-white fine solid.

Step 4: Preparation of 3-(3,3,3-trifluoro-2,2-dimethyl-propoxy)-1H-pyrazole 3-(3,3,3-trifluoro-2,2-dimethylpropoxy)-1H-pyrazole-4-carboxylic acid (1.0 equiv) was added to a reactor followed by DMF (6.0 vol, 2.6 wt equiv). The mixture was stirred at 18-22° C. DBU (0.2 equiv.) was charged to the reaction mixture at a rate of approximately 45 mL/min. The reaction temperature was then raised to 98-102° C. over 45 minutes. The reaction mixture was stirred at 98-102° C. for no less than 10 h. The reaction mixture was then cooled to −2° C. to 2° C. over approximately 1 hour and was used without isolation to make ethyl 2-chloro-6-(3-(3,3,3-trifluoro-2,2-dimethylpropoxy)-1H-pyrazol-1-yl)nicotinate.

Alternate procedure for the preparation of 2-chloro-6-[3-(3,3,3-trifluoro-2,2-dimethyl-propoxy)pyrazol-1-yl]pyridine-3-carboxylic acid

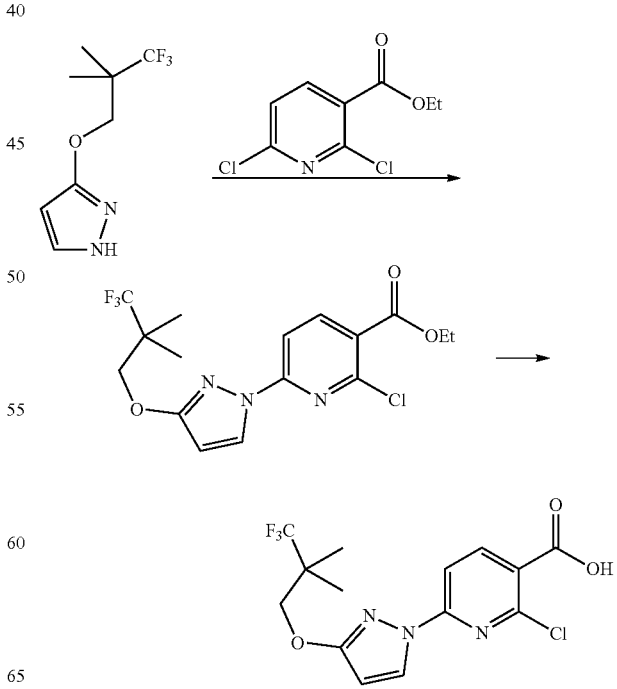

Step 1. Ethyl 2-chloro-6-(3-(3,3,3-trifluoro-2,2-dimethylpropoxy)-1H-pyrazol-1-yl)nicotinate

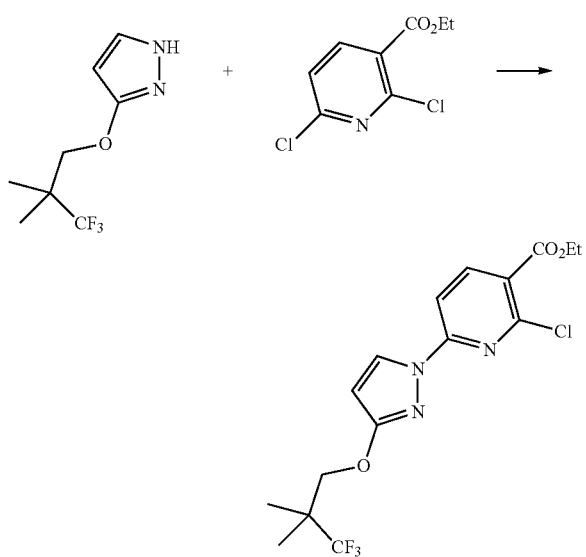

A solution of ethyl 2,6-dichloronicotinate (256 g, 1.16 mol) and 3-(3,3,3-trifluoro-2,2-dimethyl-propoxy)-1H-pyrazole (242 g, 1.16 mol) in DMF (1.53 L) was treated with potassium carbonate (209 g, 1.51 mol) and DABCO (19.6 g, 174 mmol). The resultant suspension was stirred allowed to exotherm from 14 to 25° C. and then maintained at 20-25° C. with external cooling for 3 days. The suspension was cooled to below 10° C. when water (2.0 L) was added in a thin stream while maintaining the temperature below 25° C. After the addition was complete, the suspension was stirred for an additional 1 h. The solid was collected by filtration (sintered-glass/polypad) and the filter-cake was washed with water (2×500-mL) and dried with suction for 2 h to afford water-damp ethyl 2-chloro-6-(3-(3,3,3-trifluoro-2,2-dimethylpropoxy)-1H-pyrazol-1-yl)nicotinate (512 g; 113% yield) as white powder which was used without further steps in the subsequent reaction.

Step 2. 2-chloro-6-(3-(3,3,3-trifluoro-2,2-dimethyl-propoxy)-1h-pyrazol-1-yl)nicotinic acid

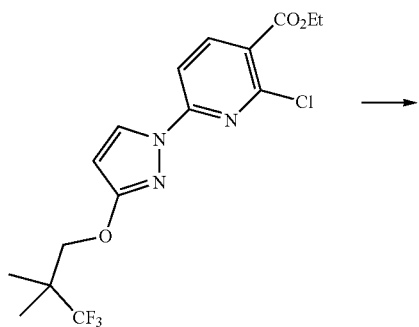

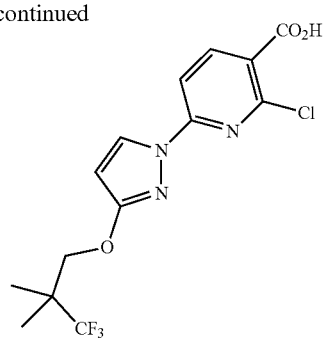

The water-damp ethyl 2-chloro-6-(3-(3,3,3-trifluoro-2,2-dimethylpropoxy)-1H-pyrazol-1-yl)nicotinate (455 g, 1.16 mol; assumed 100% yield from previous step) in EtOH (1.14 L) and THF (455 mL) was stirred at ambient temperature (17° C.) when 1 M NaOH (1.16 L, 1.16 mol) was added. The reaction mixture exothermed to 30° C. and was further warmed at 40° C. for 2 h. The solution was quenched with 1 M HCl (1.39 L, 1.39 mol) which resulted in an immediate precipitation which became thicker as the acid was added. The creamy suspension was allowed to cool to room temperature and was stirred overnight. The solid was collected by filtration (sintered-glass/poly pad). The filter-cake was washed with water (2×500-mL). The filter-cake was dried by suction for 1 h but remained wet. The damp solid was transferred to a 10-L Buchi flask for further drying (50° C./20 torr), but was not effective. Further effort to dry by chasing with i-PrOH was also ineffective. Successful drying was accomplished after the damp solid was backfilled with i-PrOAc (3 L), the suspension was heated at 60° C. (homogenization), and re-concentrated to dryness (50° C./20 torr) to afford dry 2-chloro-6-(3-(3,3,3-trifluoro-2,2-dimethyl-propoxy)-1h-pyrazol-1-yl)nicotinic acid (408 g; 97% yield for two steps) as a fine, white powder. The product was further dried in a vacuum oven (50° C./10 torr/N2 bleed) for 2 h but marginal weight loss was observed. 1H NMR (400 MHz, DMSO-d6) δ 13.64 (s, 1H), 8.49-8.36 (m, 2H), 7.77 (d, J=8.4 Hz, 1H), 6.26 (d, J=2.8 Hz, 1H), 4.28 (s, 2H), 1.24 (s, 6H). 19F NMR (376 MHz, DMSO-d6) δ-75.2. KF analysis: 0.04% water.

Preparation of Form A of Compound I

The crystalline Form A of Compound I was obtained as a result of the following synthesis. Combined 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (108 g, 207.3 mmol), (4S)-2,2,4-trimethylpyrrolidine (Hydrochloride salt) (77.55 g, 518.2 mmol), was combined with $K_2CO_3$ (143.2 g, 1.036 mol) in DMSO (432.0 mL) and 1,2-diethoxyethane (108.0 mL) in a 1-L RB flask with a reflux condenser. The resulting suspension was heated at 120° C. and was stirred at temperature overnight. Then the reaction was diluted with DCM (1.080 L) and HCl (933.0 mL of 2 M, 1.866 mol) was slowly added. The liquid phases were separated, and the aqueous phase was extracted with DCM (540.0 mL). The organic phases were combined, washed with water (540.0 mL) (3×), then dried with ($Na_2SO_4$) to afford an amber solution. Silica gel (25 g) was added and then the drying agent/silica gel was filtered off. The filter-bed was washed with DCM (3×50-mL). The organic phases were combined and concentrated (40° C./40 torr) to afford crude N-(1,3-dimethylpyrazol-4-yl)sulfonyl- 6-[3-(3,3,3-trifluoro-2,2-dimethyl-propoxy)pyrazol-1-yl]-2-[(4S)-2,2,4-trimethylpyrrolidin-1-yl]pyridine-3-carboxamide (198.6 g, 160% theory) as an off-white solid. The solid was diluted with MTBE (750 mL), warmed at 60° C. (external temperature), and mixed to a homogenous suspension. The suspension was cooled to 30° C. with stirring and the solid was collected by filtration, air-dried, and vacuum-dried to afford Compound I (111.1 g; 90%) as a fine, white powder.

The crystalline Form A of Compound I was also obtained through the following procedure. A suspension of Compound I (150.0 g, 228.1 mmol) in iPrOH (480 mL) and water (120 mL) was heated at 82° C. to obtain a solution. The solution was cooled with a J-Kem controller at a cooling rate of 10° C./h. Once the temperature reached 74° C., the solution was seeded with a sample of Compound I in crystalline Form A. Crystallization occurred immediately. The sample was cooled to −5° C., let stir for 1 h, and then the solid was collected by filtration (sintered glass/paper). The filter-cake was washed with i-PrOH (75 mL) (2×), air-dried with suction, air-dried in a drying dish (120.6 g mostly dried), vacuum-dried (55° C./300 torr/N2 bleed) for 4 h, and then RT overnight. Overnight drying afforded 118.3 g (87% yield) of a white powder.

A suspension of Compound I (116 g, 176.3 mmol) in iPrOH (371 mL) and water (93 mL) was heated at 82° C. to obtain a solution. The solution was cooled to 20° C. with a J-Kem controller at a cooling rate of 10° C./h. Once the temperature reached 74° C., the solution was seeded with a sample of Compound I in crystalline Form A. Crystallization occurred immediately. Cooling was stopped at 20° C. and the mixture was stirred overnight. The solid was collected by filtration, washed with i-PrOH (2×75 mL), air-dried with suction, and vacuum-dried (55° C./300 torr/N2 bleed) to afford Compound I, Form A (103.3 g) as a white powder.

Example 2: Synthesis of Compound II: (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

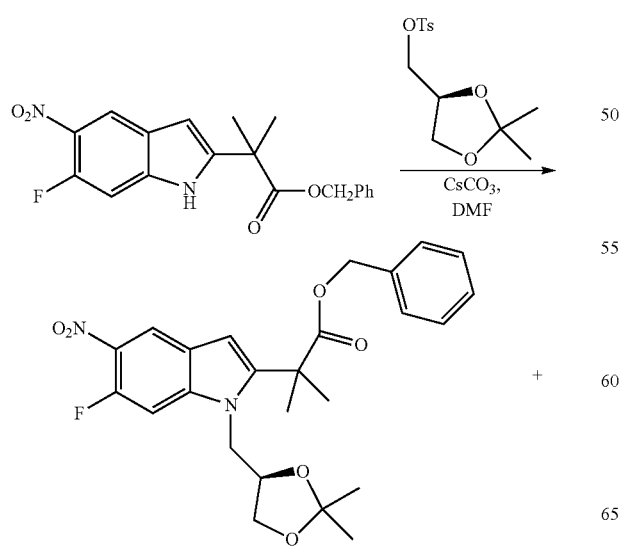

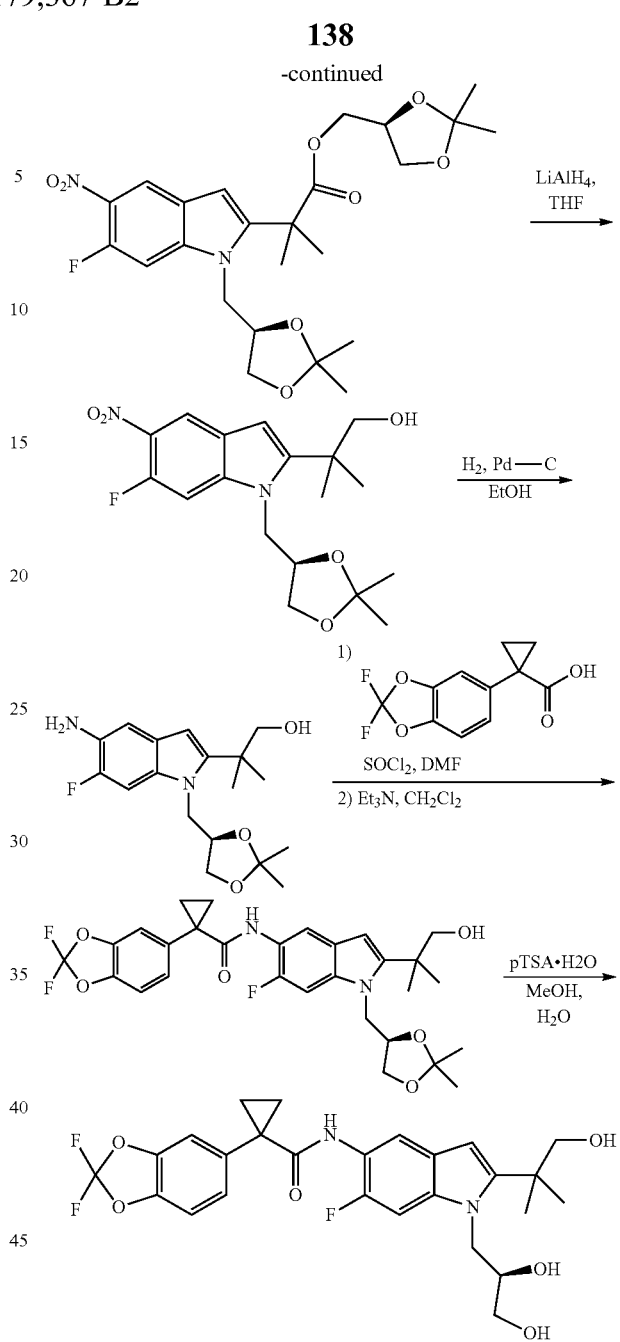

Step 1: (R)-Benzyl 2-(1-((2,2-dimethyl-1,3-dioxolan-4-yl)methyl)-6-fluoro-5-nitro-1H-indol-2-yl)-2-methylpropanoate and ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate Cesium carbonate (8.23 g, 25.3 mmol) was added to a mixture of benzyl 2-(6-fluoro-5-nitro-1H-indol-2-yl)-2-methylpropanoate (3.0 g, 8.4 mmol) and (S)-(2,2-dimethyl-1,3-dioxolan-4-yl)methyl 4-methylbenzenesulfonate (7.23 g, 25.3 mmol) in DMF (N,N-dimethylformamide) (17 mL). The reaction was stirred at 80° C. for 46 hours under a nitrogen atmosphere. The mixture was then partitioned between ethyl acetate and water. The aqueous layer was extracted with ethyl acetate. The combined ethyl acetate layers were washed with brine, dried over MgSO₄, filtered and concentrated. The crude product, a viscous brown oil which contains both of the products shown above, was taken directly to the next step without further purification. (R)-Benzyl 2-(1-((2,2-dimethyl-1,3-dioxolan-4-yl)methyl)-6-fluoro-5-nitro-1H-indol-2-yl)-2-methylpropanoate, ESI-MS m/z calc. 470.2, found 471.5 (M+1)⁺. Retention time 2.20 minutes. ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate, ESI-MS m/z calc. 494.5, found 495.7 (M+1)⁺. Retention time 2.01 minutes.

Step 2: (R)-2-(1-((2,2-dimethyl-1,3-dioxolan-4-yl)methyl)-6-fluoro-5-nitro-1H-indol-2-yl)-2-methylpropan-1-ol The crude reaction mixture obtained in step (A) was dissolved in THF (tetrahydrofuran) (42 mL) and cooled in an ice-water bath. LiAlH4 (16.8 mL of 1 M solution, 16.8 mmol) was added drop-wise. After the addition was complete, the mixture was stirred for an additional 5 minutes. The reaction was quenched by adding water (1 mL), 15% NaOH solution (1 mL) and then water (3 mL). The mixture was filtered over Celite, and the solids were washed with THF and ethyl acetate. The filtrate was concentrated and purified by column chromatography (30-60% ethyl acetate-hexanes) to obtain (R)-2-(1-((2,2-dimethyl-1,3-dioxolan-4-yl)methyl)-6-fluoro-5-nitro-1H-indol-2-yl)-2-methylpropan-1-ol as a brown oil (2.68 g, 87% over 2 steps). ESI-MS m/z calc. 366.4, found 367.3 (M+1)⁺. Retention time 1.68 minutes. ¹H NMR (400 MHz, DMSO-d6) δ 8.34 (d, J=7.6 Hz, 1H), 7.65 (d, J=13.4 Hz, 1H), 6.57 (s, 1H), 4.94 (t, J=5.4 Hz, 1H), 4.64-4.60 (m, 1H), 4.52-4.42 (m, 2H), 4.16-4.14 (m, 1H), 3.76-3.74 (m, 1H), 3.63-3.53 (m, 2H), 1.42 (s, 3H), 1.38-1.36 (m, 6H) and 1.19 (s, 3H) ppm. (DMSO is dimethylsulfoxide).

Step 3: (R)-2-(5-amino-1-((2,2-dimethyl-1,3-dioxolan-4-yl)methyl)-6-fluoro-1H-indol-2-yl)-2-methylpropan-1-ol (R)-2-(1-((2,2-dimethyl-1,3-dioxolan-4-yl)methyl)-6-fluoro-5-nitro-1H-indol-2-yl)-2-methylpropan-1-ol (2.5 g, 6.82 mmol) was dissolved in ethanol (70 mL) and the reaction was flushed with N2. Then Pd—C (250 mg, 5% wt) was added. The reaction flushed with nitrogen again and then stirred under H₂ (atm). After 2.5 hours only partial conversion to the product was observed by LCMS. The reaction was filtered through Celite and concentrated. The residue was re-subjected to the conditions above. After 2 hours LCMS indicated complete conversion to product. The reaction mixture was filtered through Celite. The filtrate was concentrated to yield the product (1.82 g, 79%). ESI-MS m/z calc. 336.2, found 337.5 (M+1)⁺. Retention time 0.86 minutes. ¹H NMR (400 MHz, DMSO-d6) δ 7.17 (d, J=12.6 Hz, 1H), 6.76 (d, J=9.0 Hz, 1H), 6.03 (s, 1H), 4.79-4.76 (m, 1H), 4.46 (s, 2H), 4.37-4.31 (m, 3H), 4.06 (dd, J=6.1, 8.3 Hz, 1H), 3.70-3.67 (m, 1H), 3.55-3.52 (m, 2H), 1.41 (s, 3H), 1.32 (s, 6H) and 1.21 (s, 3H) ppm.

Step 4: (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (1.87 g, 7.7 mmol) and thionyl chloride (1.30 mL, 17.9 mmol). After 1 hour a clear solution had formed. The solution was concentrated under vacuum and then toluene (3 mL) was added and the mixture was concentrated again. The toluene step was repeated once more and the residue was placed on high vacuum for 10 minutes. The acid chloride was then dissolved in dichloromethane (10 mL) and added to a mixture of (R)-2-(5-amino-1-((2,2-dimethyl-1,3-dioxolan-4-yl)methyl)-6-fluoro-1H-indol-2-yl)-2-methylpropan-1-ol (1.8 g, 5.4 mmol) and triethylamine (2.24 mL, 16.1 mmol) in dichloromethane (45 mL). The reaction was stirred at room temperature for 1 hour. The reaction was washed with 1N HCl solution, saturated NaHCO₃ solution and brine, dried over MgSO₄ and concentrated to yield the product (3 g, 100%). ESI-MS m/z calc. 560.6, found 561.7 (M+1)⁺. Retention time 2.05 minutes. ¹H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.51-4.48 (m, 1H), 4.39-4.34 (m, 2H), 4.08 (dd, J=6.0, 8.3 Hz, 1H), 3.69 (t, J=7.6 Hz, 1H), 3.58-3.51 (m, 2H), 1.48-1.45 (m, 2H), 1.39 (s, 3H), 1.34-1.33 (m, 6H), 1.18 (s, 3H) and 1.14-1.12 (m, 2H) ppm

Step 5: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (3.0 g, 5.4 mmol) was dissolved in methanol (52 mL). Water (5.2 mL) was added followed by p-TsOH.H₂O (p-toluenesulfonic acid hydrate) (204 mg, 1.1 mmol). The reaction was heated at 80° C. for 45 minutes. The solution was concentrated and then partitioned between ethyl acetate and saturated NaHCO₃ solution. The ethyl acetate layer was dried over MgSO₄ and concentrated. The residue was purified by column chromatography (50-100% ethyl acetate-hexanes) to yield the product. (1.3 g, 47%, ee>98% by SFC). ESI-MS m/z calc. 520.5, found 521.7 (M+1)⁺. Retention time 1.69 minutes. ¹H NMR (400 MHz, DMSO-d6) δ 8.31 (s, 1H), 7.53 (s, 1H), 7.42-7.38 (m, 2H), 7.33-7.30 (m, 2H), 6.22 (s, 1H), 5.01 (d, J=5.2 Hz, 1H), 4.90 (t, J=5.5 Hz, 1H), 4.75 (t, J=5.8 Hz, 1H), 4.40 (dd, J=2.6, 15.1 Hz, 1H), 4.10 (dd, J=8.7, 15.1 Hz, 1H), 3.90 (s, 1H), 3.65-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

Example 3: Synthesis of Compound III: N-(2,4-di-tert-butyl-5-hydroxyphenyl)-4-oxo-1,4-dihydroquinoline-3-carboxamide

Part A: Synthesis of 4-oxo-1,4-dihydroquinoline-3-carboxylic acid

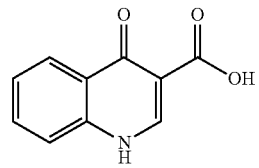 [SMILES: O=C(O)c1c[nH]c2ccccc2c1=O]

Step 1: 2-Phenylaminomethylene-malonic acid diethyl ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. ¹H NMR (DMSO-d6) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

Step 2: 4-Hydroxyquinoline-3-carboxylic acid ethyl ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous $Na_2CO_3$ solution, filtered, washed with water and dried. 4-Hydroxyquinoline-3-carboxylic acid ethyl ester was obtained as a pale brown solid (15.2 g, 70%). The crude product was used in next step without further purification.

Step 3: 4-Oxo-1,4-dihydroquinoline-3-carboxylic acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%). ¹H NMR (DMSO-d₆) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

Part B: Synthesis of N-(2,4-di-tert-butyl-5-hydroxyphenyl)-4-oxo-1,4-dihydroquinoline-3-carboxamide

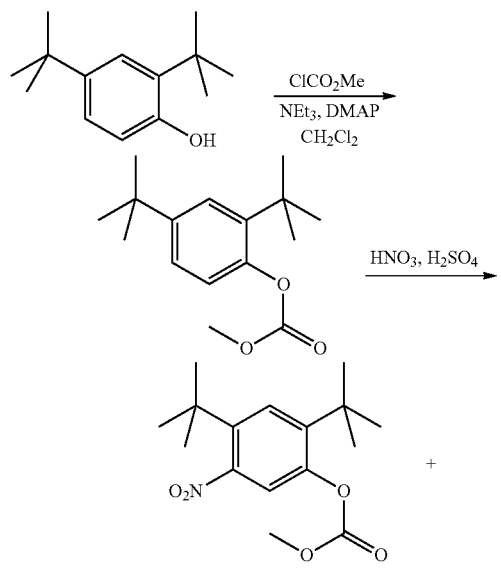

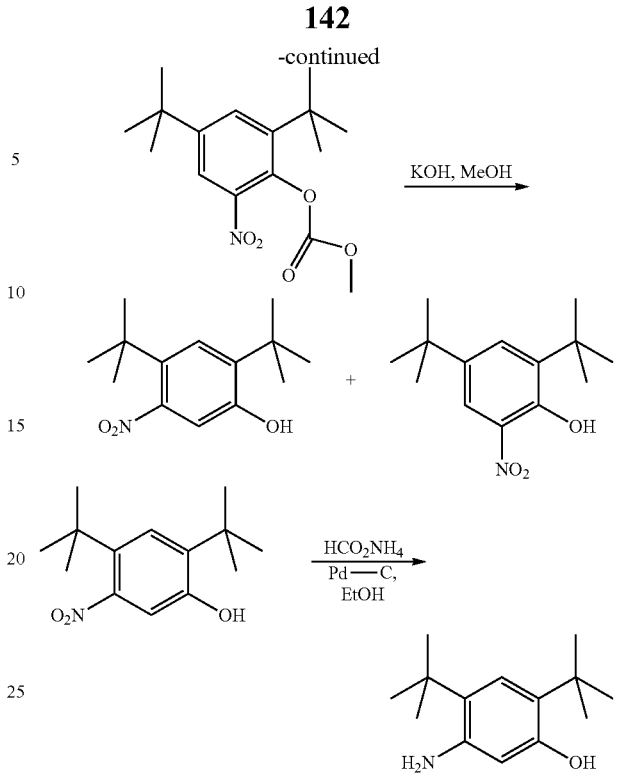

Step 1: Carbonic acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), $Et_3N$ (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1L) using 10% ethyl acetate-hexanes (~4 L) as the eluent. The combined filtrates were concentrated to yield carbonic acid 2,4-di-tert-butyl-phenyl ester methyl ester as a yellow oil (132 g, quant.). ¹H NMR (400 MHz, DMSO-d₆) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Step 2: Carbonic acid 2,4-di-tert-butyl-5-nitro-phenyl ester methyl ester and Carbonic acid 2,4-di-tert-butyl-6-nitro-phenyl ester methyl ester To a stirring mixture of carbonic acid 2,4-di-tert-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried ($MgSO_4$), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

Step 3: 2,4-Di-tert-butyl-5-nitro-phenol and 2,4-Di-tert-butyl-6-nitro-phenol The mixture of carbonic acid 2,4-di-tert-butyl-5-nitro-phenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO$_4$), concentrated and purified by column chromatography (0-5% ethyl acetate-hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-d$_6$) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, CDCl$_3$) δ 11.48 (s, 1H), 7.98 (d, J=2.5 Hz, 1H), 7.66 (d, J=2.4 Hz, 1H), 1.47 (s, 9H), 1.34 (s, 9H).

Step 4: 5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-d$_6$) δ 8.64 (s, 1H, OH), 6.84 (s, 1H), 6.08 (s, 1H), 4.39 (s, 2H, NH$_2$), 1.27 (m, 18H); HPLC ret. time 2.72 min, 10-99% CH$_3$CN, 5 min run; ESI-MS 222.4 m/z [M+H]$^+$.

Step 5: N-(5-hydroxy-2,4-di-tert-butyl-phenyl)-4-oxo-1H-quinoline-3-carboxamide

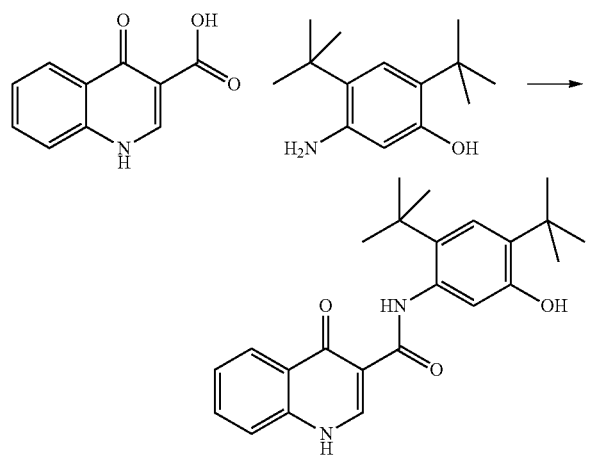

To a suspension of 4-oxo-1,4-dihydroquinolin-3-carboxylic acid (35.5 g, 188 mmol) and HBTU (85.7 g, 226 mmol) in DMF (280 mL) was added Et$_3$N (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+190, 1.71 min), the solvent was removed in vacuo. EtOH (ethyl alcohol) was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystalate. Et$_2$O (diethyl ether) was added to the solid obtained above until a slurry was formed. The mixture was stirred on a rotovapor (bath temperature 25° C.) for 15 min without placing the system under vacuum. The mixture was filtered and the solid captured. This procedure was performed a total of five times. The solid obtained after the fifth precipitation was placed under vacuum overnight to provide N-(5-hydroxy-2,4-di-tert-butyl-phenyl)-4-oxo-1H-quinoline-3-carboxamide (38 g, 52%). HPLC ret. time 3.45 min, 10-99% CH$_3$CN, 5 min run; $^1$H NMR (400 MHz, DMSO-d6) δ 12.88 (s, 1H), 11.83 (s, 1H), 9.20 (s, 1H), 8.87 (s, 1H), 8.33 (dd, J=8.2, 1.0 Hz, 1H), 7.83-7.79 (m, 1H), 7.76 (d, J=7.7 Hz, 1H), 7.54-7.50 (m, 1H), 7.17 (s, 1H), 7.10 (s, 1H), 1.38 (s, 9H), 1.37 (s, 9H); ESI-MS m/z calc'd 392.21; found 393.3 [M+H]$^+$.

Example 4: Preparation of Tablet Formulation 1 ("Tablet 1")

The intragranular components in Table 5: Compound I, the solid dispersion comprising 80 wt % substantially amorphous Compound II and 20 wt % HPMC (see PCT Publication No. WO 2015/160787, the entire contents are incorporated herein by reference), the solid dispersion comprising 80 wt % substantially amorphous Compound III-d, 19.5 wt % HPMCAS and 0.5 wt % sodium lauryl sulfate, and excipients were passed through a sieve and blended. The SDD comprising 80 wt % substantially amorphous Compound III-d, 19.5 wt % HPMCAS and 0.5 wt % sodium lauryl sulfate was made in the same manner as that for the SDD comprising 80 wt % substantially amorphous Compound III, 19.5 wt % HPMCAS and 0.5 wt % sodium lauryl sulfate as described in PCT Publication No. WO 2015/160787. The blend was granulated using a roller compactor and then milled. The milled material was added to a bin blender along with sieved extragranular components (microcrystalline cellulose and magnesium stearate) and further blended. The final blend was compressed into tablets containing the amounts in Table 5.

TABLE 5

"Tablet 1" Comprising 100 mg Compound I, 50 mg Compound II and 75 mg Compound III-d.

| | Ingredient | Amount per tablet (mg) |
|---|---|---|
| Intra-granular | Compound I | 100.0 |
| | Compound II SDD (80 wt % Compound II and 20 wt % HPMC) | 62.5 |
| | Compound III-d SDD (80 wt % Compound III-d, 19.5 wt % HPMCAS, and 0.5 wt % sodium lauryl sulfate) | 93.7 |
| | Croscarmellose Sodium | 29.3 |
| | Microcrystalline cellulose | 80.5 |
| Extra-granular | Microcrystalline cellulose | 117.1 |
| | Magnesium Stearate | 4.9 |
| Total | | 488.0 |

Example 5: Preparation of Tablet Formulation 2 ("Tablet 2")

The intragranular components in Table 6: Compound I, the solid dispersion comprising 80 wt % substantially amorphous Compound II and 20 wt % HPMC (see PCT Publication No. WO 2015/160787, the entire contents are incorporated herein by reference), the solid dispersion comprising 80 wt % substantially amorphous Compound III-d, 19.5 wt % HPMCAS and 0.5 wt % sodium lauryl sulfate, and croscarmellose sodium were passed through a sieve and blended. The SDD comprising 80 wt % substantially amorphous Compound III-d, 19.5 wt % HPMCAS and 0.5 wt % sodium lauryl sulfate was made in the same manner as that for the SDD comprising 80 wt % substantially amorphous Compound III, 19.5 wt % HPMCAS and 0.5 wt % sodium lauryl sulfate as described in PCT Publication No. WO 2015/160787. The blend was granulated using a roller compactor and then milled. The milled material was added to a bin blender along with sieved extragranular components (microcrystalline cellulose and magnesium stearate) and further blended. The final blend was compressed into tablets containing the amounts in Table 6.

TABLE 6

"Tablet 2" Comprising 100 mg Compound I, 50 mg Compound II and 75 mg Compound III-d.

| | Ingredient | Amount per tablet (mg) |
|---|---|---|
| Intra-granular | Compound I | 100.0 |
| | Compound II SDD (80 wt % Compound II and 20 wt % HPMC) | 62.4 |
| | Compound III-d SDD (80 wt % Compound III-d, 19.5 wt % HPMCAS, and 0.5 wt % sodium lauryl sulfate) | 93.8 |
| | Croscarmellose Sodium | 22.3 |
| Extra-granular | Microcrystalline cellulose | 89.1 |
| | Magnesium Stearate | 3.7 |
| Total | | 371.3 |

Example 6: Preparation of Tablet Formulation 3 ("Tablet 3")

The components in Table 7: Compound I, the solid dispersion comprising 80 wt % substantially amorphous Compound II and 20 wt % HPMC (see PCT Publication No. WO 2015/160787, the entire contents are incorporated herein by reference), the solid dispersion comprising 80 wt % substantially amorphous Compound III-d, 19.5 wt % HPMCAS and 0.5 wt % sodium lauryl sulfate, microcrystalline cellulose, and croscarmellose sodium were passed through a sieve and blended. The SDD comprising 80 wt % substantially amorphous Compound III-d, 19.5 wt % HPMCAS and 0.5 wt % sodium lauryl sulfate was made in the same manner as that for the SDD comprising 80 wt % substantially amorphous Compound III, 19.5 wt % HPMCAS and 0.5 wt % sodium lauryl sulfate as described in PCT Publication No. WO 2015/160787. Sieved magnesium stearate was added and the mixture was further blended. The final blend was compressed into tablets containing the amounts in Table 7.

TABLE 7

Tablet "3" Comprising 100 mg Compound I, 50 mg Compound II and 75 mg Compound III-d.

| Ingredient | Amount per tablet (mg) |
|---|---|
| Compound I | 100 |
| Compound II SDD (80 wt % Compound II and 20 wt % HPMC) | 62.5 |
| Compound III-d SDD (80 wt % Compound III-d, 19.5 wt % HPMCAS, and 0.5 wt % sodium lauryl sulfate) | 93.7 |
| Microcrystalline cellulose | 140.9 |
| Croscarmellose Sodium | 25.6 |
| Magnesium stearate | 4.3 |
| Total | 427.0 |

Example 7. Dissolution Testing

Figure 2B:
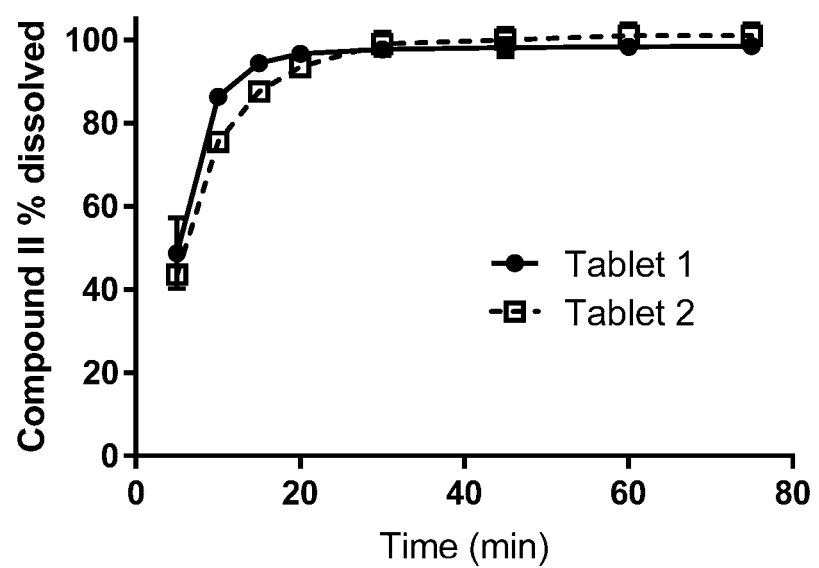
FIG. 2B is dissolution data for Compound II.
Figure 2C:
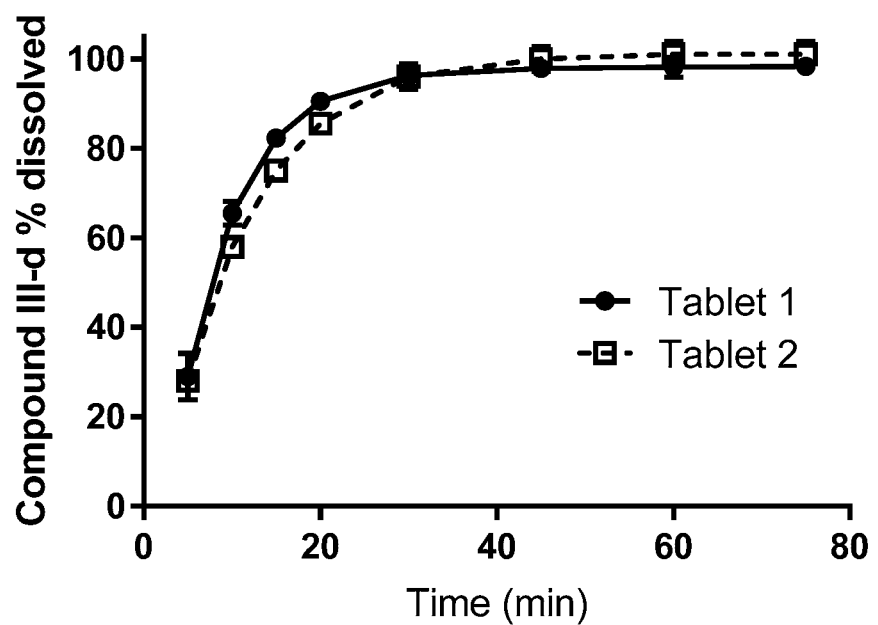
FIG. 2C is dissolution data for Compound III-d.

Dissolution testing was performed using USP Apparatus II (paddle), in 0.5% CTAB in 50 mM Acetate Buffer pH 4.5 dissolution media, following USP <711>. Samples were collected using an autosampler and filtered through 10 m PVDF filters into HPLC vials for reverse phase HPLC analysis. Dissolution results are shown in FIGS. 2A, 2B, and 2C.

Example 8. In Vivo Pharmacokinetic Study in Dogs

Figure 3A:
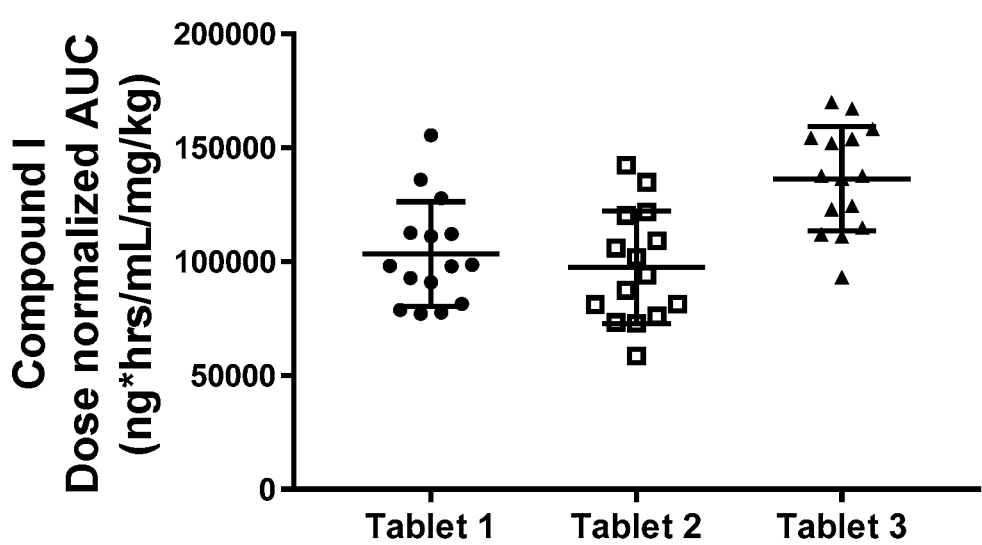
FIG. 3A shows bioavailability of Compound I for Tablet 1, Tablet 2, and Tablet 3 in a dog.
Figure 3B:
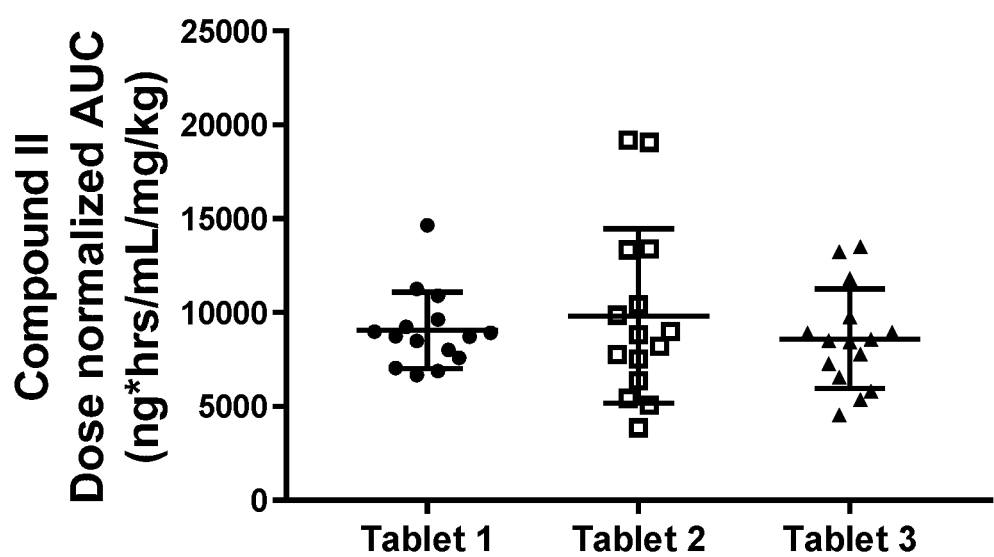
FIG. 3B shows bioavailability of Compound II for Tablet 1, Tablet 2, and Tablet 3 in a dog.
Figure 3C:
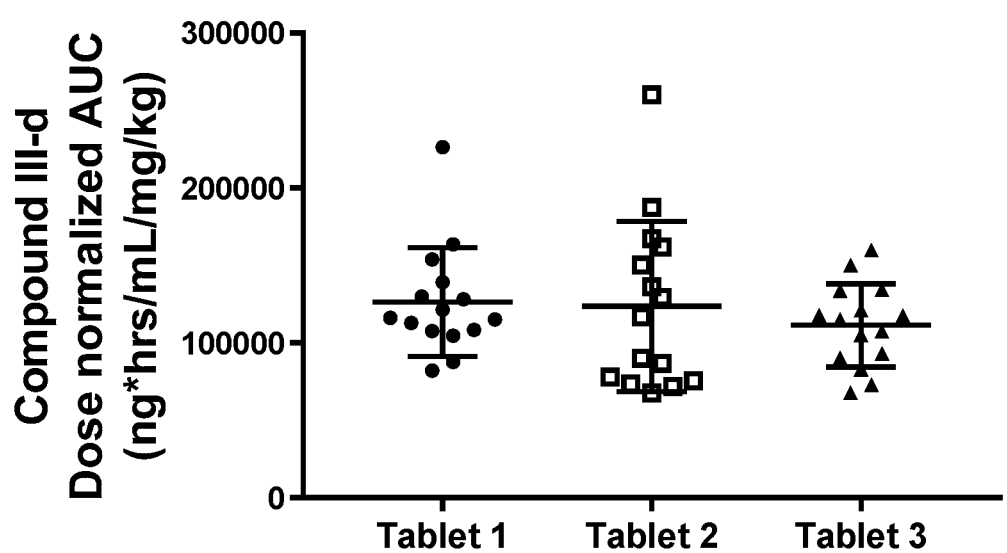
FIG. 3C shows bioavailability of Compound III-d for Tablet 1, Tablet 2, and Tablet 3 in a dog.

Male beagle dogs were fasted overnight for at least 8 hours and offered food 2 hours prior to dosing. Tablets were administered orally, and blood samples were collected pre-dose and at 0.25, 0.5, 1, 2, 4, 8, 34, 48, 72, and 96 hours post-dose. Compound I, Compound II, and Compound III-d in the plasma were quantified. Bioavailability was assessed with dose normalized AUC. Data are shown in FIGS. 3A, 3B, and 3C

Example 9: Preparation of Tablet Formulation 4 ("Tablet 4")

The intragranular components in Table 8: Compound I, the solid dispersion comprising 80 wt % substantially amorphous Compound II and 20 wt % HPMC (see PCT Publication No. WO 2015/160787, the entire contents are incorporated herein by reference), the solid dispersion comprising 80 wt % substantially amorphous Compound III, 19.5 wt % HPMCAS and 0.5 wt % sodium lauryl sulfate, and excipients were passed through a sieve and blended (see PCT Publication No. WO 2015/160787, the entire contents are incorporated herein by reference). The blend was granulated using a roller compactor and then milled. The milled material was blended with sieved extragranular components (microcrystalline cellulose and magnesium stearate). The final blend was compressed into tablets and film coated to produce final tablets containing the amounts in Table 8.

TABLE 8

"Tablet 4" Comprising 100 mg Compound I, 50 mg Compound II and 75 mg Compound III.

| | Material Name | mg per tablet |
|---|---|---|
| Intra Granular | Compound I | 100 |
| | Compound II SDD (80 wt % Compound II and 20 wt % HPMC) | 62.5 |
| | Compound III SDD (80 wt % Compound III, 19.5 wt % HPMCAS, and 0.5 wt % sodium lauryl sulfate) | 93.8 |
| | Croscarmellose sodium | 29.3 |
| | Microcrystalline cellulose | 80.5 |
| Extra Granular | Microcrystalline cellulose | 117.1 |
| | Magnesium stearate | 4.9 |
| | Total Core Tablet | 488 |
| | Film coat | 14.6 |
| | Total Coated Tablet | 502.6 |

Example 10. Dissolution Testing

Figure 5A:
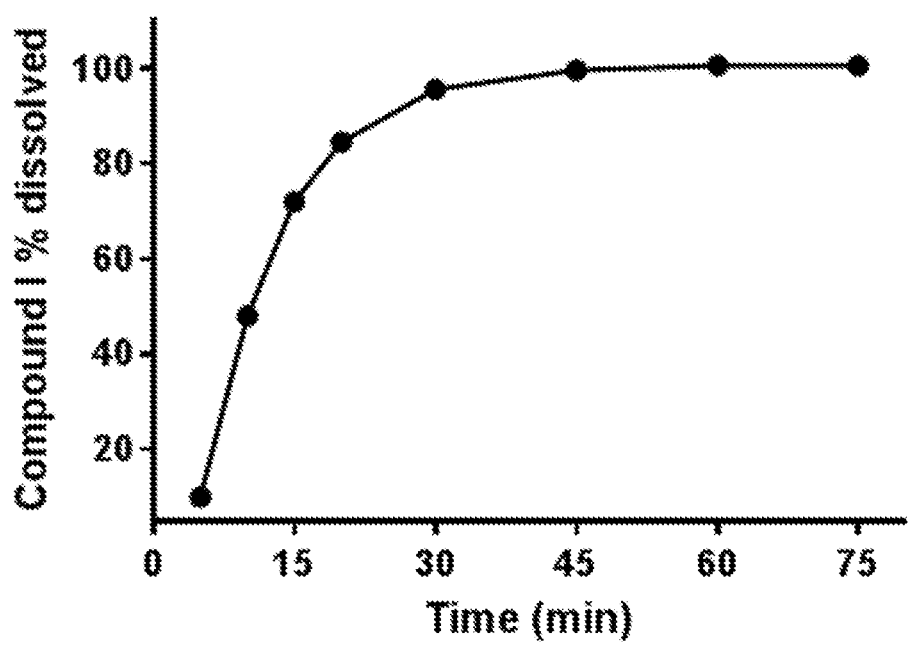
FIG. 5A is dissolution data for Compound I in Tablet 4.
Figure 5B:
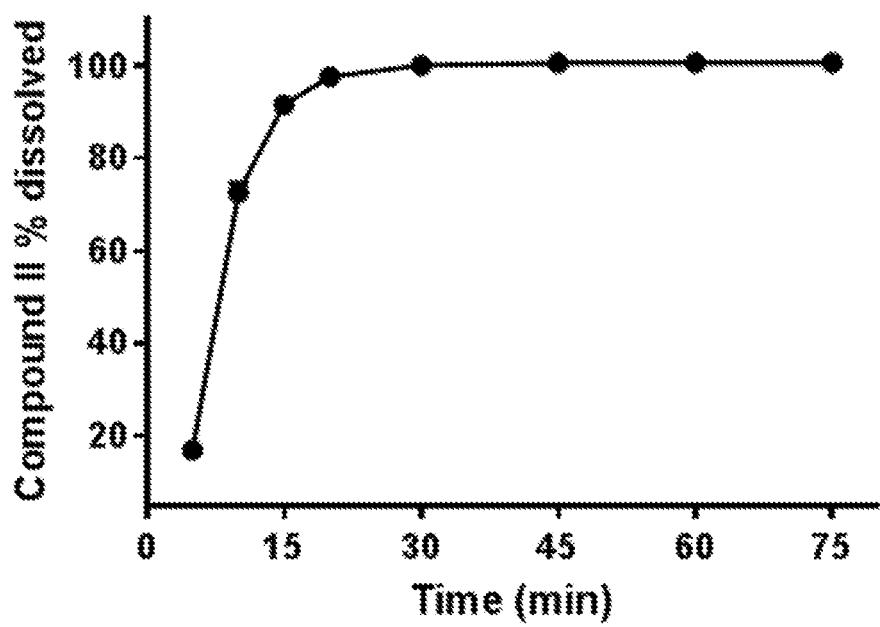
FIG. 5B is dissolution data for Compound II in Tablet 4.
Figure 5C:
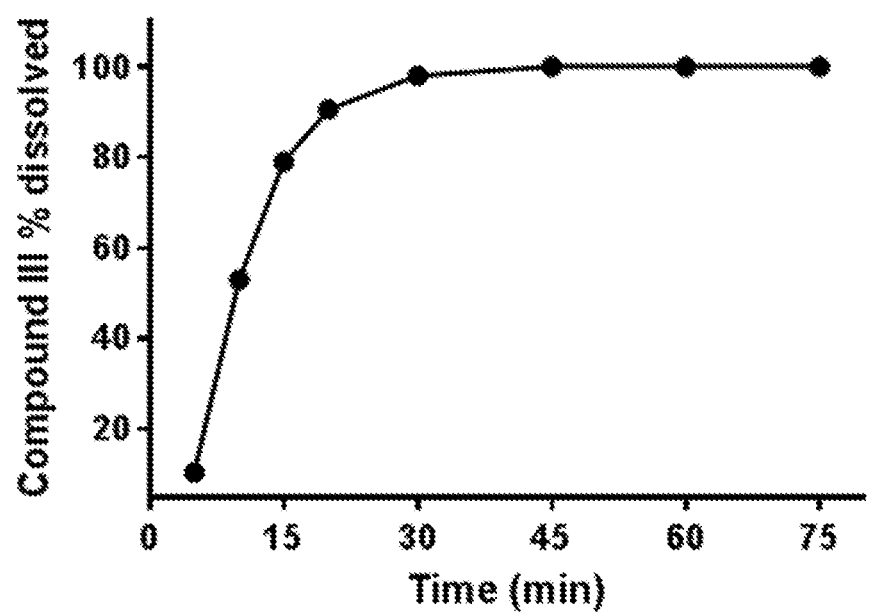
FIG. 5C is dissolution data for Compound III in Tablet 4.

Dissolution testing was performed using USP Apparatus II (paddle), in 0.5% CTAB in 50 mM Acetate Buffer pH 4.5 dissolution media, following USP <711>. Samples were collected using an autosampler and filtered through 10 m PVDF filters into HPLC vials for reverse phase HPLC analysis. Dissolution results for Tablet 4 are shown in FIGS. 5A, 5B, and 5C.

Example 11: Preparation of Tablet Formulations 5-13 ("Tablets 5, 6, 7, 8, 9, 10, 11, 12, and 13")

Tablets 5, 6, 7, 8, 9, 10, 11, 12, and 13 comprising Compounds I, II, and III, and excipients as shown in Tables 9, 10, 11, 12, 13, 14, 15, 16, and 17, respectively, can be prepared as shown above for Tablets 1, 2, 3, and 4. The solid dispersion comprising 80 wt % substantially amorphous Compound II and 20 wt % HPMC and the solid dispersion comprising 80 wt % substantially amorphous Compound III, 19.5 wt % HPMCAS and 0.5 wt % sodium lauryl sulfate can be prepared as shown in PCT Publication No. WO 2015/160787, the entire contents are incorporated herein by reference).

TABLE 9

"Tablet 5" Comprising 100 mg Compound I, 50 mg Compound II and 150 mg Compound III.

| | Ingredient | Amount per tablet (mg) |
|---|---|---|
| Intra-granular | Compound I | 100.0 |
| | Compound II SDD (80 wt % Compound II and 20 wt % HPMC) | 62.5 |
| | Compound III SDD (80 wt % Compound III, 19.5 wt % HPMCAS, and 0.5 wt % sodium lauryl sulfate) | 187.5 |
| | Croscarmellose Sodium | 29.3 |
| | Microcrystalline cellulose | 80.5 |
| Extra-granular | Microcrystalline cellulose | 117.1 |
| | Magnesium Stearate | 4.9 |
| Total | | 581.8 |

TABLE 10

"Tablet 6" Comprising 100 mg Compound I, 50 mg Compound II and 150 mg Compound III.

| | Ingredient | Amount per tablet (mg) |
|---|---|---|
| Intra-granular | Compound I | 100.0 |
| | Compound II SDD (80 wt % Compound II and 20 wt % HPMC) | 62.5 |
| | Compound III SDD (80 wt % Compound III, 19.5 wt % HPMCAS, and 0.5 wt % sodium lauryl sulfate) | 187.5 |
| | Croscarmellose Sodium | 22.3 |
| Extra-granular | Microcrystalline cellulose | 89.1 |
| | Magnesium Stearate | 3.7 |
| Total | | 465.1 |

TABLE 11

"Tablet 7" Comprising 100 mg Compound I, 50 mg Compound II and 150 mg Compound III.

| Ingredient | Amount per tablet (mg) |
|---|---|
| Compound I | 100 |
| Compound II SDD (80 wt % Compound II and 20 wt % HPMC) | 62.5 |
| Compound III SDD (80 wt % Compound III, 19.5 wt % HPMCAS, and 0.5 wt % sodium lauryl sulfate) | 187.5 |
| Microcrystalline cellulose | 140.9 |
| Croscarmellose Sodium | 25.6 |
| Magnesium stearate | 4.3 |
| Total | 520.8 |

TABLE 12

"Tablet 8" Comprising 100 mg Compound I, 50 mg Compound II and 150 mg Compound III.

| | Ingredient | Amount per tablet (mg) |
|---|---|---|
| Intra-granular | Compound I | 100 |
| | Compound II SDD (80 wt % Compound II and 20 wt % HPMC) | 62.5 |
| | Compound III SDD (80 wt % Compound III, 19.5 wt % HPMCAS, and 0.5 wt % sodium lauryl sulfate) | 187.5 |
| | Croscarmellose sodium | 40 |
| | Microcrystalline cellulose | 110 |
| Extra-granular | Microcrystalline cellulose | 160 |
| | Magnesium stearate | 6.7 |
| | Total Core Tablet | 666.7 |
| | Film coat | 20 |
| | Total Coated Tablet | 686.7 |

TABLE 13

"Tablet 9" Comprising 50 mg Compound I, 25 mg Compound II and 75 mg Compound III.

| | Ingredient | Amount per tablet (mg) |
|---|---|---|
| Intra-granular | Compound I | 50 |
| | Compound II SDD (80 wt % Compound II and 20 wt % HPMC) | 31.3 |
| | Compound III SDD (80 wt % Compound III, 19.5 wt % HPMCAS, and 0.5 wt % sodium lauryl sulfate) | 93.8 |
| | Croscarmellose sodium | 20 |
| | Microcrystalline cellulose | 55 |
| Extra-granular | Microcrystalline cellulose | 80 |
| | Magnesium stearate | 3.3 |
| | Total Core Tablet | 333.3 |
| | Film coat | 10 |
| | Total Coated Tablet | 343.3 |

TABLE 14

"Tablet 10" Comprising 50 mg Compound I, 50 mg Compound II and 150 mg Compound III.

| | Ingredient | Amount per tablet (mg) |
|---|---|---|
| Intra-granular | Compound I | 50 |
| | Compound II SDD (80 wt % Compound II and 20 wt % HPMC) | 62.5 |
| | Compound III SDD (80 wt % Compound III, 19.5 wt % HPMCAS, and 0.5 wt % sodium lauryl sulfate) | 187.5 |
| | Croscarmellose sodium | 34.3 |
| | Microcrystalline cellulose | 94.3 |
| Extra-granular | Microcrystalline cellulose | 137.1 |
| | Magnesium stearate | 5.7 |
| | Total Core Tablet | 571.4 |
| | Film coat | 17.1 |
| | Total Coated Tablet | 588.6 |

TABLE 15

"Tablet 11" Comprising 25 mg Compound I, 25 mg Compound II and 75 mg Compound III.

| | Ingredient | Amount per tablet (mg) |
|---|---|---|
| Intra-granular | Compound I | 25 |
| | Compound II SDD (80 wt % Compound II and 20 wt % HPMC) | 31.3 |
| | Compound III SDD (80 wt % Compound III, 19.5 wt % HPMCAS, and 0.5 wt % sodium lauryl sulfate) | 93.8 |
| | Croscarmellose sodium | 17.1 |
| | Microcrystalline cellulose | 47.1 |
| Extra-granular | Microcrystalline cellulose | 68.6 |
| | Magnesium stearate | 2.9 |
| | Total Core Tablet | 285.7 |
| | Film coat | 8.6 |
| | Total Coated Tablet | 294.3 |

TABLE 16

"Tablet 12" Comprising 25 mg Compound I, 50 mg Compound II and 150 mg Compound III.

| | Ingredient | Amount per tablet (mg) |
|---|---|---|
| Intra-granular | Compound I | 25 |
| | Compound II SDD (80 wt % Compound II and 20 wt % HPMC) | 62.5 |
| | Compound III SDD (80 wt % Compound III, 19.5 wt % HPMCAS, and 0.5 wt % sodium lauryl sulfate) | 187.5 |
| | Croscarmellose sodium | 31.4 |
| | Microcrystalline cellulose | 86.4 |
| Extra-granular | Microcrystalline cellulose | 125.7 |
| | Magnesium stearate | 5.2 |
| | Total Core Tablet | 523.8 |
| | Film coat | 15.7 |
| | Total Coated Tablet | 539.5 |

TABLE 17

"Tablet 13" Comprising 12.5 mg Compound I, 25 mg Compound II and 75 mg Compound III.

| | Ingredient | Amount per tablet (mg) |
|---|---|---|
| Intra-granular | Compound I | 12.5 |
| | Compound II SDD (80 wt % Compound II and 20 wt % HPMC) | 31.3 |
| | Compound III SDD (80 wt % Compound III, 19.5 wt % HPMCAS, and 0.5 wt % sodium lauryl sulfate) | 93.8 |
| | Croscarmellose sodium | 15.7 |
| | Microcrystalline cellulose | 43.2 |
| Extra-granular | Microcrystalline cellulose | 62.9 |
| | Magnesium stearate | 2.6 |
| | Total Core Tablet | 261.9 |
| | Film coat | 7.9 |
| | Total Coated Tablet | 269.8 |

Example 12: Preparation of Tablet Formulation 14 ("Tablet 14")

Tablet 14 comprising Compounds I, II, and III, and excipients as shown in Table 18 was prepared as shown above for Tablet 4. The solid dispersion comprising 80 wt % substantially amorphous Compound II and 20 wt % HPMC and the solid dispersion comprising 80 wt % substantially amorphous Compound III, 19.5 wt % HPMCAS and 0.5 wt % sodium lauryl sulfate were prepared as shown in PCT Publication No. WO 2015/160787, the entire contents are incorporated herein by reference).

TABLE 18

"Tablet 14" Comprising 50 mg Compound I, 25 mg Compound II and 37.5 mg Compound III.

| | Component | mg per tablet |
|---|---|---|
| Intragranular | Compound I | 50.0 |
| | a solid dispersion comprising: 80 wt % substantially amorphous Compound II, and 20 wt % HPMC | 31.3 |
| | a solid dispersion comprising: 80 wt % substantially amorphous Compound III, 19.5 wt % HPMCAS, and 0.5 wt % sodium lauryl sulfate | 46.9 |
| | Croscarmellose sodium | 14.6 |
| | Microcrystaline cellulose | 40.2 |
| Extragranular | Microcrystaline cellulose | 58.6 |
| | Magnesium stearate | 2.4 |
| | Total Core Tablet | 244.0 |
| | Film coat | 7.3 |
| | Total | 251.3 |

Example 13. Dissolution Testing of Tablet 14

Dissolution testing of Compound I in Tablet 14 was performed using USP Apparatus II in 1.8% Tween20 in 50 mM sodium phosphate buffer. Samples were collected and filtered through 10 m PVDF filters for HPLC analysis.

Dissolution testing of Compound II in Tablet 14 was performed using USP Apparatus II in 0.2% SDS in 50 mM sodium phosphate buffer. Samples were collected and filtered through 10 m PVDF filters for HPLC analysis.

Dissolution testing of Compound III in Tablet 14 was performed using USP Apparatus II in 0.4% SLS in 50 mM sodium phosphate buffer. Samples were collected and filtered through 10 m PVDF filters for HPLC analysis.

Figure 6A:
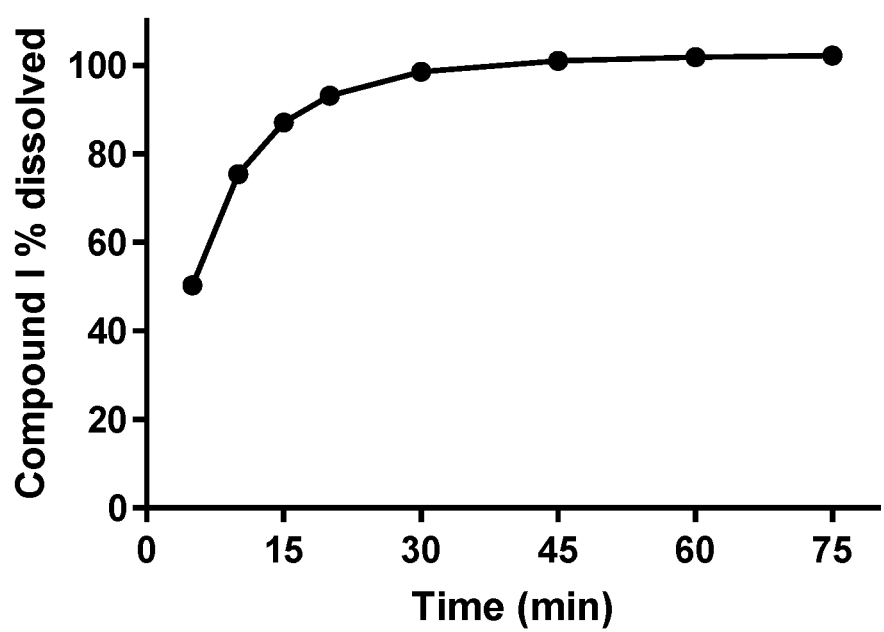
FIG. 6A is dissolution data for Compound I in Tablet 14.
Figure 6B:
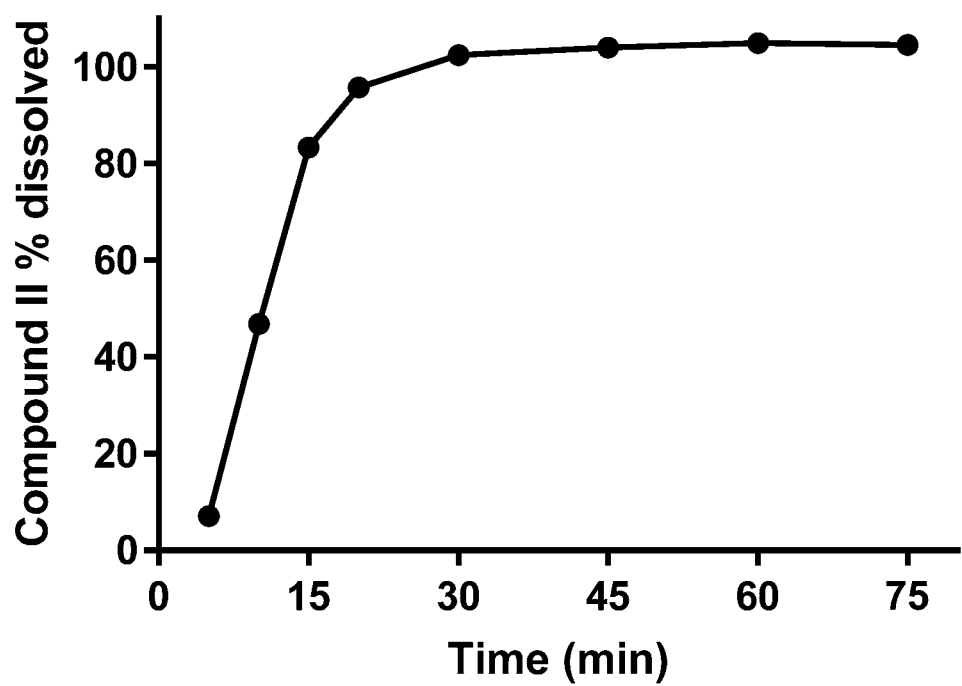
FIG. 6B is dissolution data for Compound II in Tablet 14.
Figure 6C:
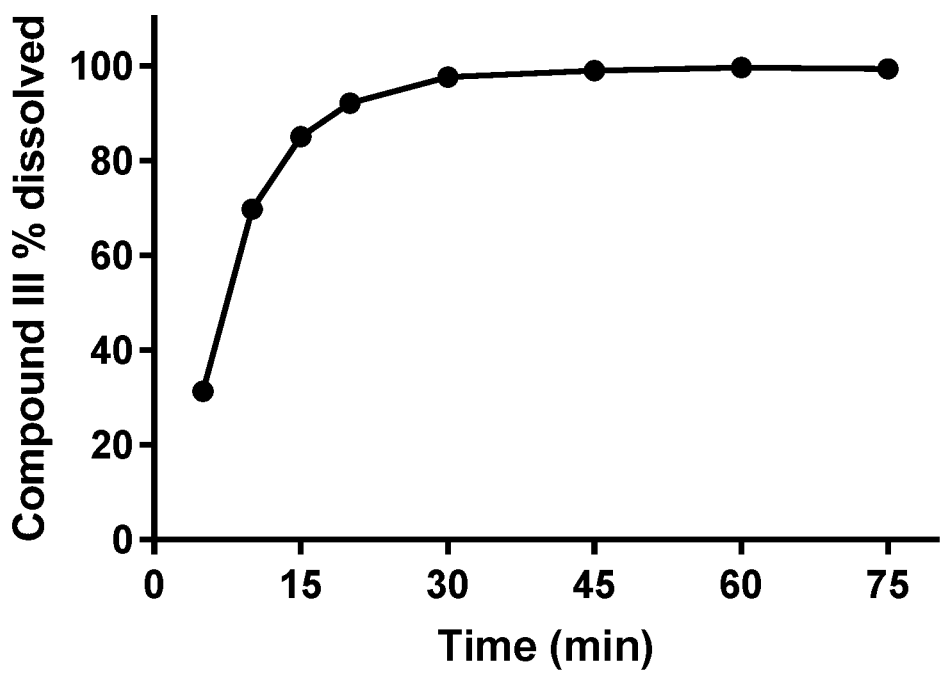
FIG. 6C is dissolution data for Compound III in Tablet 14.

Dissolution results for Tablet 14 are shown in FIGS. 6A, 6B, and 6C.

Example 14: Assays for Detecting and Measuring F508del-CFTR Modulator Properties of Compounds Membrane Potential Optical Methods for Assaying Properties of F508del-CFTR Modulators An optical assay was employed to measure changes in membrane potential to determine the CFTR modulator properties of compounds. The assay utilized fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response was the creation of a chloride ion gradient in conjunction with channel activation and concurrent with compound treatment by a single liquid addition step after the cells had previously been loaded with a voltage sensing dye.

Assay Procedure

NIH3T3 mouse fibroblasts stably expressing F508del were used for optical measurements of membrane potential. The cells were maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 $cm^2$ culture flasks. For all optical assays, the cells were seeded at 12,000 cells/well in 384-well matrigel-coated plates. For the correction assay, the cells were cultured at 37° C. for 18-24 hours and loaded with a voltage sensing dye. The cells were then activated and treated with Compound I. After 18-24 hours, fluorescence from the voltage sensing dye in the cells was measured to assess changes in the membrane potential as a read out for increase in functional F508del CFTR in the NIH3T3 cells.

Using this method, Compound I had an $EC_{50}$ of less than 3 μM and a % Efficacy of ≥100% relative to Compound II.

Ussing Chamber Assay

Ussing chamber experiments were performed on polarized airway epithelial cells expressing F508del to further characterize the F508del modulators identified in the optical assay above. Non-CF and CF airway epithelia were isolated from bronchial tissue, cultured using methods well known in the art, and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF human bronchial epithelial (HBE) cells were isolated from non-smokers that did not have any known lung disease. CF-HBE cells were isolated from patients homozygous for F508del (F508del/F508del-HBE) or heterozygous for F508del with a different disease causing mutation on the other allele.

HBE cells grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, IA). Briefly, HBE cells were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$), 10 glucose, 10 HEPES (pH adjusted to 7.35 with NaOH).

Ussing Chamber Assay Procedure

A basolateral to apical membrane Cl⁻ concentration gradient was set up as follows. Normal Ringer's solution was used on the basolateral membrane, whereas apical NaCl was replaced by equimolar sodium gluconate (titrated to pH 7.4 with NaOH) to give a large Cl— concentration gradient across the epithelium. Compound I was added either to the basolateral side 18-24 hrs prior to assay or to the apical side during the assay. Forskolin (10 μM) was added to the apical side during the assay to stimulate CFTR-mediated Cl-transport. Chloride current was measured to assess the increase in functional CFTR in the cell membrane.

In Table 20, the following meanings apply: EC50: "+++" means <2 μM; "++" means between 2 uM to 5 uM; "+" means between 5 uM to 25 uM. % Efficacy: "+" means <25%; "++" means between 25% and 100%; "+++" means >100%.

TABLE 20

| Compound | HBE EC$_{50}$ (μM) | HBE Max Eff (%) |
|---|---|---|
| Compound I | +++ | +++ |

Example 15

Compound I is a potent, efficacious, and selective next generation CFTR corrector that works by facilitating the processing and trafficking of F508del-CFTR protein to the cell surface, resulting in enhanced chloride transport.

The combination of Compound I and Compound II resulted in more than additive improvement in CFTR processing and trafficking compared to either CFTR corrector alone, suggesting that the two CFTR correctors act through different mechanisms of action, which act synergistically to increase the amount of F508del-CFTR delivered to the cell surface.

In addition, the more than additive effect of the combination of Compound I and Compound II on the processing and trafficking of CFTR suggests that the two CFTR correctors act through different mechanisms to result in the delivery of more CFTR protein to the cell surface compared to either CFTR corrector alone.

The triple combination of Compound I, Compound II, and Compound III enhanced chloride transport more than dual combinations at most concentrations of Compound I Compound 1 was administered to male Sprague Dawley rats as a single nominal intravenous (IV) dose of 3.0 mg/kg in a solution in 10% NMP, 15% EtOH, 35% PEG400, 10% Solutol, and 30% D5W. Compound 1 was also administered to male Sprague Dawley rats at single nominal oral dose (PO) of 3 mg/kg as a solution in 5% NMP, 30% PEG400, 10% TPGS, 5% PVP-K30 at 5 mL/kg dose volume.

The study design, sample tracking, data run design and individual plasma sample concentrations were stored using Watson LIMS software, Version 7.4.2 (Thermo Scientific Inc, Waltham, Mass.). Plasma concentration-time profiles of Compound 1 in Sprague Dawley rats at scheduled (nominal) sampling times were analyzed by noncompartmental pharmacokinetic methods using PK function within Watson LIMS software, Version 7.4.2 (Thermo Scientific Inc, Waltham, Mass.). Key pharmacokinetic parameters such as "area under the curve" (AUC), from the time of drug administration, time zero, extrapolated to infinity, clearance (CL), and Percent of oral bioavailability (% F) were determined. The AUC values were calculated using the linear trapezoidal rule.

In Table 21 below, Compound I is shown to have advantageous rat oral exposure (AUC) and oral bioavailability.

TABLE 21

| Compound | Rat iv CL (mL/min/kg) | Rat PO AUC (μg · hr/mL) | Rat PO AUC/dose (μg · hr/mL/mg/kg) | Rat % F |
|---|---|---|---|---|
| Compound I | 1.6 ± 0.4 | 23.5 ± 1.7 | 9.4 ± 0.7 | 84% |

OTHER EMBODIMENTS

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:
1. A pharmaceutical composition comprising
(a) 15 mg to 250 mg of Compound I:

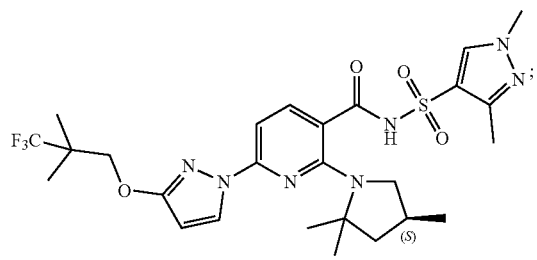

(b) a first solid dispersion comprising 10 mg to 150 mg of Compound II:

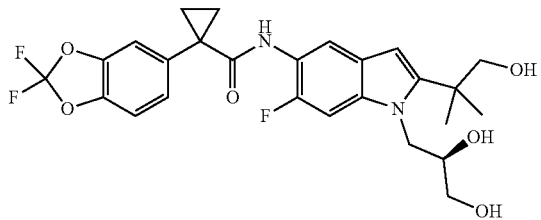 [SMILES: CC(C)(CO)c1cc2cc(NC(=O)C3(c4ccc5c(c4)OC(F)(F)O5)CC3)c(F)cc2n1C[C@@H](O)CO]

and 10 wt% to 30 wt% of a polymer relative to the total weight of the first solid dispersion; and
(c) a second solid dispersion comprising 25 mg to 200 mg of Compound III:

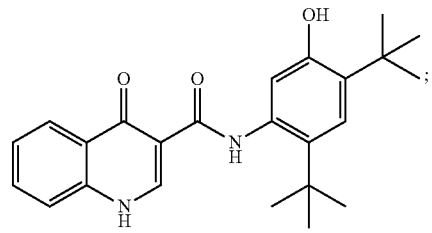 [SMILES: CC(C)(C)c1cc(C(C)(C)C)c(NC(=O)c2c[nH]c3ccccc3c2=O)cc1O]

and 10 wt% to 30 wt% of a polymer relative to the total weight of the second solid dispersion.

2. The pharmaceutical composition of claim 1, comprising
(a) 50 mg to 125 mg of Compound I; and wherein the first solid dispersion comprises 25 mg to 75 mg of Compound II; and the second solid dispersion comprises 50 mg to 175 mg of Compound III; or
(b) 70 mg to 240 mg of Compound I; and wherein the first solid dispersion comprises 30 mg to 120 mg of Compound II; and the second solid dispersion comprises 50 mg to 170 mg of Compound III; or
(c) 30 mg to 120 mg of Compound I; and wherein the first solid dispersion comprises 15 mg to 60 mg of Compound II; and the second solid dispersion comprises 20 mg to 90 mg of Compound III; or (d) 30 mg to 120 mg of Compound I; and wherein the first solid dispersion comprises 15 mg to 60 mg of Compound II; and the second solid dispersion comprises 50 mg to 170 mg of Compound III; or (e) 15 mg to 55 mg of Compound I; and wherein the first solid dispersion comprises 10 mg to 50 mg of Compound II; and the second solid dispersion comprises 20 mg to 90 mg of Compound III.

3. A pharmaceutical composition comprising:

(a) 10 wt% to 30 wt% of Compound I:

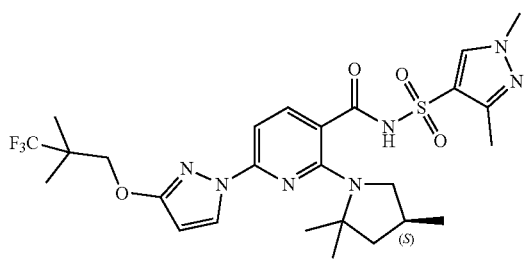

relative to the total weight of the pharmaceutical composition;

(b) 8 wt% to 30 wt% of a first solid dispersion relative to the total weight of the pharmaceutical composition, wherein the first solid dispersion comprises 70 wt% to 90 wt% of Compound II relative to the total weight of the first solid dispersion:

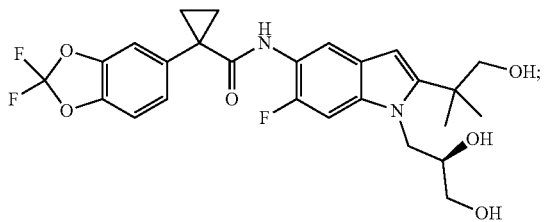

and 10 wt% to 30 wt% of a polymer relative to the total weight of the first solid dispersion; and (c) 10 wt% to 45 wt% of a second solid dispersion relative to the total weight of the pharmaceutical composition; wherein the second solid dispersion comprises 70 wt% to 90 wt% of Compound III relative to the total weight of the second solid dispersion:

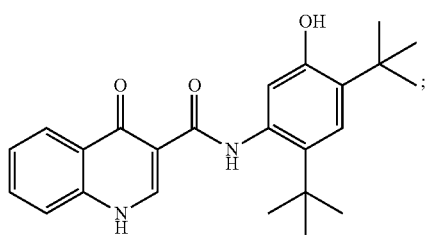 [SMILES: CC(C)(C)c1cc(C(C)(C)C)c(NC(=O)c2c[nH]c3ccccc3c2=O)cc1O]

and 10 wt% to 30 wt% of a polymer relative to the total weight of the second solid dispersion.

4. A single tablet comprising:
(a) 25 mg to 125 mg of Compound I:

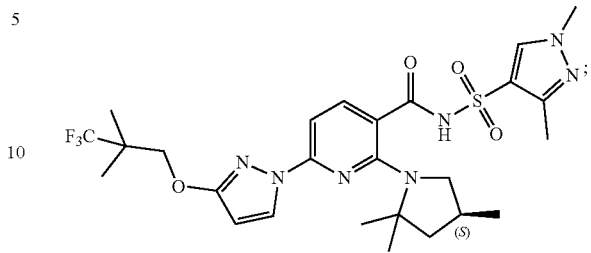

(b) 60 mg to 65 mg of a first solid dispersion comprising 80 wt% Compound II relative to the total weight of the first solid dispersion:

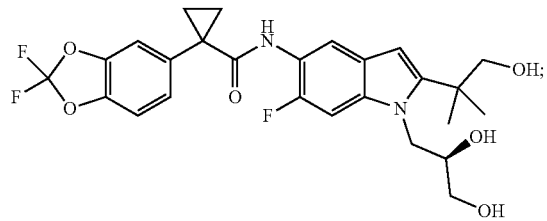 [SMILES: CC(C)(CO)c1cc2cc(NC(=O)C3(c4ccc5c(c4)OC(F)(F)O5)CC3)c(F)cc2n1C[C@@H](O)CO]

and 20 wt% of a hydroxypropyl methylcellulose relative to the total weight of the first solid dispersion; and (c) 90 mg to 95 mg, or 180 mg to 190 mg of a second solid dispersion comprising 80 wt% of Compound III relative to the total weight of the second solid dispersion:

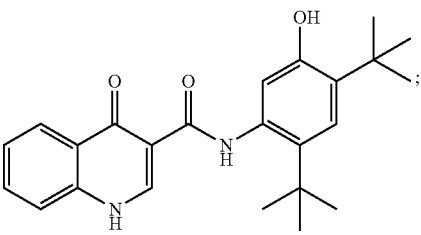 [SMILES: CC(C)(C)c1cc(C(C)(C)C)c(NC(=O)c2c[nH]c3ccccc3c2=O)cc1O]

0.5 wt% of sodium lauryl sulfate relative to the total weight of the second solid dispersion; and 19.5 wt% of a hydroxypropyl methylcellulose acetate succinate to the total weight of the second solid dispersion (d) 85 mg to 275 mg of microcrystalline cellulose;
(e) 10 mg to 35 mg of croscarmellose sodium; and
(f) 2 mg to 7 mg of magnesium stearate.

5. A single tablet of comprising:
(a) 10 mg to 110 mg of Compound I:

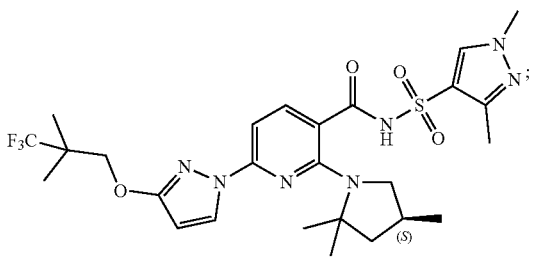

(b) 25 mg to 70 mg of a first solid dispersion comprising 80 wt% Compound II relative to the total weight of the first solid dispersion:

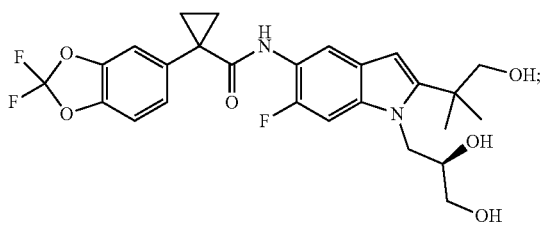 [SMILES: CC(C)(CO)c1cc2cc(NC(=O)C3(c4ccc5c(c4)OC(F)(F)O5)CC3)c(F)cc2n1C[C@@H](O)CO]

and 20 wt% of a hydroxypropyl methylcellulose relative to the total weight of the first solid dispersion; and (c) 85 mg to 195 mg, of a second solid dispersion comprising 80 wt% of Compound III relative to the total weight of the second solid dispersion:

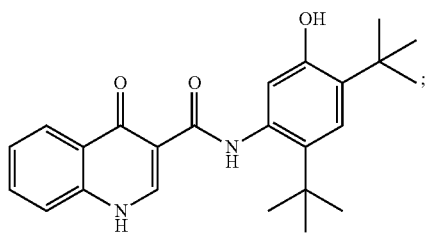 [SMILES: CC(C)(C)c1cc(C(C)(C)C)c(NC(=O)c2c[nH]c3ccccc3c2=O)cc1O]

0. 5 wt% of sodium lauryl sulfate relative to the total weight of the second solid dispersion; and 19.5 wt% of a hydroxypropyl methylcellulose acetate succinate to the total weight of the second solid dispersion (d) 10 mg to 45 mg of croscarmellose sodium; and
(e) 95 mg to 280 mg of microcrystalline cellulose; and
(f) 2 mg to 7 mg of magnesium stearate.

6. A pharmaceutical composition comprising
(a) 12 wt% to 30 wt% Compound I relative to the total weight of the pharmaceutical composition:

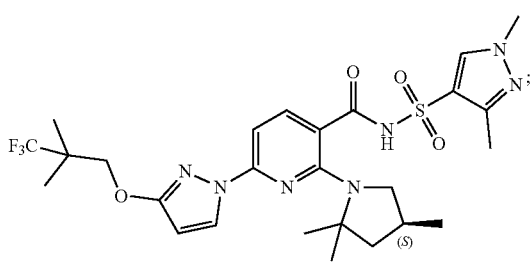

(b) 5 wt% to 15 wt% of Compound II relative to the total weight of the pharmaceutical composition:

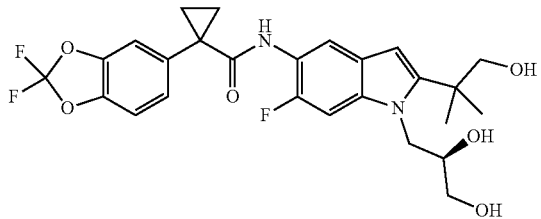 [SMILES: CC(C)(CO)c1cc2cc(NC(=O)C3(c4ccc5c(c4)OC(F)(F)O5)CC3)c(F)cc2n1C[C@@H](O)CO]

(c) 10 wt% to 25 wt% of Compound III or Compound III-d relative to the total weight of the pharmaceutical composition:

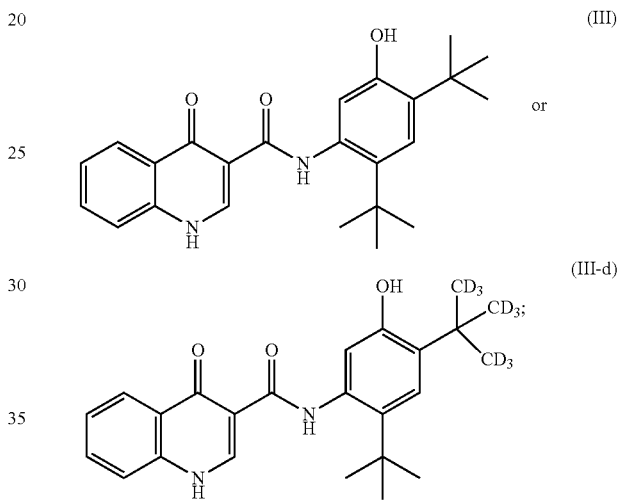

(d) 20 wt% to 45 wt% of microcrystalline cellulose relative to the total weight of the pharmaceutical composition;
(e) 3 wt% - 8 wt% of croscarmellose sodium relative to the total weight of the pharmaceutical composition; and
(f) 0.5 wt% to 2 wt% of magnesium stearate relative to the total weight of the pharmaceutical composition.

7. The pharmaceutical composition of claim 1, wherein Compound I is Crystalline Form A.

8. The pharmaceutical composition of claim 7, wherein Compound I Crystalline Form A is in substantially pure form.

9. The pharmaceutical composition of claim 7, wherein Compound I Crystalline Form A is characterized by an X-ray powder diffractogram having a signal at at least three two-theta values chosen from 6.6 ±0.2, 7.6 ±0.2, 9.6 ±0.2, 12.4 ±0.2, 13.1 ±0.2, 15.2 ±0.2, 16.4 ±0.2, 18.2 ±0.2, and 18.6 ±0.2.

10. A method of treating cystic fibrosis in a patient comprising orally administering to the patient one or more of the pharmaceutical composition of claim 1.

11. The method according to claim 10, wherein said patient having cystic fibrosis is chosen from patients with F508del/minimal function genotypes, patients with F508del/F508del genotypes, patients with F508del/gating genotypes, and patients with F508del/residual function genotypes.

12. A method of preparing the single tablet of claim 4, comprising
   (a) mixing Compound I and the first and second solid dispersions to form a first mixture; and
   (b) compressing a tablet mixture comprising the first mixture into a tablet.

13. A method of preparing the single tablet of claim 4, comprising
   (a) mixing Compound I and the first and second solid dispersions to form a first mixture;
   (b) mixing the first mixture with said microcrystalline cellulose, croscarmellose sodium and magnesium stearate to form a tablet mixture; and (c) compressing the tablet mixture into a tablet.

* * * * *